United States Patent
Krummel et al.

(10) Patent No.: US 10,428,143 B2
(45) Date of Patent: Oct. 1, 2019

(54) MODULATION OF STIMULATORY AND NON-STIMULATORY MYELOID CELLS

(71) Applicant: The Regents of the University of California, Oakland, CA (US)

(72) Inventors: Matthew Krummel, San Francisco, CA (US); Miranda Broz, San Francisco, CA (US); Denise Wolf, San Francisco, CA (US); Joshua Pollack, San Francisco, CA (US); Mikhail Biennewies, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/514,471

(22) PCT Filed: Sep. 28, 2015

(86) PCT No.: PCT/US2015/052682
§ 371 (c)(1),
(2) Date: Mar. 24, 2017

(87) PCT Pub. No.: WO2016/049641
PCT Pub. Date: Mar. 31, 2016

(65) Prior Publication Data
US 2017/0291946 A1 Oct. 12, 2017

Related U.S. Application Data

(60) Provisional application No. 62/129,883, filed on Mar. 8, 2015, provisional application No. 62/056,569, filed on Sep. 28, 2014.

(51) Int. Cl.
| | |
|---|---|
| A61K 39/00 | (2006.01) |
| C07K 16/28 | (2006.01) |
| C07K 16/24 | (2006.01) |
| C07K 16/30 | (2006.01) |
| C12N 5/071 | (2010.01) |
| C12N 5/0784 | (2010.01) |
| C12N 5/0786 | (2010.01) |
| C12N 5/09 | (2010.01) |
| G01N 33/569 | (2006.01) |

(52) U.S. Cl.
CPC ........ *C07K 16/2803* (2013.01); *C07K 16/243* (2013.01); *C07K 16/2818* (2013.01); *C07K 16/2863* (2013.01); *C07K 16/30* (2013.01); *C07K 16/3046* (2013.01); *C07K 16/3053* (2013.01); *C12N 5/0626* (2013.01); *C12N 5/0639* (2013.01); *C12N 5/0645* (2013.01); *C12N 5/0693* (2013.01); *G01N 33/56966* (2013.01); *A61K 2039/505* (2013.01); *C07K 2317/73* (2013.01); *C07K 2317/76* (2013.01)

(58) Field of Classification Search
CPC ................................................ A61K 2039/505
See application file for complete search history.

(56) References Cited

U.S. PATENT DOCUMENTS

| | | | |
|---|---|---|---|
| 6,344,339 B1 * | 2/2002 | Menrad | A61K 51/103 435/7.1 |
| 7,777,008 B2 | 8/2010 | Ponath et al. | |
| 8,231,878 B2 * | 7/2012 | Colonna | C07K 14/70503 424/178.1 |
| 8,901,281 B2 | 12/2014 | Ponath et al. | |
| 8,981,061 B2 * | 3/2015 | Colonna | C07K 16/28 530/387.9 |
| 9,696,312 B2 | 7/2017 | Suciu-Foca et al. | |
| 2010/0310560 A1 * | 12/2010 | Colonna | C07K 14/70503 424/134.1 |
| 2011/0053863 A1 | 3/2011 | Lyman et al. | |
| 2011/0262348 A1 | 10/2011 | Movahedi et al. | |
| 2012/0156280 A1 | 6/2012 | Dow et al. | |
| 2012/0276004 A1 | 11/2012 | Epstein et al. | |
| 2013/0150559 A1 | 6/2013 | Colonna et al. | |
| 2014/0045915 A1 | 2/2014 | Skog et al. | |
| 2017/0240631 A1 * | 8/2017 | Monroe | C07K 16/283 |
| 2017/0320946 A1 | 11/2017 | Colonna et al. | |
| 2018/0334977 A1 | 11/2018 | Hattar et al. | |
| 2019/0010230 A1 * | 1/2019 | Monroe | C07K 16/283 |

FOREIGN PATENT DOCUMENTS

| | | |
|---|---|---|
| WO | 2007/089942 A2 | 8/2007 |
| WO | WO2014/135245 A1 | 9/2014 |
| WO | WO2016/023019 A2 | 2/2016 |
| WO | WO2016/064895 A1 | 4/2016 |
| WO | WO2017/062672 A2 | 4/2017 |
| WO | WO2018/015573 A2 | 1/2018 |

OTHER PUBLICATIONS

Humphrey et al. (J. Bone Miner. Res. Feb. 2006; 21 (2): 237-45).*
Piccio et al. (Eur. J. Immunol. May 2007; 37 (5): 1290-301).*
Bergers et al. (Current Opinion in Genetics and Development. 2000; 10: 120-127).*
Kelland (Eur. J. Cancer. Apr. 2004; 40 (6): 827-836).*
Schuh (Toxicologic Pathology. 2004; 32 (Suppl. 1): 53-66).*
Dennis (Nature. Aug. 7, 2006; 442: 739-741).*
Gura (Science. 1997; 278: 1041-1042).*
Riemer et al. (Mol. Immunol. 2005; 42: 1121-1124).*
Jiang et al. (J. Biol. Chem. Feb. 11, 2005; 280 (6): 4656-4662).*

(Continued)

*Primary Examiner* — Stephen L Rawlings

(57) ABSTRACT

Provided herein are methods and compositions for enhancing an immune response and/or for the treatment of an immune-related condition in an individual, e.g., cancer, comprising killing, disabling, or depleting non-stimulatory myeloid cells using an antigen binding protein such as an antibody or antigen binding fragment thereof.

22 Claims, 58 Drawing Sheets
Specification includes a Sequence Listing.

(56) References Cited

OTHER PUBLICATIONS

Press et al. (J. Immunol. Dec. 15, 1988; 141 (12): 4410-4417).*
Leblond et al. (J. Biol. Chem. Apr. 5, 1991; 266 (10): 6058-67).*
Sano et al. (J. Biochem. Jan. 2007; 141 (1): 127-36).*
Wu (Clin. Can. Res. 2006; 12 (21): 6573-84).*
Bouchon et al. (J. Exp. Med. Oct. 15, 2001; 194 (8): 1111-22).*
Cheng et al. (J. Biol. Chem. Aug. 10, 2018; 293 (32): 12620-12633).*
Yao et al. (Oncotarget. May 17, 2016; 7 (20): 29620-34).*
Pettersen et al. (J. Immunol. Jun. 15, 1999; 162 (12): 7031-7040).*
Vuist et al. (Cancer Res. Sep. 15, 1990; 50 (18): 5767-5772).*
Kim et al. (Int. J. Cancer. 2002; 102: 428-434).*
Masui et al. (Cancer Res. Nov. 1986; 46 (11): 5592-5598).*
Kipps et al. (J. Exp. Med. Jan. 1, 1985; 161 (1): 1-17).*
Lewis et al. (Cancer Immunol. Immunother. Sep. 1993; 37 (4): 255-63).*
Campbell et al (Blood Reviews. 2003; 17:143-52).*
Zhang et al. (Int. J. Oncol. Dec. 2016; 49 (6): 2498-2506).*
Hamid et al., "Safety and Tumor Responses with Lambrolizumab (Anti-PD-1) in Melanoma," The New England Journal of Medicine, Jun. 2, 2013 (Jun. 2, 2013) vol. 369, No. 2, pp. 134-144 (entire document).
Li et al., Experimental animal modeling for immuno-oncology, Pharmacology & Therapeutics 173 (2017) 34-16.
San Mamed et al., Defining the optimal murine models to investigate immune checkpoint blockers and their combination with other immunotherapies, Annals of Oncology 27: 1190-1198, 2016.
Broz, M.L. et al., "Dissecting the Tumor Myeloid Compartment Reveals Rare Activating Antigen-Presenting Cells Critical for T Cell Immunity," Cancer Cell, Errata, Dec. 8, 2014, p. 938 , vol. 26, Issue 6.
PCT International Search Report and Written Opinion, PCT Application No. PCT/US2015/052682, dated Jan. 12, 2016, pages.
Saito et al., "Prognostic Significance of CD169 Lymph Node Sinus Macrophages in Patients with Malignant Melanoma", Cancer Immunology Research 3(12). Published OnlineFirst, Aug. 21, 2015.
Broz et al., "The Emerging Understanding of Myeloid Cells as Partners and Targets in Tumor Rejection", Cancer Immunology at the Crossroads: Experimental Immunotherapies. Cancer Immunology Research; 3(4) Apr. 2015.. www.aacrjournals.org. 2015. pp. 313-319.
Cook et al., "MerTK inhibition in tumor leukocytes decreases tumor growth and metastasis", J. Clin Invest. 2013; 123(8):3231-3242. vol. 123, No. 8, Aug. 2013.
Cummings et al., "Mer590, a novel monoclonal antibody targeting MER receptor tyrosine kinase, decreases colony formation and increases chemosensitivity in non-small cell lung cancer", Oncotarget, vol. 5, No. 21. www.impactjournals.com/oncotarget. pp. 10434-10445. Published Jun. 26, 2014.
Duluc, et al., "Tumor-associated leukemia inhibitory factor and IL-6 skew monocyte differentiation into tumor-associated macrophage-like cells", 2007 American Society of Hematology, Blood, Dec. 15, 2007, vol. 110, No. 13, pp. 4219.
Ford, et al., "TREM and TREM-like receptors in inflammation and disease", Current Opinion in Immunology, 2009, 21:38-46.
Taku Nagai et al., "Targeting tumor-associated macrophages in an experimental glioma model with a recombinant immunotoxin to folate receptor ß", Cancer Immunol Immunother (2009) 58:1577-1586.
Ojalvo et al., "High-Density Gene Expression Analysis of Tumor-Associated Macrophages from Mouse Mammary Tumors", The American Journal of Pathology, vol. 174, No. 3, Mar. 2009. pp. 1048-1064.
Ries, et al., "Targeting Tumor-Associated Macrophages with Anti-CSF-1R Antibody Reveals a Strategy for Cancer Therapy", Cancer Cell 25, 846-859, Jun. 16, 2014.
AEJ Rogers et al., "MER receptor tyrosine kinase inhibition impedes glioblastoma multiforme migration and alters cellular morphology", Oncogene (2012) 31, 4171-4181.
European Search Report from a co-pending application, dated Feb. 23, 2018, Application No. 15844518.9.

* cited by examiner

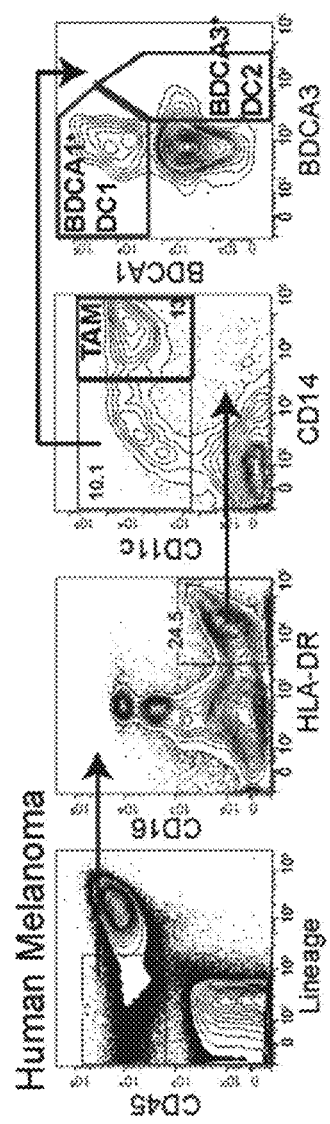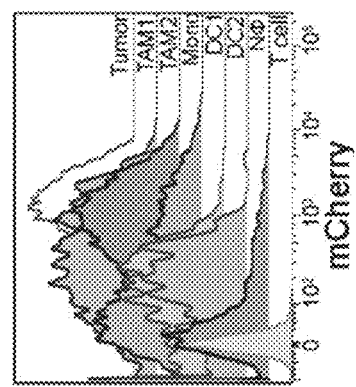

FIG. 2D Log$_2$ FC rel. to global ave. for top 1000 genes by variance
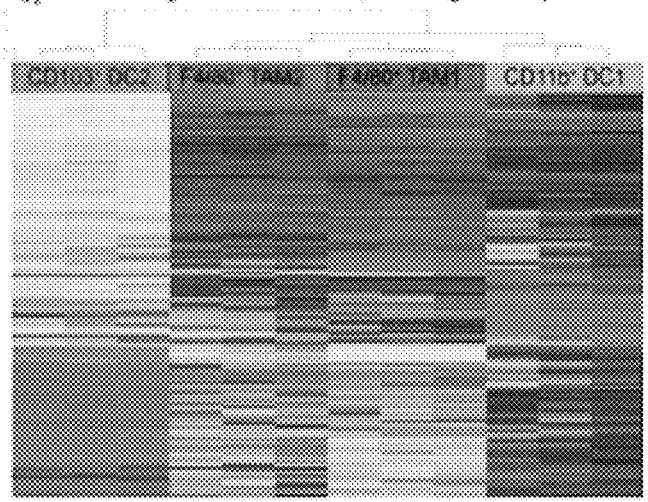
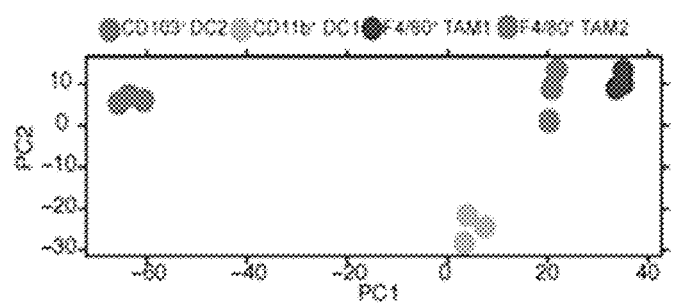
FIG. 2E
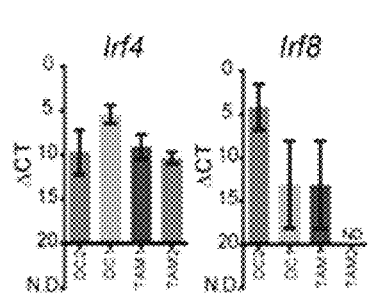
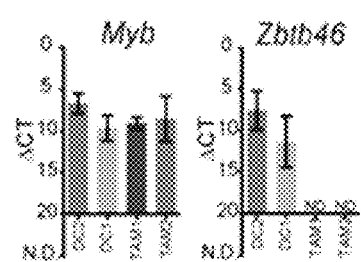
FIG. 2F
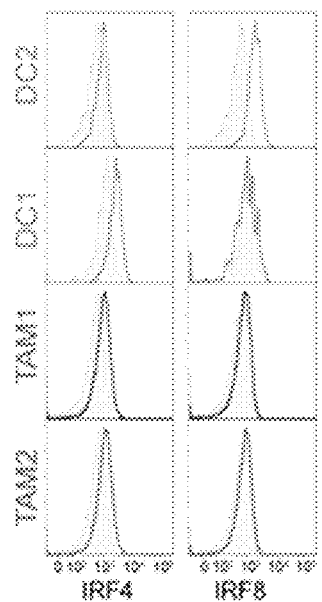
FIG. 2G

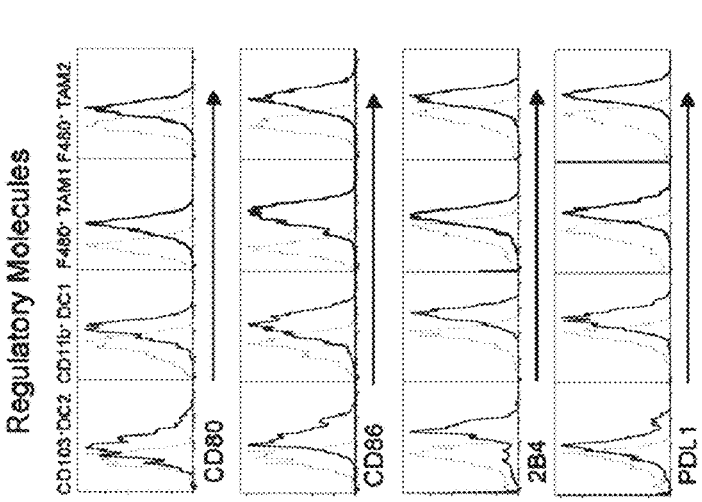
FIG. 5A
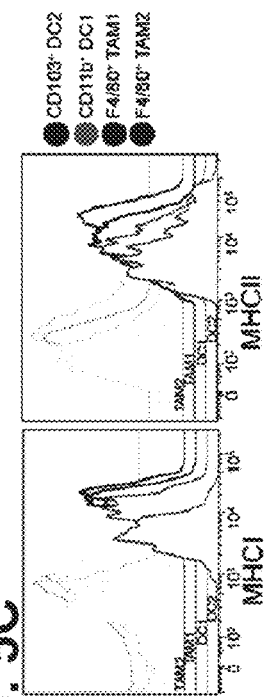
FIG. 5B
FIG. 5C

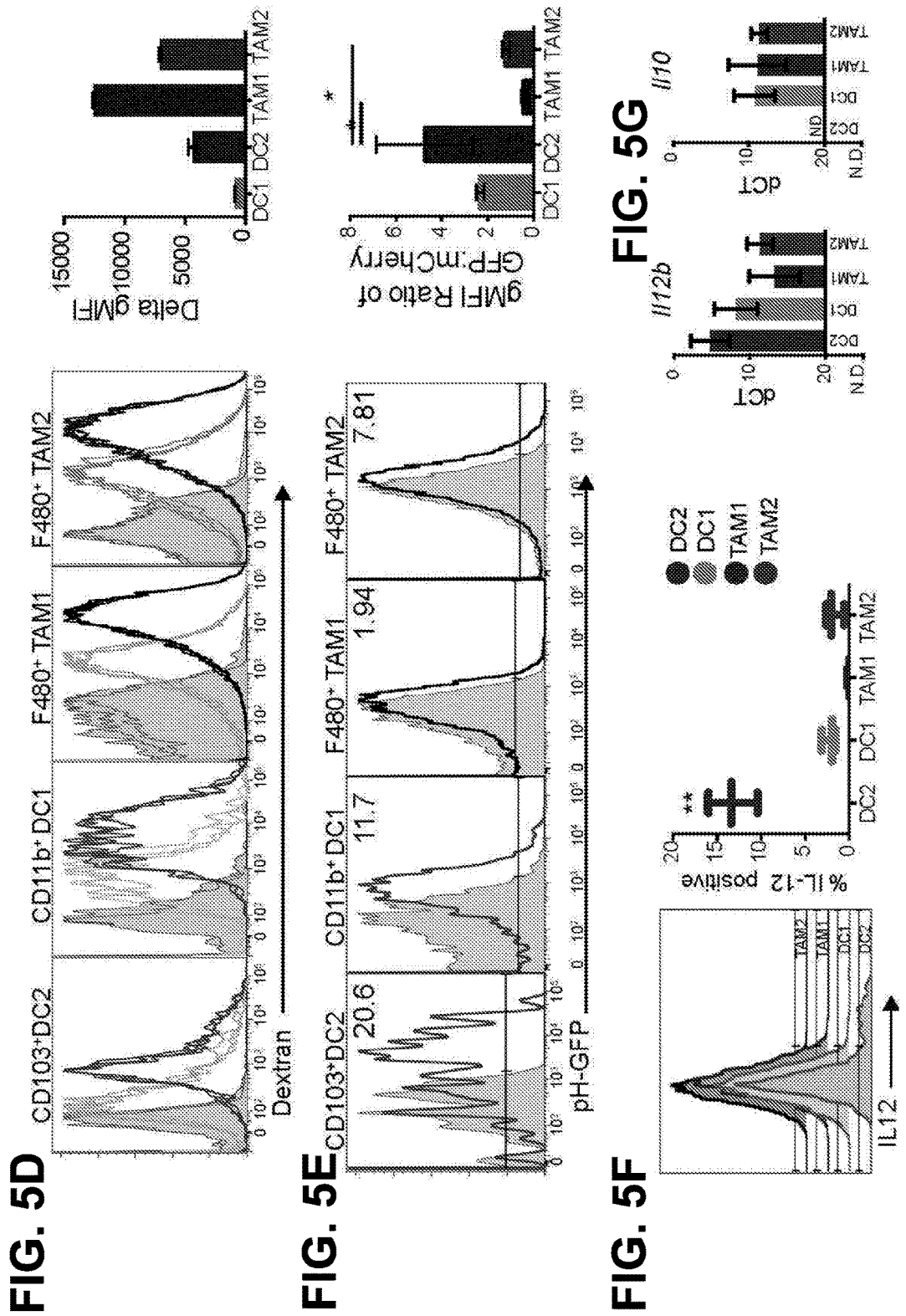

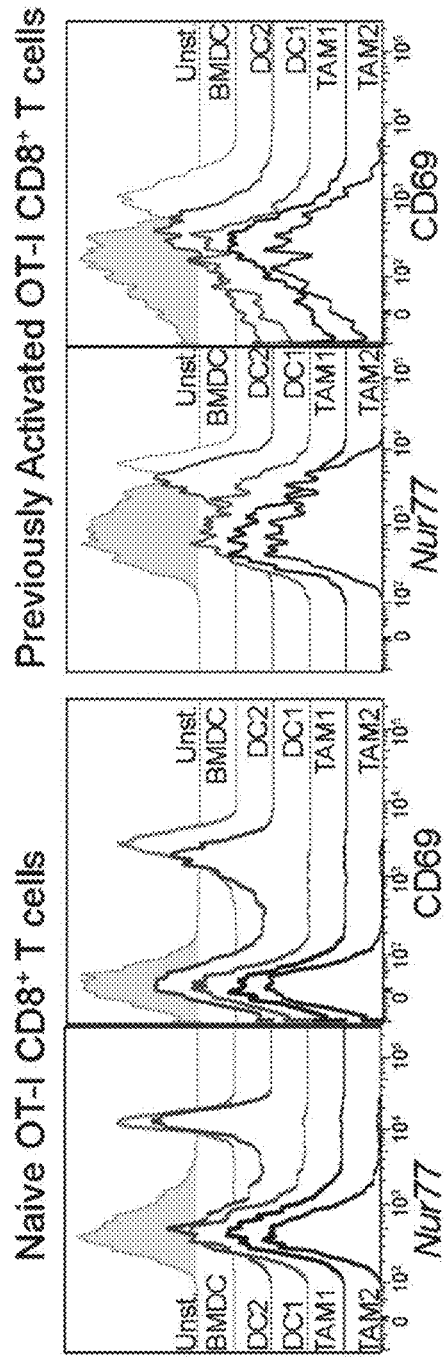
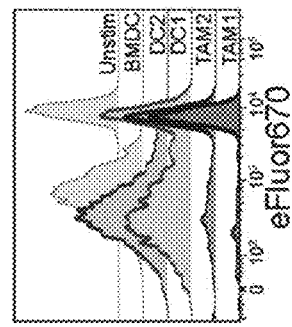
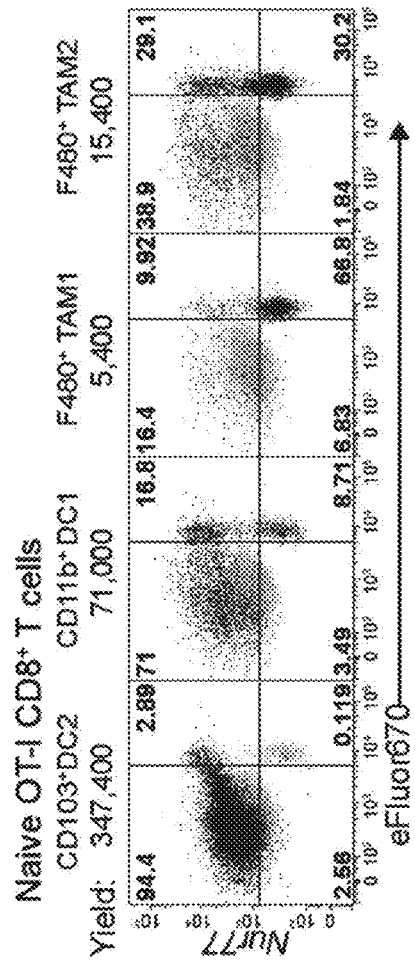
FIG. 6A
FIG. 6B
FIG. 6C

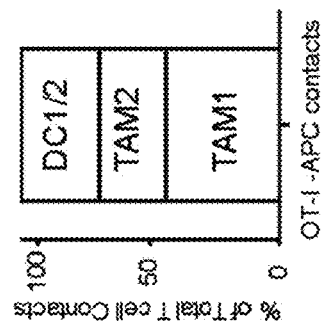
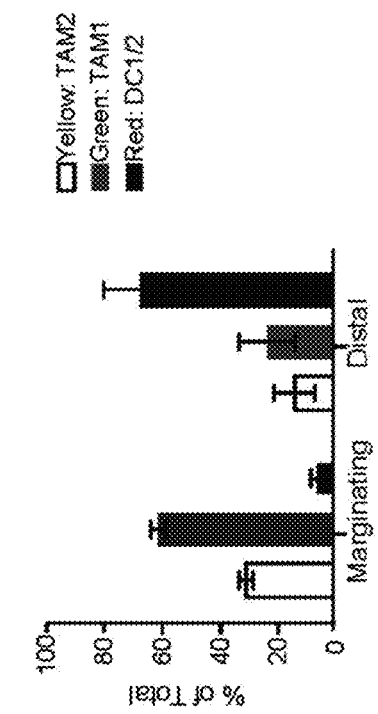
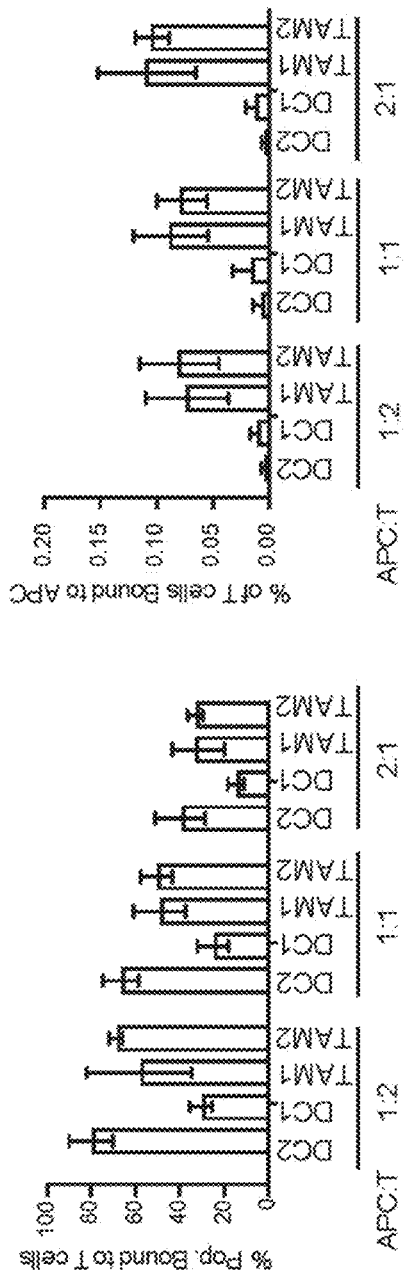

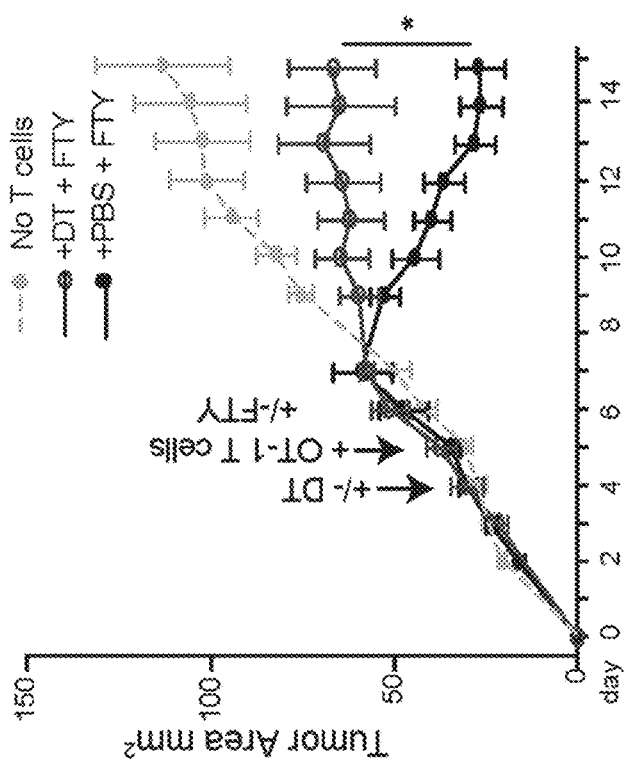

Cell Type
SDC: Stimulatory Dendritic cells (CD103+/BDCA3+)
NSM: Non-stimulatory Myeloid cells Signature Genes
Kit, Ccr7, Batf3, Flt3, Zbtb46, Irf8, Btla, Mycl1, Clec9a
C5ar1, Lyve1, Abcc3, Mrc1, Siglec1, Stab1, C1Qb, C1Qa, Tmem37, MS4A7, ApoE, Cyp4F18, Trem2, Tlr7

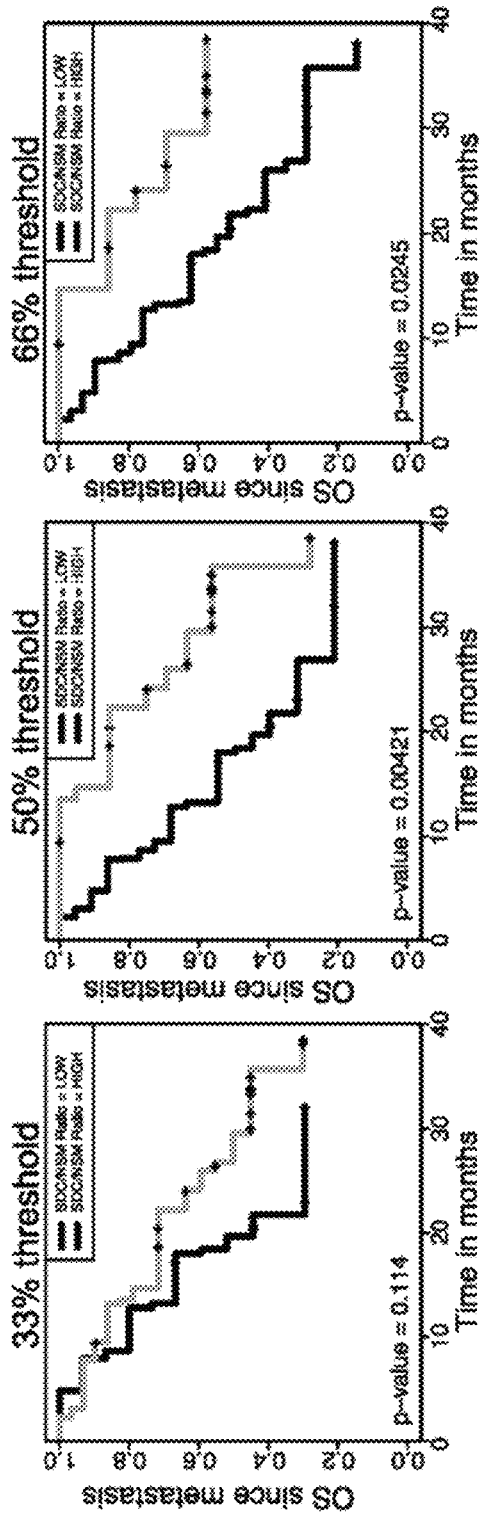
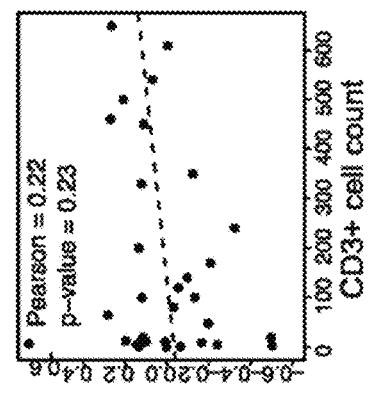
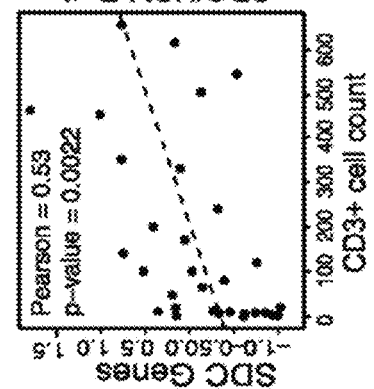
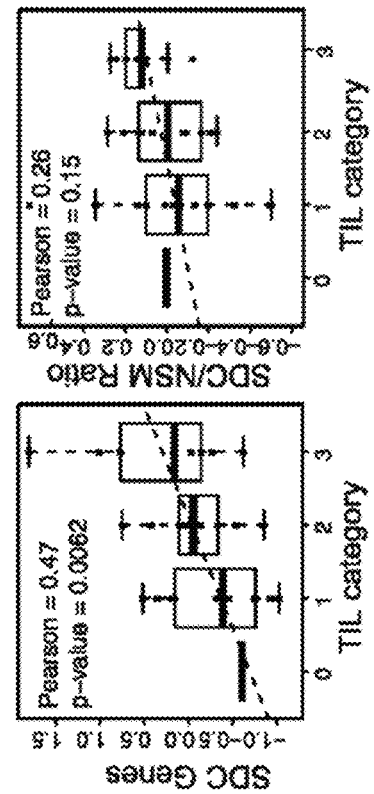

| Sample | Response | Best Objective Response (RECIST) | Primary Site | AJCC Stage | Prior Ipilimumab | Prior Targeted Therapy | Prior Radiation | Prior Chemotherapy | Baseline LDH |
|---|---|---|---|---|---|---|---|---|---|
| 1 | | -100 | Cutaneous | IV M1C | N | Y | Y | N | Normal |
| 2 | | -100 | Cutaneous | III C | Y | N | N | N | Normal |
| 3 | | -100 | Cutaneous | III C | Y | N | N | N | Normal |
| 4 | | -100 | Unknown | IV M1C | Y | N | N | N | Elevated |
| 5 | | -94 | Cutaneous | III C | N | Y | Y | N | Normal |
| 6 | | -76 | Cutaneous | IV M1C | Y | Y | N | N | Normal |
| 7 | | -73 | Cutaneous | IV M1C | Y | Y | N | Y | Normal |
| 8 | | -61 | Cutaneous | IV M1C | Y | N | N | Y | Normal |
| 9 | | -42 | Cutaneous | IV M1A | N | N | N | N | Elevated |
| 10 | | -13 | Unknown | IV M1C | Y | N | Y | Y | Normal |
| 11 | | -20 | Cutaneous | IV M1C | N | N | N | Y | Normal |
| 12 | | 0 | Cutaneous | III C | Y | Y | Y | N | Normal |
| 13 | | 5 | Acral | IV M1C | Y | Y | N | Y | Elevated |
| 14 | | 5 | Cutaneous | IV M1C | Y | N | N | N | Normal |
| 15 | | 15 | Cutaneous | IV M1C | Y | Y | N | N | Normal |
| 16 | | 27 | Cutaneous | IV M1C | Y | Y | Y | Y | Normal |
| 17 | | 33 | Cutaneous | IV M1C | Y | Y | Y | Y | Normal |
| 18 | | 80 | Cutaneous | IV M1C | N | Y | Y | N | Normal |
| 19 | | 100 | Unknown | IV M1C | Y | Y | N | Y | Normal |
| 20 | | 290 | Uveal | IV M1C | Y | N | N | N | Elevated |
| 21 | | ** | Cutaneous | IV M1B | Y | N | N | N | Elevated |
| 22 | | ** | Cutaneous | IV M1A | Y | N | N | Y | Normal |
| 23 | | ** | Unknown | IV M1C | N | N | Y | N | Normal |

FIG. 10A

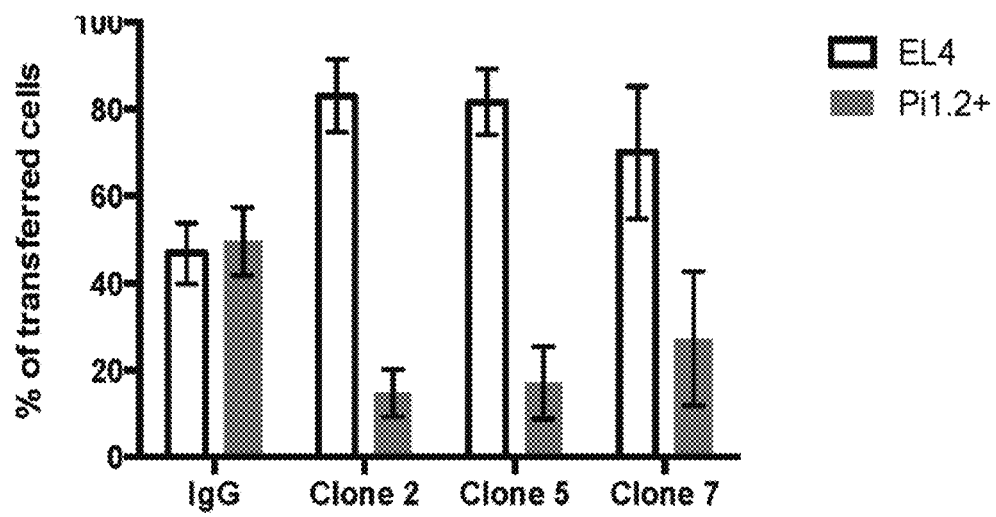
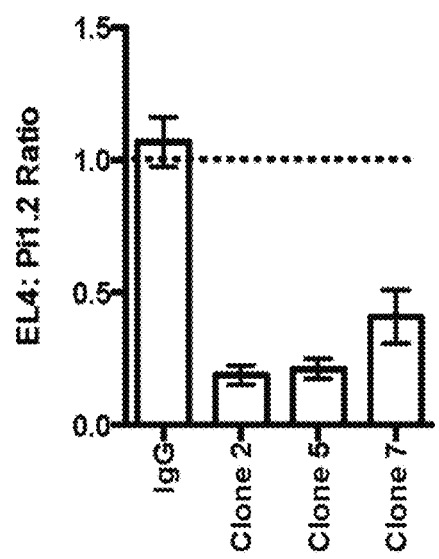
FIG. 18B

MODULATION OF STIMULATORY AND NON-STIMULATORY MYELOID CELLS

CROSS REFERENCE TO RELATED APPLICATIONS

This application claims the benefit of U.S. Provisional Application No. 62/056,569, filed Sep. 28, 2014 and U.S. Provisional Application No. 62/129,883, filed Mar. 8, 2015, each of which is hereby incorporated by reference, in its entirety, for all purposes.

STATEMENT REGARDING FEDERALLY SPONSORED RESEARCH OR DEVELOPMENT

This invention was made with government support under U01 CA141451 and U54 CA163123 awarded by the National Institutes of Health. The government has certain rights in the invention.

BACKGROUND

Immunity plays a role in preventing tumor outgrowth. A complex microenvironment can develop within the lesion, and despite the recruitment of T-cells, there is often no effective control of the developing mass. Understanding the balance between tumor elimination and tumor escape may rely on a comprehension of the differential roles myeloid cells play in the tumor microenvironment.

Myeloid populations of the tumor microenvironment prominently include monocytes and neutrophils (sometimes loosely grouped as myeloid-derived suppressor cells), macrophages, and dendritic cells. Although intra-tumoral myeloid populations, as a whole, have long been considered non-stimulatory or suppressive, it has more recently been appreciated that not all tumor-infiltrating myeloid cells are made equal.

In normal tissues, many of these myeloid cells are essential for proper functioning of both innate and adaptive immunity and notably for wound repair. However in the setting of cancer, a significant excess of macrophages and dysfunctional or skewed populations of these and other cell types are commonly described. When considered as an aggregate population defined by single markers, such as CD68 or CD163, "macrophage" infiltration is correlated with worse outcomes in subjects across multiple tumor types ((de Visser, Cancer Immunol Immunother, 2008; 57:1531-9); (Hanada et al., Int J Urol 2000; 7:263-9); (Yao et al. Clin Cancer Res, 520, 2001; 7:4021-6); (Ruffell et al., PNAS, 523 2012; 109:2796-801)). But the phenotypic and functional subsetting of macrophages from the tumor microenvironment is complicated by the similarity of macrophages and dendritic cells, and is problematic in tumor biology. A morphologic criterion has been often applied to the issue; one approach to try to differentiate dendritic cells from macrophages was based on a more spikey or dendritic morphology for the former and more veiled or bulbous morphology for the latter (Bell et al., J Exp Med 555, 1999; 190:1417-26). Other groups are trying to differentiate on the basis of genetic and cell-surface markers.

There is diversity in the antigen-presenting compartment within tumors, and T-cells can differentiate features of antigen-presenting cells (APC). Because T cells are a major driver of tumor immunity, understanding the exact features of their cognate APCs will be important. Myeloid cells are prominent among cells capable of presenting tumor-derived antigens to T-cells and thereby maintaining the latter in an activated state. Antigen presentation occurs within the tumor itself and likely influences the functions of tumor cytotoxic T-lymphocytes (CTLs). T-cell activation by antigen presenting cells (APC) is an important component in antigen-specific immune responses and tumor cell killing. As these myeloid populations represent major T-cell-interacting partners and antigen-presenting cells for incoming tumor-reactive cytotoxic T lymphocytes, understanding their distinctions may guide therapeutic avenues.

All patents, patent applications, publications, documents, and articles cited herein are incorporated herein by reference in their entireties.

SUMMARY

Described herein is a method of killing, disabling, or depleting non-stimulatory myeloid cells present in a cancer tissue of a subject, comprising contacting the non-stimulatory myeloid cells with an antibody or antigen-binding fragment thereof that binds to the non-stimulatory myeloid cells and is present in an amount effective to kill, disable, or deplete the non-stimulatory myeloid cells in the cancer tissue of the subject. In some aspects, the non-stimulatory myeloid cells are in a population of immune cells comprising stimulatory myeloid cells and non-stimulatory myeloid cells. In some aspects, the killing, disabling, or depleting of the non-stimulatory myeloid cells treats the subject by reducing the amount or volume of cancer tissue. In some aspects, the contacting increases the ratio of stimulatory myeloid cells to non-stimulatory myeloid cells in the population of immune cells. In some aspects, the contacting reduces the ratio of the non-stimulatory myeloid cells to stimulatory myeloid cells in the population of immune cells. In some aspects, the contacting enhances an immune response in the subject. In some aspects, the contacting does not substantially kill, disable, or deplete myeloid cells present outside of the cancer tissue and/or stimulatory myeloid cells present in the cancer tissue.

Also disclosed herein is a method of treating a cancer in a subject, comprising administering an antibody or antigen-binding fragment thereof that binds to non-stimulatory myeloid cells present in the cancer and is present in an amount effective to kill, disable, or deplete the non-stimulatory myeloid cells. In some aspects, the non-stimulatory myeloid cells are in a population of immune cells comprising stimulatory myeloid cells and non-stimulatory myeloid cells. In some aspects, the killing, disabling, or depleting of the non-stimulatory myeloid cells treats the subject by reducing the amount or volume of cancer tissue. In some aspects, the contacting increases the ratio of stimulatory myeloid cells to non-stimulatory myeloid cells in the population of immune cells. In some aspects, the contacting reduces the ratio of the non-stimulatory myeloid cells to stimulatory myeloid cells in the population of immune cells. In some aspects, the contacting does not substantially kill, disable, or deplete myeloid cells present outside of the cancer and/or stimulatory myeloid cells present in the cancer. In some aspects, the subject's cancer is treated by generating or enhancing an immune response to the cancer.

In some aspects, the antibody or antigen-binding fragment thereof binds to the extracellular domain of a target protein expressed on the non-stimulatory myeloid cells selected from the group consisting of TREM2, MS4A7, C5AR1, LYVE1, ABCC3, LILRB4, MRC1/CD206, SIGLEC1, STAB1, TMEM37, MERTK, and TMEM119, wherein the non-stimulatory myeloid cells are $CD45^+$, $HLA\text{-}DR^+$, $CD11c^+$, $CD14^+$, and $BDCA3^-$, wherein the antibody or antigen-binding fragment thereof kills, disables, or depletes the non-stimulatory myeloid cells via antibody-dependent cell-mediated cytotoxicity (ADCC) or complement-dependent cytotoxicity (CDC) to a level that is less than the level of non-stimulatory myeloid cells present in the cancer tissue prior to the contacting of the non-stimulatory myeloid cells with the antibody or antigen-binding fragment thereof, wherein the non-stimulatory myeloid cells are present in a population of immune cells comprising stimulatory myeloid cells that are CD45$^+$, HLA-DR$^+$, CD14$^-$, CD11c$^+$, BDCA1$^-$, and BDCA3$^+$ and the non-stimulatory myeloid cells, wherein the contacting or administering does not substantially kill, disable, or deplete myeloid cells present outside of the cancer tissue and/or stimulatory myeloid cells present in the cancer tissue, and wherein the killing, disabling, or depleting of the non-stimulatory myeloid cells treats the cancer by enhancing an immune response to the cancer tissue.

In some aspects, the non-stimulatory myeloid cells are at least one of: tumor-associated macrophages; tumor-associated dendritic cells; CD45$^+$, HLA-DR$^+$, CD11c$^+$, CD14$^+$, and BDCA3$^-$; CD45$^+$, HLA-DR$^+$, and CD14+; CD45$^+$, HLA-DR$^+$, CD14$^+$, BDCA3$^-$, CD11b$^+$, and CD11c$^+$; CD45$^+$, HLA- DR$^+$, CD14$^-$, CD11c$^+$, and BDCA1$^+$; or are not BDCA3$^+$, as determined by flow cytometry or an equivalent assay. In some aspects, the non-stimulatory myeloid cells are positive for at least one of: C5AR1, LYVE1, ABCC3, MRC1, SIGLEC1, STAB1, C1QB, C1QA, TMEM37, MERTK, C1QC, TMEM119, MS4A7, APOE, CYP4F18, TREM2, TLR7, and LILRB4; and/or are negative for at least one of: KIT, CCR7, BATF3, FLT3, ZBTB46, IRF8, BTLA, MYCL1, CLEC9A, BDCA3, and XCR1, as measured by polymerase chain reaction (PCR), gene array, flow cytometry, RNAseq, or an equivalent assay.

In some aspects, the antibody or antigen-binding fragment thereof has at least one of antibody-dependent cell-mediated cytotoxicity (ADCC) activity, complement-dependent cytotoxicity (CDC) activity, and antibody-mediated phagocytosis activity. In some aspects, the antibody is at least one of a monoclonal antibody, an antagonistic antibody, a polyclonal antibody, an IgG1 antibody, an IgG3 antibody, an afucosylated antibody, a bispecific antibody, a human antibody, a humanized antibody, a chimeric antibody, a full length antibody, and an antigen binding fragment. In some aspects, the antibody or antigen-binding fragment thereof is not an IgG2 antibody or wherein the antibody or antigen-binding fragment thereof is not an IgG4 antibody. In some aspects, the antibody or antigen-binding fragment thereof is conjugated. In some aspects, the antibody or antigen-binding fragment thereof is conjugated to at least one therapeutic agent selected from the group consisting of a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide, an antisense molecule, a siRNA, a second antibody and a second antibody fragment. In some aspects, the antibody or antigen-binding fragment thereof selectively binds at least one of TREM2, MS4A7, C5AR1, LYVE1, ABCC3, LILRB4, MRC1/CD206, SIGLEC1, STAB1, TMEM37, MERTK, and TMEM119. In some aspects, the antibody or antigen-binding fragment thereof does not selectively bind LILRB4.

In some aspects, the contacting or administering induces at least one of death of the non-stimulatory myeloid cells, apoptosis of the non-stimulatory myeloid cells, lysis of the non-stimulatory myeloid cells, phagocytosis of the non-stimulatory myeloid cells, and growth arrest in the non-stimulatory myeloid cells.

In some aspects, the stimulatory myeloid cells comprise cells that are at least one of CD45$^+$, HLA-DR$^+$, CD14$^-$, CD11c$^+$, BDCA1$^-$, and BDCA3$^+$; CD45$^+$, HLA-DR$^+$, CD14$^-$, CD11c$^+$, and BDCA3$^+$; CD45$^+$, HLA-DR$^+$, and BDCA3$^+$; CD45$^+$, HLA-DR$^+$, CD14$^-$, and BDCA3$^+$; and CD45$^+$, HLA-DR$^+$, CD11c$^+$, and BDCA3$^+$, as determined by flow cytometry or an equivalent assay. In some aspects, the stimulatory myeloid cells are negative for at least one of: C5AR1, LYVE1, ABCC3, MRC1, SIGLEC1, STAB1, C1QB, C1QA, TMEM37, MERTK, C1QC, TMEM119, MS4A7, APOE, CYP4F18, TREM2, TLR7, and LILRB4; and/or are positive for at least one of: KIT, CCR7, BATF3, FLT3, ZBTB46, IRF8, BTLA, MYCL1, CLEC9A, BDCA3, and XCR1, as measured by polymerase chain reaction (PCR), gene array, flow cytometry, RNAseq, or an equivalent assay.

In some aspects, the non-stimulatory myeloid cells are in a population of immune cells comprising stimulatory myeloid cells and non-stimulatory myeloid cells.

In some aspects, the cancer tissue is a solid cancer or a liquid cancer. In some aspects, the cancer is selected from the group consisting of: melanoma, kidney, hepatobiliary, head-neck squamous carcinoma (HNSC), pancreatic, colon, bladder, glioblastoma, prostate, lung, and breast.

In some aspects, the subject is a human subject. In some aspects, the subject has previously received, is concurrently receiving, or will subsequently receive an immunotherapy. In some aspects, the immunotherapy is at least one of: an immunotherapy that inhibits a checkpoint inhibitor; an immunotherapy that inhibits a checkpoint inhibitor of T cells; anti-PD1; anti-PDL1; anti-CTLA4; adoptive T cell therapy; CAR-T cell therapy; a dendritic cell vaccine; a monocyte vaccine; an antigen binding protein that binds both a T cell and an antigen presenting cell; a BiTE antigen binding protein; a toll-like receipt ligand; and a cytokine.

In some aspects, the methods enhance an immune response in the subject. In some aspects, the immune response is an immunotherapy-based immune response. In some aspects, the immunotherapy-based immune response is targeted against the cancer tissue.

In some aspects, the methods further comprise administering an agent that enhances the activity of or increases the number of stimulatory myeloid cells. In some aspects, the agent is FLT3L.

In some aspects, the methods treat cancer in the subject.

In some aspects, the contacting or administering increases the ratio of stimulatory myeloid cells to non-stimulatory myeloid cells in the population of immune cells. In some aspects, the contacting or administering results in the subject having greater than 1-4, 1-2, 1, 1.37, 1.6, 2, 3, or 4% stimulatory myeloid cells present in the tumor of total CD45+, HLA-DR+ cells present in the tumor.

In some aspects, the methods further include determining the number of stimulatory myeloid cells and/or non-stimulatory myeloid cells in a biological sample from the subject. In some aspects, the determining step is used to determine whether the subject would benefit from administration of the antibody or antigen binding fragment thereof. In some aspects, the determining step is used to monitor the effectiveness of the administration of the antibody or antigen binding fragment thereof.

In some aspects, the methods further include determining the expression level of at least one of C5AR1, LYVE1, ABCC3, MRC1, SIGLEC1, STAB1, C1QB, C1QA, TMEM37, MERTK, C1QC, TMEM119, MS4A7, APOE, CYP4F18, TREM2, TLR7, and LILRB4 in a biological sample from the subject. In some aspects, the methods further include determining the expression level of at least one of KIT, CCR7, BATF3, FLT3, ZBTB46, IRF8, BTLA, MYCL1, CLEC9A, BDCA3, and XCR1 in a biological sample from the subject.

In some aspects, the antibody or antigen-binding fragment thereof is in a pharmaceutical composition comprising the antibody or antigen-binding fragment thereof and a pharmaceutically acceptable excipient. In some aspects, the composition is sterile.

In some aspects, the antibody or antigen-binding fragment thereof binds to the extracellular domain of a target protein expressed on the non-stimulatory myeloid cells selected from the group consisting of TREM2, MS4A7, C5AR1, LYVE1, ABCC3, LILRB4, MRC1/CD206, SIGLEC1, STAB1, TMEM37, MERTK, and TMEM119, wherein the non-stimulatory myeloid cells are CD45$^+$, HLA-DR$^+$, CD11c$^+$, CD14$^+$, and BDCA3$^-$, wherein the antibody or antigen-binding fragment thereof kills, disables, or depletes the non-stimulatory myeloid cells via antibody-dependent cell-mediated cytotoxicity (ADCC) or complement-dependent cytotoxicity (CDC) to a level that is less than the level of non-stimulatory myeloid cells present in the cancer tissue prior to the contacting of the non-stimulatory myeloid cells with the antibody or antigen-binding fragment thereof, wherein the non-stimulatory myeloid cells are present in a population of immune cells comprising stimulatory myeloid cells that are CD45$^+$, HLA-DR$^+$, CD14$^-$, CD11c$^+$, BDCA1$^-$, and BDCA3$^+$ and the non-stimulatory myeloid cells, and wherein the killing, disabling, or depleting of the non-stimulatory myeloid cells treats the cancer.

Also disclosed herein is a method of enhancing a subject's immune response to a tumor, comprising administering an effective amount of a treatment to the subject which enhances the abundance of stimulatory myeloid cells in the tumor or decreases the abundance of non-stimulatory myeloid cells in the tumor, wherein the treatment enhances the immune response to the tumor, optionally wherein the immune response reduces the volume of the tumor.

Also disclosed herein is a method of improving the efficacy of a cancer immunotherapy treatment in a subject having a tumor, comprising administrating an effective amount of a treatment to the subject which enhances the abundance of stimulatory myeloid cells in the tumor or decreases the abundance of non-stimulatory myeloid cells in the tumor, wherein the subject has previously received, is concurrently receiving, or will subsequently receive the cancer immunotherapy.

In some aspects, the methods comprise systemic administration or enhancement of FLT3L. In some aspects, the methods comprise systemic administration of one or more antibodies that result in elimination or reduction of non-stimulatory myeloid cells, selectively sparing stimulatory myeloid cells. In some aspects, the methods comprise treatment of a subject's autologous bone-marrow or blood cells with FLT3L while simultaneously blocking the expression or action of CSF1. In some aspects, the methods comprise enhancing expression of IRF8, Mycl1, or BATF3 or ZBTB46 in bone-marrow or blood progenitor populations.

Also disclosed herein is a method of determining the presence or absence of non-stimulatory myeloid cells in a sample from a subject, comprising: contacting a population of immune cells comprising the non-stimulatory myeloid cells and stimulatory myeloid cells with an antibody or antigen-binding fragment thereof that binds to the non-stimulatory myeloid cells; determining the presence of complexes indicating the binding of the antibody to non-stimulatory myeloid cells; optionally quantifying the number of non-stimulatory myeloid cells in the population; and optionally treating the subject with an antibody or antigen-binding fragment thereof that binds to the non-stimulatory myeloid cells.

Also disclosed herein is a method of determining the presence or absence of stimulatory myeloid cells in a sample from a subject, comprising: contacting a population of immune cells comprising the stimulatory myeloid cells and non-stimulatory myeloid cells with an antibody or antigen-binding fragment thereof that binds to the stimulatory myeloid cells; determining the presence of complexes indicating the binding of the antibody to stimulatory myeloid cells; optionally quantifying the number of stimulatory myeloid cells in the population; and optionally treating the subject.

Also disclosed herein is a method of quantifying non-stimulatory myeloid cells in a tumor sample, comprising measuring the number of cells which are at least one of: tumor-associated macrophages; tumor-associated dendritic cells; CD45$^+$, HLA-DR$^+$, and CD14$^+$; CD45$^+$, HLA-DR$^+$, CD14$^+$, BDCA3$^-$, CD11b$^+$, and CD11c$^+$; CD45$^+$, HLA-DR$^+$, CD14$^-$, CD11c$^+$, and BDCA1$^+$; or are not BDCA3$^+$.

Also disclosed herein is a method of quantifying stimulatory myeloid cells present in a tumor sample, comprising measuring the number of cells that are at least one of CD45$^+$, HLA-DR$^+$, CD14$^-$, CD11c+, and BDCA3$^+$; CD45$^+$, HLA-DR$^+$, and BDCA3$^+$; CD45$^+$, HLA-DR$^+$, CD14$^-$, and BDCA3$^+$; and CD45$^+$, HLA-DR$^+$, CD11c$^+$, and BDCA3$^+$.

In some aspects, the cells are quantified by a cell sorting method. In some aspects, the cell sorting method is selected from the group consisting of fluorescence activated cell sorting, flow-cytometry, magnetic-activated cell sorting, microraft sorting, and affinity-based cell separation.

Also disclosed herein is a method of quantifying non-stimulatory myeloid cells in a tumor sample, comprising measuring the expression of at least one of non-stimulatory myeloid cell markers: C5AR1, LYVE1, ABCC3, MRC1, SIGLEC1, STAB1, C1QB, C1QA, TMEM37, MERTK, C1QC, TMEM119, MS4A7, APOE, CYP4F18, TREM2, TLR7, and LILRB4.

Also disclosed herein is a method of quantifying stimulatory myeloid cells present in a tumor sample, comprising measuring the expression of at least one of stimulatory myeloid cell markers: KIT, CCR7, BATF3, FLT3, ZBTB46, IRF8, BTLA, MYCL1, CLEC9A, BDCA3, and XCR1.

In some aspects, the expression of the markers is measured by quantitative PCR. In some aspects, the quantification of marker gene expression is accomplished using an oligonucleotide array comprising immobilized probes for marker gene sequences.

In some aspects, the tumor sample is obtained from a tumor by needle biopsy, punch biopsy, or surgical excision of the tumor.

Also disclosed herein is a method of assessing cancer status in a patient, comprising the steps of obtaining a tumor sample from the subject; and measuring the abundance of stimulatory myeloid cells in the tumor sample derived from the subject.

In some aspects, the cancer status assessed is the likelihood of cancer recurrence; and wherein an elevated abundance of stimulatory myeloid cells in the tumor sample is indicative of a reduced likelihood of cancer recurrence. In some aspects, the cancer status assessed is the amenability of the subject to immunotherapy treatment; and wherein an elevated abundance of stimulatory myeloid cells in the tumor sample is indicative of an increased likelihood that the subject will respond positively to immunotherapy treatment. In some aspects, the cancer status assessed is the effectiveness of an immunotherapy treatment; and wherein an elevated abundance of stimulatory myeloid cells in the tumor sample is indicative of the immunotherapy treatment being effective. In some aspects, the cancer status assessed is expected cancer survival time; and wherein an elevated abundance of stimulatory myeloid cells in the tumor sample is indicative of an increased expected cancer survival time.

In some aspects, an elevated abundance of stimulatory myeloid cells is an abundance which exceeds the median or mean abundance of stimulatory myeloid cells observed in a pool of representative tumor samples. In some aspects, the abundance of stimulatory myeloid cells is measured as the ratio of stimulatory myeloid cells to non-stimulatory myeloid cells present in the sample. In some aspects, the abundance of stimulatory myeloid cells is measured as the ratio of stimulatory myeloid cells to total myeloid cells present in the sample. In some aspects, the abundance of stimulatory myeloid cells is measured as the ratio of stimulatory myeloid cells to total HLA-DR$^+$ cells present in the sample. In some aspects, an elevated abundance of stimulatory myeloid cells is defined as greater than 1.37 stimulatory myeloid cells per 100 HLA-DR$^+$ cells. In some aspects, the immunotherapy treatment is an anti-PD1 treatment. In some aspects, the anti-PD1 treatment is the administration of nivolumab or pembromizulab. In some aspects, the subject has melanoma.

Also disclosed herein is a method of assessing the effectiveness of a treatment to increase the abundance of stimulatory myeloid cells in tumors, comprising the steps of: administering the treatment to one or more subjects having cancer; and measuring the abundance of stimulatory myeloid cells in one or more tumor samples derived from the one or more subjects, wherein an increased abundance of stimulatory myeloid cells in the one or more tumor samples is indicative that the agent is effective.

In some aspects, an increased abundance of stimulatory myeloid cells is defined as a greater abundance of stimulatory myeloid cells in the one or more tumor samples than was observed in one or more tumor samples obtained from the one or more subjects prior to administration of the treatment. In some aspects, an increased abundance of stimulatory myeloid cells is defined as a greater abundance of stimulatory myeloid cells in the one or more tumor samples from treated subjects than is observed in a pool of representative tumor samples from untreated subjects.

An anti-LILRB4 antibody or antigen-binding fragment thereof that comprises one or more sequences shown in Table BB or a variant thereof having at least 80, 90, or 95% sequence identity to a sequence shown in Table BB, optionally wherein the antibody or antigen-binding fragment thereof comprises each of the CDRs of the CDR sequences shown in Table BB, optionally wherein the antibody or antigen-binding fragment thereof comprises each of the variable domains shown in Table BB, and optionally wherein the antibody or antigen-binding fragment thereof comprises the full length sequences shown in Table BB.

An antibody or antigen-binding fragment thereof which binds a LILRB4 protein and is capable of specifically killing, depleting, or disabling non-stimulatory myeloid cells.

In some aspects, the antibody or antigen-binding fragment thereof binds to the extracellular domain of LILRB4, wherein the antibody or antigen-binding fragment thereof kills, disables, or depletes non-stimulatory myeloid cells via antibody-dependent cell-mediated cytotoxicity (ADCC) or complement-dependent cytotoxicity (CDC).

In some aspects, the antibody or antigen-binding fragment thereof has at least one of antibody-dependent cell-mediated cytotoxicity (ADCC) activity, complement-dependent cytotoxicity (CDC) activity, and antibody-mediated phagocytosis activity. In some aspects, the antibody is at least one of a monoclonal antibody, an antagonistic antibody, a polyclonal antibody, an IgG1 antibody, an IgG3 antibody, an afucosylated antibody, a bispecific antibody, a human antibody, a humanized antibody, a chimeric antibody, a full length antibody, and an antigen binding fragment. In some aspects, the antibody or antigen-binding fragment thereof is not an IgG2 antibody or wherein the antibody or antigen-binding fragment thereof is not an IgG4 antibody. In some aspects, the antibody or antigen-binding fragment thereof is conjugated. In some aspects, the antibody or antigen-binding fragment thereof is conjugated to at least one therapeutic agent selected from the group consisting of a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide, an antisense molecule, a siRNA, a second antibody and a second antibody fragment. In some aspects, the antibody or antigen-binding fragment thereof comprises a sequence that is at least 95% identical to a sequence set forth in Table BB.

A pharmaceutical composition comprising an anti-LILBR4 antibody or antigen-binding fragment thereof disclosed herein and a pharmaceutically acceptable excipient.

In some aspects, the composition is sterile.

In some aspects, an anti-LILBR4 antibody or antigen-binding fragment thereof disclosed herein is used in a method disclosed herein.

BRIEF DESCRIPTION OF THE DRAWINGS

FIG. 1. Rare DC and abundant macrophages in mouse and human tumors. (FIG. 1C) Histogram of tumor-derived mCherry fluorescence, by tumor-infiltrating immune cells in B78chOVA. (FIG. 1D) Representative cytometry of digested human melanoma metastatic biopsy identifying corollary DC and TAM populations defined by CD45$^+$ Lin$^-$ (CD3e, CD56, CD19) HLA-DR$^+$ and split by CD14, BDCA1 and BDCA3. Double negative cells likely reflect B cells escaping lineage gate, immature monocytes or pDC. (FIG. 1E) Relative proportions of tumor infiltrating myeloid cells as a % of total CD45$^+$ cells for PyMTchOVA and B78chOVA models. Pooled data from individual tumors, presented as mean±SEM from (n=5) mice. (FIG. 1F) Frequency of DC and TAM populations infiltrating human metastatic melanoma presented as a % of total CD45$^+$ cells. Pooled data from multiple patients, presented as mean±SEM from (n=4) biopsies. For FIG. 1C the histogram for each cell type from front to back is: T cell, Nφ, DC2, DC1, Mono, TAM2, TAM1, and Tumor, respectively.

FIG. 2. Surface and transcriptional profiling highlights distinct lineages of tumor DCs and macrophages. All data (FIG. 2A-G) is from the ectopic B78chOVA tumor model. Cell lineages are defined as per FIG. 1. (FIG. 2D) Global transcriptional profiles revealed by RNAseq of FACS-purified populations from biological triplicates. Data displayed as a heat map of $Log_2$ fold change relative to the global average of the top 1000 genes by maximum variance between DC1, DC2, TAM1, and TAM2. (FIG. 2E) PCA of DC1, DC2, TAM1, and TAM2 populations based on RNAseq global transcriptional profiles. (FIG. 2F) qRT-PCR analysis of expression of Irf4, Irf8, Myb, and Zbtb46 (zDC) from sorted APC populations. Data presented as mean ΔCt±SEM calculated from biological triplicates (n=3), (N.D. not detected). (FIG. 2G) Intracellular staining for Irf4 and Irf8 in tumor APC populations as compared to the respective isotype (grey). For FIG. 2E each cluster of three dots from left to rights is: CD103+DC2, CD11b+DC1, F4/80+ TAM1, and F4/80+ TAM2, respectively.

FIG. 3. Differential Irf4, Irf8 and Batf3 requirements for tumor infiltrating APC populations. All data is representative flow cytometric analysis of CD11b+ DC1 and CD103+ DC2 populations (gated on CD45+, Ly6C−, MHCII+, and CD24+) Data shown as mean±SEM. Statistical significance indicated by *p<0.05, p<0.01, *p<0.001; ns=not statistically significant.

FIG. 5. Unique antigen processing and presentation capabilities of CD103+ DC2. All data (FIG. 5A-G) is from the ectopic B78chOVA tumor model. (FIG. 5A) Heat map of $Log_2$ transformed expression from RNAseq across populations for selected genes involved in cross presenting, cytokine and chemokine production, and costimulation. Color scale defined as, light grey=bottom $20^{th}$ percentile, dark grey=top $80^{th}$ percentile, with $20^{th}$-$80^{th}$ percentile graduated and centered ($50^{th}$ percentile). Data from biological triplicates of sorted cells. (FIG. 5B) Cytometry of surface protein levels of ligands for T cell regulatory molecules (dark line) as compared to respective isotypes (grey shaded). (FIG. 5C) Cytometry of MCHI and MHCII (dark lines; front four lines) expression compared to respective isotype (shaded; back four lines). For FIG. 5C each line from front to back of colored is CD103+ DC2, CD11b+ DC1, F4/80+ TAM1, and F4/80+ TAM2, respectively. For FIG. 5C each line from front to back of shaded is CD103+ DC2, CD11b+ DC1, F4/80+ TAM1, and F4/80+ TAM2, respectively. (FIG. 5D) Cytometry of ex vivo dextran uptake across populations. Grey=no dextran, light histogram=dextran binding at 4 C and dextran uptake at 37 C=dark histogram, displayed in triplicate. Delta geometric Mean Fluorescence Intensity (gMFI) for each population plotted as mean±SEM. Data are representative of 2 independent experiments (n=6). (FIG. 5E) Cytometry analysis of relative pH of endocytic compartments across populations. B78 tumor cells were transfected with the ratiometric pH construct, N1-mCherry-pHlourin. pHluorin, a pH sensitive GFP derivative quenches at acidic pH. Representative histograms show florescence of pHluorin in mCherry+ cells, where less pH-GFP represents a more acidic environment. Grey histograms are respective populations from a non-pHluorin expressing control tumor (B78parental). Data summarized as the ratio of gMFI between GFP and mCherry fluorescence. Data presented as mean ratio±SEM, pooled from 3 independent experiments. (FIG. 5F) Intracellular cytokine stain of IL12 in populations. % of IL12+ cells quantified across each population, data pooled from 2 independent experiments, (n=3), plotted as mean±SEM. Statistical significance indicated by *p<0.05. For FIG. 5F each line from front to back is CD103+ DC2, CD11b+ DC1, F4/80+ TAM1, and F4/80+ TAM2, respectively. (FIG. 5G) Transcript levels, measured by qPCR for cytokine Il12b and Il10 transcripts. Data presented as mean ΔCt±SEM calculated from biological triplicates (n=3) of individual tumors, (N.D. not detected).

FIG. 6. CD103+ DCs are superior T cell stimulators for naïve and activated CD8+ T cells. All data (FIG. 6A-G) is from the ectopic B78chOVA tumor model. T cells+ BMDC (shaded grey; rear most), T cells+ BMDC+SL8 (unshaded grey; second rear most), T cells+ tumor APCs (respective colored histograms). Plated at 20,000 T cells: 4,000 APC ratio. Representative flow plots from 4 independent experiments, unless noted. (FIG. 6A) Flow cytometry of early activation markers, Nur77 and CD69 (12 hrs) on naïve or previously activated OT-I CD8$^+$ T cells cultured on sorted APC populations directly from tumors. For FIG. 6A each line from front to back is F4/80+ TAM2, F4/80+ TAM1, CD11b+ DC1, and CD103+ DC2, respectively. (FIG. 6B) Representative cytometry of Naïve OT-I CD8$^+$ T cell proliferation, measured by dye dilution of eFluor670 plotted against Nur77 (as measure of TCR triggering), at 72 hours following co-culture with tumor APC populations. Total cell yield counts listed above graphs. (FIG. 6C) Histogram overlay of Naive T cell proliferation between tumor APCs. For FIG. 6C each line from front to back is F4/80+ TAM1, F4/80+ TAM2, CD11b+ DC1, and CD103+ DC2, respectively.

FIG. 7. Intravital and slice imaging reveals CD11b$^+$ DC1 and CD103$^+$ DC2 are sparse near tumor margins yet can interact with T cells when present there. (FIG. 7A) Quantification of proximal/distal location of the APCs within the tumor. Data pooled from 4 independent imaging runs, presented as mean±SEM. For FIG. 7A the bars for each group are from left to right: TAM2, TAM1, and DC1/2, respectively. (FIG. 7B) APC-T cell contacts in vivo as a % of total T cell couples observed. Accumulated data of 4 different positions imaged for 30 minutes in 2 independent intravital 2 photon imaging runs. Contacts were scored manually by counting physical contact made between T cells and red, yellow and green APCs. Placement of bar represents the APC of contact (Top: CD103$^+$, CD11b$^+$ DC1, Bottom: TAM1, Middle: TAM2). (FIG. 7C) Ex vivo T cell coupling assay with digested tumor positively selected for CD45$^+$ cells with previously activated OT-I CD8$^+$ T cell. Data calculated as % of T cells couples within each of the populations (left), and as a total % of T cell couples (right). Data pooled from 2 independent experiments, plotted as mean±SEM. For FIG. 7C each bar of each group from left to right is: DC2, DC1, TAM1, and TAM2, respectively.

FIG. 8. Rare CD103 DC2 population at the tumor is required for efficient adoptive CTL therapy. (FIG. 8A) Tumor growth curve plotted as tumor area (mm$^2$) over time for EG7.1 in zDC-DTR hosts. Arrows indicate time of i.p. D.T./PBS administration, and i.v. transfer of 5×10$^6$ previously activated OT-I CD8$^+$ T cells, on day 4 and 5 respectively. DT/PBS was subsequently administered every 3$^{rd}$ day and FTY-720/Saline was subsequently administered every other day throughout time course. Light grey dashed line (top) shows EG7.1 growth in a zDC-DTR host without transfer of T cells. EG7.1 regression upon transfer of activated CD8$^+$ T cells and FTY-720 treatment (black line; bottom) or with additional DT-mediated DC depletion (dark grey-line; middle). Representative data presented as mean tumor area±SEM (n=4) from 2 independent experiments. Statistical significance indicated by *p<0.05. (FIG. 8B) Comparison of prognostic value of CD103$^+$/CD103$^-$ Ratio Gene Signal as compared to the individual genes (either CD103$^+$ specific, green, or TAM1/TAM2/Cd11b DC1 specific genes, red) for TCGA human samples in a multivariate COX proportional hazards survival analysis adjusting for cancer type as a covariate. Data expressed as Hazard Ratio (HR) with 95% confidence intervals, where a value <1 means increased Overall Survival (OS); >1 means decreased OS for genes with BH p-values<0.05. (FIG. 8C) Comparison of the prognostic value of the CD103$^+$/CD103$^-$ Ratio Gene Signal as compared to several published prognostic gene signatures for TCGA human samples for in a multivariate COX proportional hazards survival analysis adjusting for cancer type as a covariate. Data expressed as Hazard Ratio (HR) with 95% confidence intervals, where a value <1 means increased Overall Survival (OS); >1 means decreased OS for genes with BH p-values<0.05.

FIG. 9. Transcriptional abundance of CD103$^+$ and BDCA3$^+$ genes associates with increased post-recurrence survival in metastatic melanoma. (FIG. 9C) Kaplan-Meier plot for post recurrence survival of metastatic melanoma patients for CD103$^{+/-}$ ratio gene expression. Data are parsed into "high" (light grey; top line of each plot) and "low" (black; bottom line of each plot) bins at 33%, 50%, and 66% stringency thresholds for levels of expression of the CD103$^{+/-}$ ratio genes. FIG. 9D-E. Class-based measures of TIL category and FIG. 9F-G. histological measures of peri-tumoral CD3+ T cell numbers from {Bogunovic et al, 2009} were plotted versus SDC gene signature (FIG. 9D,F) and SDC/NSM ratio (FIG. 9E,G).

FIG. 10. Flow cytometric quantification of tumor-infiltrating APC populations in human metastatic melanoma. (FIG. 10A) Human metastatic melanoma biopsy patient table. Table of patient identifier, age, sex, and location of tumor biopsy, as well as prior treatment (if known) for each patient. All patients listed received anti-PD-1 immunotherapy at UCSF. Prior history is coded as naïve, 0 or treated, 1. ** indicates rapid progression that precluded additional scans.

FIG. 11. Cellular abundance of BDCA3+ DCs in human melanoma predicts anti-PD1 responsiveness. Patients binned as either responders (grey, including partial or complete responses) or non-responders (black, including stable disease and progressive disease).

FIG. 12. Requirements of CD103+ DCs for anti-PD1 efficacy in a mouse model of melanoma.

Figure 1A:
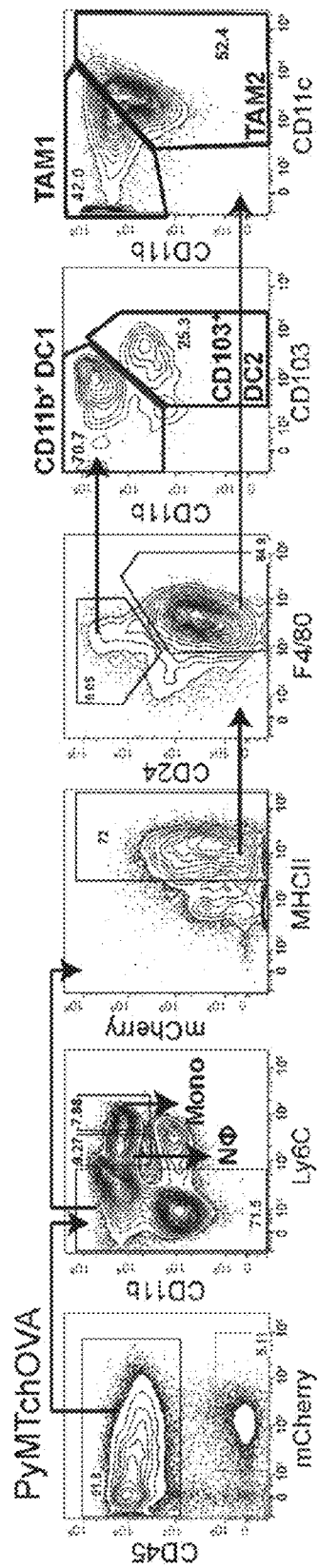
(FIG. 1A) Flow cytometry and gating of tumor APC populations from digested and CD45 enriched PyMTchOVA tumors. A-C: Representative of greater than 5 independent experiments.

These and other aspects and advantages of the present invention will become apparent from the subsequent detailed description and claims. It is to be understood that one, some, or all of the properties of the various embodiments described herein may be combined to form other embodiments of the present invention.

DETAILED DESCRIPTION

For purposes of interpreting this specification, the following definitions will apply and whenever appropriate, terms used in the singular will also include the plural and vice versa. In the event that any definition set forth below conflicts with any document incorporated herein by reference, the definition set forth shall control.

It is understood that aspects and embodiments of the invention described herein include "comprising," "consisting," and "consisting essentially of" aspects and embodiments.

For all compositions described herein, and all methods using a composition described herein, the compositions can either comprise the listed components or steps, or can "consist essentially of" the listed components or steps. When a composition is described as "consisting essentially of" the listed components, the composition contains the components listed, and may contain other components which do not substantially affect the condition being treated, but do not contain any other components which substantially affect the condition being treated other than those components expressly listed; or, if the composition does contain extra components other than those listed which substantially affect the condition being treated, the composition does not contain a sufficient concentration or amount of the extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed. As a non-limiting specific example, when a composition is described as 'consisting essentially of' a component, the composition may additionally contain any amount of pharmaceutically acceptable carriers, vehicles, or diluents and other such components which do not substantially affect the condition being treated.

The term "optionally" is meant, when used sequentially, to include from one to all of the enumerated combinations and contemplates all subcombinations.

An "effective amount" or "therapeutically effective amount" as used herein refers to an amount of therapeutic compound, such as an anti-NSM antigen binding agent or anti-NSM antibody, administered to an individual, either as a single dose or as part of a series of doses, which is effective to produce or contribute to a desired therapeutic effect, either alone or in combination with another therapeutic modality. Examples of a desired therapeutic effect is enhancing an immune response, slowing or delaying tumor development; stabilization of disease; amelioration of one or more symptoms. An effective amount may be given in one or more dosages.

The term "treating" as used herein, refers to retarding or reversing the progress of a condition, such as cancer. The term "treatment," as used herein, refers to the act of treating a condition, such as cancer.

An "individual" or "subject" as used herein refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments, the individual is human. In some embodiments, the individual is mouse.

The term "about" as used herein refers to the usual error range for the respective value readily known to the skilled person in this technical field. Reference to "about" a value or parameter herein includes (and describes) embodiments that are directed to that value or parameter per se.

It must be noted that, as used in the specification and the appended claims, the singular forms "a," "an" and "the" include plural referents unless the context clearly dictates otherwise.

For any of the structural and functional characteristics described herein, methods of determining these characteristics are known in the art.

Non-Stimulatory Myeloid Cells (NSMs)

Provided herein are methods and compositions for disabling and/or detecting non-stimulatory myeloid cells (NSMs) comprising the use of an anti-NSM antibody. Also provided herein are methods and compositions for targeting and/or detecting non-stimulatory myeloid cells expressing a NSM protein.

Also provided herein are methods and compositions for disabling and/or detecting non-stimulatory myeloid cells comprising the use of antibody directed at a non-human homolog of human NSM protein, in that non-human individual.

As used herein, non-stimulatory myeloid cells are myeloid cells that are not sufficiently effective at stimulating an immune response (e.g. not as effective at stimulating an anti-tumor response in a tumor microenvironment compared to stimulatory myeloid cells). In some embodiments, non-stimulatory myeloid cells are not as effective at presenting an antigen (e.g. a tumor antigen) to T-cells or not as effective at stimulating tumor specific T-cell responses as compared to a stimulatory myeloid cell. In some embodiments, non-stimulatory myeloid cells can display a decreased ability to uptake, process, and/or present tumor-associated antigens to a T cell as compared to a stimulatory myeloid cell. Non-stimulatory myeloid cells may contain a reduced ability or no ability to re-prime cytotoxic T lymphocytes or in some cases cannot stimulate effective tumor-cell killing. Non-stimulatory myeloid cells may display lower expression of gene and cell-surface markers involved in antigen processing, antigen presentation and/or antigen co-stimulation including, without limitation, CD80, CD86, MHCI, and MHCII compared to stimulatory myeloid cells.

Non-stimulatory myeloid cells, when compared to stimulatory myeloid cells, may display the lower expression of genes associated with cross-presentation, co-stimulation, and/or stimulatory cytokines, including, without limitation, any one or more of TAP1, TAP2, PSMB8, PSMB9, TAPBP, PSME2, CD24a, CD274, BTLA, CD40, CD244, ICOSL, ICAM1, TIM3, PDL2, RANK, FLT3, CSF2RB, CSF2RB2, CSF2RA, IL12b, XCR1, CCR7, CCR2, CCL22, CXCL9, and CCL5, and increased expression of anti-inflammatory cytokine IL-10. In some embodiments non-stimulatory myeloid cells are dependent on the transcription factor IRF4 and the cytokines GM-CSF or CSF-1 for differentiation and survival. In some embodiments, non-stimulatory myeloid cells can contribute to tumoral angiogenesis by secreting vascular endothelial growth factor (VEGF) and nitric oxide synthase (NOS) and support tumor growth by secreting epidermal growth factor (EGF).

In some embodiments, non-stimulatory myeloid cells are tumor-associated macrophages (TAM) or dendritic cells (DC). In some embodiments, the non-stimulatory myeloid cell is not a dendritic cell (DC).

In some embodiments, non-stimulatory myeloid cells are tumor-associated macrophages (TAMs). TAMs are macrophages present near or within cancerous tumors, and are derived from circulating monocytes or resident tissue macrophages.

In some embodiments the non-stimulatory myeloid cells and the stimulatory myeloid cells are distinguished on the basis of the markers they express, or the markers they selectively express. The expression of a cell surface markers can be described as '+' or 'positive'. The absence of a cell surface marker can be described as '−' or 'negative'. The expression of a cell surface marker can be further described as 'high' (cells expressing high levels of the makers) or 'low' (cells expressing low levels of the markers), which indicates the relative expression of each marker on the cell surface. The level of markers may be determined by various methods known in the art, e.g. immuno-staining and FACS analysis, or gel electrophoresis and Western blotting.

In some embodiments, non-stimulatory myeloid cells are dendritic cells (DCs). In some embodiments, dendritic cells can be distinguished by a spikey or dendritic morphology. In one embodiment, the non-stimulatory dendritic cell is at least CD45+, HLA-DR+, CD14−, CD11c+, and BDCA1+ (also referred to as DC1 cells). In one embodiment, the non-stimulatory dendritic cell is not CD45+, HLA-DR+, CD14−, CD11c+, and BDCA3+(also referred to as DC2 cells). In one embodiment a dendritic cell that is CD45+, HLA-DR+, CD14−, CD11c+, and BDCA3+ is a stimulatory-myeloid cell.

In some embodiments, non-stimulatory myeloid cells are tumor associated macrophages. In some embodiments, for example in humans, the non-stimulatory tumor associated macrophages are at least CD45+, HLA-DR+, CD14+. In some embodiments the non-stimulatory tumor associated macrophages are at least $CD45^+$, $HLA-DR^+$, $CD14^+$, $CD11b^+$. In some embodiments the non-stimulatory tumor associated macrophages are at least $CD45^+$, $HLA-DR^+$, $CD14^+$, $CD11c^+$. In some embodiments the non-stimulatory tumor associated macrophages are at least $CD45^+$, $HLA-DR^+$, $CD14^+$, $BDCA3^-$. In some embodiments the non-stimulatory tumor associated macrophages are at least $CD45^+$, $HLA-DR^+$, $CD14^+$, $BDCA3^-$, $CD11b^+$. In some embodiments the non-stimulatory tumor associated macrophages are at least $CD45^+$, $HLA-DR^+$, $CD14^+$, $BDCA3^-$, $CD11c^+$. In some embodiments the non-stimulatory tumor associated macrophages are at least $CD45^+$, $HLA-DR^+$, $CD14^+$, $CD11b^+$, and $CD11c^+$. In some embodiments the non-stimulatory tumor associated macrophages are at least $CD45^+$, $HLA-DR^+$, $CD14^+$, $BDCA3^-$, $CD11b^+$, and $CD11c^+$.

In some embodiments the methods and compositions of the present invention are useful for targeting TAMs and DCs in other mammals, for example in mice. In such embodiments, mice TAMs and DCs are contacted with a NSM antibody. In one embodiment, for example in mice, the tumor-associated macrophage is at least CD45+, HLA-DR+, CD14+, $CD11b^{high}$, and $CD11c^{low}$ (also referred to as TAM1). In one embodiment, for example in mice, tumor-associated macrophages are at least $CD45^+$, $HLA-DR^+$, $CD14^+$, $CD11b^{low}$, and $CD11c^{high}$ (also referred to as TAM2). The term "$CD11b^{high}$ macrophages", as used herein, relates to macrophages expressing high levels of CD11b. The term "$CD11b^{low}$ macrophages," as used herein, relates to macrophages that express on their surface a level of CD11b that is substantially lower than that of $Cd11b^{high}$ macrophages. The term "$CD11c^{high}$", as used herein, relates to macrophages expressing high levels of CD11c. The term "$CD11c^{low}$ macrophages", as used herein, relates to macrophages that express on their surface a level of CD11c that is substantially lower than that of $Cd11c^{high}$ macrophages.

In some embodiments, the non-stimulatory myeloid cells of the invention include one or more of TAM and DC1 cells.

In some embodiments, for example in mice, the non-stimulatory myeloid cells of the invention include one or more of TAM1, TAM2, and DC1 cells. In such embodiments the non-stimulatory myeloid cells of the invention are contacted with a NSM antibody.

In some embodiments, the non-stimulatory myeloid cells are localized within the margins of the tumoral lesions or in the transformed tumor ducts, where they come into contact with cognate T-cells. In one embodiment, the localization of the non-stimulatory myeloid cell is modified, so that the cells are no longer localized at the tumor margin or are no longer in contact with T-cells.

In some embodiments, the non-stimulatory myeloid cells are in a population of immune cells comprising stimulatory myeloid cells and non-stimulatory myeloid cells. In some embodiments, the non-stimulatory myeloid cells are in a population of immune cells comprising only non-stimulatory myeloid cells. The populations of immune cells of the present invention may be pure, homogenous, heterogeneous, derived from a variety of sources (e.g. diseased tissue, tumor tissue, healthy tissue, cell banks), maintained in primary cell cultures, maintained in immortalized cultures, and/or maintained in ex vivo cultures.

In some embodiments, the non-stimulatory myeloid cells are tumor-associated macrophages.

In some embodiments, the non-stimulatory myeloid cells are dendritic cells.

In some embodiments, the non-stimulatory myeloid cells are $CD45^+$, $HLA-DR^+$, $CD14^-$, $CD11c^+$, and $BDCA1^+$. In some embodiments, the non-stimulatory myeloid cells comprise cells that are $CD45^+$, $HLA-DR^+$, $CD14^-$, $CD11c^+$, and $BDCA1^+$. In some embodiments, the non-stimulatory myeloid cells consist of cells that are $CD45^+$, $HLA-DR^+$, $CD14^-$, $CD11c^+$, and $BDCA1^+$. In some embodiments, the non-stimulatory myeloid cells consist essentially of cells that are $CD45^+$, $HLA-DR^+$, $CD14^-$, $CD11c^+$, and $BDCA1^+$.

In some embodiments, the non-stimulatory myeloid cells are $CD45^+$, $HLA-DR^+$, $CD14^+$, $BDCA3^-$. In some embodiments, the non-stimulatory myeloid cells comprise cells that are $CD45^+$, $HLA-DR^+$, $CD14^+$, $BDCA3^-$. In some embodiments, the non-stimulatory myeloid cells consist of cells that are $CD45^+$, $HLA-DR^+$, $CD14^+$, $BDCA3^-$. In some embodiments, the non-stimulatory myeloid cells consist essentially of cells that are CD45$^+$, HLA-DR$^+$, CD14$^+$, BDCA3$^-$.

In some embodiments, the non-stimulatory myeloid cells are CD45$^+$, HLA-DR$^+$, CD14$^+$, CD11b+. In some embodiments, the non-stimulatory myeloid cells comprise cells that are CD45$^+$, HLA-DR$^+$, CD14$^+$, CD11b$^+$. In some embodiments, the non-stimulatory myeloid cells consist of cells that are CD45$^+$, HLA-DR$^+$, CD14$^+$, CD11b$^+$. In some embodiments, the non-stimulatory myeloid cells consist essentially of cells that are CD45$^+$, HLA-DR$^+$, CD14$^+$, CD11b$^+$.

In some embodiments, the non-stimulatory myeloid cells are CD45$^+$, HLA-DR$^+$, CD14$^+$, CD11c$^+$. In some embodiments, the non-stimulatory myeloid cells comprise cells that are CD45$^+$, HLA-DR$^+$, CD14$^+$, CD11c$^+$. In some embodiments, the non-stimulatory myeloid cells consist of cells that are CD45$^+$, HLA-DR$^+$, CD14$^+$, CD11c$^+$. In some embodiments, the non-stimulatory myeloid cells consist essentially of cells that are CD45$^+$, HLA-DR$^+$, CD14$^+$, CD11c$^+$.

In some embodiments, the non-stimulatory myeloid cells are CD45$^+$, HLA-DR$^+$, CD14$^+$, BDCA3$^-$, and CD11c$^+$. In some embodiments, the non-stimulatory myeloid cells comprise cells that are CD45$^+$, HLA-DR$^+$, CD14$^+$, BDCA3$^-$, and CD11c$^+$. In some embodiments, the non-stimulatory myeloid cells consist of cells that are CD45$^+$, HLA-DR$^+$, CD14$^+$, BDCA3$^-$, and CD11c$^+$. In some embodiments, the non-stimulatory myeloid cells consist essentially of cells that are CD45$^+$, HLA-DR$^+$, CD14$^+$, BDCA3$^-$, and CD11c$^+$.

In some embodiments, the non-stimulatory myeloid cells are CD45$^+$, HLA-DR$^+$, CD14$^+$, BDCA3$^-$, CD11b$^+$. In some embodiments, the non-stimulatory myeloid cells comprise cells that are CD45$^+$, HLA-DR$^+$, CD14$^+$, BDCA3$^-$, CD11b$^+$. In some embodiments, the non-stimulatory myeloid cells consist of cells that are CD45$^+$, HLA-DR$^+$, CD14$^+$, BDCA3$^-$, CD11b$^+$. In some embodiments, the non-stimulatory myeloid cells consist essentially of cells that are CD45$^+$, HLA-DR$^+$, CD14$^+$, BDCA3$^-$, CD11b+.

In some embodiments, the non-stimulatory myeloid cells are CD45$^+$, HLA-DR$^+$, CD14$^+$, CD11b+, and CD11c$^+$. In some embodiments, the non-stimulatory myeloid cells comprise cells that are CD45$^+$, HLA-DR$^+$, CD14$^+$, CD11b$^+$, and CD11c$^+$. In some embodiments, the non-stimulatory myeloid cells consist of cells that are CD45$^+$, HLA-DR$^+$, CD14$^+$, CD11b$^+$, and CD11c$^+$. In some embodiments, the non-stimulatory myeloid cells consist essentially of cells that are CD45$^+$, HLA-DR$^+$, CD14$^+$, CD11b$^+$, and CD11c$^+$.

In some embodiments, the non-stimulatory myeloid cells are CD45$^+$, HLA-DR$^+$, CD14$^+$, BDCA3$^-$, CD11b$^+$, and CD11c$^+$. In some embodiments, the non-stimulatory myeloid cells comprise cells that are CD45$^+$, HLA-DR$^+$, CD14$^+$, BDCA3$^-$, CD11b$^+$, and CD11c$^+$. In some embodiments, the non-stimulatory myeloid cells consist of cells that are CD45$^+$, HLA-DR$^+$, CD14$^+$, BDCA3$^-$, CD11b$^+$, and CD11c$^+$. In some embodiments, the non-stimulatory myeloid cells consist essentially of cells that are CD45$^+$, HLA-DR$^+$, CD14$^+$, BDCA3$^-$, CD11b$^+$, and CD11c$^+$.

In some embodiments, the non-stimulatory myeloid cells are not CD45$^+$, HLA-DR$^+$, CD14$^-$, CD11c$^+$, and BDCA3$^+$. In some embodiments, the non-stimulatory myeloid cells comprise cells that are not CD45$^+$, HLA-DR$^+$, CD14$^-$, CD11c$^+$, and BDCA3$^+$.

In some embodiments, for example in mice, the non-stimulatory myeloid cells are CD45$^+$, HLA-DR$^+$, CD14$^+$, CD11b$^{high}$, and CD11c$^{low}$. In some embodiments, for example in mice, the non-stimulatory myeloid cells comprise cells that are CD45$^+$, HLA-DR$^+$, CD14$^+$, CD11b$^{high}$, and CD11c$^{low}$. In some embodiments, for example in mice, the non-stimulatory myeloid cells consist of cells that are CD45$^+$, HLA-DR$^+$, CD14$^+$, CD11b$^{high}$, and CD11c$^{low}$. In some embodiments, for example in mice, the non-stimulatory myeloid cells consist essentially of cells that are CD45$^+$, HLA-DR$^+$, CD14$^+$, CD11b$^{high}$, and CD11c$^{low}$. In such embodiments the non-stimulatory mice myeloid cells are contacted with a NSM antibody.

In some embodiments, for example in mice, the non-stimulatory myeloid cells are CD45$^+$, HLA-DR$^+$, CD14$^+$, CD11b$^{low}$, and CD11c$^{high}$. In some embodiments, for example in mice, the non-stimulatory myeloid cells comprise cells that are CD45$^+$, HLA-DR$^+$, CD14$^+$, CD11b$^{low}$, and CD11c$^{high}$. In some embodiments, for example in mice, the non-stimulatory myeloid cells consist of cells that are CD45$^+$, HLA-DR$^+$, CD14$^+$, CD11b$^{low}$, and CD11c$^{high}$. In some embodiments, for example in mice, the non-stimulatory myeloid cells consist essentially of cells that are CD45$^+$, HLA-DR$^+$, CD14$^+$, CD11b$^{low}$, and CD11c$^{high}$. In such embodiments the non-stimulatory mice myeloid cells are contacted with a NSM antibody.

In some embodiments, the non-stimulatory myeloid cells are in a cancer tissue.

In some embodiments, the population of immune cells is in a cancer tissue.

In some embodiments, the non-stimulatory cells and stimulatory myeloid cells are in a cancer tissue.

In some embodiments, the biological sample comprises a population of immune cells comprising non-stimulatory myeloid cells and stimulatory myeloid cells.

NSM cells can refer collectively to DC1, TAM1, and TAM2 cells present in tumor tissues and which may be distinguished from other cell types by their expression of NSM cell markers. For example, genes and associated proteins which are expressed or translated in greater abundance in NSM cells than SDC's may act as NSM markers. An exemplary NSM marker is CD11b. Additional exemplary NSM markers are listed in Table A. NSM cells can express TREM2, MS4A7, C5AR1, LYVE1, ABCC3, LILRB4, MRC1/CD206, SIGLEC1, STAB1, TMEM37, MERTK, and TMEM119 on their cell surface. In some aspects, NSM cells do not express at least one of KIT, CCR7, BATF3, FLT3, ZBTB46, IRF8, BTLA, MYCL1, CLEC9A, BDCA3, and XCR1.

In one embodiment, NSM cells are tumor infiltrating myeloid cells which express one or more of the NSM marker genes listed in Table A. In another embodiment, NSM cells are tumor myeloid cells which express three or more of the NSM markers listed in Table A. In another embodiment, NSM cells are tumor myeloid cells that express most or all of the NSM markers listed in Table A. In another embodiment, NSM cells are identified as tumor myeloid cells expressing MRC1, MS4A7, C1QC, APOE, C1QB, C1QA, and C5AR1.

TABLE A

| SDC Markers | NSM Markers |
| --- | --- |
| KIT | C5AR1 |
| CCR7 | LYVE1 |
| BATF3 | ABCC3 |
| FLT3 | MRC1 |
| ZBTB46 | SIGLEC1 |
| IRF8 | STAB1 |
| BTLA | C1QB |
| MYCL1 | C1QA |
| CLEC9A | TMEM37 |
| BDCA3 | MERTK |
| XCR1 | C1QC |
|  | TMEM119 |

TABLE A-continued

| SDC Markers | NSM Markers |
|---|---|
| | MS4A7 |
| | APOE |
| | CYP4F18 |
| | TREM2 |
| | TLR7 |
| | LILRB4 |

Stimulatory Myeloid Cells

As used herein, stimulatory myeloid cells (also called SDCs in certain aspects) are myeloid cells that are effective at stimulating an immune response (e.g. more effective at stimulating an anti-tumor response in a tumor microenvironment compared to non-stimulatory myeloid cells). In some embodiments, stimulatory myeloid cells are effective at presenting an antigen (e.g. a tumor antigen) to T-cells or are effective at stimulating tumor specific T-cell responses as compared to a non-stimulatory myeloid cell. In some embodiments, stimulatory myeloid cells can display an increased ability to uptake, process, and/or present tumor-associated antigens to a T cell as compared to a non-stimulatory myeloid cell. Stimulatory myeloid cells can have an increased ability to re-prime cytotoxic T lymphocytes or in some cases stimulate effective tumor-cell killing relative to non-stimulatory myeloid cells. Stimulatory myeloid cells may display higher expression of gene and cell-surface markers involved in antigen processing, antigen presentation and/or antigen co-stimulation including, without limitation, CD80, CD86, MHCI, and MHCII compared to non-stimulatory myeloid cells.

Exemplary stimulatory myeloid cell markers are listed in Table A. For example, in human SDC's, the expression of Xcr1, Clec9a, and BDCA3 (CD141) are markers of SDC identity. It will be noted that in mice, CD103 can also be used as a strong marker of SDC identity, although it is not expressed in human SDC's.

In one embodiment, SDC's are tumor infiltrating myeloid cells having dendritic cell identity and which also express one or more of the SDC markers listed in Table A. In another embodiment, SDC's are tumor infiltrating myeloid cells having dendritic cell identity and which also express two, three, four, five, six, seven, eight, nine or all of the SDC markers listed in Table A. In another embodiment, SDC's are identified as tumor infiltrating myeloid dendritic cells expressing BDCA3, KIT, CCR7, BATF3, FLT3, ZBTB46, IRF8, BTLA, MYCL1, XCR1 and CLEC9A. SDC's cells can express at least one of KIT, CCR7, BATF3, FLT3, ZBTB46, IRF8, BTLA, MYCL1, CLEC9A, BDCA3, and XCR1. In some embodiments, SDC's do not substantially express TREM2, MS4A7, C5AR1, LYVE1, ABCC3, LILRB4, MRC1/CD206, SIGLEC1, STAB1, TMEM37, MERTK, and/or TMEM119 on their cell surface. In some embodiments, SDC's do not substantially express C5AR1, LYVE1, ABCC3, MRC1, SIGLEC1, STAB1, C1QB, C1QA, TMEM37, MERTK, C1QC, TMEM119, MS4A7, APOE, CYP4F18, TREM2, TLR7, and/or LILRB4. Flow cytometry and PCR, among other art recognized assays, can be used to assess expression of a marker disclosed herein.

Stimulatory myeloid cells can be CD45$^+$, HLA-DR$^+$, CD14$^-$, CD11c$^+$, and BDCA3$^+$. Stimulatory myeloid cells can be CD45$^+$, HLA-DR$^+$, and BDCA3$^+$. Stimulatory myeloid cells can be CD45$^+$, HLA-DR$^+$, CD14$^-$, and BDCA3$^+$. Stimulatory myeloid cells can be CD45$^+$, HLA-DR$^+$, CD11c$^+$, and BDCA3$^+$.

Antibodies

The present application provides antibodies and compositions comprising an antibody which binds a NSM protein including antibodies that disable non-stimulatory myeloid cells.

The present application provides antibodies and compositions comprising an antibody which binds a NSM protein including antibodies that disable non-stimulatory myeloid cells.

As used herein, an "antibody" or "immunoglobulin" refers to a polypeptide substantially encoded by an immunoglobulin gene or set of immunoglobulin genes, or analyte-binding fragments thereof, which specifically bind and recognize an analyte (e.g., antigen). The recognized immunoglobulin genes include the kappa, lambda, alpha, gamma, delta, epsilon and mu constant region genes, as well as the myriad immunoglobulin variable region genes. Light chains are classified as either kappa or lambda. The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG$_2$, IgG$_3$, IgG$_4$, IgA1, and IgA$_2$. The heavy chain constant domains that correspond to the different classes of immunoglobulins are called α, δ, ε, γ, and μ, respectively.

An exemplary immunoglobulin (antibody) structural unit is composed of two pairs of polypeptide chains, each pair having one "light" (about 25 kD) and one "heavy" chain (about 50-70 kD). The N-terminal domain of each chain defines a variable region of about 100 to 110 or more amino acids primarily responsible for antigen recognition. The terms variable light chain (VL) and variable heavy chain (VH) refer to these light and heavy chain domains respectively. The IgG1 heavy chain comprises of the VH, CH1, CH2 and CH3 domains respectively from the N to C-terminus. The light chain comprises of the VL and CL domains from N to C terminus. The IgG1 heavy chain comprises a hinge between the CH1 and CH2 domains. In certain embodiments, the immunoglobulin constructs comprise at least one immunoglobulin domain from IgG, IgM, IgA, IgD, or IgE connected to a therapeutic polypeptide. In some embodiments, the immunoglobulin domain found in an antibody provided herein, is from or derived from an immunoglobulin based construct such as a diabody, or a nanobody. In certain embodiments, the immunoglobulin constructs described herein comprise at least one immunoglobulin domain from a heavy chain antibody such as a camelid antibody. In certain embodiments, the immunoglobulin constructs provided herein comprise at least one immunoglobulin domain from a mammalian antibody such as a bovine antibody, a human antibody, a camelid antibody, a mouse antibody or any chimeric antibody.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen-binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

As used herein, the term "single-chain" refers to a molecule comprising amino acid monomers linearly linked by peptide bonds. In a particular such embodiment, the C-terminus of the Fab light chain is connected to the N-terminus of the Fab heavy chain in the single-chain Fab molecule. As described in more detail herein, an scFv has a variable domain of light chain (VL) connected from its C-terminus to the N-terminal end of a variable domain of heavy chain (VH) by a polypeptide chain. Alternately the scFv comprises of polypeptide chain where in the C-terminal end of the VH is connected to the N-terminal end of VL by a polypeptide chain.

The "Fab fragment" (also referred to as fragment antigen-binding) contains the constant domain (CL) of the light chain and the first constant domain (CH1) of the heavy chain along with the variable domains VL and VH on the light and heavy chains respectively. The variable domains comprise the complementarity determining loops (CDR, also referred to as hypervariable region) that are involved in antigen-binding. Fab' fragments differ from Fab fragments by the addition of a few residues at the carboxy terminus of the heavy chain CH1 domain including one or more cysteines from the antibody hinge region.

The "Single-chain Fv" or "scFv" includes the VH and VL domains of an antibody, wherein these domains are present in a single polypeptide chain. In one embodiment, the Fv polypeptide further comprises a polypeptide linker between the VH and VL domains which enables the scFv to form the desired structure for antigen-binding. For a review of scFv see Pluckthun in The Pharmacology of Monoclonal Antibodies, vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

The "Single domain antibodies" or "sdAb" format is an individual immunoglobulin domain. Sdabs are fairly stable and easy to express as fusion partner with the Fc chain of an antibody (Harmsen M M, De Haard H J (2007). "Properties, production, and applications of camelid single-domain antibody fragments". Appl. Microbiol Biotechnol. 77(1): 13-22).

The term "Fc domain" or "Fc region" herein is used to define a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat et al, Sequences of Proteins of Immunological Interest, 5th Ed. Public Health Service, National Institutes of Health, Bethesda, Md., 1991. An "Fc polypeptide" of a dimeric Fc as used herein refers to one of the two polypeptides forming the dimeric Fc domain, i.e. a polypeptide comprising C-terminal constant regions of an immunoglobulin heavy chain, capable of stable self-association. For example, an Fc polypeptide of a dimeric IgG Fc comprises an IgG CH2 and an IgG CH3 constant domain sequence. An Fc can be of the class IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$.

The terms "Fc receptor" and "FcR" are used to describe a receptor that binds to the Fc region of an antibody. For example, an FcR can be a native sequence human FcR. Generally, an FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Immunoglobulins of other isotypes can also be bound by certain FcRs (see, e.g., Janeway et al., Immuno Biology: the immune system in health and disease, (Elsevier Science Ltd., NY) (4th ed., 1999)). Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976); and Kim et al., J. Immunol. 24:249 (1994)).

Modifications in the CH2 domain can affect the binding of FcRs to the Fc. A number of amino acid modifications in the Fc region are known in the art for selectively altering the affinity of the Fc for different Fcgamma receptors. In some aspects, the Fc comprises one or more modifications to promote selective binding of Fc-gamma receptors.

Exemplary mutations that alter the binding of FcRs to the Fc are listed below:

S298A/E333A/K334A, S298A/E333A/K334A/K326A (Lu Y, Vernes J M, Chiang N, et al. J Immunol Methods. 2011 Feb. 28; 365(1-2): 132-41);

F243L/R292P/Y300L/V305I/P396L, F243L/R292P/Y300L/L235V/P396L (Stavenhagen J B, Gorlatov S, Tuaillon N, et al. Cancer Res. 2007 Sep. 15; 67(18):8882-90; Nordstrom J L, Gorlatov S, Zhang W, et al. Breast Cancer Res. 2011 Nov. 30; 13(6):R123);

F243L (Stewart R, Thom G, Levens M, et al. Protein Eng Des Sel. 2011 September; 24(9):671-8.), S298A/E333A/K334A (Shields R L, Namenuk A K, Hong K, et al. J Biol Chem. 2001 Mar. 2; 276(9):6591-604);

S239D/I332E/A330L, S239D/I332E (Lazar G A, Dang W, Karki S, et al. Proc Natl Acad Sci USA. 2006 Mar. 14; 103(11):4005-10);

S239D/S267E, S267E/L328F (Chu S Y, Vostiar I, Karki S, et al. Mol Immunol. 2008 September; 45(15):3926-33); S239D/D265S/S298A/I332E, S239E/S298A/K326A/A327H, G237F/S298A/A330L/I332E, S239D/I332E/S298A, S239D/K326E/A330L/I332E/S298A, G236A/S239D/D270L/I332E, S239E/S267E/H268D, L 234F/S267E/N325L, G237F/V266L/S267D and other mutations listed in WO2011/120134 and WO2011/120135, herein incorporated by reference. *Therapeutic Antibody Engineering* (by William R. Strohl and Lila M. Strohl, Woodhead Publishing series in Biomedicine No 11, ISBN 1 907568 37 9, October 2012) lists mutations on page 283.

In some embodiments an antibody described herein includes modifications to improve its ability to mediate effector function. Such modifications are known in the art and include afucosylation, or engineering of the affinity of the Fc towards an activating receptor, mainly FCGR3a for ADCC, and towards C1q for CDC. The following Table B summarizes various designs reported in the literature for effector function engineering.

Methods of producing antibodies with little or no fucose on the Fc glycosylation site (Asn 297 EU numbering) without altering the amino acid sequence are well known in the art. The GlymaX® technology (ProBioGen AG) is based on the introduction of a gene for an enzyme which deflects the cellular pathway of fucose biosynthesis into cells used for antibody production. This prevents the addition of the sugar "fucose" to the N-linked antibody carbohydrate part by antibody-producing cells. (von Horsten et al. (2010) Glycobiology. 2010 December; 20 (12): 1607-18. Another approach to obtaining antibodys with lowered levels of fucosylation can be found in U.S. Pat. No. 8,409,572, which teaches selecting cell lines for antibody production for their ability to yield lower levels of fucosylation on antibodys Antibodys can be fully afucosylated (meaning they contain no detectable fucose) or they can be partially afucosylated, meaning that the isolated antibody contains less than 95%, less than 85%, less than 75%, less than 65%, less than 55%, less than 45%, less than 35%, less than 25%, less than 15% or less than 5% of the amount of fucose normally detected for a similar antibody produced by a mammalian expression system.

Thus, in one embodiment, an antibody described herein can include a dimeric Fc that comprises one or more amino acid modifications as noted in Table B that confer improved effector function. In another embodiment, the antibody can be afucosylated to improve effector function.

TABLE B

CH2 domains and effector function engineering

| Reference | Mutations | Effect |
|---|---|---|
| Lu, 2011, Ferrara 2011, Mizushima 2011 | Afucosylated | Increased ADCC |
| Lu, 2011 | S298A/E333A/K334A | Increased ADCC |
| Lu, 2011 | S298A/E333A/K334A/K326A | Increased ADCC |
| Stavenhagen, 2007 | F243L/R292P/Y300L/V305I/P396L | Increased ADCC |
| Nordstrom, 2011 | F243L/R292P/Y300L/L235V/P396L | Increased ADCC |
| Stewart, 2011 | F243L | Increased ADCC |
| Shields, 2001 | S298A/E333A/K334A | Increased ADCC |
| Lazar, 2006 | S239D/I332E/A330L | Increased ADCC |
| Lazar, 2006 | S239D/I332E | Increased ADCC |
| Bowles, 2006 | AME-D, not specified mutations | Increased ADCC |
| Heider, 2011 | 37.1, mutations not disclosed | Increased ADCC |
| Moore, 2010 | S267E/H268F/S324T | Increased CDC |

Fc modifications reducing FcγR and/or complement binding and/or effector function are known in the art. Recent publications describe strategies that have been used to engineer antibodies with reduced or silenced effector activity (see Strohl, W R (2009), Curr Opin Biotech 20:685-691, and Strohl, W R and Strohl L M, "Antibody Fc engineering for optimal antibody performance" In Therapeutic Antibody Engineering, Cambridge: Woodhead Publishing (2012), pp 225-249). These strategies include reduction of effector function through modification of glycosylation, use of IgG2/IgG4 scaffolds, or the introduction of mutations in the hinge or CH2 regions of the Fc. For example, US Patent Publication No. 2011/0212087 (Strohl), International Patent Publication No. WO 2006/105338 (Xencor), US Patent Publication No. 2012/0225058 (Xencor), US Patent Publication No. 2012/0251531 (Genentech), and Strop et al ((2012) J. Mol. Biol. 420: 204-219) describe specific modifications to reduce FcγR or complement binding to the Fc.

Specific, non-limiting examples of known amino acid modifications to reduce FcγR or complement binding to the Fc include those identified in the following table:

TABLE C

Modifications to reduce FcγR or complement binding to the Fc

| Company | Mutations |
|---|---|
| GSK | N297A |
| Ortho Biotech | L234A/L235A |
| Protein Design labs | IGG2 V234A/G237A |
| Wellcome Labs | IGG4 L235A/G237A/E318A |
| GSK | IGG4 S228P/L236E |
| Alexion | IGG2/IGG4combo |
| Merck | IGG2 H268Q/V309L/A330S/A331S |
| Bristol-Myers | C220S/C226S/C229S/P238S |
| Seattle Genetics | C226S/C229S/E3233P/L235V/L235A |
| Amgen | *E. coli* production, non glyco |
| Medimune | L234F/L235E/P331S |
| Trubion | Hinge mutant, possibly C226S/P230S |

In some embodiments, the antibody has antibody-dependent cellular cytotoxicity (ADCC) activity. ADCC can occur when antibodies bind to antigens on the surface of pathogenic or tumorigenic target-cells. Effector cells bearing Fc gamma receptors (FcγR or FCGR) on their cell surface, including cytotoxic T-cells, natural killer (NK) cells, macrophages, neutrophils, eosinophils, dendritic cells, or monocytes, recognize and bind the Fc region of antibodies bound to the target-cells. Such binding can trigger the activation of intracellular signaling pathways leading to cell death. In particular embodiments, the antibody's immunoglobulin Fc region subtypes (isotypes) include human IgG1 and IgG3. As used herein, ADCC refers to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., *Proc. Natl. Acad. Sci. (USA)* 95:652-656 (1998).

In some embodiments, the antibody has complement-dependent cytotoxicity (CDC) activity. Antibody-induced CDC is mediated through the proteins of the classical complement cascade and is triggered by binding of the complement protein C1q to the antibody. Antibody Fc region binding to C1q can induce activation of the complement cascade. In particular embodiments, the antibody's immunoglobulin Fc region subtypes (isotypes) include human IgG1 and IgG3. As used herein, CDC refers to the ability of a molecule to lyse a target in the presence of complement. The complement activation pathway is initiated by the binding of the first component of the complement system (C1q) to a molecule (e.g. polypeptide (e.g., an antibody)) complexed with a cognate antigen. To assess complement activation, a CDC assay, e.g. as described in Gazzano-Santoro et al., *J. Immunol. Methods* 202:163 (1996), may be performed.

Anti-NSM antibodies can target at least 1, 2, 3, 4, or more of TREM2, MS4A7, C5AR1, LYVE1, ABCC3, LILRB4, MRC1/CD206, SIGLEC1, STAB1, TMEM37, MERTK, and TMEM119. Anti-NSM antibodies can target TREM2. Anti-NSM antibodies can target MS4A7. In some aspects, anti-NSM antibodies do not target one or more of TREM2, MS4A7, C5AR1, LYVE1, ABCC3, LILRB4, MRC1/CD206, SIGLEC1, STAB1, TMEM37, MERTK, and/or TMEM119. In some aspects, anti-NSM antibodies do not target LILRB4. In some aspects, anti-NSM antibodies do not bind TREM2. In some aspects, anti-NSM antibodies do not bind MS4A7. In some aspects, anti-NSM antibodies do not bind C5AR1. In some aspects, anti-NSM antibodies do not bind LYVE1. In some aspects, anti-NSM antibodies do not bind ABCC3. In some aspects, anti-NSM antibodies do not bind LILRB4. In some aspects, anti-NSM antibodies do not bind MRC1/CD206. In some aspects, anti-NSM antibodies do not bind SIGLEC1. In some aspects, anti-NSM antibodies do not bind STAB1. In some aspects, anti-NSM antibodies do not bind TMEM37. In some aspects, anti-NSM antibodies do not bind MERTK. In some aspects, anti-NSM antibodies do not bind TMEM119. In some aspects, anti-NSM antibodies do not bind TLR7.

In some embodiments, an antibody has antibody-dependent cellular phagocytosis (ADCP) activity. ADCP can occur when antibodies bind to antigens on the surface of pathogenic or tumorigenic target-cells. Phagocytic cells bearing Fc receptors on their cell surface, including monocytes and macrophages, recognize and bind the Fc region of antibodies bound to target-cells. Upon binding of the Fc receptor to the antibody-bound target cell, phagocytosis of the target cell can be initiated. ADCP can be considered a form of ADCC.

In some embodiments, the antibodies are capable of forming an immune complex. For example, an immune complex can be a tumor cell covered by antibodies.

In some aspects, an anti-NSM antibody does not substantially bind myeloid cells present outside of cancer tissue. In some aspects, an anti-NSM antibody does not substantially bind stimulatory myeloid cells present in cancer tissue.

In some embodiments the antibodies are monoclonal antibodies.

In some embodiments the antibodies are polyclonal antibodies.

In some embodiments the antibodies are produced by hybridomas. In other embodiments, the antibodies are produced by recombinant cells engineered to express the desired variable and constant domains.

In some embodiments the antibodies may be single chain antibodies or other antibody derivatives retaining the antigen specificity and the lower hinge region or a variant thereof.

In some embodiments the antibodies may be polyfunctional antibodies, recombinant antibodies, human antibodies, humanized antibodies, fragments or variants thereof. In particular embodiments, the antibody fragment or a derivative thereof is selected from a Fab fragment, a Fab'2 fragment, a CDR and ScFv.

A human antibody includes all antibodies that have variable and constant regions derived from human immunoglobulin sequences. In one embodiment, all of the variable and constant domains are derived from human immunoglobulin sequences (a fully human antibody). These antibodies may be prepared in a variety of ways including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies can be found in U.S. Pat. Nos. 6,054,297, 5,886,152 and 5,877,293.

A chimeric antibody refers to an antibody that contains one or more regions from one antibody and one or more regions from one or more other, distinct antibodies.

In some embodiments, antibodies are specific for surface antigens, such as NSM protein. In some embodiments, therapeutic antibodies are specific for tumor antigens (e.g., molecules specifically expressed by tumor cells). In particular embodiments, the therapeutic antibodies may have human or non-human primate IgG1 or IgG3 Fc portions.

In some embodiments, an antibody is bound to, or conjugated to an effector molecule. In particular embodiments, an antibody is conjugated to at least one therapeutic agent selected from the group consisting of a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide, an antisense molecule, a siRNA, a second antibody and a second antibody fragment.

In some embodiments, an antibody is an agonistic antibody. An agonistic antibody can induce (e.g., increase) one or more activities or functions of NSMs after the antibody binds an NSM protein expressed on the cell. The agonistic antibody may bind to and activate NSMs, causing changes in proliferation of the cell or modifying antigen presentation capabilities. The agonistic antibody may bind to and activate NSMs, triggering intracellular signaling pathways that lead to modified cell growth or apoptosis.

In some embodiments, an antibody is an antagonistic antibody. An antagonistic antibody can block (e.g. decrease) one or more activities or functions of NSMs after the antibody binds a NSM protein expressed on the cell. For example, the antagonist antibody may bind to and block ligand binding to one or more NSM proteins, preventing differentiation and proliferation of the cell or modifying antigen presentation capabilities. The antagonist antibody may bind to and prevent activation of a NSM protein by its ligand, modifying intracellular signaling pathways that contribute to cell growth and survival.

In some embodiments an antibody is a depleting antibody. A depleting antibody is one that would kill a non-stimulatory myeloid cell upon contact through the antibody's interaction with other immune cells of molecules. For example, antibodies, when bound to cells bearing NSM proteins, could engage complement proteins and induce complement-dependent cell lysis. Antibodies, when bound to cells bearing NSM proteins, could also trigger neighboring cells bearing Fc receptors to kill them by antibody-dependent cellular cytotoxicity (ADCC).

In some embodiments, an antibody is a neutralizing antibody, and the antibody neutralizes one or more biological activities of NSMs. In some embodiments, NSM protein is expressed on the surface of non-stimulatory myeloid cells and the antibody recognizes the extracellular domain of NSM protein.

In some embodiments an antibody is selective for NSMs (preferentially binds to NSM). In certain embodiments, an antibody that selectively binds to NSMs has a dissociation constant (Kd) of range of 0.0001 nM to 1 µM. In certain embodiments, an antibody specifically binds to an epitope on a NSM protein that is conserved among the protein from different species. In another embodiment, selective binding includes, but does not require, exclusive binding.

In one embodiment an anti-NSM antibody bound to its target is responsible for causing the in vivo depletion of non-stimulatory myeloid cells to which it is bound. In some embodiments, effector proteins induced by clustered antibodies can trigger a variety of responses, including release of inflammatory cytokines, regulation of antigen production, endocytosis, or cell killing. In one embodiment the antibody is capable of recruiting and activating complement or mediating antibody-dependent cellular cytotoxicity (ADCC) in vivo, or mediating phagocytosis by binding Fc receptors in vivo. The antibody may also deplete non-stimulatory myeloid cells by inducing apoptosis or necrosis of the non-stimulatory myeloid cell upon binding.

In some embodiments, an antibody is an IgG1 antibody.
In some embodiments, an antibody is an IgG3 antibody.
In some embodiments, an antibody is not an IgG2 antibody.
In some embodiments, an antibody is not an IgG4 antibody.

In some embodiments the disabling of non-stimulatory myeloid cells is in vitro and is achieved: a) by killing of the non-stimulatory myeloid cells; b) magnetic bead depletion of the non-stimulatory myeloid cells; or c) Fluorescence-activated cell sorting (FACS) sorting of the non-stimulatory myeloid cells.

In certain embodiments, an antibody provided herein has a dissociation constant (Kd) of range of 0.0001 nM to 1 µM. For example, Kd of the antibody may be about 1 µM, about 100 nM, about 50 nM, about 10 nM, about 1 nM, about 500 pM, about 100 pM, or about 50 pM to any of about 2 pM, about 5 pM, about 10 pM, about 15 pM, about 20 pM, or about 40 pM.

In some embodiments, for in vivo administration of anti-NSM antibodies described herein, normal dosage amounts may vary from about 10 ng/kg up to about 100 mg/kg of an individual's body weight or more per day, preferably about 1 mg/kg/day to 10 mg/kg/day, depending upon the route of administration. For repeated administrations over several days or longer, depending on the severity of the disease or disorder to be treated, the treatment is sustained until a desired suppression of symptoms is achieved. An exemplary dosing regimen comprises administering an initial dose of an anti-NSM antibody of about 2 mg/kg, followed by a weekly maintenance dose of about 1 mg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, and about 2/mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the anti-NSM antibody administered, can vary over time independently of the dose used.

In certain embodiments an antibody is conjugated to a drug, e.g., a toxin, a chemotherapeutic agent, an immune modulator, or a radioisotope. Several methods of preparing ADCs (antibody drug conjugates) are known in the art and are described in U.S. Pat. No. 8,624,003 (pot method), U.S. Pat. No. 8,163,888 (one-step), and U.S. Pat. No. 5,208,020 (two-step method), for example. An antibody or antigen-binding fragment thereof can be conjugated to at least one agent including a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide, an antisense molecule, a siRNA, a second antibody, and a second antibody fragment that is antigen binding.

Proteins, Nucleotides, and Homologs

Provided herein are methods and compositions for disabling and/or detecting non-stimulatory human myeloid cells that express NSM proteins. In some embodiments, the invention is directed to disabling and/or detecting non-stimulatory myeloid cells from non-human mammalian cells that express a NSM protein homolog. For example, NSM proteins in the mouse can express a comparable restricted pattern of expression as its human homolog. Thus in one embodiment, provided herein are methods and compositions for disabling and/or detecting non-stimulatory mouse myeloid cells that express an NSM protein. Also provided herein are similar methods and compositions for disabling and/or detecting non-stimulatory cells from any individual that expresses a homolog of a NSM protein, with a similar expression pattern, which cells exhibit a comparable pattern of expression as that of the NSM protein.

NSM proteins or nucleotides can include at least one or more of C5AR1, LYVE1, ABCC3, MRC1, SIGLEC1, STAB1, C1QB, C1QA, TMEM37, MERTK, C1QC, TMEM119, MS4A7, APOE, CYP4F18, TREM2, TLR7, and LILRB4, and homologs thereof. SDC proteins or nucleotides can include at least one or more of KIT, CCR7, BATF3, FLT3, ZBTB46, IRF8, BTLA, MYCL1, CLEC9A, BDCA3, and XCR1, and homologs thereof. Cell surface NSM proteins can include at least one or more of TREM2, MS4A7, C5AR1, LYVE1, ABCC3, LILRB4, MRC1/CD206, SIGLEC1, STAB1, TMEM37, MERTK, and TMEM119. Cell surface NSM proteins can be targeted by one or more anti-NSM antibodies, alone or in combination. Generally NSMs are positive for NSM proteins or nucleotides and negative for SDC proteins or nucleotides; conversely SDCs are generally positive for SDC proteins or nucleotides and negative for NSM proteins or nucleotides.

The antigen-binding constructs described herein comprise at least one polypeptide. Also described are polynucleotides encoding the polypeptides described herein. The antigen-binding constructs are typically isolated.

As used herein, "isolated" means an agent (e.g., a polypeptide or polynucleotide) that has been identified and separated and/or recovered from a component of its natural cell culture environment. Contaminant components of its natural environment are materials that would interfere with diagnostic or therapeutic uses for the antigen-binding construct, and may include enzymes, hormones, and other proteinaceous or non-proteinaceous solutes. Isolated also refers to an agent that has been synthetically produced, e.g., via human intervention.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, praline, serine, threonine, tryptophan, tyrosine, and valine) and pyrrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as β-alanine, ornithine, etc.; and chemically synthesized compounds having properties known in the art to be characteristic of amino acids. Examples of non-naturally occurring amino acids include, but are not limited to, α-methyl amino acids (e.g. α-methyl alanine), D-amino acids, histidine-like amino acids (e.g., 2-amino-histidine, β-hydroxy-histidine, homohistidine), amino acids having an extra methylene in the side chain ("homo" amino acids), and amino acids in which a carboxylic acid functional group in the side chain is replaced with a sulfonic acid group (e.g., cysteic acid). The incorporation of non-natural amino acids, including synthetic non-native amino acids, substituted amino acids, or one or more D-amino acids into the proteins of the present invention may be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class II-restricted presentation to T helper cells, and are therefore, less likely to induce humoral immune responses in the whole organism.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Also included in the invention are polynucleotides encoding polypeptides of the antigen-binding constructs. The term "polynucleotide" or "nucleotide sequence" is intended to indicate a consecutive stretch of two or more nucleotide molecules. The nucleotide sequence may be of genomic, cDNA, RNA, semisynthetic or synthetic origin, or any combination thereof.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles described herein.

Conservative substitution tables providing functionally similar amino acids are known to those of ordinary skill in the art. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and [0139] 8) Cysteine (C), Methionine (M) (see, e.g., Creighton, Proteins: Structures and Molecular Properties (W H Freeman & Co.; 2nd edition (December 1993)

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the present invention, including homologs from species other than human, may be obtained by a process comprising the steps of screening a library under stringent hybridization conditions with a labeled probe having a polynucleotide sequence described herein or a fragment thereof, and isolating full-length cDNA and genomic clones containing said polynucleotide sequence. Such hybridization techniques are well known to the skilled artisan.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are known to those of ordinary skill in the art. Optimal alignment of sequences for comparison can be conducted, including but not limited to, by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

One example of an algorithm that is suitable for determining percent sequence identity and sequence similarity are the BLAST and BLAST 2.0 algorithms, which are described in Altschul et al. (1997) Nuc. Acids Res. 25:3389-3402, and Altschul et al. (1990) J. Mol. Biol. 215:403-410, respectively. Software for performing BLAST analyses is publicly available through the National Center for Biotechnology Information available at the World Wide Web at ncbi.nlm.nih.gov. The BLAST algorithm parameters W, T, and X determine the sensitivity and speed of the alignment. The BLASTN program (for nucleotide sequences) uses as defaults a wordlength (W) of 11, an expectation (E) or 10, $M=5$, $N=-4$ and a comparison of both strands. For amino acid sequences, the BLASTP program uses as defaults a wordlength of 3, and expectation (E) of 10, and the BLOSUM62 scoring matrix (see Henikoff and Henikoff (1992) Proc. Natl. Acad. Sci. USA 89:10915) alignments (B) of 50, expectation (E) of 10, $M=5$, $N=-4$, and a comparison of both strands. The BLAST algorithm is typically performed with the "low complexity" filter turned off.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability ($P(N)$), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or less than about 0.01, or less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to hybridization of sequences of DNA, RNA, or other nucleic acids, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, Laboratory Techniques in Biochemistry and Molecular Biology—Hybridization with Nucleic Probes, "Overview of principles of hybridization and the strategy of nucleic acid assays" (1993).

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches. The engineered proteins are expressed and produced by standard molecular biology techniques.

By "isolated nucleic acid molecule or polynucleotide" is intended a nucleic acid molecule, DNA or RNA, which has been removed from its native environment. For example, a recombinant polynucleotide encoding a polypeptide contained in a vector is considered isolated. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts, as well as positive and negative strand forms, and double-stranded forms. Isolated polynucleotides or nucleic acids described herein, further include such molecules produced synthetically, e.g., via PCR or chemical synthesis. In addition, a polynucleotide or a nucleic acid, in certain embodiments, includes a regulatory element such as a promoter, ribosome binding site, or a transcription terminator.

The term "polymerase chain reaction" or "PCR" generally refers to a method for amplification of a desired nucleotide sequence in vitro, as described, for example, in U.S. Pat. No. 4,683,195. In general, the PCR method involves repeated cycles of primer extension synthesis, using oligonucleotide primers capable of hybridising preferentially to a template nucleic acid.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

A derivative, or a variant of a polypeptide is said to share "homology" or be "homologous" with the peptide if the amino acid sequences of the derivative or variant has at least 50% identity with a 100 amino acid sequence from the original peptide. In certain embodiments, the derivative or variant is at least 75% the same as that of either the peptide or a fragment of the peptide having the same number of amino acid residues as the derivative. In certain embodiments, the derivative or variant is at least 85% the same as that of either the peptide or a fragment of the peptide having the same number of amino acid residues as the derivative. In certain embodiments, the amino acid sequence of the derivative is at least 90% the same as the peptide or a fragment of the peptide having the same number of amino acid residues as the derivative. In some embodiments, the amino acid sequence of the derivative is at least 95% the same as the peptide or a fragment of the peptide having the same number of amino acid residues as the derivative. In certain embodiments, the derivative or variant is at least 99% the same as that of either the peptide or a fragment of the peptide having the same number of amino acid residues as the derivative.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

In some aspects, an antibody or protein disclosed herein comprises an amino acids sequence that is at least 80, 85, 90, 91, 92, 93, 94, 95, 96, 97, 98, 99, or 100% identical to a relevant amino acid sequence or fragment thereof set forth in the Table(s) or accession number(s) disclosed herein. In some aspects, an isolated antibody or protein disclosed herein comprises an amino acids sequence encoded by a polynucleotide that is at least 80, 85, 90, 91, 92, 93, 94, 95, 96, 97, 98, 99, or 100% identical to a relevant nucleotide sequence or fragment thereof set forth in Table(s) or accession number(s) disclosed herein.

Pharmaceutical Compositions

The present application provides compositions comprising the antibodies including pharmaceutical compositions comprising any one or more of the antibodies described herein with one or more pharmaceutically acceptable excipients. In some embodiments the composition is sterile. The pharmaceutical compositions generally comprise an effective amount of an antibody.

These compositions can comprise, in addition to one or more of the antibodies disclosed herein, a pharmaceutically acceptable excipient, carrier, buffer, stabiliser or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

Whether it is a polypeptide, antibody, nucleic acid, small molecule or other pharmaceutically useful compound that is to be given to an individual, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc., is within the responsibility of general practitioners and other medical doctors, and typically takes account of the disorder to be treated, the condition of the individual subject, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

Methods

Methods of Use

In one aspect, the present application provides methods of contacting non-stimulatory myeloid cells with an anti-NSM antibody, such as a human antibody, which results in the disabling of the non-stimulatory myeloid cells.

In another aspect, the present application provides methods of contacting non-stimulatory myeloid cells with an anti-NSM mouse antibody, which results in the disabling of the non-stimulatory myeloid cells.

In some embodiments the non-stimulatory cells are one or more of DC1 cells, and TAM cells.

In some embodiments, the present application provides methods of disabling non-stimulatory myeloid cells, comprising contacting the non-stimulatory myeloid cells with a NSM antibody, thereby killing the non-stimulatory myeloid cells. Disabling refers to rendering a cell partially or completely non-functional. In some embodiments, the disabling of the non-stimulatory myeloid cells leads to inducing growth arrest in the cells. In some embodiments, the disabling of the non-stimulatory myeloid cells leads to apoptosis in the cells. In some embodiments, the disabling of the non-stimulatory cells leads to lysis of the cells, as for example by complement dependent cytotoxicity (CDC) or antibody-dependent cell cytotoxicity (ADCC). In some embodiments, the disabling of the non-stimulatory myeloid cells leads to necrosis in the cells. In some embodiments, the disabling of the non-stimulatory myeloid cells leads to inducing growth arrest in the cells. In some embodiments, the disabling of the non-stimulatory myeloid cells leads to inactivating the cells. In some embodiments, the disabling of the non-stimulatory myeloid cells leads to neutralizing the activity of a NSM protein in the cells. In some embodiments, the disabling of the non-stimulatory myeloid cells leads to reduction in proliferation of the cells. In some embodiments, the disabling of the non-stimulatory myeloid cells leads to differentiation of the cells. In some embodiments, the disabling of the non-stimulatory myeloid cells leads to a decrease in the cells' ability to act as inhibitory antigen presenting cells or leads to an increase in the cells' ability to act as activating antigen-presenting cells. In some embodiments, the disabling of the non-stimulatory myeloid cells leads to the mislocalization of the cells within tumor tissue or tumor microenvironment (TME). In some embodiments, the disabling of the non-stimulatory myeloid cells leads to an altered spatial organization of the cells within tumor tissue or tumor microenvironment. In some embodiments, the disabling of the non-stimulatory myeloid cells leads to an altered temporal expression of the cells within tumor tissue or TME. In some embodiments, the method further comprises removing the non-stimulatory myeloid cells.

In any and all aspects of disabling non-stimulatory myeloid cells as described herein, any increase or decrease or alteration of an aspect of characteristic(s) or function(s) is as compared to a cell not contacted with an anti-NSM antibody.

In another aspect, the present application provides methods of contacting non-stimulatory myeloid cells with an anti-NSM antibody, which results in the modulation of function of the non-stimulatory myeloid cells. The modulation can be any one or more of the following. In some embodiments the non-stimulatory cells are one or more of DC1 cells, TAM1 cells, and TAM2 cells. In some embodiments, the modulation of function leads to the disabling of non-stimulatory myeloid cells. In some embodiments, the modulation of function of the non-stimulatory myeloid cells leads to an increase in the cells' abilities to stimulate both native and activated CD8+ T-cells, for example, by increasing the ability of non-stimulatory cells to cross-present tumor antigen on MHCI molecules to naive CD8+ T-cells. In some embodiments, the modulation increases the T-cell stimulatory function of the non-stimulatory myeloid cells, including, for example, the cells' abilities to trigger T-cell receptor (TCR) signaling, T-cell proliferation, or T-cell cytokine production. In one embodiment, the survival of the non-stimulatory cell is decreased or the proliferation of the non-stimulatory cell is decreased. In one embodiment, the ratio of stimulatory myeloid cells to non-stimulatory myeloid cells is increased.

In any and all aspects of decreasing the function of non-stimulatory myeloid cells as described herein, any increase or decrease or alteration of an aspect of characteristic(s) or function(s) is as compared to a cell not contacted with an anti-NSM antibody.

In some embodiments, the present application provides methods of killing (also referred to as inducing cell death)

non-stimulatory myeloid cells, comprising contacting the non-stimulatory myeloid cells with an anti-NSM antibody, thereby killing the non-stimulatory myeloid cells. In some embodiments the killing is increased relative to non-stimulatory myeloid cells that have not been contacted with an anti-NSM antibody. In some embodiments, the contacting induces apoptosis in the non-stimulatory myeloid cells. In some embodiments, the contacting induces apoptosis in the non-stimulatory myeloid cells. In some embodiments, the non-stimulatory myeloid cells are in a population of immune cells comprising non-stimulatory myeloid cells and stimulatory myeloid cells. In some embodiments, the method further comprises removing the non-stimulatory myeloid cells. In some embodiments, 10%-80% of the cells are killed. In some embodiments, at least 10%, 20%, 30%, 40%, 50%, 60%, 70%, or 80% of the cells are killed.

In some embodiments, the present application provides methods of increasing the ratio of stimulatory myeloid cells to non-stimulatory myeloid cells in a population of immune cells comprising stimulatory myeloid cells and non-stimulatory myeloid cells, comprising contacting the population of immune cells with an anti-NSM antibody. In some embodiments the ratio is increased relative to a population of cells that have not been contacted with an anti-NSM antibody. In some embodiments the ratio of DC2 cells to DC1 cells is increased. In some embodiments the ratio of DC2 cells to TAM1 cells is increased. In some embodiments the ratio of DC2 cells to TAM2 cells is increased. In some embodiments the ratio of DC2 cells to TAM1+ TAM2 cells is increased. In some embodiments the ratio of DC2 cells to TAM1+DC1 cells is increased. In some embodiments the ratio of DC2 cells to DC1+ TAM2 cells is increased. In some embodiments the ratio of DC2 cells to DC1+ TAM1+ TAM2 cells is increased. In some embodiments, at least the ratio is increased by 10%, 20%, 30%, 40%, 50%, 60%, 70%, 80%, 90%, or 100%.

In some embodiments the ratio of stimulatory myeloid cells to non-stimulatory myeloid cells prior to contacting ranges from 0.001:1-0.1:1. In some embodiments the ratio of stimulatory myeloid cells to non-stimulatory myeloid cells following the contacting ranges from 0.1:1-100:1.

In some embodiments, the non-stimulatory myeloid cells are reduced in number. In some embodiments the stimulatory myeloid cells are DC2 cells. In some embodiments, the non-stimulatory myeloid cells are killed, for example by necrosis, or apoptosis. In some embodiments, the non-stimulatory myeloid cells are induced to undergo growth arrest. In some embodiments the non-stimulatory myeloid cells no longer proliferate. In some embodiments the spatial localization of the non-stimulatory myeloid cells is altered, and the ratio is increased in a particular region of the TME. In some embodiments the temporal expression of the non-stimulatory myeloid cells is altered, and the ratio is increased during a particular time during the development of the tumor.

In some embodiments, the contacting is in vitro. In some embodiments, the contacting is in vivo. In some particular embodiments, the contacting is in vivo in a human. In some embodiments, the contacting is effected by administering an anti-NSM antibody. In some embodiments, the individual receiving the antibody (such as a human) has cancer.

In another aspect, the invention provides methods of treating an immune-related condition (e.g., cancer) in an individual comprising administering to the individual an effective amount of a composition comprising an anti-NSM antibody. In another aspect, the invention provides methods of enhancing an immune response in an individual comprising administering to the individual an effective amount of a composition comprising an anti-NSM antibody. In some embodiments these methods are further provided in combination with other co-therapies such as a PDL blockade therapy, a CTLA4 blockade therapy, generalized checkpoint blockade therapy in which inhibitory molecules on T cells are blocked, adoptive T-cell therapy, CAR T-cell therapy, dendritic cell or other cellular therapies, as well as conventional chemotherapies.

In some embodiments, the method further comprises determining the expression level of NSM protein in a biological sample from the individual. In some embodiments the biological sample includes, but is not limited to a body fluid, a tissue sample, an organ sample, urine, feces, blood, saliva, CSF and any combination thereof. In some embodiments the biological sample is derived from a tumor tissue. In some embodiments, the expression level comprises the mRNA expression level of mRNA encoding NSM protein. In some embodiments, the expression level of NSM protein comprises the protein expression level of NSM. In some embodiments the expression level of NSM protein is detected in the sample using a method selected from the group consisting of FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometery, HPLC, qPCR, RT-qPCR, multiplex qPCR or RT-qPCR, RNA-seq, microarray analysis, SAGE, MassARRAY technique, and FISH, and combinations thereof.

In another aspect, the present application provides methods for determining the presence or absence of non-stimulatory myeloid cells in general, or for determining the presence or absence of particular non-stimulatory myeloid cells (for example DC1 cells, TAM1 cells, and/or TAM2 cells) comprising: contacting a population of cells comprising non-stimulatory myeloid cells with an anti-NSM antibody; and quantifying the number non-stimulatory myeloid cells. In another aspect, the present application provides methods for determining the presence or absence of non-stimulatory myeloid cells comprising: contacting a population of immune cells comprising non-stimulatory myeloid cells and stimulatory myeloid cells with an anti-NSM antibody; detecting a complex or moiety indicating the binding of the antibody to the cell and optionally quantifying the number of non-stimulatory myeloid cells in the population. In another aspect, methods of determining the relative ratio of non-stimulatory myeloid cells to stimulatory myeloid cells are provided, comprising: contacting a population of immune cells comprising non-stimulatory myeloid cells and stimulatory myeloid cells with an anti-NSM antibody; quantifying the number of stimulatory myeloid cells and non-stimulatory myeloid cells; and determining the relative ratio of non-stimulatory myeloid cells to stimulatory myeloid cells.

In embodiments described herein for detection and/or quantification, an anti-NSM antibody binds to a NSM protein, but does not necessarily have to affect a biological response, such as ADCC, although it may have an effect on a biological response.

In another aspect, the present invention provides methods for identifying an individual who may respond to immunotherapy (e.g. with an anti-NSM antibody) for the treatment of an immune-related condition (e.g. cancer) comprising: detecting the expression level of NSM protein in a biological sample from the individual; and determining based on the expression level of NSM protein, whether the individual may respond immunotherapy, wherein an elevated level of NSM protein in the individual relative to that in a healthy individual indicates that the individual may respond to immunotherapy. In some embodiments, these methods may also be used for diagnosing an immune-related condition (e.g. cancer) in the individual and are based the expression level of NSM protein, wherein an elevated level of NSM protein in the individual relative to that in a healthy individual indicates that the individual suffers from cancer. In some embodiments, the expression level comprises the mRNA expression level of mRNA encoding NSM protein. In other embodiments, the expression level of NSM protein comprises the protein expression level of NSM protein. In some embodiments the expression level of NSM protein is detected in the sample using a method selected from the group consisting of FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometery, HPLC, qPCR, RT-qPCR, multiplex qPCR or RT-qPCR, RNA-seq, microarray analysis, SAGE, MassARRAY technique, and FISH, and combinations thereof. In these embodiments, an anti-NSM antibody binds to the NSM protein, but does not necessarily have to effect a biological response, such as ADCC. In some embodiments the biological sample is derived from a tumor tissue. In some embodiments the biological sample includes, but is not limited to a body fluid, a tissue sample, an organ sample, urine, feces, blood, saliva, CSF and any combination thereof.

Also disclosed herein is a method of enhancing a subject immune response to tumors or enhancing the efficacy of immunotherapy treatments. In general, a treatment that increases the abundance of SDC's will improve subject outcome, such as recurrence-free survival time, and will enhance the efficacy of cancer immunotherapy treatments. A treatment can increase the relative or absolute abundance of SDC cells in a subject's tumor. A treatment can decreases the relative or absolute abundance of NSM cells in a subject's tumor.

Exemplary methods of the general treatment strategy include increasing the numbers of SDC's by systemic introduction of Flt3L. Another method is treatment of a subject's autologous bone-marrow or blood cells with Flt3L while simultaneously blocking CSF1. Expression, for example by retrovirus, of SDC transcription factors such as IRF8, Mycl1 or BATF3 or ZBTB46 in bone-marrow or blood progenitor populations may also be used to drive SDC development. Another strategy of treatment includes the systematic elimination of NSM cells while selectively sparing the SDC. This can generate an overall favorable change in the ratio of these populations. Elimination of NSM cells may be accomplished by any means, including the administration (systemic or localized to the tumor) of antibodies against NSM surface proteins.

In some embodiments, SDC-enhancing treatments are applied as a therapeutic treatment to better enable the subject's native immune system in controlling or eradicating the cancer. In another embodiment, the SDC-enhancing treatments of the invention are applied in combination with a therapeutic treatment such as an immunotherapy treatment (such application being prior to, concurrent with, or after the immunotherapy treatment) wherein the SDC-enhancing treatment acts as an accessory or adjuvant treatment to increase the efficacy of the therapeutic treatment.

Methods of Administration

In some embodiments, the methods provided herein are useful for the treatment of an immune-related condition in an individual. In one embodiment, the individual is a human and the antibody is a NSM antibody. In another embodiment, the individual is a mouse and the antibody is a NSM antibody.

In some embodiments, the methods provided herein (such as methods of enhancing an immune response or effecting the disabling of non-stimulatory myeloid cells) are useful for the treatment of cancer and as such an individual receiving an anti-NSM antibody or an anti-NSM antibody has cancer. In some embodiments, the cancer is a solid cancer. In some embodiments, the cancer is a liquid cancer. In some embodiments, the cancer is immunoevasive. In some embodiments, the cancer is immunoresponsive. In particular embodiments, the cancer is selected from the group consisting of melanoma, kidney, hepatobiliary, head-neck squamous carcinoma (HNSC), pancreatic, colon, bladder, prostate, lung, glioblastoma, and breast.

In some embodiments the immune-related condition is an immune-related condition associated with the expression of NSM protein on non-stimulatory myeloid cells (in humans) or the expression of a homolog of NSM protein in a non-human species. In some embodiments the immune-related condition is an immune-related condition associated with the overexpression of NSM protein on non-stimulatory myeloid cells, as compared to stimulatory myeloid-cells. In some embodiments the overexpression of the NSM mRNA or the NSM protein is about at least 2 fold, 5 fold, 10 fold, 25 fold, 50 fold, or 100 fold higher as compared to stimulatory myeloid cells.

In some embodiments, an antibody is administered intravenously, intramuscularly, subcutaneously, topically, orally, transdermally, intraperitoneally, intraorbitally, by implantation, by inhalation, intrathecally, intraventricularly, or intranasally. An effective amount of an anti-NSM antibody may be administered for the treatment of cancer. The appropriate dosage of the anti-NSM antibody may be determined based on the type of cancer to be treated, the type of the anti-NSM antibody, the severity and course of the cancer, the clinical condition of the individual, the individual's clinical history and response to the treatment, and the discretion of the attending physician.

Detection and Quantification of SDC and NSM Cells

The invention encompasses any methodology for the quantification of SDC's and/or NSMs cells. Various embodiments are directed to the identification and quantification of SDC's and/or NSM cells, e.g., in a tumor sample. A tumor sample may be any tissue comprising tumor cells obtained from a patient, as known in the art, for example, a portion of a tumor removed for a biopsy (e.g. needle biopsy or punch biopsy, e.g. a 4 mm punch biopsy) or substantially whole tumors which have been surgically excised, including primary or metastatic cells. It will be noted that the abundance of SDC's is greater in distal regions of a tumor than marginal regions. In a typical sample, this differential will be averaged out and should not affect results. However, if an excessive amount of marginal material is included in the sample, this could sway results towards an undercount of SDC abundance.

In an embodiment, the numbers of SDC's and NSM cells in a sample are directly quantified by fluorescence activated cell sorting (FACS), similar flow-cytometry methodologies, magnetic-activated cell sorting, microraft sorting, affinity-based cell separation methods, and other means of isolating specific cell types from a mixed population of cells. For example, a tumor sample may be digested with enzymes to create a single cell suspension, as known in the art. Then the cells can be labeled with antibodies specific to protein or carbohydrate markers unique to each cell type. Next, various gating protocols based on the various labels can be utilized to separate the cell fractions by FACS, or similar methodologies, as known in the art. For example, as described in the Examples, labeling the single cell suspension from digested tumors with fluorescently tagged antibodies allowed FACS isolation of the dendritic cell fraction from other cell types within the sample and the separation of SDC and NSM cell pools. As known in the art, labeling of either extracellular or intracellular marker proteins may be used in such methodologies.

For example, in one FACS protocol, the various cell types of the tumor myeloid compartment may be sorted as follows. Those cells expressing CD11b and Ly6C represent monocytes and neutrophils and can be removed by such expression. High CD24 expression and low F4/80 expression may be used to distinguish the dendritic cells (SDC's and DC1 cells) from tumor macrophages cells (TAM1 and TAM2). The two tumor macrophage populations can be separated from each other by their differential expression of CD11b and CD11c, with TAM1 cells being "CD11b high", "MHC Class II low" and "CD11c low," while TAM2 cells are "CD11b low", "MHC Class II high" and "CD11c high." Tumor macrophages in humans characteristically express CD14 whereas DCs typically do not. Examples of distinguishing surface markers that assist in distinguishing the two dendritic populations from one another and from macrophages include CD103, XCR1, Clec9a and CD11b in mouse or CD14, BDCA3, XCR1 and Clec9a in human. For example, the two dendritic cell populations may be separated in mouse tumors by their differential expression of CD11b (absent in SDC's, present in NSM cells) and CD103 (absent in NSM cells, present in SDC's). Similarly, the SDCs in humans express BDCA3, XCR1, and Clec9a whereas non-stimulatory DCs express BDCA1 and macrophages express CD14.

In another embodiment, direct histological analysis of tissue samples is used to determine the presence, prevalence, and relative abundance of SDC's compared to other cell types. For example, tissue sections may be stained with labeled antibodies against SDC markers and comprising antigens, and labeled antibodies against NSM markers and comprising antigens. Analysis of labeled tissue sections by quantitative fluorescence microscopy may then be applied for the quantification of SDC's and NSM cells in the sample, as well as visualization of the relative physical distribution and localization of such cells in the sample.

In another embodiment, the abundance of SDC's and/or the abundance of NSM cells in a sample is determined indirectly by observing gene expression patterns in the bulk tumor sample, obviating the need to separate the sample into cell fractions. Quantitative analysis of SDC and NSM genetic markers in bulk tumor tissue is utilized as a surrogate measure of the ratio of SDC's to NSM cells present in the tumor. For example, in one embodiment, the entire transcriptome of the cells within the tumor sample is assayed to determine the ratio of expression of SDC marker genes to the expression of NSM marker genes. It will be understood that such quantification of marker gene expression can be accomplished utilizing any number of tools known in the art for the analysis of gene expression.

In one embodiment, assessment of marker gene expression in a tumor sample is carried out using quantitative PCR methodologies, as known in the art. Such methodologies can be performed using whole tumor-transcriptome protocols, as known in the art, and primer pairs uniquely capable of amplifying marker gene sequences. Given the known sequences of the marker genes, it is readily within the skill of one in the art to generate primers thereto. It will be understood, as known in the art, that reference to a "gene sequence" of a particular gene, in the context of quantifying expression, will refer to whole or partial nucleic acid sequences corresponding to or complementary to mRNA (or cDNA generated therefrom) produced by that gene when expressed.

In another embodiment, expression of maker genes can be measured using DNA array technology, as known in the art. Probes which bind maker gene transcripts may readily be generated by one of skill in the art utilizing the known sequences of the marker genes, and may be utilize in any number of gene expression chips and analysis platforms.

In another embodiment, SDC and NSM cell quantification is accomplished by monitoring the presence or activity of downstream genes and proteins defined as genes and proteins which are regulated by a marker gene or its translation product, and whose activity varies predictably in response to marker gene expression. In another embodiment, functional assays are used to identify or quantify SDC and NSM cells, for example, by differential immunological activity. For example, SDC's are efficient at cross-presenting tumor antigens and are potent activators of CD8 T cells, whereas NSM cells are not. Similarly, while NSM cells display highly phagocytic behavior, SDCs are less robust phagocytes, in comparison.

Abundance and Screening

Various embodiments of the invention are directed to determining the abundance of SDC's in a tumor. The abundance of such cells may be assessed by various measures. Such measurements may comprise relative measurements or absolute measurements, and may comprise direct or indirect measurement. For example, relative abundance may be determined by measuring the ratio of SDC's to NSM cells in the sample; the ratio of SDC's to the number of DC1 cells in the sample; or the ratio of SDC's to all cell types within the sample, the ratio of SDC's to total myeloid cells in the sample, or the ratio of SDC's to HLA-DR$^+$ cells in the sample. In some embodiments, the absolute abundance of SDC's is determined, for example, as a measure of the total number of SDC's per ml of tumor tissue or per microgram of tumor tissue. Indirect measures include assessing the levels of gene expression of SDC marker genes, alone or in comparison with the expression levels of markers to other cell types such as NSM cells.

In various embodiments, the abundance of SDC's in a subject's tumor comprises a prognostic indicator, a diagnostic indicator, or a treatment selection indicator.

Various embodiments are directed to comparative measures, such as an "elevated" or "increased" abundance of SDC's. Such comparative measures may be made by comparing a sample from a subject to representative samples. Representative samples may comprise, for example, samples derived from the same subject at an earlier point in time, samples derived from like subjects (e.g. matched in age, gender, health indicators, cancer progression, cancer type, etc.), or samples derived from like tumors (e.g. matched as to tumor type, tumor stage, and other measures of tumor progression). In some embodiments, for example, wherein the efficacy of a treatment is being assessed, an elevated abundance is defined as an abundance greater than that observed in representative samples from untreated subjects. In some embodiments, a measure of typical or average SDC abundance is used as a baseline for determining what constitutes an elevated or increased abundance, for example, the mean, median, or similar statistical measure of SDC's in representative samples may be used. Various statistical methodologies known in the art may be used to define quantities that are significantly elevated or increased.

In one embodiment, the abundance of SDC's in a subject's tumor comprises a prognostic indicator wherein the subject's outcome is predicted based upon the abundance of SDC's in the subject's tumor, wherein an elevated abundance is indicative of a higher probability of a positive outcome. Exemplary measures of outcome include likelihood of recurrence free-survival, predicted time of recurrence free survival, predicted time of overall survival, risk of relapse, quality of life indicators, etc. For example, in one embodiment, the ratio of SDC's to NSM cells in the tumor sample, measured either directly or indirectly, is utilized as the measure of SDC abundance and predicted time of recurrence-free survival is the measure of subject outcome. For example, the mean or median SDC marker gene expression to NSM marker gene expression ratio observed in a pool of like tumor samples may serve as a threshold value, and if an individual subject's measured ratio exceeds said threshold, the subject is found to have an increased probability of recurrence-free survival.

In another embodiment, the abundance of SDC's in a subject's tumor is an indicator of the subject's likelihood of responding positively to immunotherapy treatment, wherein an elevated abundance of SDC's in a tumor sample derived from the subject is indicative of a higher probability of a positive response to immunotherapy. For example, in one embodiment, the ratio of SDC's to NSM cells in the tumor sample, measured directly or indirectly, is utilized as the measure of SDC abundance. For example, the mean or median SDC marker gene expression to NSM marker gene expression ratio observed in a pool of like tumor samples may serve as a threshold value, and if an individual subject's measured ratio is below said threshold, the subject is found to have an decreased probability of positively responding to immunotherapy.

Predicting which subjects will be more likely amenable to treatment with an immunotherapy method advantageously allows for selection of the proper therapeutic intervention. Subjects found less likely to respond to immunotherapy treatment may be directed to other treatment modalities, while subjects more likely to respond to immunotherapy can be treated accordingly. The treatment selection indicators of the invention are applicable to predicting responsiveness or non-responsiveness to any cancer immunotherapy known in the art. For example, one class of cancer immunotherapies is known as "checkpoint blockade" treatments. The mammalian immune system comprises various "checkpoints," which are self-limiting inhibitory pathways which normally act to attenuate immune responses and prevent autoimmune reactions. Tumors have been shown to hijack these pathways such that the anti-tumor immune response is suppressed. Various therapeutic strategies, known as checkpoint blockades involve the use of ligands, such as antibodies, to block these control points and inhibit tumor suppression of immune responses and to rescue the anti-tumor immune response. Another class of immunotherapies encompasses the cell based strategies, for example the removal of cells such as dendritic cells from the subject and the ex-vivo proliferation and activation of such cells against tumor antigens. The activated cells are then reintroduced to the body to enhance the subject's immune response against the tumor.

The disclosures contained herein provide the art with novel relationships between the abundance of SDC's and subject outcome and/or subject amenability to immunotherapeutic treatment. The invention broadly encompasses any applications of these concepts. It is within the skill of one in the art to implement the inventive concepts by developing predictive relationships between specific measures of SDC abundance and specific measures of subject outcome or amenability to specific immunotherapy treatments, for any specific type or subtype of cancer. Such predictive relationships may encompass any statistical regimen which embodies the phenomenon that increased SDC abundance is indicative of an improved subject outcome or an increased amenability to immunotherapeutic treatment.

In one embodiment, the invention comprises a predictive relationship wherein the ratio of SDC marker gene expression to NSM marker gene expression is used as a measure of SDC abundance relative to NSM immune cell abundance, and an elevated proportion of SDC's is predictive of a greater likelihood of subject survival. For example, as described in the examples, a large pool of gene expression data from 3602 tumor samples, representing 12 different cancer types (data from TCGA pan-cancer project) was analyzed, wherein associated subject survival data was available for each tumor sample. For each sample, the mean observed expression level (measured in relative units of intensity in the normalized dataset) of all SDC marker genes in Table A was calculated and taken as a measure of SDC dendritic immune cell abundance. Likewise, the observed mean expression level of all NSM marker genes in Table A was calculated for each sample and taken as a measure of NSM immune cell abundance. The ratio of SDC to NSM cell abundance signals for each sample was then calculated, transformed logarithmically, and Z-score normalized to render a median of 0 and standard deviation of 1 across the entire dataset. For each cancer type, a median SDC to NSM gene marker gene expression ratio value was calculated. For each cancer type, the pool of samples was divided into "high" SDC to NSM ratio or "low" SDC to NSM ratio, with the high pool encompassing all samples with a standardized ratio above the median value for the entire population of like samples (matched on the basis of cancer type), and the low pool encompassing all samples with a standardized ratio below the median value. The Kaplan-Meier method was used to assess association between overall survival and the SDC/NSM signature ratio as a dichotomous variable (split across median, per cancer). As depicted in the figures, the data clearly show that overall survival rates are substantially increased in the high pool compared to the low pool.

Accordingly, the ratio of SDC marker gene expression to NSM gene expression in a sample is predictive of overall survival time for the subject from which the sample is derived, wherein an elevated ratio is indicative of increased overall survival. In this case, an "elevated" ratio is defined as a ratio exceeding the median ratio value for that type of cancer. Accordingly, in one embodiment, the invention comprises a method of predicting greater overall survival time for a subject (relative to subjects with low SDC/NSM signature ratio) by: (1) calculating the z-scored, log-transformed ratio of mean SDC marker gene expression to mean NSM gene expression in a tumor sample derived from the subject; and then comparing the subject's observed ratio to a threshold value representing the median SDC marker gene expression to NSM gene expression ratio value for the tumor sample's type of cancer; wherein a greater than average overall survival time is indicated if the sample ratio value exceeds the threshold value.

It will be appreciated that the exemplary method of calculating SDC abundance presented herein is illustrative and may be modified in various ways. For example, subsets of genes from Table A may be used. For example, in one embodiment, the SDC markers BDCA3, KIT, CCR7, BATF3, FLT3, ZBTB46, IRF8, BTLA, MYCL1, and CLEC9A, and the NSM markers MRC1, MS4A7, C1QC, APOE, C1QB, C1QA, and C5AR1 are used. Likewise, the specific mathematical operations utilized to calculate gene expression ratios may be altered, for example log transformed values may be summed and averaged rather than averaged values being log transformed, and so on. So long as the specific methodology is representative of the ratio of SDC marker gene expression level to NSM marker gene expression level in the sample, the exact nature of and sequence of mathematical operations utilized to calculate the ratio are not essential.

In alternative embodiments, NSM abundance may be measured as the number of NSM cells per total live tumor cells, the number of NSM cells per total tumor immune cells the number of NSM cells per unit volume of tumor sample, or the number of NSM cells per unit mass (e.g. mg) of tumor sample. Likewise, SDC abundance may be measured as the number of SDC cells per total live tumor cells, the number of SDC cells per total tumor immune cells the number of SDC cells per unit volume of tumor sample, or the number of SDC cells per unit mass (e.g. mg) of tumor sample.

Total myeloid cells in a sample may be assessed as the total CD11b+ cells in the sample. Total myeloid cells in the sample may be defined as total cells expressing CD14 plus the total cells expressing CD16 plus the total cells expressing HLA.

In one embodiment, the abundance of SDC cells is assessed as a percentage of HLA-DR positive myeloid cells in the sample expressing an SDC marker by flow cytometric methods. For example, the SDC marker may be BDCA3 or XCR1 or Clec9a.

It has been advantageously discovered by the inventors of the present disclosure that the abundance of CD14 expressing (CD14+) macrophages and monocytes may be used as a measure of non-stimulatory cell abundance or to stratify subject pools for the purposes of more accurately prognosing cancer outcome or assessing treatment efficacy. The CD14+ macrophages may be competing with stimulatory dendritic cells and thus the balance of CD14+ cells to SDC cells in the myeloid pool may be an important determinant of cancer outcome. The proportion of CD14+ cells may modulate the effects of SDC abundance. In one implementation, an alternative measure of NSM abundance is defined as the abundance of CD14+ myeloid cells in a sample. In one embodiment, CD14+ myeloid cell abundance is measured as the percentage of total CD11b+ myeloid cells expressing CD14. In another embodiment, the percentage of HLA-DR positive cells that express CD14 is used as a measure of CD14+ cell abundance. In another embodiment, CD14+ myeloid cell abundance is measured as the percentage of total immune cells expressing CD45. In another embodiment, CD14+ myeloid cell abundance is measured as the number of CD14+ cells per gram of sample tissue or a like measure.

In one implementation of the invention, SDC abundance is measured as the percentage of myeloid cells expressing HLA-DR+ which are also expressing an SDC marker, for example, BDCA3 or XCR1. In one embodiment, the SDC abundance so measured is utilized as a prognostic indicator, an indicator of treatment efficacy, or an indicator of a subject's amenability to a specific treatment wherein an elevated abundance of SDC's is indicative of a positive prognosis, a positive response to treatment, or a higher likelihood of amenability to a specific treatment, and a lower abundance of SDC's is indicative of a poor prognosis, an ineffective treatment, or a lower probability of amenability to a specific treatment. For example, an SDC (for example, BDCA3+ cell) abundance of 1-4, 1-2, 1, 2, 3, 4, 5, or 1.37% or greater of HLA-DR+ cells may be considered an elevated abundance of SDC's. For example, subjects having tumors with 1-5, 1-4, 1-2, 1, 2, 3, 4, 5, or 1.37% or greater HLA-DR+ comprising SDC cells have a greater than 50% probability of responding positively to an immunotherapy treatment such as anti-PD1, for example a greater than 85% probability of responding positively.

In one embodiment, the treatment being assessed is an immunostimulatory or immunotherapy treatment. For example, the treatment may comprise a treatment which targets programmed cell death protein 1 (PD1) or programmed cell death ligand 1 (PD-L1). For example anti-PD1 treatments include nivolumab (Opdivo™), pembromizulab (Keytruda™). Another similar treatment is the targeting of CTLA-4, for example with ipilimumab (Yervoy™). In one embodiment, the likelihood that a subject will respond to an anti PD1 therapy is assessed by measuring the abundance of SDC cells in the subject's tumor, for example wherein the abundance of SDC cells is assessed as a percentage of HLA-DR+ myeloid cells that express an SDC marker (for example BDCA3), wherein an elevated abundance of SDC cells is indicative that the subject will respond favorably to the anti-PD1 treatment and a lower abundance of SDC cells in the tumor is indicative that the subject will respond poorly to the anti-PD1 treatment. In one example, an elevated abundance of SDC cells is defined as 4% or greater of HLA-DR+ myeloid cells and a lower abundance of SDC cells is defined as less than 4% of HLA-DR+ myeloid cells in the tumor sample. In one embodiment, the subject is a melanoma subject. The above methodology may similarly be utilized to assess the efficacy of an anti-PD1 treatment, with an observed increase in the abundance of SDC cells following treatment being indicative of the treatment being effective. Likewise, putative inhibitors of PD1 may be identified as agents which increase the abundance of SDC cells, for example, measured as the percentage of HLA-DR+ cells which are BDCA3+ cells.

In one embodiment, the invention comprises a screening method for identifying a composition (or other type of treatment modality) which enhances the abundance of SDC's. For example, an animal having a tumor may be exposed to a putative enhancer of SDC abundance and then, using the tools and methods of the invention, the abundance of SDC's may be assessed, wherein an enhancement of SDC abundance, compared, for example, to untreated controls or to samples derived from the same subjects prior to treatment, is indicative of the treatment being an effective enhancer of SDC abundance. Such SDC abundance may comprise any measure of SDC abundance, including relative and absolute measures of SDC, for example the ratio of SDC's to NSM cells, or indirect measurements thereof.

Kits and Articles of Manufacture

The present application provides kits comprising any one or more of the antibody compositions described herein. In some embodiments, the kits further contain a component selected from any of secondary antibodies, reagents for immunohistochemistry analysis, pharmaceutically acceptable excipient and instruction manual and any combination thereof. In one specific embodiment, the kit comprises a pharmaceutical composition comprising any one or more of the antibody compositions described herein, with one or more pharmaceutically acceptable excipients.

In one aspect, kits can be made up of reagents, biological materials, and other components for facilitating the measurement of SDC and NSM cells. For example, in one embodiment a kit can include antibodies, including fluorescently labeled antibodies, which are directed to myeloid cells, common dendritic cell markers, SDC cell markers, and NSM cell markers to facilitate FACS or other cell sorting or flow cytometric methodologies for the quantification of SDC and/or NSM cells within a sample. For example, a kit comprising differentially-labeled antibodies to CD45, CD11c, Ly6C, MHCII, CD24, F4/80, CD11b and CD103 in mouse may be used, while antibodies to CD45, CD11c, CD14, HLA-DR, BDCA1 and BDCA3 in human may be used to facilitate FACS isolation of SDC and NSM fractions.

In another embodiment, a set of PCR primers can be included in a kit for the amplification of one or more SDC gene markers or one or more NSM gene markers. In one embodiment, the PCR primer kit comprises a set of primers capable of uniquely amplifying one, two, three, four, five, six, seven, eight, nine, or all of the SDC markers listed in Table A and one, two, three, four, five, six, seven, eight, nine, or more than nine of the NSM markers listed in Table A. In another embodiment, a PCR primer kit comprises a set of primers capable of uniquely amplifying BDCA3, KIT, CCR7, BATF3, FLT3, ZBTB46, IRF8, BTLA, MYCL1, CLEC9A, MRC1, MS4A7, C1QC, APOE, C1QB, C1QA, and C5AR1.

Kits can include two or more probes, comprising SDC or NSM gene marker sub-sequences for the binding and/or labeling of SDC or NSM transcripts or cDNA. In another embodiment, a kit comprises a microarray or other solid substrate having on it immobilized probes comprising one or more SDC or NSM marker gene sequences for the binding and quantification of tumor infiltrating SDC or NSM transcripts or cDNA derived therefrom. In one embodiment, an array comprises a set of probes corresponding to one, two, three, four, five, six, seven, eight, nine, or all of the SDC markers listed in Table A; and/or one, two, three, four, five, six, seven, eight, nine, or more than nine of the NSM markers listed in Table A. In another embodiment, an array comprises a set of probes corresponding to BDCA3, KIT, CCR7, BATF3, FLT3, ZBTB46, IRF8, BTLA, MYCL1, CLEC9A, MRC1, MS4A7, C1QC, APOE, C1QB, C1QA, and C5AR1.

A kit can comprise a set of PCR primers capable of uniquely amplifying KIT, CCR7, BATF3, FLT3, ZBTB46, IRF8, BTLA, MYCL1, and CLEC9A gene sequences in a sample. A kit can comprise a set of PCR primers capable of uniquely amplifying C5AR1, LYVE1, ABCC3, MRC1, SIGLEC1, STAB1, C1QB, C1QA, TMEM37, MERTK, C1QC, TMEM119, MS4A7, APOE, CYP4F18, TREM2, and TLR7 gene sequences in a sample. A kit can comprise a set of PCR primers capable of uniquely amplifying MRC1, MS4A7, C1QC, APOE, C1QB, C1QA, and C5AR1 gene sequences in a sample. An oligonucleotide array can comprise immobilized probes capable of binding KIT, CCR7, BATF3, FLT3, ZBTB46, IRF8, BTLA, MYCL1, BDC3A, XRC1 and CLEC9A gene sequences. An oligonucleotide array can comprise immobilized probes capable of binding C5AR1, LYVE1, ABCC3, MRC1, SIGLEC1, STAB1, C1QB, C1QA, TMEM37, MERTK, C1QC, TMEM119, MS4A7, APOE, CYP4F18, TREM2, and TLR7 gene sequences. An oligonucleotide array can comprise immobilized probes capable of binding MRC1, MS4A7, C1QC, APOE, C1QB, C1QA, and C5AR1 gene sequences.

The present application also provides articles of manufacture comprising any one of the antibody compositions or kits described herein. Examples of an article of manufacture include vials (including sealed vials).

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B (1992).

Example 1: Materials and Methods of Examples 1-9

Mouse Tumors

PyMT-ChOVA transgenic C57BL/6 founder mice were as described (Engelhardt et al., 2012) and offspring were screened for the PyMT-ChOVA transgene by PCR and monitored for tumors and used at 20-30 weeks of age. B78ChOVA is a variant of B78 (Graf et al., 1984), generated and used as described in supplemental methods. All additional strain information can be found in supplemental methods. All mice were maintained under SPF conditions and treated in accordance with NIH and American Association of Laboratory Animal Care standards, and consistent with the care regulations of the UCSF.

Flow Cytometry

All antibodies were purchased from BD Pharmingen, eBioscience, Invitrogen, BioLegend®, the UCSF hybridoma core, or were produced in the Krummel Lab. For surface staining cells were incubated with anti-Fc receptor antibody (clone 2.4G2) and stained with antibodies in PBS+2% FCS for 30 min on ice. Viability was assessed by staining with fixable Live/Dead Zombie (BioLegend®) or DAPI. For intracellular staining, mice were injected with 10 ug/gram of body weight with Brefeldin A (Cayman) 6 hrs prior to harvest, cells were stained with antibodies against surface markers, then fixed with 2% PFA for 10 min at 25° C. and permeabilized with 0.2% Saponin then stained with target antibody. All flow cytometry was performed on a BD Fortessa flow cytometer. Analysis of flow cytometry data was done using Flowjo (Treestar). Cell sorting was performed using a BD FACS Aria II.

TCGA Bioinformatics Analysis

Clinical expression analysis uses genome-wide mRNA levels (Illumina mRNA-seq) from 3602 patient tumor samples representing 12 cancer types (845 breast, 265 ovarian, 303 head & neck squamous, 122 bladder, 168 glioblastoma, 190 colon, 173 AML, 72 rectal, 355 lung adenocarcinoma, 259 lung squamous, 480 kidney, and 370 uterine cancers), normalized and combined into a single dataset by the TCGA PanCancer working group as published (Cancer Genome Atlas Research et al., 2013; Hoadley et al., 2014) (data is in the TCGA Data Portal https://tcga-data.nci.nih.gov/tcga/ and available as syn1715755 on https://www.synapse.org/). The $CD103^+/CD103^-$ ratio signature is calculated as the log of the mean expression of $CD103^+$ DC genes divided by the mean expression of the CD103-DC genes, followed by zscore standardization (mean=0, sd=1; gene list in FIG. 8C). We also evaluate published T cell (Palmer et al., 2006), proliferation (Wolf et al., 2014), CSR/wound (Chang et al., 2005), and gamma interferon (Viigimaa et al., 2010) signatures as published, along with a CD8/CD68 expression ratio (DeNardo et al., 2011). Overall survival data was obtained from the TCGA portal (downloaded June 2013) (Cancer Genome Atlas Research et al., 2013) and survival analysis performed using Cox Proportional Hazards modeling in a multivariate model adjusting for cancer type. Log rank p-values are used to assess significance after adjusting for multiple comparisons using the Benjamini-Hochberg method (Bejamini and Hochberg, 1995). Kaplan-Meier survival plots are generated using the Survival package in R. In the all-data KM plot (FIG. 8E), we 'adjusted' for cancer type by classifying each sample as 'high' or 'low' using that cancer types' median value of the $CD103^+/CD103^-$ ratio signature.

Mouse Strain Information

OT-I mice, specific for ovalbumin peptide SIINFEKL (SL8) in the context of H-2Kb (Hoquist et al., 1994) were interbred with CD45.1, Nur77-eGFP mice (Moran et al., 2011) and Cd2-RFP mice (Veiga-Fernandes et al., 2007), or with Actin-CFP mice (Hadjantonakis et al., 2002) to produce genomically encoded, fluorescent or congenically labeled T cells for adoptive transfer, imaging and activation experiments.

For modulating populations of myeloid cells in tumors, the following mouse strains were used: C57BL/6 purchased from Simonsen, Irf4$^{f/f}$×CD11c-Cre (Klein et al., 2006), (Williams et al., 2013) kindly gifted to us by Anne Sperling at University of Chicago, Irf8$^{-/-}$ FVBN (Ouyang et al., 2011) kindly gifted to us by Scott Kogan at UCSF, Zbtb46-DTR (Meredith et al., 2012), Csf2rb$^{-/-}$ (Robb et al., 1995), and Csf3r$^{-/-}$ (Liu et al., 1996).

For visualization of APCs within tumors, PyMT-ChOVA transgenic mice were interbred with $Cx_3$crl-eGFP (Jung et al., 2000) and Cd11c-mCherry mice (Khanna et al., 2010) and resulting F1 offspring bearing both transgenes were used for imaging experiments.

Cell Lines, Cell Culture, Plasmids, and Transfection

The following tumor cell lines were cultured under standard conditions prior to injection into mice. B16-F10 (Fidler, 1975), B16-GMCSF (Dranoff et al., 1993), B16-FLT3L (Curran and Allison, 2009) kindly provided by Larry Fong, B78-parental (Graf et al., 1984), B78chOVA, B78 parental transfected with a ChOVA fusion construct identical to that used in PyMTChOVA (Engelhardt et al) using standard methods, EL4 (Hyman et al., 1972), EG7 (Moore et al., 1988), EG7-chOVA, Vo-PyMT-Luciferase-FVB kindly gifted to us from Zena Werb at UCSF (Halpern et al., 2006), and LLC kindly gifted to us by Lewis Lanier at UCSF (Bertram and Janik, 1980). B78p-mCherry-pHlourin were generated by transfection of B78-parental cells with Lipofectamine according to the manufacturer's instructions of the N1-mCherry-pHlourin construct (Koivusalo et al., 2010; Webb et al., 2011; Choi et al., 2013).

Briefly adherent cells were cultured at 37° C./%5 CO2 in DMEM plus 10% FCS with Pen/Strep/Glut on tissue-culture treated plastic plates and split every other day. Suspension cells were cultured in RPMI-1640 plus 10% FCS and Pen/Strep/Glut in flasks and split every other day.

Ectopic Tumor Injection

Tumor cell lines were harvested and washed 3 times with PBS, then mixed at a 1:1 ratio with growth factor-reduced Matrigel™ Matrix (BD Biosciences) for a final injection volume of 50 ul. 100,000 tumor cells (unless otherwise stated) were injected in the right flank of shaved mice subcutaneously and allowed to grow for 14-21 days before use.

Tumor Digestion

PyMT-chOVA and etopic B78chOVA tumors were dissected from mice and total weight of removed tumor tissue was determined. Tumors were then minced using scalpels and digested with 500 U/ml Collagenase IV (Sigma), 100 U/ml Collagenase I (Worthington) and 200 mg/ml DNAse I (Roche) per 0.3 grams of tumor weight for 3×30 minute intervals in a 25 ml Erlenmeyer with a stir bar and placed in a 37° C. incubator with 5% CO2 on a stir plate. After each 30-minute interval, tumor was then passed through a 70 um cell strainer to remove large pieces of undigested tumor, and remaining chunks were reintroduced to digest while isolated single cells were kept on ice. CD45-Biotin magnetic positive selection (StemSep™) was then performed at 4° C. to enrich for total tumor immune infiltrate.

Human Samples

Tissue was vigorously minced with surgical scissors and transferred to a 25 ml Erlenmeyer with magnetic stir bar with 3 mg/ml Collagenase A (Roche) and 50 U/ml DNase I (Roche) per 0.3 g of tissue for 1 hour at 37° C./5% CO2 with constant agitation. Samples are then filtered through a 70 um filter, spun down and resuspended for staining (Ruffell et al., 2012). For all human samples, informed consent was obtained from all subjects and work was performed in accordance with IRB approval (IRB number 13-12246, Dec. 6, 2013-Dec. 5, 2014).

Cell Isolation

OT-I Naïve $CD8^+$ T cells were isolated from lymph nodes and spleen of 6- to 12-week-old mice. Selection was carried out with a negative CD8 isolation kit (Stemcell Technologies) following manufacturer's instructions. BMDCs were generated by culture of bone marrow cells for 8-11 days plated at 1-2×10^6 cells/ml in IMDM with 10% FCS with GM-CSF (granulocyte-macrophage colony-stimulating factor). IL-4 was added for the final 2 days of culture and LPS was added 12 hours before use to fully mature the BMDC.

eFlour670 Labeling of T Cells

OT-I $CD8^+$ T cells were incubated in RPMI without FCS with 2 uM efluor670 (eBioscience) for 15 minutes at 37° C. eFluor670 was then quenched with 2 ml FCS and washed in RPMI 10% FCS 3 times before use.

Bulk Activation of T Cells (CTL Generation)

OT-I TCR transgenic lymph node cells were stimulated with B6 splenocytes pulsed with 100 ng/ml SL8 peptide for 30 minutes, then washed 3×. Two days following stimulation and again four days after stimulation, cells were expanded in the presence of 2 U/ml recombinant human IL-2 and used for experiments 2-3 days later.

T Cell Proliferation Assays

Lymph node cells from OT-I TCR transgenic mice were isolated and were enriched for Naïve $CD8^+$ T cells by StemSep™ CD8 enrichment (Stemcell technologies) or and/or bulk activation cultures of CTL were used. Lymph node cells from OT-II TCR transgenic mice were isolated and were enriched for Naïve CD4⁺ T cells by StemSep™ CD4 enrichment (Stemcell technologies). 20,000 enriched naïve CD8 cells or day 5 previously activated OT-1 T cells or Naïve CD4 cells labeled with 2 uM eFluor670 were mixed with either 4,000 BMDCs pulsed with or without 25 ng/ml of SL8 peptide (OT-I), or 1 ug/ml pOVA 323-339 peptide (OT-II), or 4,000 unpulsed Tumor APCs (unless otherwise noted) in 96 well V-bottom plates for either 12, 48 or 72 hrs at 37° C./5% CO2, at which point activation was measured by CD69/Nur77 upregulation and efluor670 dilution via flow cytometry.

Coupling Assay

Coupling assays were performed as described (Friedman et al., 2006). Briefly labeled T cells were mixed with stained single cell suspension from tumor digests for 30 min-1 hour and then fixed with 2% PFA for flow cytometry. Coupling percentages were calculated as the number of T cell couples over the total number of T cells.

In Vivo Multiphoton Microscopy Imaging and Surgery

Animals were kept under anesthesia using isofluorane on a heated microscopy stage and depth of anesthesia was monitored in regular intervals according to institutional guidelines. Before surgery, animals were injected i.v. with 100 ug Evans Blue in PBS and 1 ml of Ringer's Lactate i.p. The mammary glands were exposed surgically and tumors were imaged through a modified version of a suction window we described earlier (Thornton et al.). Intravital imaging was performed using a custom-built two-photon setup equipped with two infrared lasers (MaiTai: Spectra Physics, Chameleon: Coherent) The MaiTai laser was tuned to 870 nm or 910 nm for simultaneous excitation of CFP and GFP, or GFP alone, respectively. Chameleon laser excitation was tuned to 1030 nm for excitation of mCherry. Emitted light was detected using a 25×1.2NA water lens (Zeiss) coupled to a 6-color detector array (custom; utilizing Hamamatsu H9433MOD detectors), alternating laser excitation was used to yield 12 detection channels. Emission filters used were: violet 417/50, blue 475/23, green 510/42, yellow 542/27, red 607/70, far red 675/67. The microscope was controlled by the MicroManager software suite, z-stack images were acquired with 4-fold averaging and z-depths of 3 μM. Data analysis was performed using the Imaris software suite (Bitplane).

Ex Vivo Tumor Slice Staining and Multiphoton Imaging

Animals were euthanized and tumors were harvested. Obstructing fat was removed and tumors were embedded in 2% low-melting agarose in PBS (SeaPlaque™, Lonza). 300 μM thick sections were prepared using a Compresstome VF-200, Precisionary Instruments Inc. tissue slicer. Slices were attached to plastic coverslips using Vetbond (3M) and stained with Alexa647-labelled rat anti-CD11b antibody in RPMI supplemented with 5% rat serum for 2 hours at 37° C./5% CO2. Slices were washed in RPMI and imaged using a Nikon A1R confocal microscope.

RNA Extraction, Fluidigm and RNA Sequencing 4,000-20,000 cells were sorted directly into 300 ul of Trizol™ LS, flash frozen and immediately stored at −80° c. until extraction. RNA was extracted by phenol-chloroform method and ethanol precipitation. Samples were then DNase I treated and cDNA was synthesized using Superscript III® (Invitrogen). For nanoliter qPCR Fluidigm analysis cDNA was pre-amplified (12 cycles) though a Target Specific Amplification with 2× Taqman® PreAmp Master Mix (Applied Biosystems) and then treated with Exonuclease I to remove unincorporated primers. Samples and primers (target primers were designed using Harvard primer bank: http://pga.mgh.harvard.edu/primerbank/) were then loaded onto a 48.48 Dynamic Array with 2× SsoFast™ EvaGreen® Super Mix (Bio-Rad) and run on the BioMark HD. For RNA sequencing, samples were extracted using the Arcturus PicoPure™ RNA isolation kit (Life Technologies), biolanalyzed and submitted to the UCSF Genomics Core. Libraries were prepared using the Nugen Ovation® kit and subsequently sequenced on an Illumina HiSeq 2500 machine. Single-end, 50 base pair reads were generated to yield ~405 million reads with and average depth of 33.7 million reads/sample. Reads were aligned to the mouse genome (USCS mm 10) and those that mapped uniquely to known mRNAs were used to assess differential expression. For analysis and assessing differential expression Tophat (Trapnell et al., 2009) was used to perform alignments and DESeq (Anders and Huber, 2010) was used to perform the differential expression analysis.

Tumor Growth

For tumor growth curves, tumor area (mm²) was measured with calipers as tumor width×tumor height, over the indicated time periods.

Diphtheria Toxin, FTY-720, and αCSF-1 Treatment

D.T. was purchased from Sigma-Aldrich. For transient D.T. ablation DTR mice were injected i.p. with 20 ng D.T. per gram of body weight, and mice were euthanized 24 hrs after D.T. injection for analysis. For long-term ablation, mice were initially injected i.p. with 20 ng/gram DT, and then maintained on 4 ng/gram every third day thereafter.

FTY720 was purchased from Cayman and reconstituted in saline and stored at 1 mg/ml aliquots at −20 C. 200 ul of FTY was injected i.p. at a final concentration of 100 ug/ml in saline every other day over the indicated time periods.

Neutralizing αCSF-1 antibody, clone 5A1, and isotype Rat IgG2a was purchased purified from the UCSF Antibody Core. Animals were treated initially with 1 mg of antibody by i.p. injection and analyzed 3 days later. To maintain depletion over time, mice were subsequently given 0.5 mg i.p. doses every 5 days thereafter.

GMP Progenitor Preparation and Adoptive Transfers

All bones (including femurs, tibias, humeri, ulnas, radii and pelvis) were harvested into sort buffer (PBS+2% FCS) and crushed with a mortal and pestle and repeatedly washed with HBSS and then passed through a 70 um filter. Cells where then RBC lysed with 175 mM Ammonium Chloride for 5 min at 37° C. and then washed and ficolled with a 3 ml underlay of Histopaque®-1110 (Sigma) to select for live cells and remove remaining bone debris. Bone marrow cells were enriched for CD117 positive cells using CD117 Microbeads (Miltenyi Biotec) and positively selected on an AutoMACS. Cells were then stained with a lineage cocktail of unconjugated Rat antibodies (CD4, CD8, Mac1, Gr-1, CD5, Ter119, and CD3) for 30 minutes on ice followed by a wash and stain with an anti-Rat fluorescently conjugated secondary for 30 minutes on ice. Cells were then washed and stained with the progenitor master mix (Ckit-APC-cy7, Sca1-PB, CD34-FITC, and FCgR-PerCPCy5.5) for 30 minutes on ice, washed and sorted on Live, cKit+ Sca1−, CD34+ FcgR+ for GMPs using a BD FACs AriaII.

Dextran Uptake Assay

Tumors were digested and CD45 positive selected as described above and then plated at $1 \times 10^6$ cells per well in 96 well rounds bottom plates and incubated with or without 1 mg/ml Dextran-Pacific Blue™ (10,000 MW) at either 4° C. or 37° C. for 30 min in triplicate. Plates were tapped every 5 minutes. Plates were then washed 3 times and stained with surface antibodies and analyzed immediately by flow cytometry. Dextran uptake was measured as the geometric mean fluorescence intensity of dextran binding at 4° C. subtracted from the geometric mean fluorescence intensity of dextran uptake at 37° C.

Cell Tracking and Imaging Analysis

Data was visualized and analyzed using Imaris Software (Bitplane). Individual T cells were identified and tracked by Imaris. CD11c mcherry DCs was calculated using isosurfaces of masked DCs from MATLAB segmentation. Contact duration was determined by calculated track duration of masked T cell-DC couples that were tracked using Imaris.

Antibody Clones

Mouse Ab Clones: CD45 clone 30-F11, CD45.1 clone A20, CD45.2 clone 104, CD11b clone M1/70, CD11c clone N418, CD103 clone 2E7, CD24 clone M1/69, CD90.2 clone 30-H12, Ly6C clone HK1.4, MHCII clone N22, F4/80 clone BM8, CD69 clone H1.2F3, CD135 cone A2F10, CD117 clone 2B8, CD26 clone H194-112, CD206 clone C068C2, CD64 clone X54-5/7.1, MerTK clone Y323, CD301b clone 11A10-B7-2 kindly gifted to us by Akiko Iwasaki from Yale University, PDL2 clone TY25, IRF4 clone M17 and IRF8 clone T14 kindly gifted to us by Roger Sciammas from University of Chicago, IL12 clone C17.8, CD80 clone 16-10A1, CD86 clone GL1, 2B4 clone m2B4, and PDL1 clone 10F.9G2.

Human Ab Clones: CD45 clone H130, CD3e clone OKT3, HLADR clone L243, CD56 clone CMSSB, CD19 clone H1B19, CD14 clone 61D3, CD16 clone CB16, CD11c clone 3.9, BDCA1 clone L161, and BDCA3 clone AD5-14H12.

Statistical Analysis

Statistical analyses were performed using GraphPad Prism software. Unless specifically noted all data are representative of >3 separate experiments. Error bars represent SEM calculated using Prism, and are derived from triplicate experimental conditions. Specific statistical tests used were paired and unpaired T tests and all p values less than 0.05 were considered statistically significant.

Example 2: Surface Markers Delineate Rare Tumoral DC Subsets from Abundant Macrophages To dissect the tumor infiltrating myeloid populations, an 11-color flow cytometry panel was devised and progressive gating strategy using a spontaneous breast tumor model, PyMTChOVA (Engelhardt et al., 2012), engineered along with the initiating oncogene to independently co-express fluorescent mCherry protein and ovalbumin. We profiled the tumoral $CD45^+$ compartment, many of which had phagocytosed tumor antigen and thus exhibit mCherry fluorescence (FIG. 1A). Subgating all hematopoietic cells by the myeloid-specific marker CD11b and the monocyte-marker Ly6C allowed removal of neutrophils and monocytes (data not shown). Within the $MHCII^+$ cells, DCs were distinguished from Macrophages based on $CD24^{hi}$ and $F4/80^{lo}$ expression, neither of which, alone, are typically sufficient to make this distinction. Subsequently, DCs were found to parse into two populations based on differential expression of CD11b and CD103, as has been observed in healthy peripheral tissues (Hashimoto et al., 2011). We found these populations in two mouse models of melanoma (B78ChOVA (a variant of B16 expressing mCherry and OVA), FIG. 1B and BRAF V600E, data not shown), across mouse strains (e.g. FVB PyMT; data not shown), and in ectopic tumors (Lewis Lung Carcinoma; data not shown). We refer to these DC populations as "$CD11b^+$ DC1" and "$CD103^+$ DC2" henceforth for ease of discrimination and discussion.

Figure 1B:
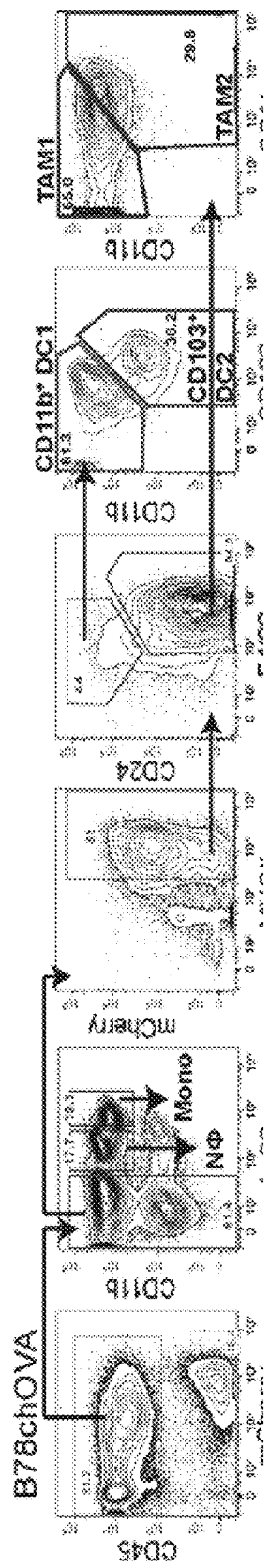
(FIG. 1B) Cytometry of tumor APC populations in ectopic B78ChOVA tumors.

Parsing of the $F4/80^{hi}$ $CD24^{lo}$ compartment also revealed two types of macrophages, identified by differential expression of CD11c and CD11b. CD11c $CD11b^{hi}$ (heretofore "TAM1") and $CD11c^{hi}$ $CD11b^{lo}$ cells ("TAM2") appear to broadly correspond to similarly delineated $MHCII^{hi}$ and $MHCII^{lo}$ populations (Movahedi et al., 2010) (see also FIG. 5c). While CD11c, otherwise a 'protoypical' DC marker, was highest on DCs it was highly expressed in TAM2 and to a lesser extent in TAM1 (data not shown). These populations existed across all models examined although the prevalence of each and their ability to be unambiguously distinguished varied slightly (FIG. 1A-B, and data not shown). We therefore applied our lineage and function studies to one example of spontaneous (PyMTChOVA) and ectopic tumor model (B78ChOVA), except where indicated.

mCherry loading and retention, derived from the tumor, was assessed for each of these populations. This revealed that the uptakehi cells, localized to the tumor margin in our previous report and then identified only by CD11c (Engelhardt et al., 2012), were best captured in the TAM1 and TAM2 gates (FIG. 1c and data not shown). Comparatively, $CD11b^+$ DC1s and $CD103^+$ DC2s took up or retained less mCherry while some monocytes but few neutrophils showed evidence of modest antigen loading.

$CD11b^+$ and $CD103^+$ DC subsets have been found in many peripheral mouse tissues and their counterparts have been identified in peripheral human tissues, defined by expression of BDCA1 and BDCA3, respectively (Dzionek et al., 2000; Haniffa et al., 2012). We found that an equivalent TAM/DC distinction was also possible in human metastatic melanoma samples using these markers (FIG. 1D). $CD16-HLADR^+$ $CD11c^+$ $CD14^+$ cells representing all TAMs were distinct from $CD16-HLADR^+$ $CD11c^+$ $CD14^-$ DC populations, which were in turn parsed by differential expression of BDCA1 ("DC1") and BDCA3 ("DC2"). Common across mouse models (FIG. 1E) and human melanoma biopsies (FIG. 1F) is the presence and rarity of the CD11b+/BDCA1 DC1 and $CD103^+$/BDCA3 DC2 populations, with DC2 being particularly sparse.

Example 3: Protein and Transcriptional Delineation of Tumor DCs and Macrophages

Figure 2A:
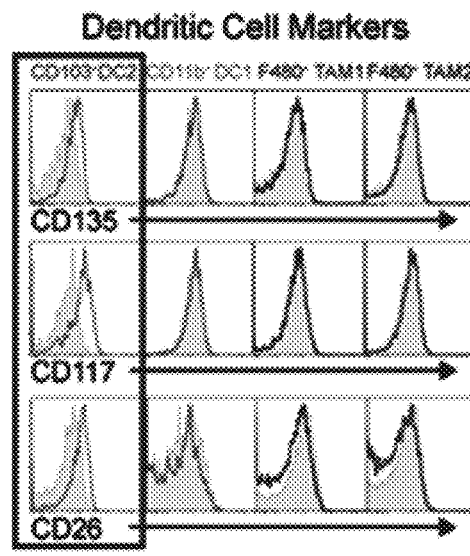
(FIG. 2A) Expression of a panel of DC specific markers compared to respective isotype (grey shaded). A black box outlines the CD103+ DC2 population, showing unique expression.
Figure 2B:
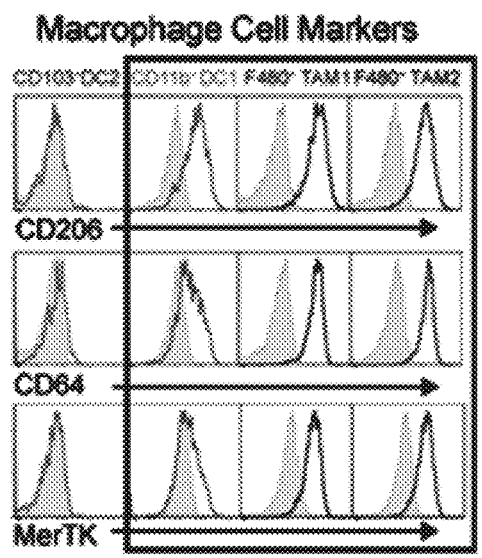
(FIG. 2B) Differential expression of macrophage specific markers (colored) with corresponding isotypes (grey shaded). A black box outlines the CD11b+ DC1, TAM1, and TAM2 populations, showing unique expression.
Figure 2C:
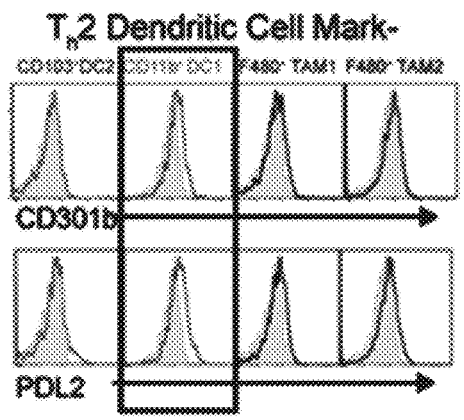
(FIG. 2C) Specific expression of DC-$T_h2$ makers (colored), by CD11b+ DC1 populations compared to respective isotype (grey shaded). A black box outlines CD11b+ DC1, which shows unique expression.

To validate our gating strategies we applied panels of antibodies defined by the ImmGen consortium (Gautier et al., 2012; Miller et al., 2012). Consistent with our assignment of "DC", $CD103^+$ DC2 expressed CD135 (Flt3), CD117 (cKit) and CD26 whereas both TAM populations did not in the B78chOVA and PyMTchOVA models. (FIG. 2A and data not shown). Surprisingly, $CD11b^+$ DC1 did not express detectable levels of DC markers and actually segregated more with TAM1 and TAM2 by virtue of expression of several "macrophage" markers including CD206, CD64 and MerTK (FIG. 2B and data not shown). CD11b+DC1, however, slightly expressed CD301b and PDL2, both of which have been used to define IRF4 dependent "$DC_{Th}2$" populations found in the skin (FIG. 2C and data not shown) (Gao et al., 2013; Kumamoto et al., 2013).

To further delineate these APCs, we analyzed the gene expression profiles of sorted cells from B78chOVA tumors using RNAseq. As shown in FIG. 2D, blocks of genes clearly segregate the four populations, with TAM1, TAM2 and $CD11b^+$ DC1 being the most similar by PCA analysis (FIG. 2E) and $CD103^+$ DC2 the most distinct. Amongst the genes most differentially expressed, DC lineage-defining transcription factors Irf8 (Tamura et al., 2005) and Zbtb46 (zDC) (Meredith et al., 2012) were specific for $CD103^+$ DC2 alone, or both DCs respectively, whereas Irf4 was modestly enriched in CD11b⁺ DC1 and all of which were validated by RT-qPCR (FIG. 2F). This was also confirmed at the protein level by intracellular flow cytometry for IRF4/8 (FIG. 2G and data not shown). All populations expressed Myb, which indicates hematopoietic stem cell origin as opposed to deriving from tissue precursors, seeded from the yolk-sac (Schulz et al., 2012). Unique surface phenotypes and expression of key transcription factors were replicated in the PyMTchOVA model (data not shown).

Figure 3A:
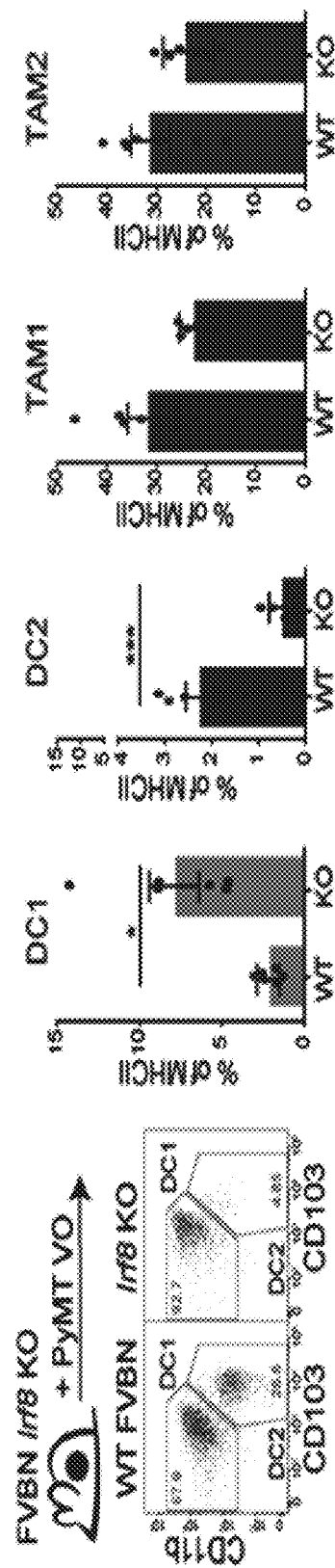
(FIG. 3A) Ectopic PyMT-VO tumors from an Irf8−/− (KO) compared to control (WT). Relative cell proportions as a % of total MHCII+ cells. Data pooled from individual mice (n=6) from 2 independent experiments.
Figure 3B:
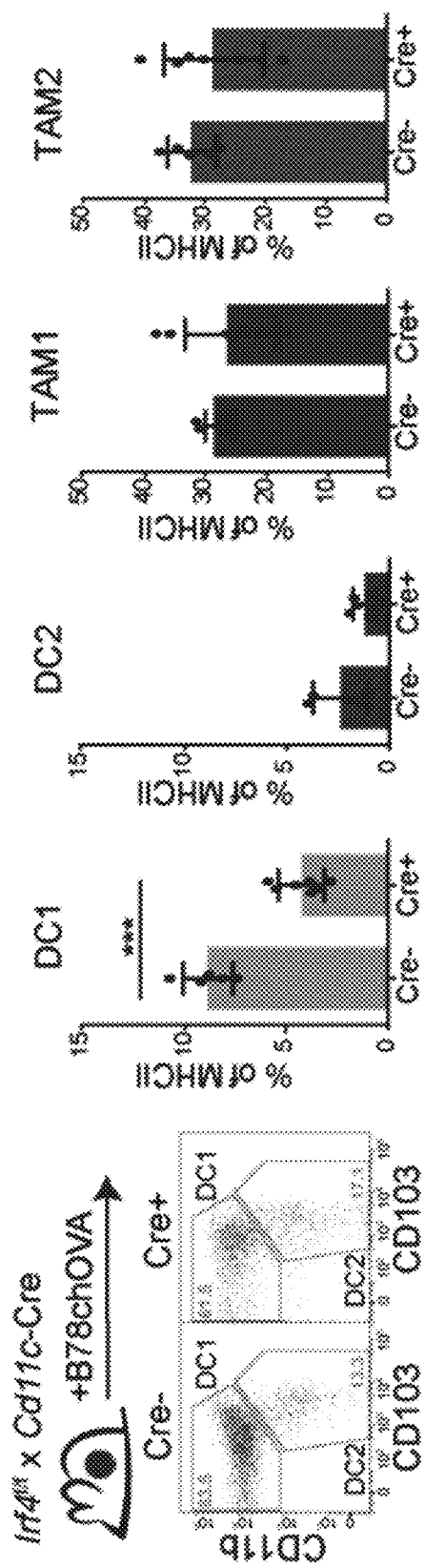
(FIG. 3B) Ectopic B78chOVA tumors in Irf4$^{f/f}$×CD11c-CRE+ host compared to Cre-negative littermates. Relative cell proportions as a % of total MHCII+ cells. Data pooled from individual mice (n=7) from 2 independent experiments.
Figure 3C:
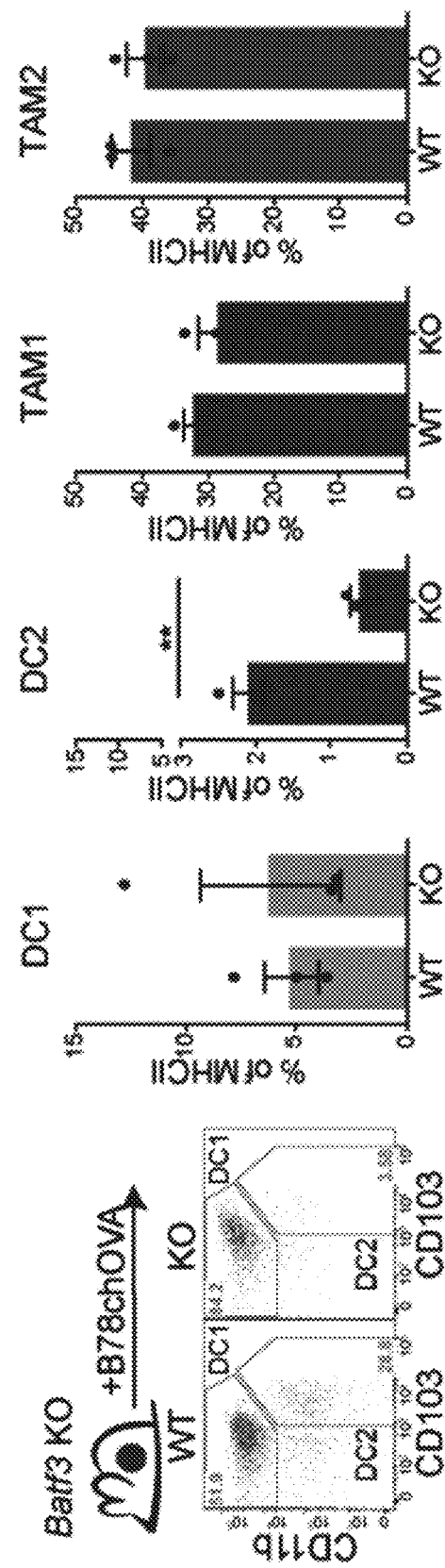
(FIG. 3C) Ectopic B78chOVA tumors in Batf3 KO, compared to WT. Relative cell proportions graphed as a % of total MHCII+. Data pooled from individual mice (n=6).
Figure 3D:
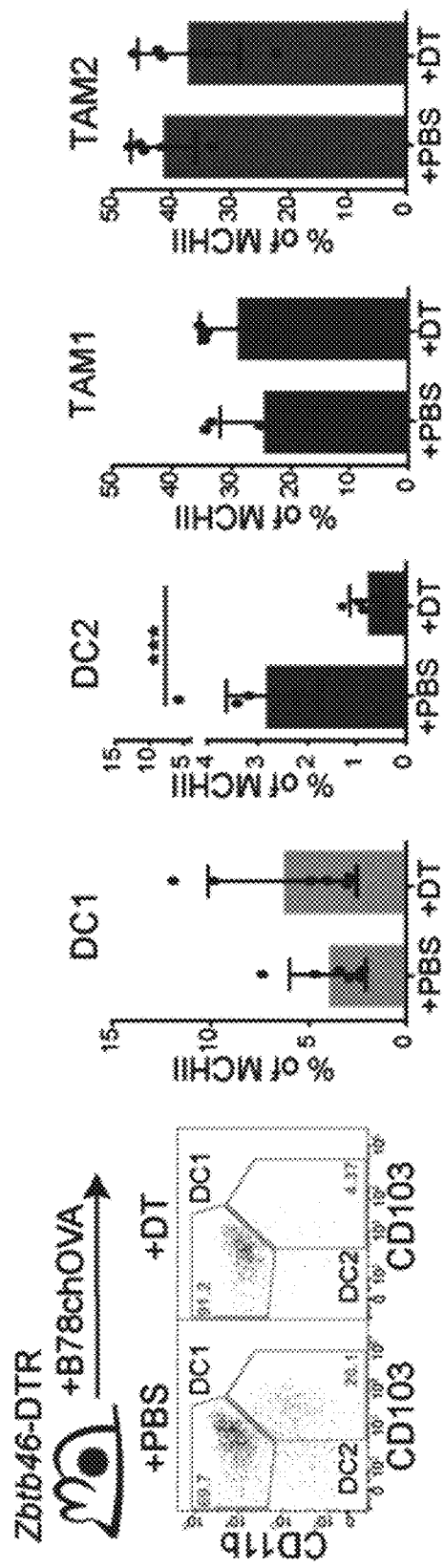
(FIG. 3D) Ectopic B78chOVA tumors in Zbtb46-DTR mice, receiving acute 24 hour depletion with DT or PBS. Relative cell proportions graphed as a % of total MHCII+ cells. Data pooled from individual mice (n=6) from 2 independent experiments.

As these intratumoral populations may derive through distinct tumor-specific mechanisms and not rely on these transcription factors as they do in some conventional tissues, we investigated Irf8, Irf4, Batf3 and zDC dependency using knockout or transcription factor-driven Diphtheria toxin receptor (DTR) mice. We took advantage of various ectopic tumors, due to the vagaries and length of breeding these alleles to a spontaneous model. Using an ectopic PyMT breast tumor model, we found that loss of Irf8 specifically ablated the CD103⁺ DC2s but did not affect TAM1 or TAM2 and mildly enriched the percentage of CD11b⁺ DC1, perhaps as a result of compensation (FIG. 3A). Conversely, conditional deletion of Irf4, driven by CD11c-Cre (Williams et al., 2013) resulted in the specific reduction in CD11b⁺ DC1 with little change in the others in the B78chOVA model (FIG. 3B). In agreement with RNAseq data, Batf3 deficient animals also lacked tumoral CD103⁺ DC2 populations in a B78chOVA model, without effect on CD11b⁺ DC1, TAM1 or TAM2 proportions (FIG. 3C). Finally, when a zDC-driven DTR allele was used, we somewhat unexpectedly found a specific and significant reduction in CD103⁺ DC2 with little or no changes in the CD11b⁺ DC1 or TAM1/TAM2 populations in B78chOVA tumors (FIG. 3D). This may represent vagaries of the DTR allele or subtle but significant variations in zDC expression. Taken together, we conclude that CD103⁺ DC2 represent a distinct lineage of APC as compared to CD11b⁺ DC1 and the highly abundant TAM1/TAM2 in the tumor.

Example 4: CD103⁺ DC2 are Programmed by Distinct Cytokines

APCs derive from bone marrow (BM) precursors and their differentiation into DC/macrophage subsets depends on specific cytokines. To determine the cytokines driving differentiation into these populations we queried Colony Stimulating Factor (CSF) receptor expression across models by qPCR. Whereas Csf1r (M-CSFR) was found exclusively in TAM1, TAM2 and CD11b⁺ DC1, Csf2rb (GM-CSFR) was uniquely expressed in the DC1 and DC2 subsets, and Csf3r (G-CSF) was absent in all (FIG. 4A). Using either neutralizing antibody treatment or cytokine receptor deficient mice with ectopic tumors, we functionally tested CSF cytokine reliance of the APCs at the tumor.

Figure 4B:
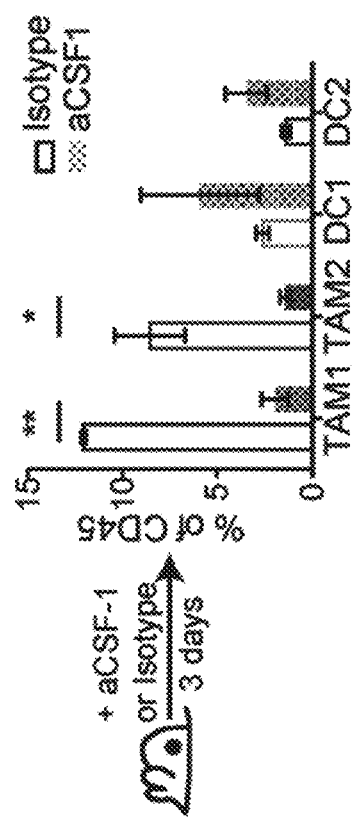
(FIG. 4B) Cytometry of tumor APCs after 3 days of αCSF-1 block (dotted) compared to isotype (filled) treated tumor animals. Quantified as % of total tumor CD45+ cells, pooled from individual mice (n=6) from 2 independent experiments shown as mean±SEM. Statistical significance indicated by *p<0.05, p<0.01, *p<0.001; ns=not statistically significant (FIG. 4C) Schematic of BM progenitor adoptive transfer and contributions to BM, spleen, and tumor.
Figure 4A:
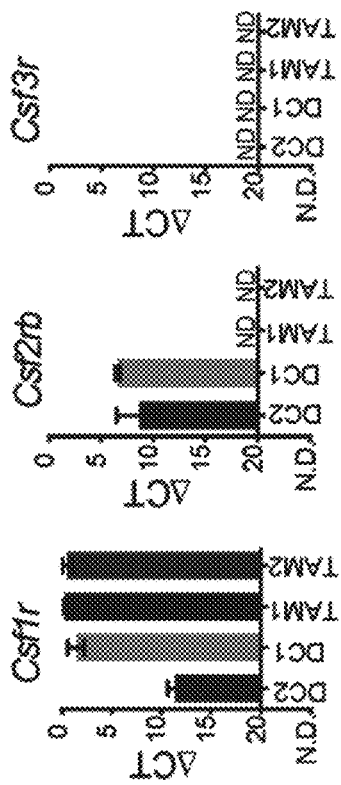
(FIG. 4A) qPCR of CSF1R, CSF2Rb, and CSF3R expression from sorted APCs. Data presented as mean ΔCt±SEM calculated from biological triplicates (n=3) of individual B78chOVA tumors (N.D. not detected).
Figure 4C:
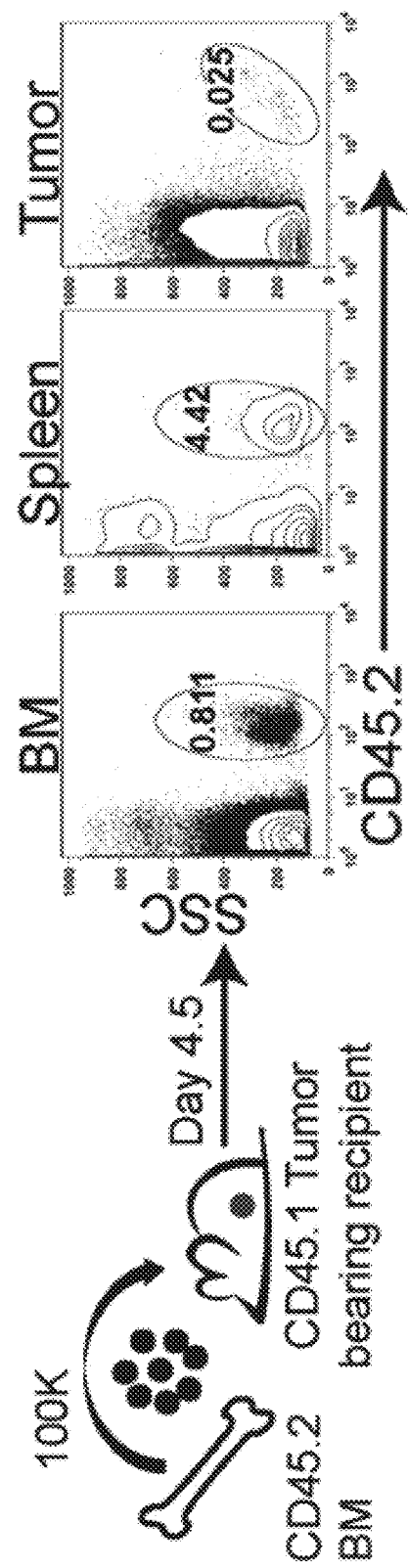
FIG. 4. Differential reliance on M-CSF and GM-CSF cytokines by tumor-infiltrating APC populations.
(FIG. 4D) Representative cytometry of tumor arriving congenic cells. Gated on CD45.2 and following the gating strategy of FIG. 1A.
(FIG. 4E) Competitive BM adoptive transfer of WT vs. GMCSFR KO GMP progenitors into B78chOVA tumor recipients. Repopulation efficiency plotted as % of total transferred cells. Representative gating of tumor arriving GMP cells, WT (left bar for each of BM, Spleen, and Tumor), KO (right bar for each of BM, Spleen, and Tumor). Quantification of tumor arriving DCs, defined by CD24+ CD11c+. Data pooled from 2 independent experiments, plotted as mean±SEM from individual tumors (n=6).
(FIG. 4F) Cytometry of CD11b+ DC1 and CD103+ DC2 populations (gated on CD45+, Ly6C− MHCII+, CD24+) between ectopic B16-F10, B16-GMCSF and B16-FLT3L cytokine expressing tumors. Populations presented as % of total MHCII+ cells for each tumor. Data are pooled from 3 independent experiments, plotted as mean±SEM from individual tumors (n=6). For each group in FIG. 4F (right panel) the bar represented from left to right is: DC2, DC1, TAM1, and TAM2, respectively.
Figure 4D:
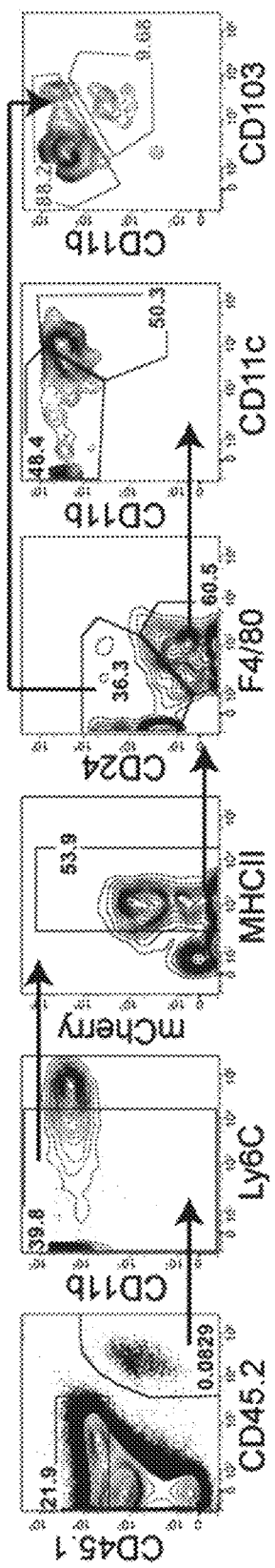
Figure 4E:
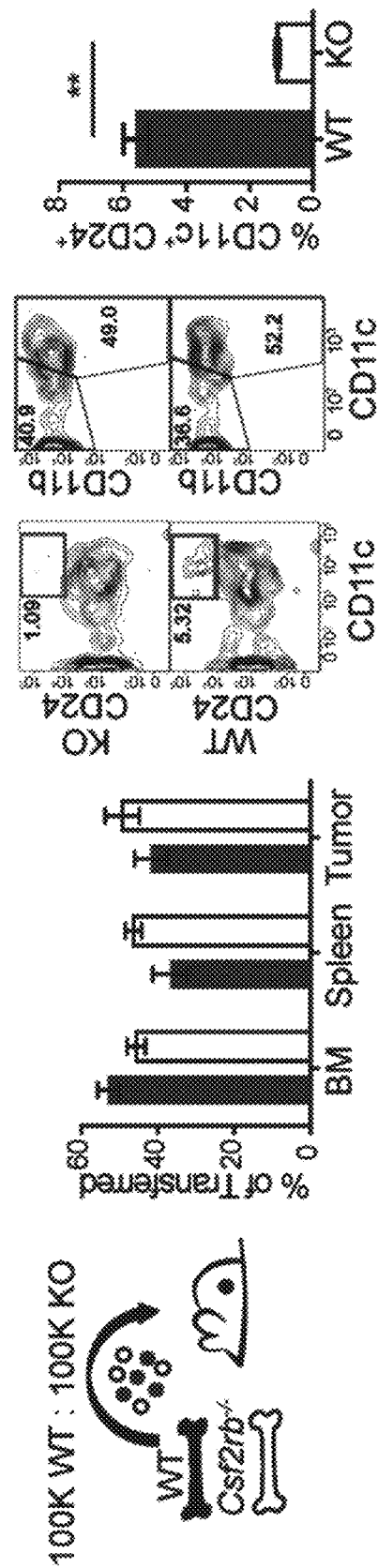

While TAM1 and TAM2 cells critically relied upon CSF-1 for their maintenance, as has been shown previously (Wyckoff et al., 2004), CD11b⁺ DC1 and CD103⁺ DC2 populations were uniquely independent of CSF1 (FIG. 4B). For use of cytokine receptor deficient mice, we developed a congenic adoptive transfer model, whereby Granulocyte Macrophage Progenitors (GMP) were transferred into ectopic tumor-bearing hosts and repopulation was tracked in the BM, spleen and tumor (FIG. 4C). At the tumor GMP-derived cells populated all myeloid compartments, confirming GMP origin of CD11b⁺ DC1, CD103⁺ DC2, TAM1, and TAM2 (FIG. 4D). By use of the GMP adoptive system with a competitive transfer, we found a selective inability of Csf2rb⁻/⁻ cells to reconstitute DCs at the tumor, here defined as the sum of DC1/DC2 using CD24⁺ CD11c⁺ gating. We found no effect on TAM1 and TAM2 repopulation, suggesting a unique requirement of CSF2 (GM-CSF) for tumoral DC development (FIG. 4E) while no requirement for CSF-3 was found for any of the four APCs (data not shown).

Figure 4F:
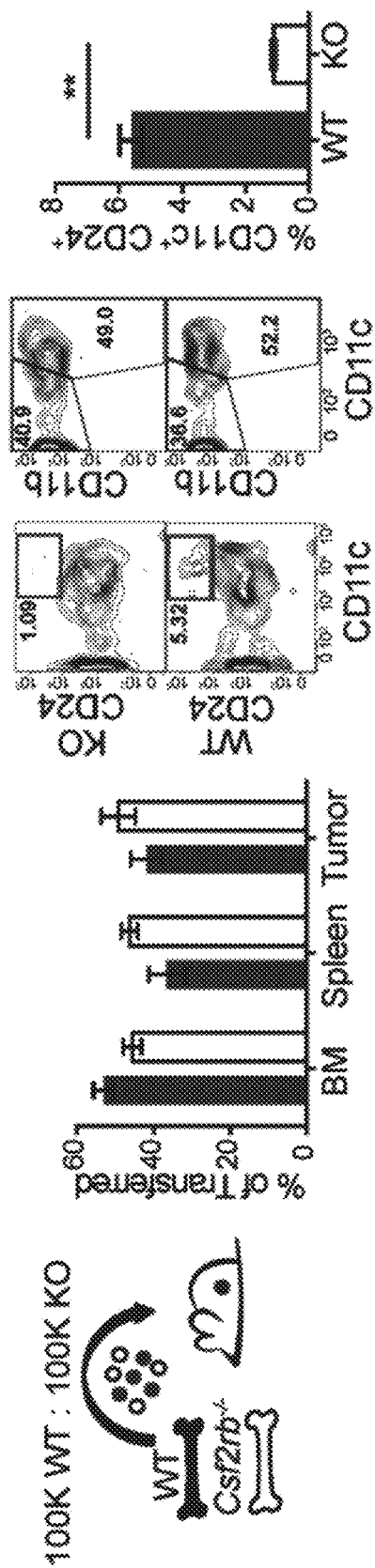

As DCs are prototypically driven by GM-CSF or FLT3-ligand (FLT3L), we assessed cytokine sufficiency to drive DC populations at the tumor using B16 melanoma tumor models engineered to express GMCSF or FLT3L. While GMCSF expression by the tumor drastically skewed the proportion of CD11b⁺ DC1, FLT3L expressing tumors drove unique expansion of the rare CD103⁺ DC2 at the tumor (FIG. 4F).

Example 5: Unique Antigen Processing and Presentation Capabilities of CD103⁺ DC2

Having established the lineage requirements of the different APCs we then assessed their ability to initiate, engage and sustain T cell responses. To parse the cells with regard to antigen processing, presentation, and costimulation we analyzed transcript and protein levels of genes involved in these pathways using RNASeq data from FIG. 2. Differences were considerable, across broad swaths of potential APC function (FIG. 5A). Notably, while surface levels of molecules involved in regulating T cell responses including CD80, CD86 and 2B4 were comparable between populations, CD103⁺ DC2s showed distinct transcriptional signatures consistent with heightened cross presentation, enhanced costimulation, and increased expression of chemokines that would be expected to enhance T cell interactions (FIG. 5A, B and data not shown). There were no major differences in MHCI and MHCII expression between the APCs with the exception of slightly reduced MHCI on CD103⁺ DC2 (FIG. 5C). However, significant differences in phagocytic capacity were observed in CD103⁺ DC2s compared to TAM1/TAM2, measured exogenously by ex vivo dextran uptake from ectopic tumors (FIG. 5D).

As DC maturation and phagocytic capacity are often inversely correlated, we hypothesized that the decreased phagocytic capacity of CD103⁺ DC2 might correspond to a more mature DC with increased cross-presentation of antigen (Guermonprez et al., 2002). Efficient cross presentation of antigen in DCs relies upon Nox2 to regulate phagasomal pH, which thereby prevents destruction of T cell peptides. Prior to this work, this was previously determined using a ratiometric assay comparing intracellular fluorescence intensity of a pH-sensitive and pH-insensitive fluorophore following phagocytosis (Savina et al., 2006). We therefore generated a B78 (melanoma) tumor line expressing a fusion of a pH-sensitive GFP (pHluorin, quenched below pH 6.5) and a pH insensitive fluorophore (mCherry). By analyzing pHluorin intensity alone within the mCherry⁺ compartment of each population, we found that only the 'DC' populations maintained pHluorin in an alkaline (fluorescent) environment; comparing the ratio of pHluorin and mCherry signals showed that CD103⁺ DC2 maintained the most basic endocytic compartment while TAM1 and TAM2 populations displayed highly acidic and therefore degradative phagocytic pathways (FIG. 5E). In addition to the increased alkaline phagosomal lumen of CD103⁺ DC2, these cells demonstrated differential expression of the pro-inflammatory cytokine IL-12 and absence of anti-inflammatory IL-10 (FIG. 5F, G and data not shown). Together, all of these features suggest CD103+ DC2 are highly poised for efficient antigen cross-presentation to CD8+ T cells.

Figure 6E:
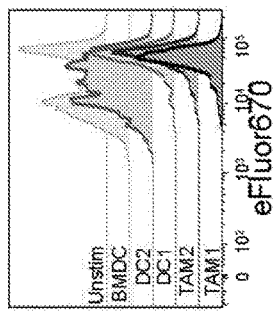
(FIG. 6E) Histogram overlay of previously activated OT-I CD8$^+$ T cell proliferation across tumor APCs. For FIG. 6E each line from front to back is F4/80+ TAM1, F4/80+ TAM2, CD11b$^+$ DC1, and CD103+ DC2, respectively.
Figure 6G:
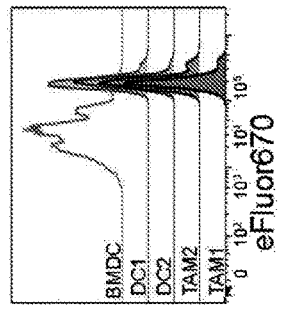
(FIG. 6G) Histogram overlay of Naïve OT-II CD4$^+$ T cell proliferation across tumor APCs. For FIG. 6G each line from front to back is F4/80+ TAM1, F4/80+ TAM2, CD11 b+DC1, and CD103+ DC2, respectively.
Figure 6D:
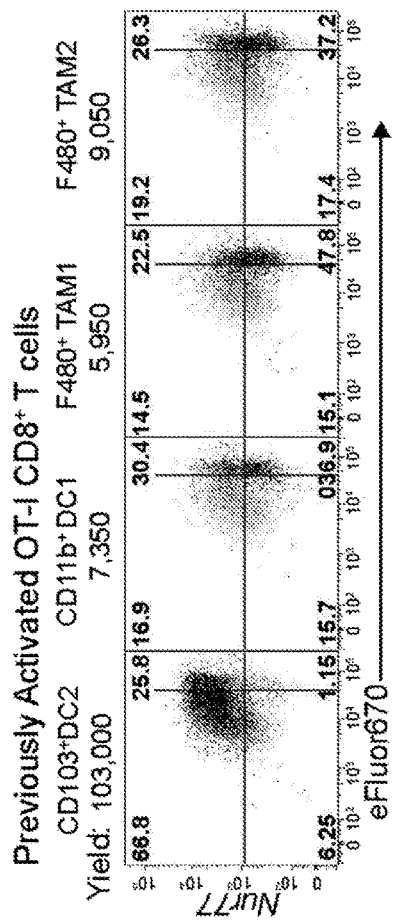
(FIG. 6D) Representative cytometry of T cell proliferation, measured by dye dilution of eFluor670 plotted against Nur77, at 72 hours for previously activated OT-I CD8$^+$ T cell blasts cultured on tumor APC populations. Total cell yield counts listed above graphs.

Example 6: CD103+ DC2 are Superior Stimulators of Naïve and Activated CD8+ T Cells Previously, we found that the aggregate antigen-ingesting myeloid compartment could stimulate naïve but not previously activated CD8+ T cells when taken directly from tumors (Engelhardt et al., 2012). However, based on the unique cross-presentation phenotype of CD103+ DC2, we sought to test the T cell stimulatory capacity of each population, freshly isolated from tumors. After 12 hours of coculture with ovalbumin-specific OT-I CD8+ T cells, the CD103+ DC2 population was the only population capable of robustly inducing TCR signaling, as evidenced by upregulation of early T cell activation markers Nur77 and CD69 in both naïve and previously activated OT-I CD8+ T cells. Importantly, this was consistent in both ectopic and spontaneous mouse models (FIG. 6A and data not shown). Extended coculture of dye-labeled OT-I CD8+ T cells revealed that CD11b+ DC1 and CD103+ DC2 populations were the most robust stimulators of naive CD8+ T cell proliferation, and demonstrated that nearly the entire stimulatory capacity previously identified in phagocytosing tumor myeloid cells lies specifically within these DC (FIG. 6B-C, and data not shown). Interestingly, CD103+ DC2 were uniquely capable of inducing strong proliferation of established CTLs, which were not stimulated by the other populations, indicating CD103+ DC2 were superior cross presenting stimulators of CTLs in the tumor (FIG. 6D-E and data not shown, respectively).

Figure 6F:
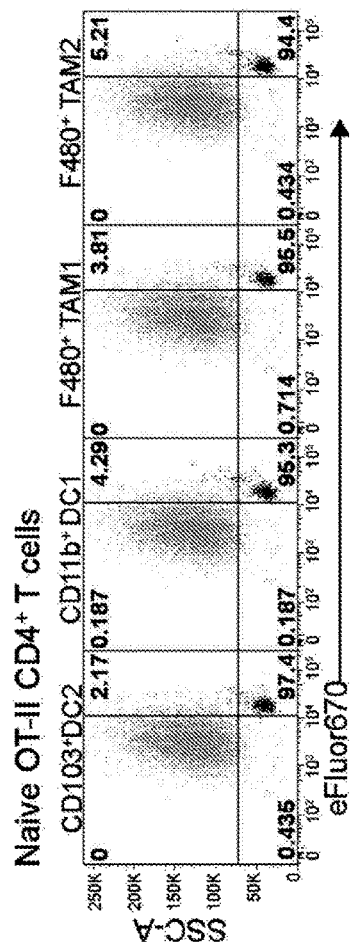
(FIG. 6F) Representative cytometry of T cell proliferation, measured by dye dilution of eFluor670, at 72 hours for Naive OT-II CD4$^+$ T cells cultured on tumor APC populations. Representative flow plots from 2 independent experiments.

Ultimately, at their normally low frequencies in total tumor isolate, CD103+ DC2 remain unable to drive proliferation of CTLs (data not shown (Engelhardt et al., 2012)). Additionally, none of the APC subsets induced CD4+ T cell proliferation directly from the tumor. (FIG. 6F-G and data not shown). However exogenous peptide did restore DC1 and DC2 capacity to stimulate proliferation, suggesting these DCs may not be inherently incapable of CD4 T cell stimulation (data not shown). Critically, this identifies the unique capacity of CD103+ DC2 within the tumor to uptake, process, and cross-present tumor antigen to robustly stimulate CTLs. This challenges the simple concept that tumors contain only weak or suppressive myeloid populations.

Example 7: CD103+ DC2 Localization and T Cell Interactions Revealed by Intravital Imaging Given the unique ability of the rare CD103+ DC2s to stimulate T cells, we sought to understand the spatial organization of these cells within tumor and their interaction dynamics with T cells both in vivo and in vitro. To differentiate these populations in living spontaneous tumors in vivo, the PyMTchOVA allele was crossed on to Cx$_3$crl-eGFP and Cd11c-mCherry alleles, generating three uniquely fluorescent populations in the myeloid compartment (data not shown). Both DC subsets (DC1/DC2) were specifically marked red (CD11c-mCherry only), while TAM1 and TAM2 populations were green (Cx$_3$crl-eGFP only) and yellow (CD11c-mCherry and Cx$_3$crl-eGFP), respectively. Using this fluorescent approach, with 2-photon intravital imaging, we observed that TAM1 and TAM2 populations are preferentially marginating tightly on tumoral lesions. This zone is one where we had previously found T cells to be preferentially captured (Engelhardt et al., 2012). In contrast, red DC subsets typically, were found in separate collagen-rich zones distal to the tumor lesions, making up nearly 70% of all distally localized APC (FIG. 7A and data not shown).

Since this approach did not fully differentiate between CD11b+ DC1 and CD103+ DC2 cells amongst those on the margins of tumor foci, we sought to determine whether the few red DCs might preferentially represent exclusively one or the other subset. To delineate the subsets in situ, we utilized live tumor slice imaging, with anti-CD11b antibody staining. Using this, we could distinguish CD11b+ DC1 from CD103+ DC2 subsets in situ in the presence of the red/green fluorescent reporters and found that, both CD11b+ and CD11b− DCs were present at these locations (data not shown). We conclude that while TAMs generally represent the dominant cell type at the tumor margin, pro-CTL stimulatory APCs nevertheless can be found there, albeit in very low numbers.

Our previous data demonstrated that incoming CTLs engaged in arrest behavior at the tumor margin and we sought to determine whether these might be taking place with DCs or TAMs or both. In vivo T cell dynamics were analyzed in the red/green reporter system by adoptive transfer of Actin-CFP labeled OT-I CD8+ T cells into spontaneous breast tumor bearing mice, for either intravital or live slice imaging. We observed stable T cell interactions largely confined to the tumor margins, as previously described (Boissonnas et al., 2013; Engelhardt et al., 2012) (FIG. 7B and data not shown). Although TAM1 interactions dominated all interactions scored, DCs and TAM2s were also well represented in T cell arrests. This demonstrates that DC1/2 in the tumor-proximal regions are not incapable nor physically excluded from engaging T cells within tumors but did raise a fundamental question of whether either is intrinsically more capable of engaging T cells.

To answer this, we divorced APC selection from the physical constraints of the tissue and digested tumor to make single-cell suspension and introduced in vitro activated OT-I CTLs and allowed them to form antigen-specific couples. We then quantified the percentage of each APC population that was occupied with a T cell by flow cytometry. This revealed that OT-I T cells couple preferentially with CD103+ DC2 and TAM1/2 subsets (FIG. 7C left panel). However, due to the high frequency of TAM1/2, most T cell-APC couples are formed with TAM1/2 cells (FIG. 7C right panel). We conclude that DC2 contribute to T cell interactions in tumors and, when present near the margin are capable of competing for T cell occupancy.

Example 8: Rare Tumor CD103+ DC2 Allow Efficient Adoptive T Cell Therapy

We were surprised to find that the proportions of CD11b+ DC1 and CD103+ DC2 were nearly inverted in a spontaneously regressing EG7 tumor cell line, hereto after referred to as EG7.2, as compared to a fully aggressive and outgrowing line EG7.1. While the aggressively growing line maintained the relative proportions of DCs we observed in all other aggressive tumors (data not shown), the spontaneously regressing model contained unusually high numbers of the CD103+ DC2 (data not shown). We also observed increased tumor growth in the Irf8 KO tumor model, which lack CD103+ DC2, but not in the Irf4 conditional KO model (data not shown). Together, suggesting DC2 tumoral abundance may play an important role in tumor control, however the differences in outgrowth may represent many variances in these lines, beyond their populations of myeloid cells and their ability to stimulate CTLs. Therefore to formally test whether the CD103+ DC2 are necessary for efficient CTL mediated tumor regression, we turned to the outgrowing EG7.1 tumor model and performed adoptive T cell therapy of activated tumor specific T cells to analyze regression (Helmich and Dutton, 2001). We performed these experiments in zDC-DTR mice, which permitted us to specifically ablate CD103$^+$ DC2 in the tumor (FIG. 3D). In order to isolate the effect of the CD103$^+$ DC2 to the site of the tumor, and eliminate any effect of LN priming, we specifically designed the experiment to include two strategies, (1) use of activated OT-I CD8$^+$ CTL blasts, which do not require priming in the LN and typically do not traffic there, and (2) treatment of animals with the S1P$_1$R antagonist, FTY-720, which prevents LN exit of rare transferred CTL T cells that traffic to the LN. The effect of FTY-720 alone had minimal effects on transferred CTLs to mediate tumor regression (data not shown). However, we found that ablation of CD103$^+$ DC2s in the context of FTY-720 had a significant effect on the ability of CTLs to mediated efficient tumor regression, massively slowing T cell mediation tumor regression (FIG. 8A).

Example 9: Signatures of Intratumoral CD103$^+$ DC2 Abundance Predict Outcome Across Human Cancer To determine if a critical role for CD103$^+$ DC2 abundance translated to human tumors, we took advantage of TCGA array data (Cancer Genome Atlas Research et al., 2013; Hoadley et al., 2014) that quantifies relative gene expression from numerous human cancer types with matched outcome data. We used our RNAseq data to select for high level transcripts that characterized CD103$^+$ DC2 and also selected a subset of genes that characterized TAM1/TAM2/CD11b$^+$ DC1 cells but were deficient in CD103$^+$ DC2 (FIG. 8B top and bottom genes, respectively). We identified human homologs of those mouse genes and assayed expression of these 'signatures' in patient TCGA data from all cancer types to assess prognostic associations. In a Proportional Hazards survival analysis, adjusting the model for cancer type as a co-variate, we observed that the individual genes from these populations had only modest prognostic benefits (expressed as Hazard Ratio (HR)). However, a highly significant association with increased survival (BH p=0.00019) was observed when we defined a ratio of the CD103$^+$ and CD103$^-$ gene expression data and used this as a continuous variable within the Cox analysis (FIG. 8B).

This analysis shows that the cell type we identified, when ratioed with its functional opposite, generates a very strong prognostic value for outcome across human cancers. Comparing this 'signature' to other previously described 'immune scores' shows that the ratio of CD103$^+$/CD103$^-$ genes provides the strongest pro-immune survival signal compared to other current analyses of TCGA data including those based on total T cell abundance (Palmer et al., 2006) and that made by bulk ratio of CD8 T cells to macrophages (CD8/CD68 DeNardo et al., 2011) (FIG. 8C). Our score also compares favorably, though opposite in prognosis, for those immune scores associated with poor outcome. It is also notable that CSF-1 expression in tumors in these patients also anti-correlates with the CD103/BDCA3 gene ratio measure, although it likewise anti-correlates with total tumor Flt3L levels (data not shown).

Figure 8D:
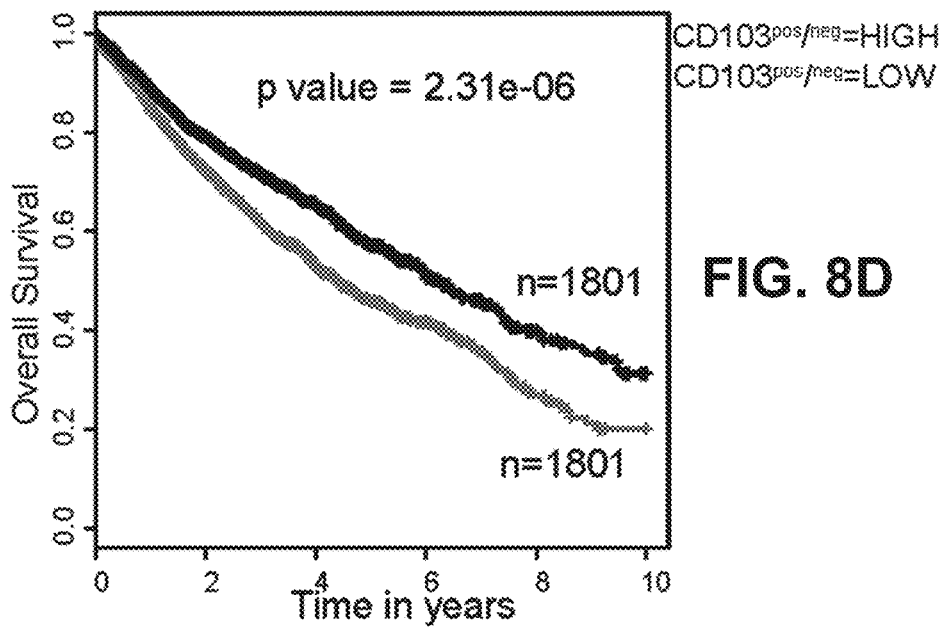
(FIG. 8D) K-M plot across all 12 cancers in Human TCGA data set, adjusting for cancer type. Data Parsed on HIGH CD103$^+$/CD103$^-$ gene Ratio (black, n=1801) and LOW CD103$^+$/CD103$^-$ Ratio expressers (grey, n=1801), with a p-value=1.76e-07.
Figure 8E:
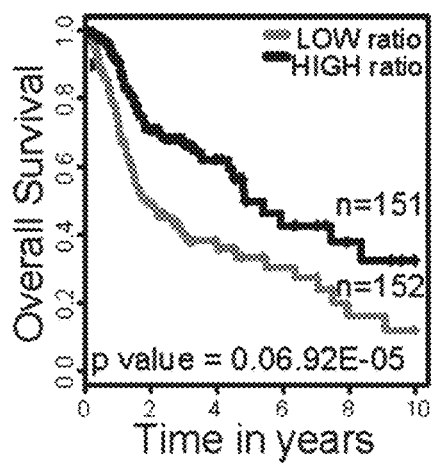
(FIG. 8E) K-M plot for overall survival of Breast Cancer patients in TCGA data set. Data Parsed on HIGH CD103$^+$/CD103$^-$ gene Ratio (black, n=422) and LOW CD103$^+$/CD103$^-$ Ratio expressers (grey, n=423), with a p-value=0.0255.
Figure 8F:
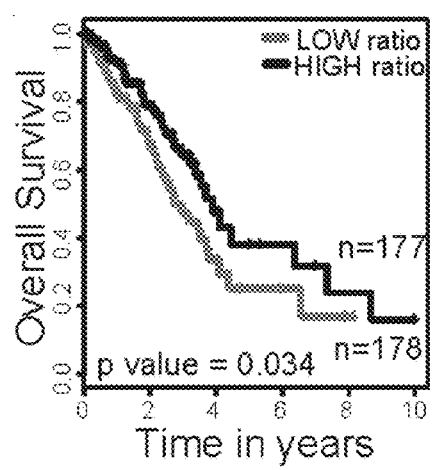
(FIG. 8F) K-M plot for overall survival of Head and Neck Squamous Cell Carcinoma patients in TCGA data set. Data Parsed on HIGH CD103$^+$/CD103$^-$ gene Ratio (black, n=151) and LOW CD103$^+$/CD103$^-$ Ratio expressers (grey, n=152), with a p-value=0.000207.
Figure 8G:
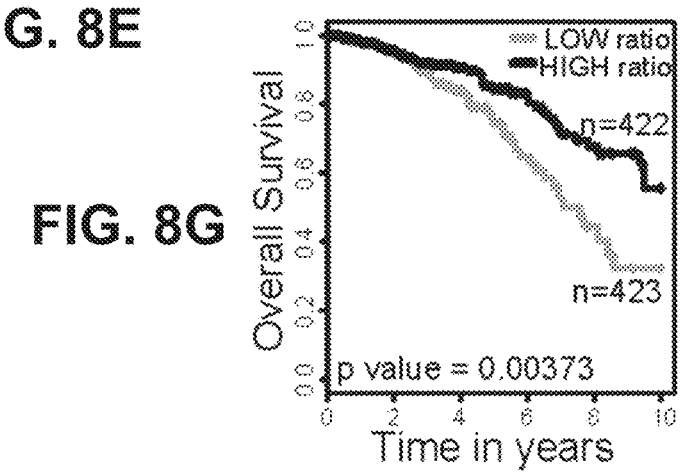
(FIG. 8G) K-M plot for overall survival of Lung Adenocarcinoma patients in TCGA data set. Data Parsed on HIGH CD103$^+$/CD103$^-$ gene Ratio (black, n=177) and LOW CD103$^+$/CD103$^-$ Ratio expressers (grey, n=178), with a p-value=0.000874.

Finally, we sought to analyze the TCGA data within individual cancer types. Adjusting for cancer type, a Kaplan-Meier (K-M) plot for all 12 cancers in this dataset shows the overall benefit in tumors with a high CD103$^+$/CD103$^-$ gene-expression profile (FIG. 8D; and data not shown). The extent of this association is particularly profound in Breast Cancer, Head-Neck Squamous Cell Carcinoma, and Lung Adenocarcinoma (FIG. 8E-G). Overall, this represents an unexpectedly strong immune signature, the more so as it was derived entirely from empirical immunoprofiling in mouse tumor models.

Example 10: Materials and Methods for Example 11

Melanoma Bioinformatics Analysis

The melanoma data set GSE19234 (n=44) was pre-processed by quantile normalizing in the R environment prior to evaluating the signature and assessing associations with survival (Cox proportional hazards). Bogunovic, D., et al. Immune profile and mitotic index of metastatic melanoma lesions enhance clinical staging in predicting patient survival. Proc Natl Acad Sci USA 106, 20429-20434 (2009). SDC/NSM ratio signature is calculated as the log of the mean expression of SDC genes divided by the mean expression of the NSM genes, followed by zscore standardization (mean=0, sd=1; gene list in FIG. 1A). Survival analyses were performed using Cox Proportional Hazards modeling. Log rank p-values are used to assess significance after adjusting for multiple comparisons using Benjamini-Hochberg method.[20] Kaplan-Meier survival plots were generated using the Survival package in R and we classified each sample as 'high' or 'low' using the 33%, 50% (Median), or 66% value of the SDC or SDC/NSM ratio signature.

Patients and Samples

Patients were enrolled in this study if they had histologically confirmed stage IV or III unresectable metastatic melanoma. Patients were consented for tissue collection under a UCSF IRB approved protocol (UCSF CHR #13-12246). The study enrollment period started from December 2012 to February 2015. Patients were treated with the following PD-1/PDL-1 axis blocking monoclonal antibodies: pembrolizumab (Keynote 001, 002, 006 or expanded access program or commercial supply) or nivolumab (commercial supply). Cutaneous/subcutaneous tumors were biopsied with either a punch (4 mm or 6 mm), a surgical excision (sample K10) and all other tumor biopsies were with core biopsies (16 g or 18 g) exclusively. An additional sample was sent for pathology evaluation. Biopsies (n=21) were collected prior to infusion of anti-PD 1. The fresh biopsy samples were immediately placed in a sterile container on saline soaked gauze and placed in a container of wet ice and transported to the laboratory for evaluation. All response evaluation was with radiologic imaging using the Response Evaluation Criteria in Solid Tumors version 1.1 (RECIST). Complete Response was defined as a complete regression of all target and non-target lesions, Partial Response was defined as regression of target lesions >30% with no new lesions appearing, Stable disease was defined as <30% decrease or <20% increase in the size of target lesions. Progressive disease was defined as increase in target lesions >20% or appearance of new lesions >1 cm in size. Patients with complete or partial response were classified as "responders" while those with stable disease or progressive disease were classified as "non-responders". In cases when progression was defined clinically (e.g. new lesions) without the benefit of a follow-up scan, the patient was categorized as a responder and the RECIST was indicated as 'x'.

Human Tissue Digestion

Tissue was vigorously minced with surgical scissors and transferred to a 25 ml Erlenmeyer flask with a magnetic stir bar and with 3 mg/ml collagenase A (Roche) and 50 U/ml DNase I (Roche) per 0.3 g of tissue for 1 hour at 37° C. with 5% $CO_2$ with constant agitation. Samples are then filtered through a 70 um filter, spun down, and re-suspended for staining. Ruffell, B., et al. Leukocyte composition of human breast cancer. Proc Natl Acad Sci USA 109, 2796-2801 (2012).

Flow Cytometry and Ab Clones

All antibodies were purchased from BD Pharmingen, eBioscience, Invitrogen, BioLegend®, the UCSF hybridoma core, or were produced in the Krummel Lab. For surface staining cells were incubated with human anti-Fc receptor antibody cocktail (clones 3G8, FUN-2, and 10.1, BioLegend®) and stained with antibodies in PBS+2% FCS+2 mM EDTA for 30 min on ice. Viability was assessed by staining with fixable Live/Dead Zombie NIR™ or Aqua (BioLegend®). All flow cytometry was performed on a BD Fortessa flow cytometer. Analysis of flow cytometry data was done using FlowJo (Treestar) software. Cell sorting was performed using a BD FACS Aria II.

Mouse antibodies against human antigens: CD45 clone H130, CD3e clone OKT3, HLA-DR clone L243, CD56 clone CMSSB, CD19 clone H1B19, CD14 clone 61D3, CD16 clone CB16, CD11c clone 3.9, BDCA1 clone L161, and BDCA3 clone AD5-14H12.

Cell Lines and Cell Culture

B78ChOVA is a variant line of B78, generated by standard transfection procedures with the ChOVA fusion construct identical to that used to generate the PyMTchOVA cell line. Graf, L. H., Jr., Kaplan, P. & Silagi, S. Efficient DNA-mediated transfer of selectable genes and unselected sequences into differentiated and undifferentiated mouse melanoma clones. *Somatic cell and molecular genetics* 10, 139-151 (1984) and Engelhardt, J. J., et al. Marginating dendritic cells of the tumor microenvironment cross-present tumor antigens and stably engage tumor-specific T cells. *Cancer Cell* 21, 402-417 (2012). Briefly, adherent cells were cultured at 37° C. with 5% $CO_2$ in DMEM plus 10% FCS with Penicillin, Streptomycin, and Glutamine on tissue culture-treated plastic plates and split every other day. Suspension cells were cultured in RPMI-1640 plus 10% FCS and Pen/Strep/Glut in tissue culture T25 and T75 flasks and split every other day.

Mouse Tumors

All mice were maintained under SPF conditions and treated in accordance with NIH and American Association of Laboratory Animal Care standards, and consistent with IACUC UCSF protocols.

Tumor cell lines were harvested and washed 3 times with PBS, then mixed at a 1:1 ratio with growth factor-reduced Matrigel™ Matrix (BD Biosciences) in a final volume of 50 ul. One hundred fifty thousand tumor cells were injected subcutaneously in the right shaved flank and allowed to grow for 14-21 days.

Mouse Strains

For modulating populations of myeloid cells in tumors, wildtype C57BL/6 purchased from Simonsen and Zbtb46-DTR C57BL/6 mice were obtained from SImonsen. Meredith, M. M., et al. Expression of the zinc finger transcription factor zDC (Zbtb46, Btbd4) defines the classical dendritic cell lineage. *J Exp Med* 209, 1153-1165 (2012). Zbtb46-DTR BM chimeras were generated following standard procedures using 8 week-old C57BL/6 male recipients receiving lethal irradiation (2 doses of 5.5 Gy) and $2-5 \times 10^6$ Zbtb46-DTR BM cells. Mice were kept on antibiotic water for 4 weeks and used for experiments at 8 weeks post-reconstitution.

Tumor Growth

For tumor growth curves, tumor area ($mm^2$) was measured with electronic calipers as tumor width× tumor height, over the indicated time periods.

Diphtheria Toxin, Anti-PD-1, and Anti-CTLA-4 Treatment

DT was purchased from Sigma-Aldrich. For transient DT ablation in DTR mice were injected i.p. with 20 ng DT per gram of body weight, and mice were euthanized 24 hours after DT injection for analysis. For long-term ablation, mice were initially injected i.p. with 20 ng/gram DT, and then maintained on 4 ng/gram every third day thereafter for up to 15 days.

Purified anti-PD-1 (clone RMPI-14) and anti-CTLA-4 (clone 9H10) were purchased from BioXcell and injected i.p with 100 ug of each antibody as a combined therapy with three treatments at days 5, 8 and 11 of tumor growth.

Statistical Analysis

Statistical analyses were performed using GraphPad Prism software. Unless specifically noted, all data are representative of >3 independent experiments. Error bars represent S.E.M. calculated using Prism, and are derived from triplicate experimental conditions. Specific statistical tests used were paired and unpaired T tests and all p values <0.05 were considered statistically significant.

Example 11: Intratumoral BDCA3+ DCs Predict Outcome to Anti-PD1 Checkpoint Therapy in Human Melanoma Intratumoral APCs are extremely diverse in their phenotype and the myeloid system contributes multiple populations resembling both macrophages and dendritic cells. However, it has long been suspected that whilst 'macrophages' are inhibitory to tumor progression (DeNardo et al., and Hanada et al.), that perhaps intratumoral dendritic cells are stimulatory (Sandel et al.). Efforts to understand this in explicit detail has been significantly hindered by a lack of clear distinction between these cell types. Recently, we undertook high-dimensional flow-cytometry together with RNAseq in order to differentiate intratrumoral myeloid cells. We found that, indeed, a small population of cross-presenting dendritic cells was highly stimulatory for CTL but that other bona-fide "dendritic cell" subsets as well as the very abundant macrophage populations failed to stimulate tumor-antigen reactive CD8 T cells. The rare stimulatory dendritic cells (SDC) were defined in the mouse by expression of the integrin CD103 and in the human by expression of CD141/BDCA3 (Broz et al.).

Figures 9A, 9B:
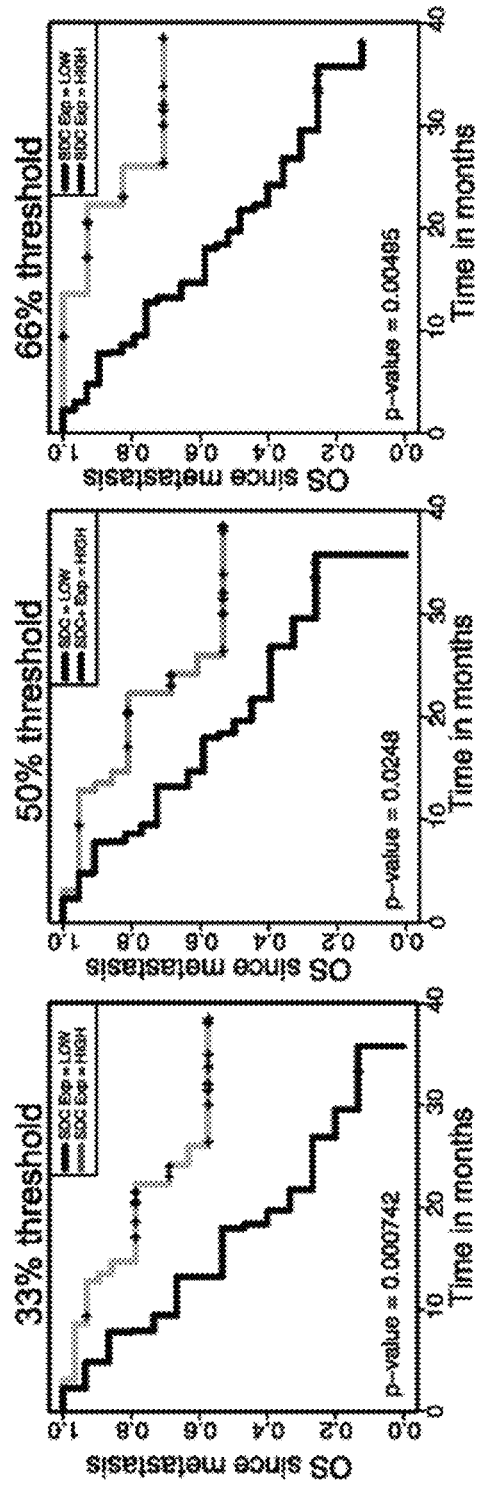
(FIG. 9A) Comparison of the prognostic value of the CD103$^+$ genes, CD103$^{+/-}$ Ratio, and the individual genes using the metastatic melanoma data set in a COX proportional hazards survival analysis. Data are expressed as Hazard Ratio (HR) with 95% Confidence Intervals, where <1 means increased overall survival (OS) since time of metastasis (post-recurrence survival) and >1 means decreased OS since time of metastasis with BH-adjusted p values <0.05.
(FIG. 9B) Kaplan-Meier plot for post recurrence survival of metastatic melanoma patients for CD103$^+$ gene list expression. Data are parsed into "high" (light grey; top line of each plot) and "low" (black; bottom line of each plot) bins at 33%, 50%, and 66% stringency thresholds for levels of expression of the CD103$^+$ genes.

To specifically address the role of these rare immune-stimulatory DC populations in human melanoma, we initially took advantage of two 'signature' gene sets whose RNA was either dramatically enriched in mouse SDC as compared to all remaining Non-Stimulatory Myeloid (NSM, comprising macrophages and non-stimulatory DC) antigen-presenting cell subsets or conversely the gene set which is preferentially expressed in the NSM (FIG. 9A). We then queried a well-annotated dataset of 44 metastatic melanoma patients that encompassed both RNA expression analysis, tumor mitotic index, clinical staging of disease and survival in metastatic melanoma patients (Bogunovic et al). We undertook analysis of the RNA abundance, analyzing for either the individual SDC genes, the mean of all SDC genes or the ratio of SDC/NSM genes. These latter two could be considered measures of overall SDC abundance and relative SDC/NSM cellular abundance, respectively (Broz et al.).

Of the 9 SDC signature genes, 7 had a significant prognostic benefit, expressed as a hazard ratio (HR) (Table 1, below) and both the SDC signature and SDC/NSM ratio signature had highly significant predictive value.

| Gene/Signature | Coefficient | p value | BH p value |
| --- | --- | --- | --- |
| MYCL | −1.763 | 6.20E−05 | 0.0008519 |
| All SDC Genes | −1.379 | 8.52E−05 | 0.0008519 |
| BTLA | −1.114 | 0.0002445 | 0.001834 |
| SDC/NSM Ratio | −3.26 | 0.0005485 | 0.002742 |
| FLT3 | −1.176 | 0.0008321 | 0.003492 |
| CCR7 | −0.4115 | 0.0009313 | 0.003492 |
| IRF8 | −0.373 | 0.005329 | 0.01776 |
| BATF3 | −0.6643 | 0.02956 | 0.08062 |
| XCR1 | −0.732 | 0.0372 | 0.093 |

To better visualize these prognostic associations, Kaplan-Meier (K-M) plots were generated for either the SDC genes or the SDC/NSM ratio where patients were binned into 'high' or 'low' signature expression with increasing stringency cut points at either a 33%, 50%, or 66% binned thresholds of expression (FIG. 9B, C). These analyses demonstrated increasing odds of survival when selecting for the highest levels of expression; the top 33% of SDC or SDC/NSM tumors have the most statistically significant increase in survival since time of metastasis. This supports the hypothesis that increased abundance of stimulatory BDCA3+ DCs in tumors better supports survival, even in the absence of therapy.

In considering the relationship between this relationship and T cell immunity, we further took advantage of curated information on the abundance of TILs in the profiled tumors to relate the SDC and SDC/NSM signatures to parse data on TIL infiltration. This analysis revealed (FIG. 9D-G), that class-based measures of TIL category and measures of peri-tumoral CD3+ T cell numbers were both highly correlated with the SDC gene signature and, to a lesser but still very significant extent, with the SDC/NSM ratio.

These relationships suggested an inter-relationship between SDC abundance, T cell function and overall survival. We sought to query this relationship as it might relate to checkpoint blockade. But, since the SDC and SDC/NSM signatures are only surrogates for the populations themselves, we sought to directly measure these populations from melanoma biopsies in the context of clinical trials of checkpoint therapies to see how they relate.

Figure 10B:
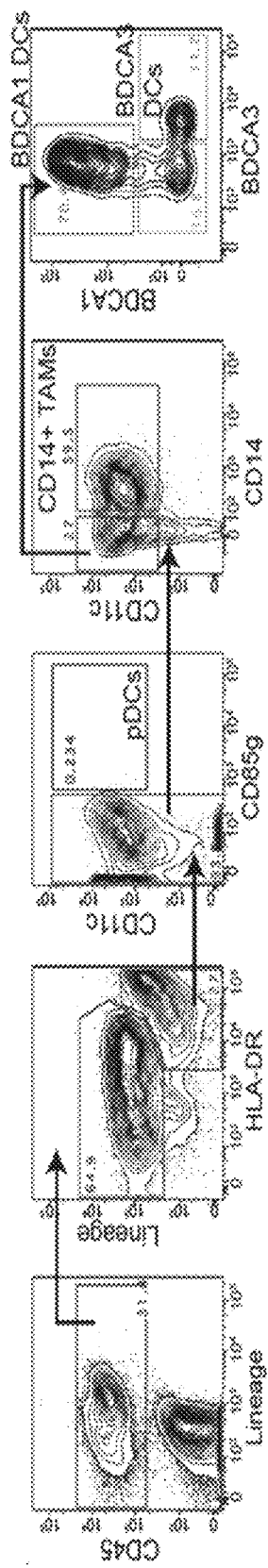
(FIG. 10B) Representative flow cytometric gating strategy for human metastatic melanomas to define tumor-infiltrating myeloid subsets. Data are representative of a patient with prominent BDCA3+ and BDCA1+ DC populations, gated on singlets and live cells. (pDCs, CD14+ TAMs, BDCA1+ DCs, BDCA3+, CD14− TAMs).
Figure 10C:
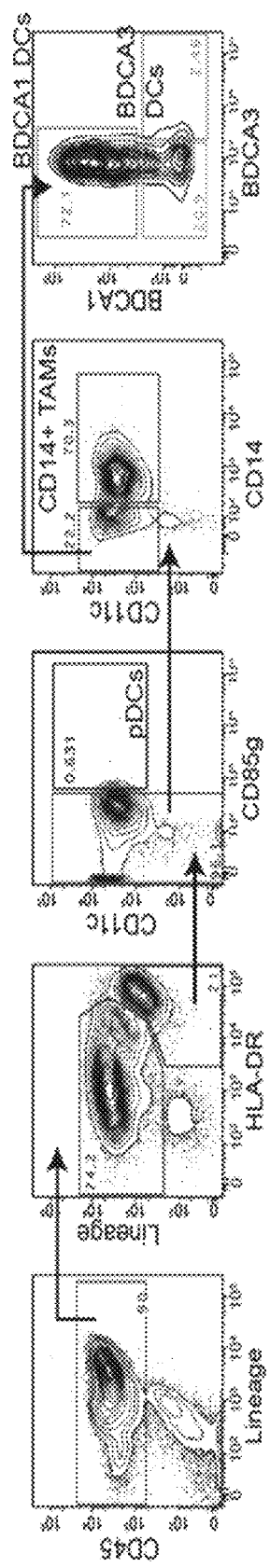
(FIG. 10C) Representative flow cytometric gating strategy for human metastatic melanomas to define tumor-infiltrating myeloid subsets. Data are representative of a patient without a prominent BDCA3+ DC population, gated on singlets and live cells. (pDCs, CD14+, BDCA1+ DCs, BDCA3+ DCs, CD14− TAMs).
Figure 10D:
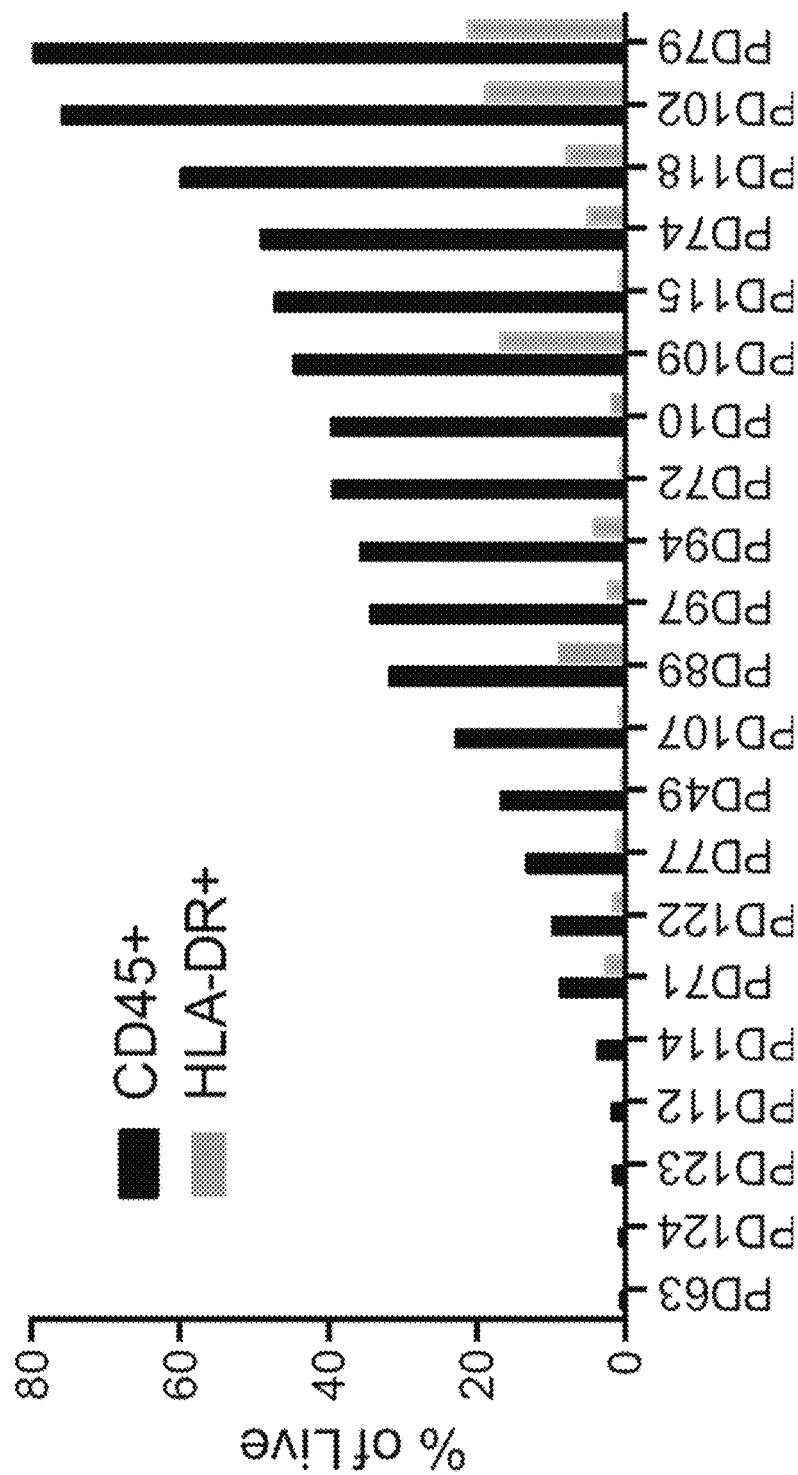
(FIG. 10D) Frequencies of CD45+(black; left bar of each group) and HLA-DR+ (grey; right bar of each group) cells as a percent of total live cells across patient biopsies.
Figure 10E:
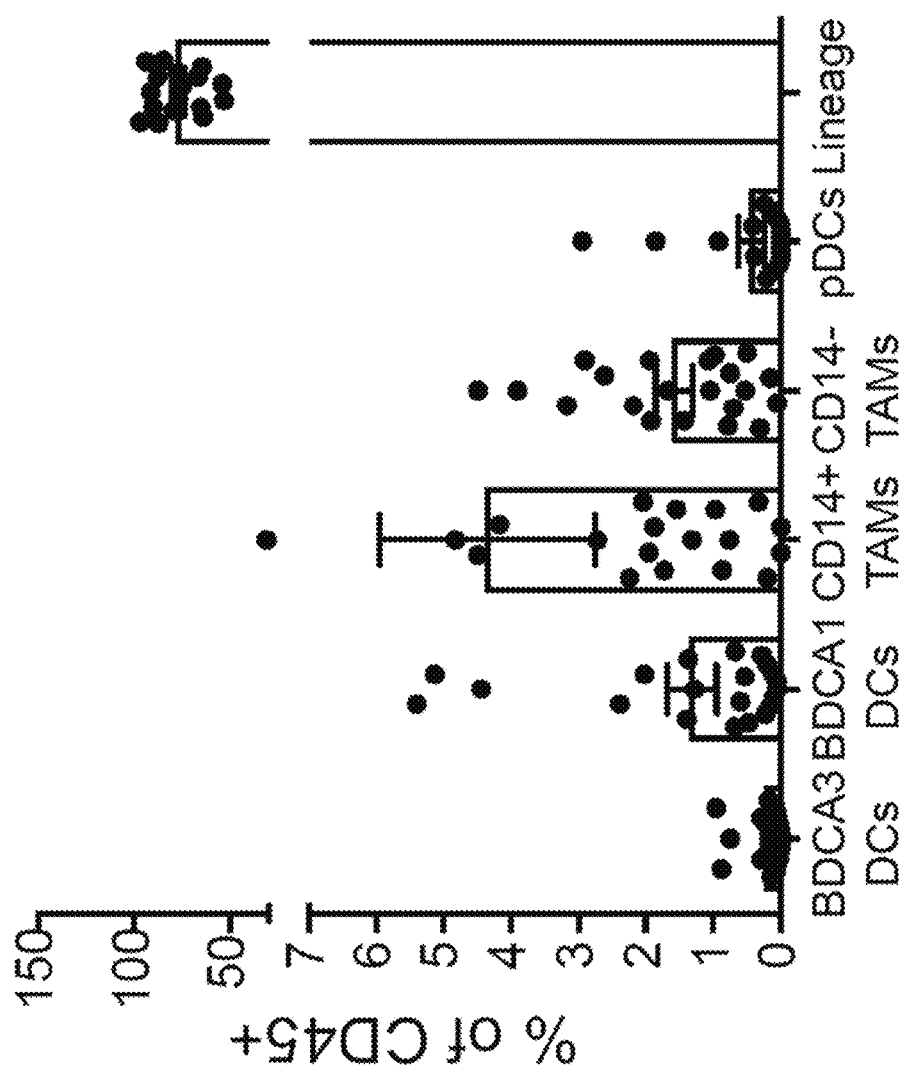
(FIG. 10E) Frequencies of tumor-infiltrating immune populations across patient biopsies as defined by the gating strategy. Data are presented as frequency of total CD45+ cells, mean±S.E.M. across patients. pDCs, CD14+ TAMs, BDCA1+ DCs, BDCA3+ DCs, CD14− TAMs, Lineage markers (CD3e, CD56, CD19).

To test this end, we analyzed tumor biopsies from 21 metastatic melanoma patient's biopsy samples using flow cytometry and then tracked their progress in response to anti-PD-1 therapy. Among the 21 patients, 5 were female and 16 were male with an average age of 61.6 years, and biopsies were taken from a variety of locations and tissues (FIG. 10A). For each of these patients, biopsies were digested enzymatically and analyzed by flow cytometry to quantify the proportion of immune cell infiltrates in the tumor. We designed a comprehensive flow panel to dissect the human myeloid infiltrates using the markers CD45, HLA-DR, CD3, CD19, CD56, CD11c, CD11b, CD85g, CD14, BDCA1, and BDCA3. Using these markers we were able to progressively gate the immune compartment of these tumors identify BDCA3+ DCs, BDCA1+ DCs, CD14+ TAMs, and CD14-TAMs subset (FIG. 10B, C). And we found patients with significant populations of BDCA3+ SDC (FIG. 10B) as well as those with significantly fewer (FIG. 10C). Tumors also varied significantly in the overall quantity of CD45+ cell infiltration and in the proportion of cells expressing HLA-DR (FIG. 10D). Most melanomas were highly enriched for overall abundance of lymphocytes ('lineage') (FIG. 10E). And when HLA-DR+ cells were parsed, as in FIG. 10C/D, into myeloid sub-populations these also demonstrated quite significant heterogeneity across patient biopsies (FIG. 10E).

Figure 11A:
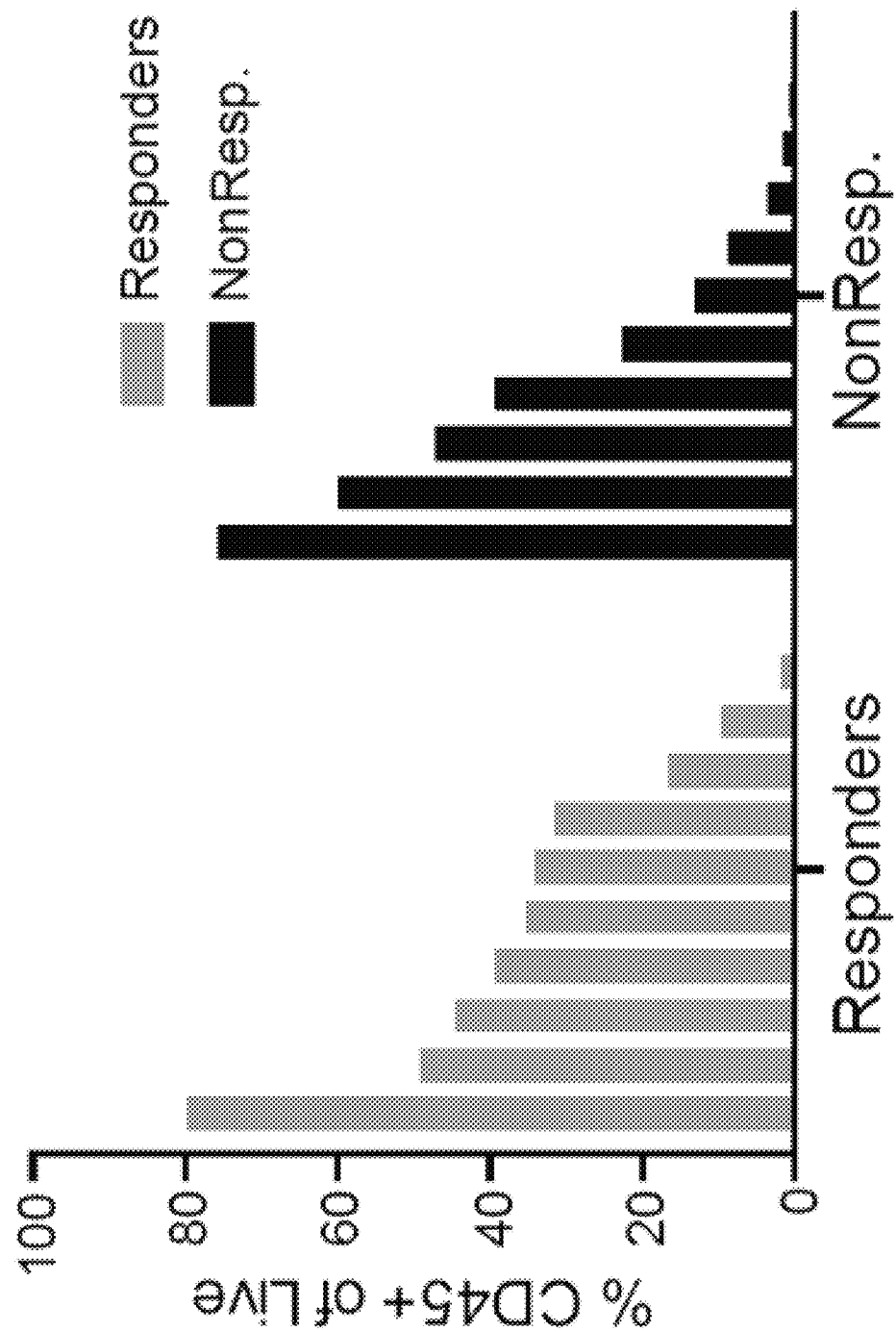
(FIG. 11A) Waterfall plot of percentage of CD45+ cells of total live cells in individual patients, separated by responders and non-responders.
Figure 11B:
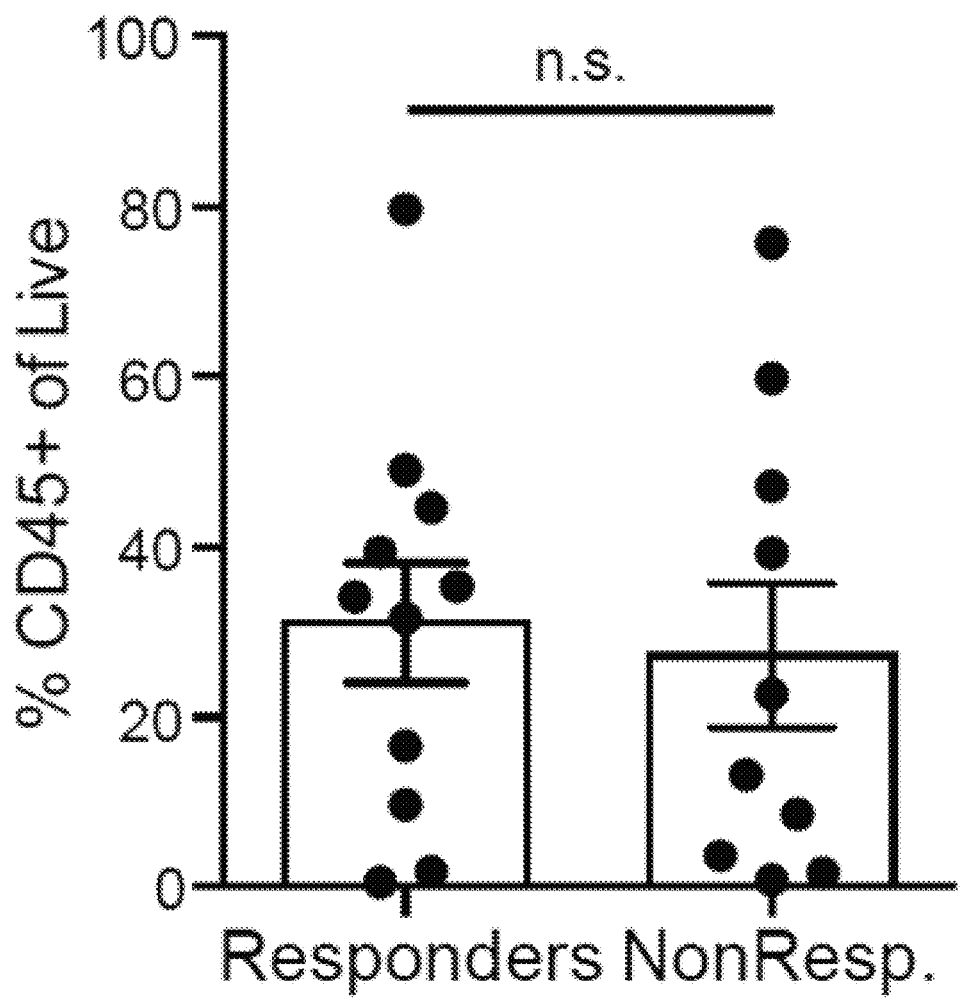
(FIG. 11B) Quantified frequency of responders (grey) and non-responders (black) for percentage of CD45+ cells of total live cells in the tumor. Data were pooled across patients and presented as mean±S.E.M., n.s.=not significant.
Figure 11C:
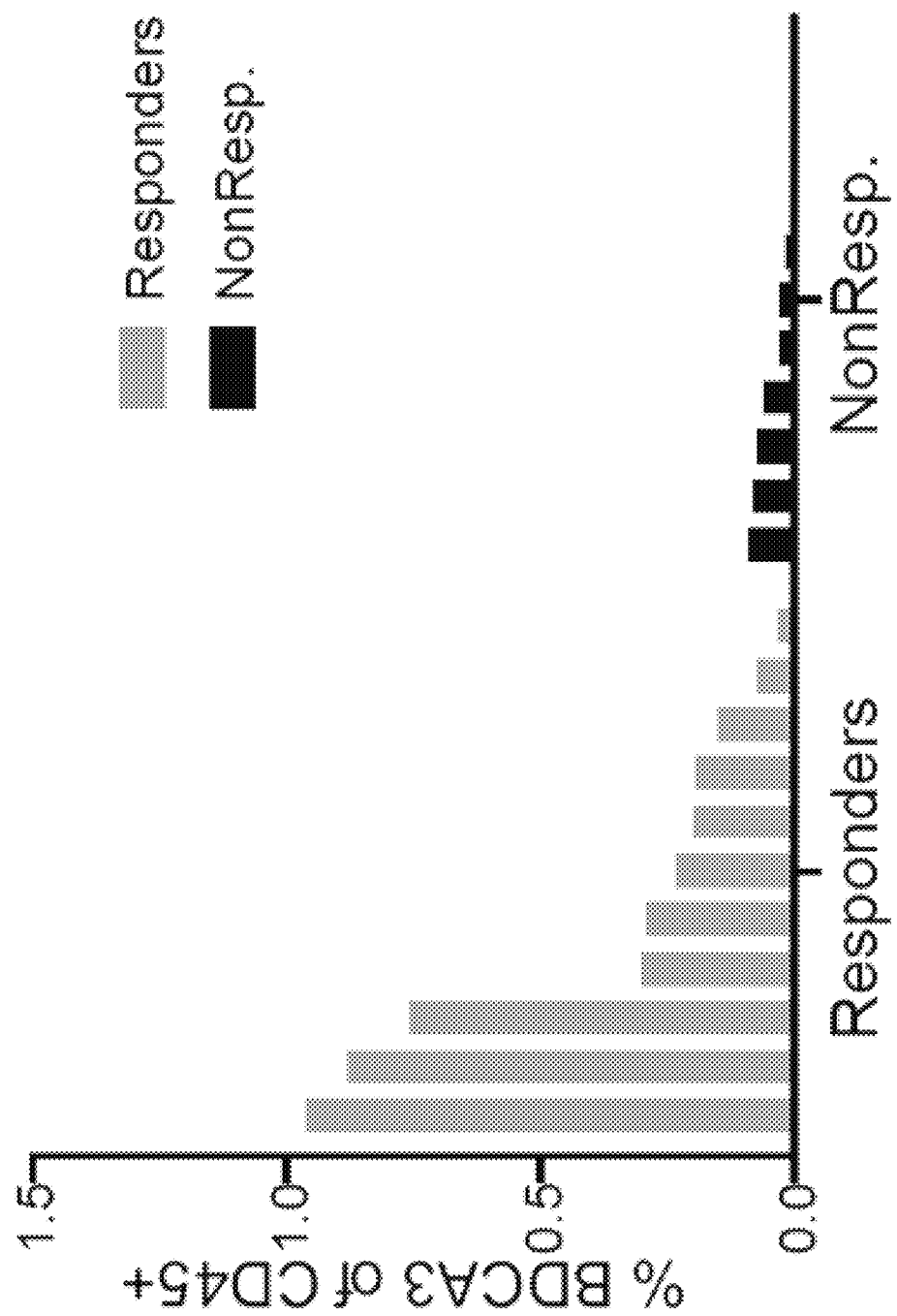
(FIG. 11C) Waterfall plot percentage of BDCA3+ DCs of total CD45+ cells in the tumor in individual patients, separated by responders and non-responders.
Figure 11D:
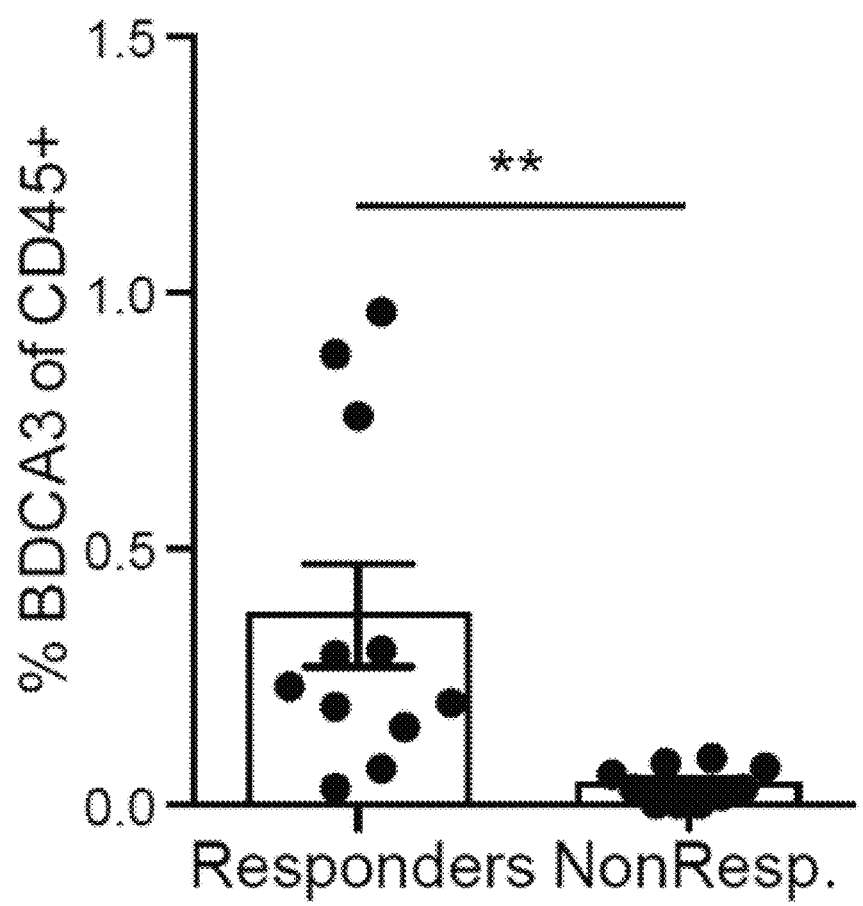
(FIG. 11D) Quantified frequency of responders (grey) and non-responders (black) for percentage of BDCA3+ DCs of total CD45+ cells in tumors. Data were pooled across patients and presented as mean±S.E.M., **p=0.0056.
Figure 11E:
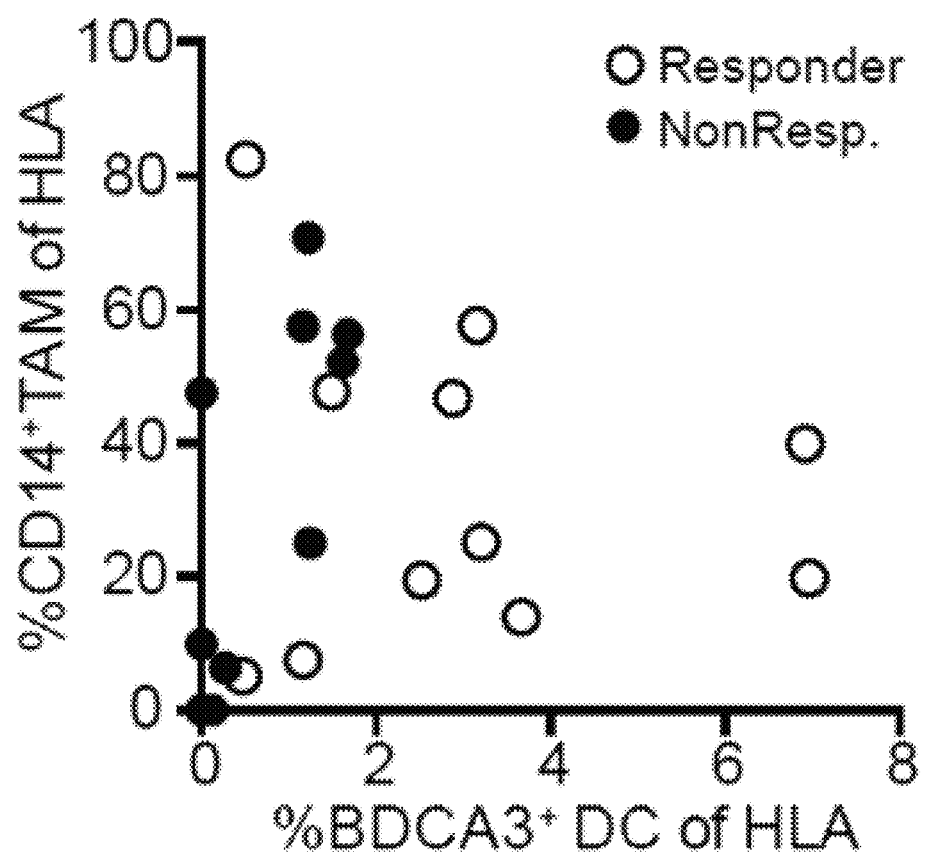
(FIG. 11E) Scatter plot of frequencies of BDCA3+ DCs and CD14+ TAMs as a proportion of total HLA-DR+ cells in the tumor, with responders indicated by open circles and non-responders indicated by closed circles.
Figure 11F:
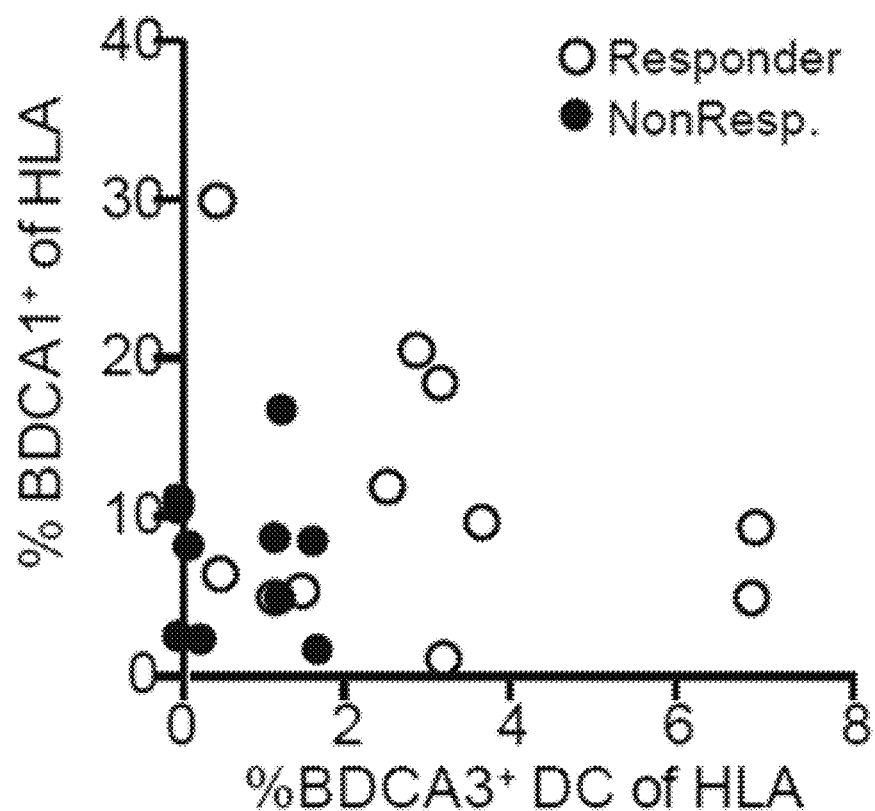
(FIG. 11F) Scatter plot of frequencies of BDCA3+ DCs and BDCA1+ DCs as a proportion of total HLA-DR+ cells in the tumor, with responders indicated by open circles and non-responders indicated by closed circles.
Figure 11G:
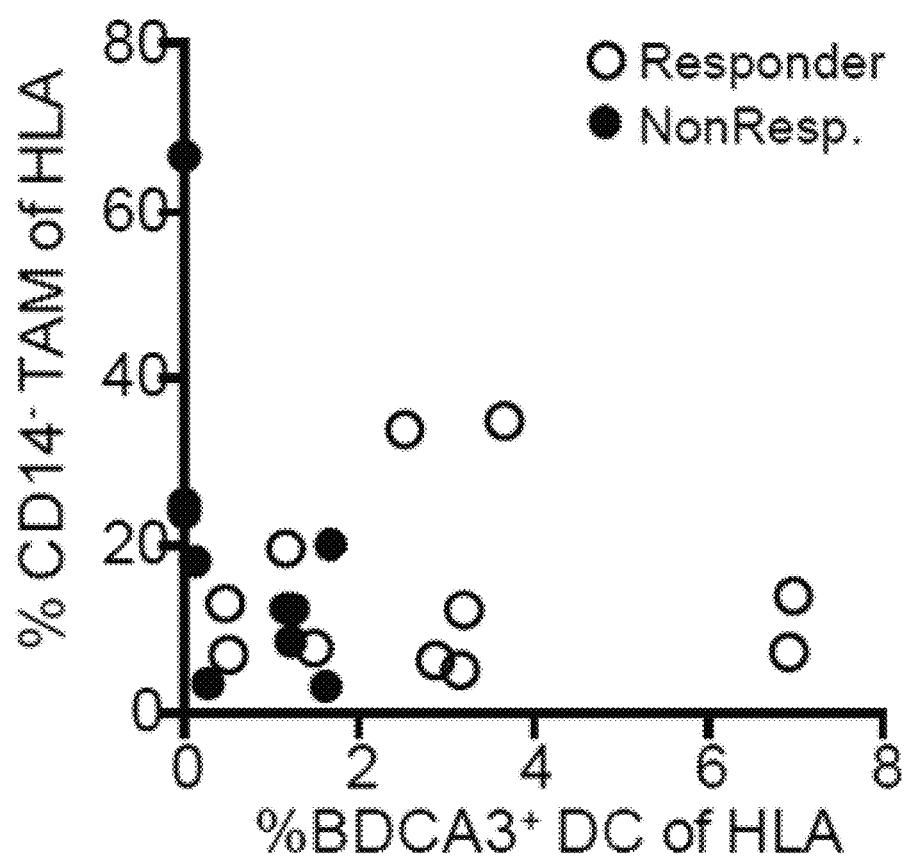
(FIG. 11G) Scatter plot of frequencies of BDCA3+ DCs and CD14− TAMs as a proportion of total HLA-DR+ cells in the tumor, with responders indicated by open circles and non-responders indicated by closed circles.

To examine the association of these immune myeloid infiltrates with patient responses we parsed patients into groups either as 'non-responders', defined as either stable or progressive disease, or 'responders', defined as partial or complete responses to anti-PD-1 therapy (see FIG. 10A and methods). By this approach, there was no significant difference in the percentage of total CD45+ immune cell infiltrates between responding and non-responding patients, and both groups, in fact, had similar average percentage of CD45+ cells with similar variability around the mean (FIG. 11A, B and data not shown). Similarly, there was no relationship apparent between the overall frequency of lymphocytes cells and outcome (data not shown) Comparatively, when BDCA3+ DCs were quantified across response groups as either a proportion of total immune cells (gating on CD45+ cells, FIG. 11C-D) or total APCs (gating on HLA-DR+ cells, data not shown) then the anti-PD-1 responding patients had statistically significant higher frequencies of BDCA3+ DCs in their tumors. Together, these finding suggest that while the total immune cell infiltration of tumors does not predict immunotherapy responsiveness, possibly because the total CD45+ population contains both pro-versus anti-tumoral players in the TME, the proportion of stimulatory BDCA3+ DCs can, in fact, predict immunotherapy efficacy for anti-PD-1. While there were clear examples of responders with relatively low numbers of BDCA3, an absolute cutoff above 2% of HLA-DR+ provides 95% confidence for responder status using this sample size.

We sought to further examine this data to understand if this positive relationship could be further improved by considering the precise identity of the remaining myeloid populations; specifically the abundance or either CD14+ TAMs or the alternative DC population marked by BDCA1 or CD14− TAMs. We plotted individual patients by their percentage of BDCA3+ cells versus each of those and coded each according to the responder status. While responders still parsed into BDCA3+ high regions of this plot, we found no obvious trends with the other populations (FIG. 11 E-G). Again, these finding indicate that the presence of BDCA3 is a strong indicator of being able to raise a solid antitumoral response but that other factors may play a role in permitting a few patients to respond despite having lower levels. Future studies should focus on intratumoral localization of the BDCA3+ cells as a possible explanation; at present, antibodies for these perform poorly in our hands and will thus need to be developed for future studies.

Figure 12A:
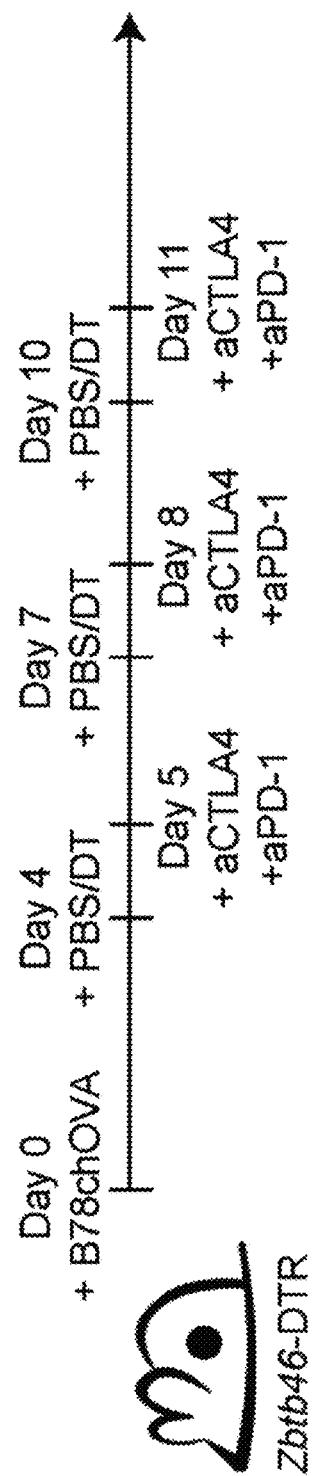
(FIG. 12A) Schematic of mouse and tumor model with combined immunotherapy treatment regimen.
Figure 12B:
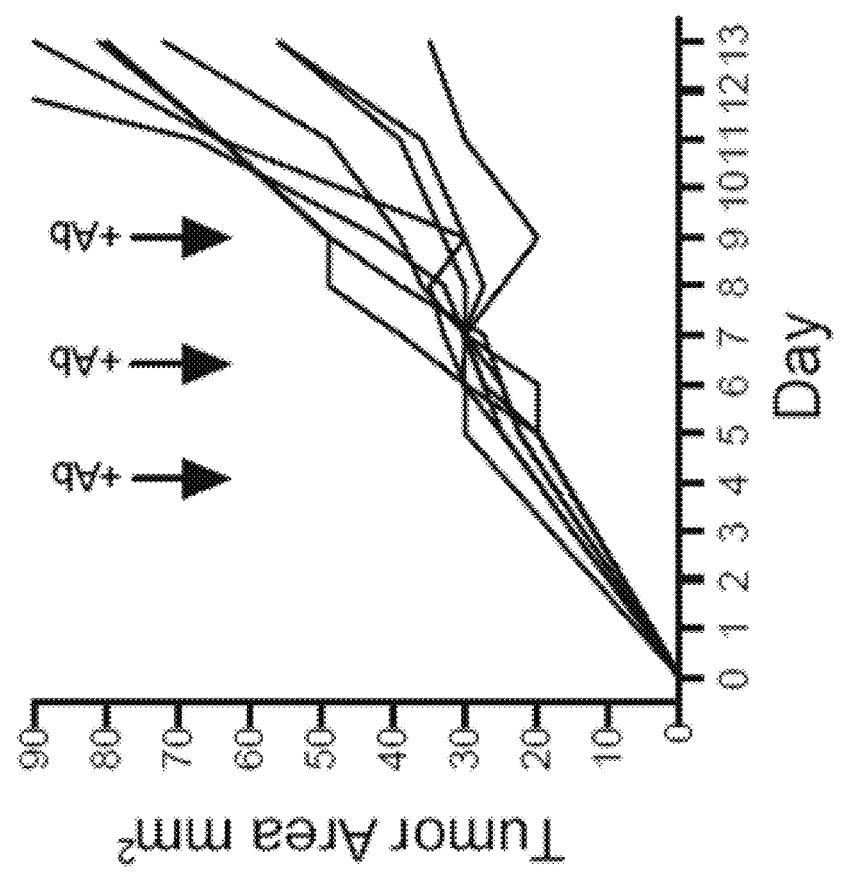
(FIG. 12B) Tumor area (mm$^2$) of individual B78chOVA tumors in B6 control mice (left most graph) receiving 100 ug control Armenian hamster IgG and 100 ug control rat IgG2a i.p. at days 5, 8, and 11 of tumor growth. Data were pooled form 2 independent experiments, n=8.
Figure 12C:
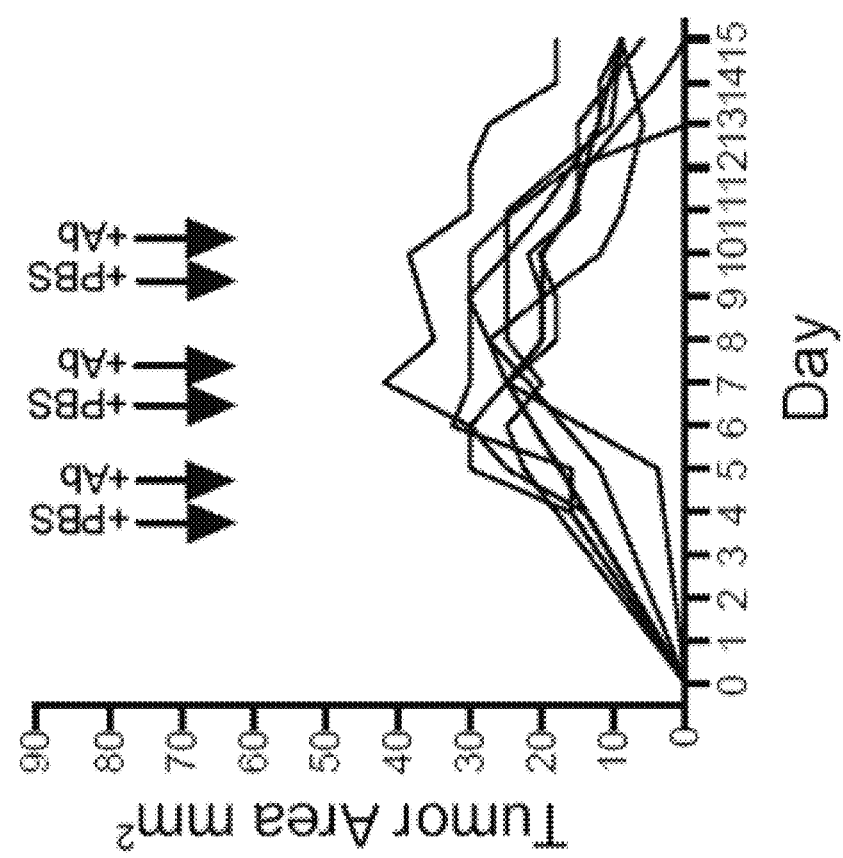
(FIG. 12C) Tumor area (mm$^2$) of individual B78chOVA tumors in Zbtb46-DTR BM chimeras mice (middle graph) receiving 100 ug anti-CTLA-4 and 100 ug anti-PD-1 at days 5, 8, and 11 of tumor growth, with injection of PBS on days 4, 7, and 10. Data were pooled form 2 independent experiments, n=8.
Figure 12D:
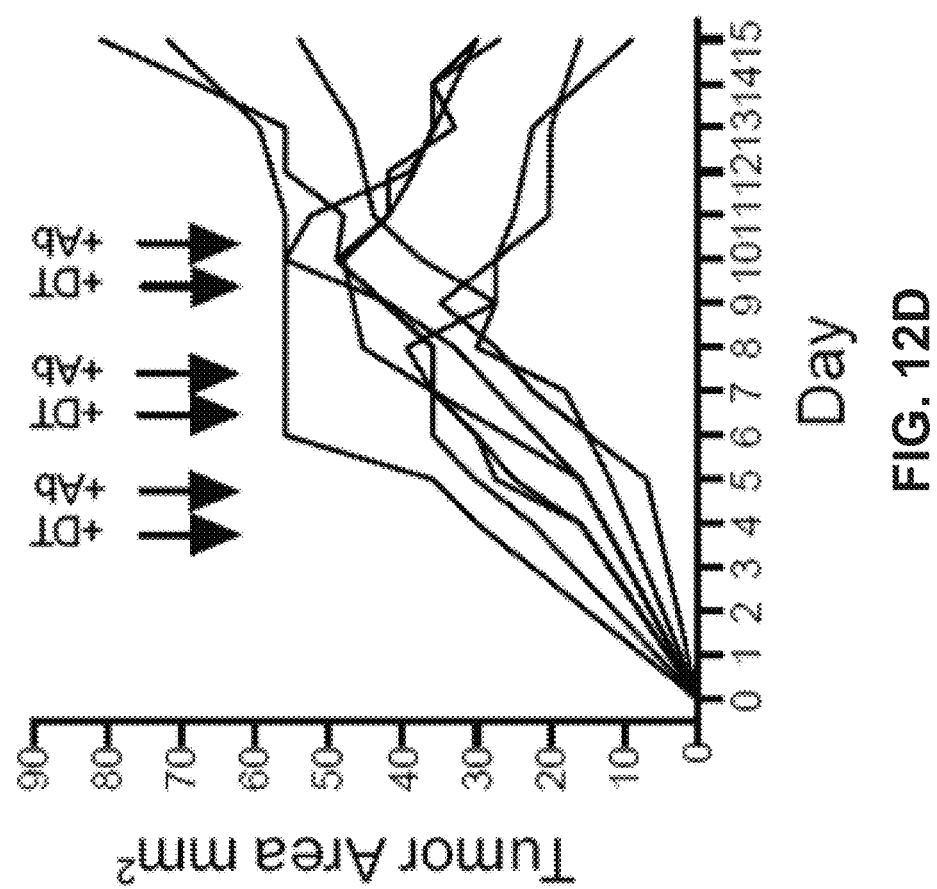
(FIG. 12D) Tumor area (mm$^2$) of individual B78chOVA tumors in Zbtb46-DTR BM chimeras mice (right most graph) receiving 100 ug anti-CTLA-4 and 100 ug anti-PD-1 at days 5, 8, and 11 of tumor growth, with injection of DT on days 4, 7 and 10. Data were pooled form 2 independent experiments, n=8.

Having established a strong association between BDCA3+ DC abundance and responsiveness to immunotherapy, we addressed whether this association represented a functional requirement of this stimulatory DC population for checkpoint blockade therapies, or simply represented a 'signature' of responsiveness. To test this we turned to a tractable mouse model of melanoma, the B78chOVA cell line[7], which is a modified variant of the B16 melanoma that expresses mCherry florescent protein and ovalbumin. In conjunction with this tumor model we used Zbtb46-DTR BM chimeric mice, which we've previously shown to preferentially ablate (CD103+) SDCs (Broz et al.). In mouse models in our hands, monotherapy with just anti-PD1 was ineffectual in melanoma. We thus used the ablation model to examine whether deletion of CD103+ SDC would prevent the efficacy of a combined immunotherapy regimen of anti-PD-1 and anti-CTLA-4 (FIG. 12A). Zbtb46-DTR BM chimera mice were either treated with or anti-PD-1 and anti-CLTA-4 or with isotype-matched control antibodies, using a three dosed treatment regimen at days 5, 8, and 11, and with either DT or PBS injections starting at day and we confirmed that DT treatment alone had no effect on tumor growth in this model (data not shown). We found that while untreated melanoma tumors progressively grew out, those treated with the combined immunotherapies rapidly regressed after 7-8 days, and were nearly fully eradicated by day 15 (FIG. 12B, C). Comparatively, when mice were depleted of $CD103^+$ DCs in the context of this potent immunotherapy, the rapid tumor regression was lost, and the efficacy of dual therapy was abrogated, suggesting a functional requirement of the $CD103^+$ DCs for immunotherapeutic effect (FIG. 12D).

Thus, we've established a powerful predictive and prognostic benefit of the specific SDC (CD103 or $BDCA3^+$) population in both mouse and human tumor tissues. Generically, these findings further highlight the importance of fully understanding the immune landscape of tumor tissues as revealed in previous studies (DeNardo et al and Fridman et al). 'Immuno-scoring' (Ascierto et al) is becoming accepted as a new diagnostic marker for several cancers; however, going beyond this, our study reveals the necessity of increasingly detailed immunoprofiling of human tumors to identify rare populations of immune cells that may modulate T cells in the microenvironment. Stratification will need to use continuous refinements of signatures revealed in primary studies followed by development of tests amenable to biopsies and our study highlights that in future, high dimensional imaging, for example by mass-ion beam technologies may represent one such method (Angelo et al).

Example 12: Materials and Methods for Below Examples

Tumor Digestion

Tumors were dissected from mice and total weight of removed tumor tissue was determined. Tumors were then minced using scalpels and digested with 20 ul/ml of Liberase™ TL (Roche) from 5 mg/ml stock solution and 200 mg/ml DNAse I (Roche) per 0.3 grams of tumor weight for 30 minutes in a 50 ml conical and placed in a 37° C. shaker with 5% $CO_2$. After 30 minutes, tumor was then passed through a 70 um cell strainer and live cells were enriched by a Ficoll® Paque Plus (GE) density gradient. Live cells were collected from interface and washed into staining buffer (PBS+2% FCS+2 mM EDTA).

Mouse Bone Marrow and Spleen Isolation

Femurs and tibias were removed and bone marrow was extruded using with PBS/2% FCS/2 mM EDTA and a 25G needle/syringe. Spleens were dissected from mice and minced using scalpels. Tissue fragments were digested with 500 U/ml Collagenase IV (Worthington), 100 U/ml Collagenase I (Worthington) and 200 mg/ml DNAse I (Roche) in a 50 ml conical at 37° C. shaker. Digested tissue was then filtered through a 70 um cell strainer. Red blood cells were lysed in both bone marrow and spleen with 0.8% $NHCl_4$ for 5 minutes and then washed into staining buffer (PBS+2% FCS+2 mM EDTA).

Human Tumor Samples

Tissue was vigorously minced with surgical scissors and transferred to a 50 ml conical with 20 ul/ml of Liberase™ TL (Roche) from a 5 mg/ml stock solution and 200 mg/ml DNAse I (Roche) per 0.3 grams of tumor weight for 30 minutes at 37° C./5% $CO_2$ with constant agitation. Samples are then filtered through a 70 um filter, spun down and resuspended for staining (Ruffell et al., 2012). For all human samples, informed consent was obtained from all subjects and work was performed in accordance with IRB approval (IRB number 13-12246, Dec. 6, 2013-Dec. 5, 2014).

Flow Cytometry and Ab Clones

All antibodies were purchased from BD Pharmingen, eBioscience, Invitrogen, BioLegend®, Human Protein Atlas or were produced in the Krummel Lab or at Precision Immune Inc. For surface staining cells were incubated with anti-Fc receptor antibody (clone 2.4G2) as well as 500 nm human IgG1 Fc and stained with primary antibodies in PBS+2% FCS+2 nM EDTA for 30 min on ice. Followed by 2 washes in PBS+2% FCS+2 mM EDTA and appropriate secondary antibody staining for 30 min on ice. Viability was assessed by staining with fixable Live/Dead Zombie Aqua™ (BioLegend®) or Zombie NIR™ or DAPI. All flow cytometry was performed on a BD Fortessa flow cytometer. Analysis of flow cytometry data was done using FlowJo (Treestar) software.

Anti-Mouse Ab Clones: CD45 clone 30-F11, CD11b clone M1/70, CD11c clone N418, CD103 clone 2E7, CD24 clone M1/69, CD90.2 clone 30-H12, Ly6C clone HK1.4, MHCII clone M5/114.15.2, F4/80 clone BM8, CD64 clone X54-5/7.1.

NSM Markers: MS4A7 (polyclonal, from Human Protein Atlas, product number: HPA017418), MS4A6A (polyclonal from Human Protein Atlas, product number HPA011391). Rat anti-mouse CD88 (C5aR) clone 20/70, anti-LILRB4 clone (Pi1.5 Clone 1), Anti-Trem2 (Pi1.2 clone 2, 5 or 7), CD206 clone C068C2, MerTK clone Y323.

SDC: Anti-CCR7 clone 4B12 (mouse), anti-CCR7 clone 3D12 (human), Anti-XCR1 clone ZET (mouse), CD135 cone A2F10 (mouse), CD117 clone 2B8 (mouse).

Anti-Human Ab Clones: CD45 clone H130, CD3e clone OKT3, HLADR clone L243, CD56 clone CMSSB, CD19 clone H1B19, CD14 clone 61D3, CD16 clone CB16, CD11c clone 3.9, BDCA1 clone L161, and BDCA3 clone AD5-14H12. TREM2 (clone 237920).

Secondary antibodies: anti-human-Fab-A488, anti-Rat-A488, and anti-Goat-A488, all purchased from Jackson Immunoresearch.

To produce the anti-TREM2 antibodies, purified protein antigens corresponding to the extracellular domains of the human and mouse TREM2 were produced as Fc fusions and purchased from R&D Systems (Minneapolis, Minn.). These antigens were diluted in phosphate buffered saline (PBS) at pH 7.4 and immobilized in 96-well immunoplates by adsorption overnight at 4 C. Immunoplates were then blocked with bovine serum albumin (BSA) and incubated with naïve synthetic Fab-phagemid library for at least 2 hours at room temperature. Unbound phage were removed by extensive washing with PBS+0.05% Tween-20. Bound phage were eluted using 0.1 N HCl. Eluted phage were neutralized with 1 M Tris-Cl pH 8.0 and amplified by passage through a bacterial host by trans complementation with helper phage M13KO7. Amplified phage were concentrated from the bacterial supernatant by precipitation by addition of 1/5 volume of PEG-8000, 2.5 M NaCl, incubation on ice for 20 minutes and centrifugation at >17,600×g for 20 minutes. Precipitated phage were resuspended in PBS containing 0.5% BSA and 0.05% Tween-20 and used for subsequent rounds of selection on adsorbed mouse, human or both antigens. After three to five rounds of selection, phage were produced from individual clones grown in a 96-well format and the culture supernatants were used in phage ELISAs to detect specific binding clones. Clones that bound to antigen but not to bovine serum albumin or to human Fc control were subjected to DNA sequence analysis. Pi1.2 Clones 2, 5, and 7 were selected and tested. These clones were found to bind to mouse and human extracellular TREM2 and not bind mouse and human extracellular TREM1 (data not shown). TREM1 (triggering receptor expressed on myeloid cells 1) has accession number NM_018643.3 as available on Sep. 25, 2015 via the NCBI website.

The antibody library was obtained from the University of Toronto. See Persson et al., CDR-H3 Diversity is Not Required for Antigen Recognition by Synthetic Antibodies. *J Mol Biol.* 2013 Feb. 22; 425(4): 803-811, herein incorporated by reference for this express purpose and all purposes. Various synthetic antibody libraries are also described in U.S. Pat. No. 7,985,840 B2, herein incorporated by reference; and various book chapters (Fellouse and Sidhu, "Making antibodies in bacteria," in: Making and Using Antibodies, Howard and Kaser, eds. Taylor and Francis, 2007, herein incorporated by reference.

LILRB4 antibodies were produced using methods similar to those described above or those described in WO2013080055, herein incorporated by reference. The clone 1 sequences are shown in Table BB.

Cell Lines and Cell Culture

MC38 cells were cultured by standard cell culture practices. Briefly, adherent cells were cultured at 37° C. with 5% $CO_2$ in DMEM plus 10% FCS with Penicillin, Streptomycin, and Glutamine on tissue culture-treated plastic plates and split every other day. EL4 suspension cells were cultured at 37° C. with 5% $CO_2$ in RPMI-1640 plus 10% FCS with Penicillin, Streptomycin, and Glutamine in tissue culture flasks and split every other day.

Mouse Tumors

All mice were maintained under SPF conditions and treated in accordance with NIH and American Association of Laboratory Animal Care standards, and consistent with IACUC UCSF protocols.

Tumor cell lines were harvested and washed 3 times with PBS, and injected at a final injection volume of 50 ul. One hundred fifty thousand tumor cells were injected subcutaneously in the right shaved flank and allowed to grow for 14-21 days in 6-8 weeks old C57BL/6 male mice.

Tumor Growth

For tumor growth curves, tumors were measured with electronic calipers as tumor width×tumor height, over the indicated time periods and tumor volume ($mm^3$) was calculated as V=(L×W×W)/2.

Antibody Treatment

Purified anti-PD-1 (clone RMPI-14) purchased from BioXcell, human IgG1 Fc (purchased form BioXcell), or in house produced antibody clones were injected IP at 200 ug over four treatments at days 5, 8 and 11 and 14 of tumor growth with the exception of anti-TREM2 (Pi1.2) (clone 2) which was injected at 40, 20, 20 and 40 ug on the respective days.

Transducant Generation

Cell lines were generated by lentiviral transduction using GeneCopoeia lentiviral vectors and LentiPack HIV Packaging Systems. Following manufactures instructions, infected cell lines were cultured in a selectable antibiotic (Puromycin) as well as sorted for expression of target protein by FACS.

Dye Labeling of Cells

Cells were incubated in RPMI without FCS with 0.5 uM eFluor670 (eBioscience) or 0.5 uM CMTMR (Thermo) for 15 minutes at 37° C. Dyes were then quenched with 2 ml FCS and washed in RPMI 10% FCS 3 times before use.

Intraperitoneal Depletion Assay $2 \times 10^{6}$ dye labeled cells each of parental and target expressing transducant cell line were injected IP into WT B6 male mice. After four hours, animals were injected with 500 ug of depleting or control antibodies. After 24-36 hours, transferred cells were recovered by peritoneal lavage, and enumerated by flow cytometry.

Statistical Analysis

Statistical analyses were performed using GraphPad Prism software. Unless specifically noted, all data are representative of >3 independent experiments. Error bars represent S.E.M. calculated using Prism, and are derived from triplicate experimental conditions. Specific statistical tests used were paired and unpaired T tests and all p values <0.05 were considered statistically significant.

Example 13: Presence of NSMs and SDCs in Multiple Human Tumors

Figure 13A:
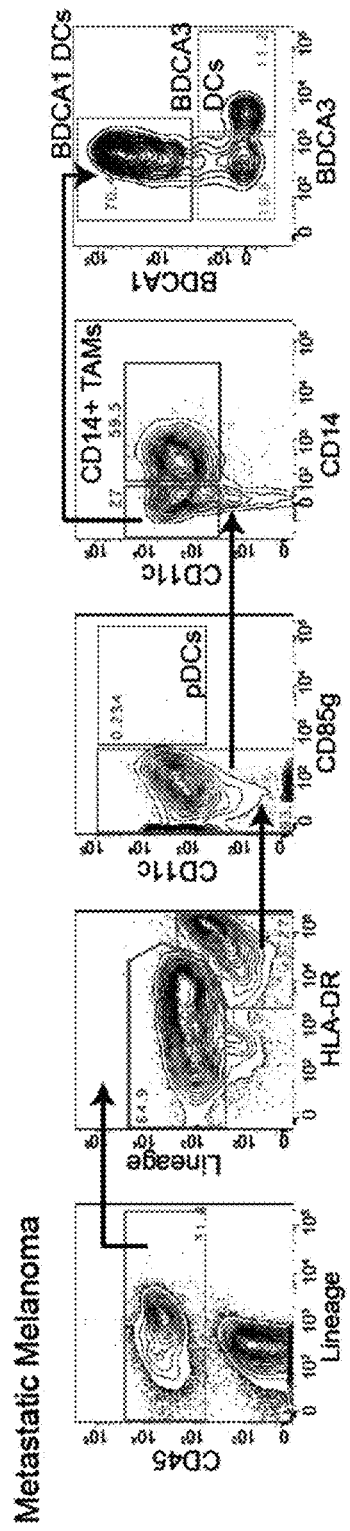
FIG. 13A, B, C shows that progressive gating identified both the NSM population and the SDC populations in all displayed human tumor types, as analyzed by flow cytometry (metastatic melanoma, head and neck squamous cell carcinoma (HNSC), and colon carcinoma).
Figure 13B:
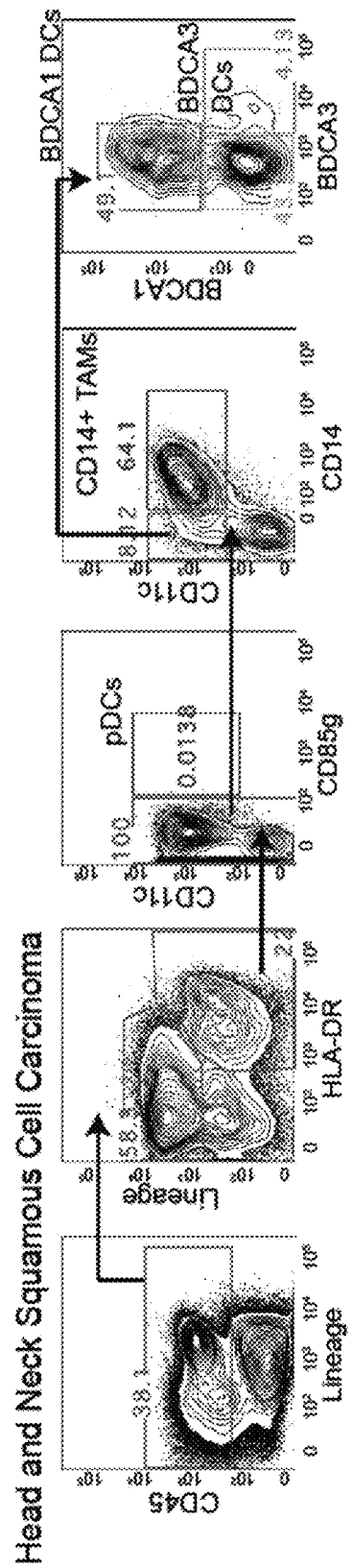
Figure 13C:
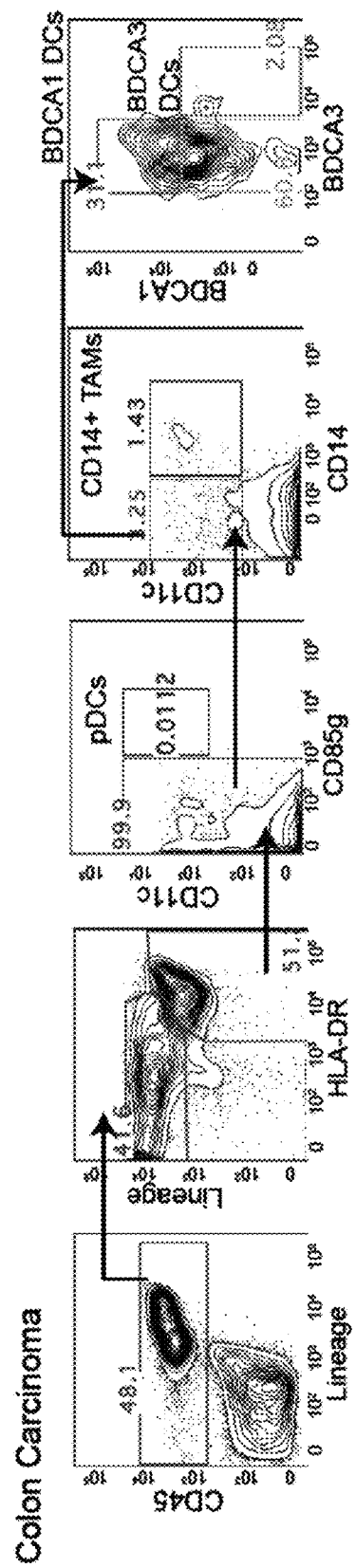

It was next determined whether NSMs and SDCs exist across multiple different human tumor types. Human tumor tissue biopsies from metastatic melanoma, head and neck squamous cell carcinoma (HNSC), and colon carcinoma were analyzed by flow cytometry for the presence of SDC and NSM populations. Representative flow plots show that progressive gating identified both the NSM population and the SDC population in all displayed human tumor types (metastatic melanoma, head and neck squamous cell carcinoma (HNSC), and colon carcinoma). See FIG. 13.

Example 14: NSM Protein Expression and Binding in Mouse Tumor

It was next determined whether certain NSM proteins are expressed on the cell surface of NSMs and whether those NSM proteins can be bound by anti-NSM antibodies. It was also determined whether certain NSM proteins are expressed on SDCs.

Figure 14A:
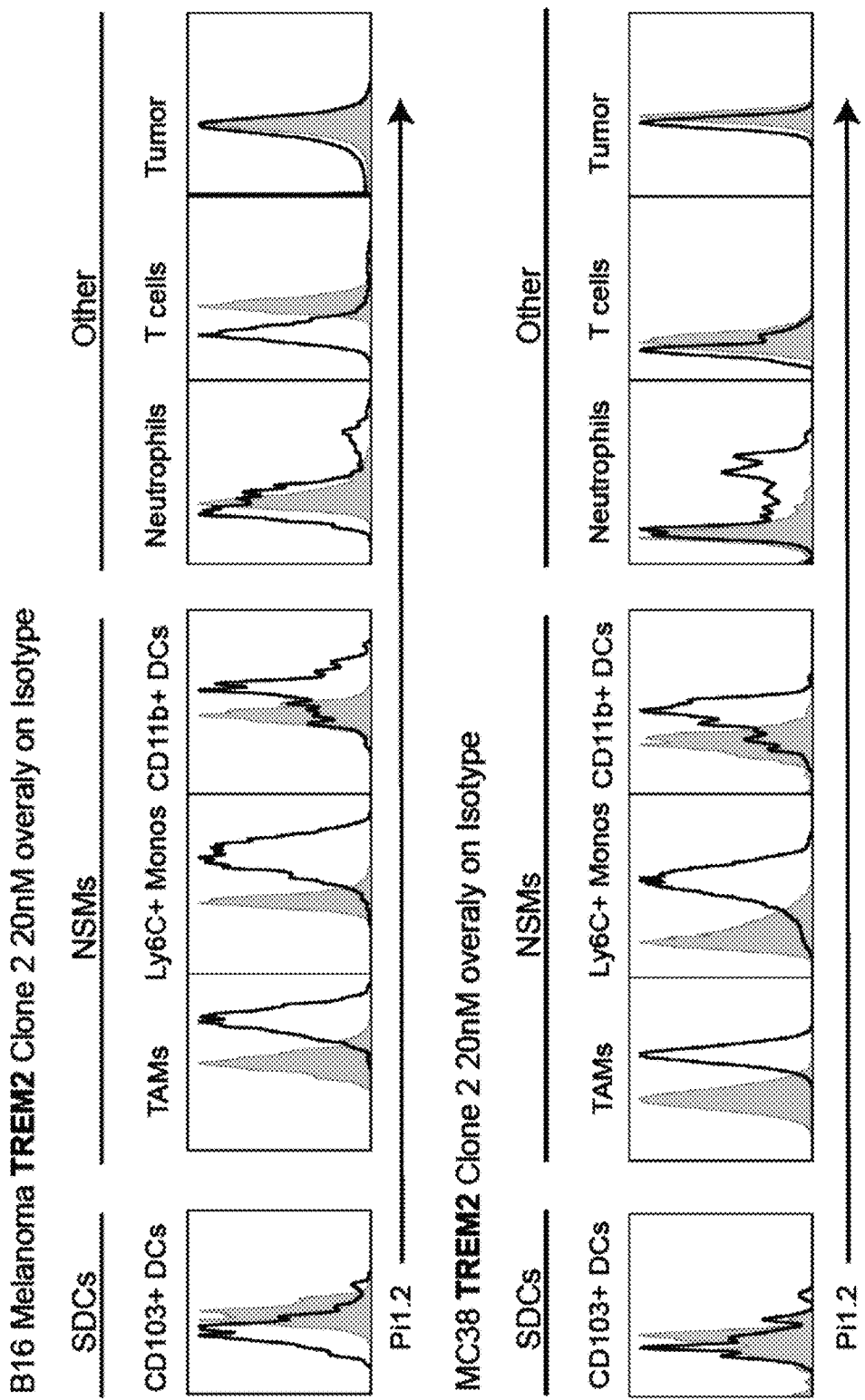
FIG. 14A, B, C shows labeling of the indicated cell subsets in the tumor microenvironment with various NSM markers including TREM2, across the B16-F10 and MC38 ectopic mouse tumor models, as well as MS467, LILRB4 and CD88 staining as analyzed by flow cytometry. Staining patterns for all NSM markers reveal high specificity for NSM populations (TAMs, Ly6C+ monocytes, CD11b+ DCs) without staining the SDCs (CD103+ DCs). Populations previously gated as in FIG. 1A, B gating strategy. The secondary control for each population is in shaded grey while the staining for NSM markers is over-laid by a solid black histogram for each population.
Figure 14B:
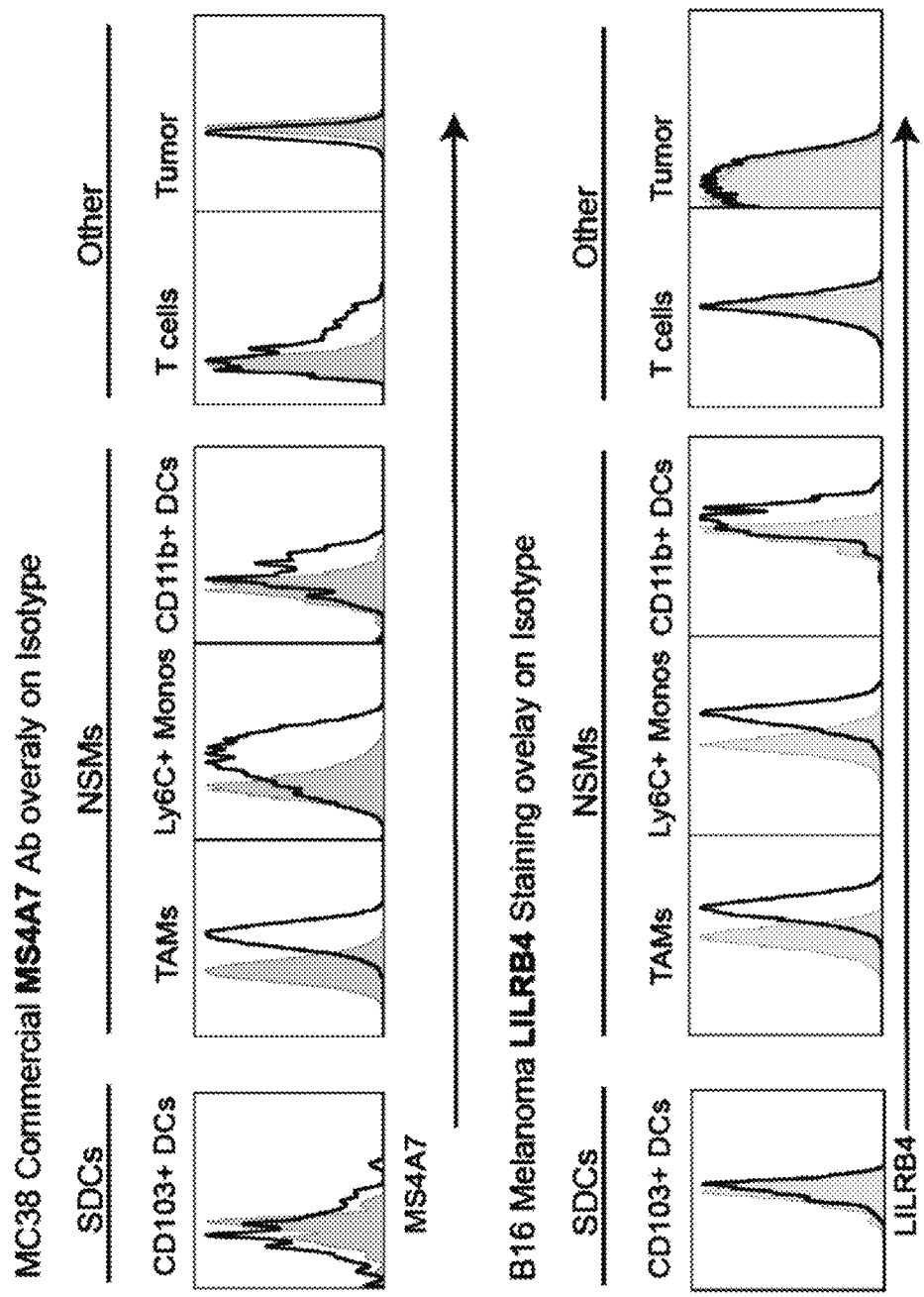
Figure 14C:
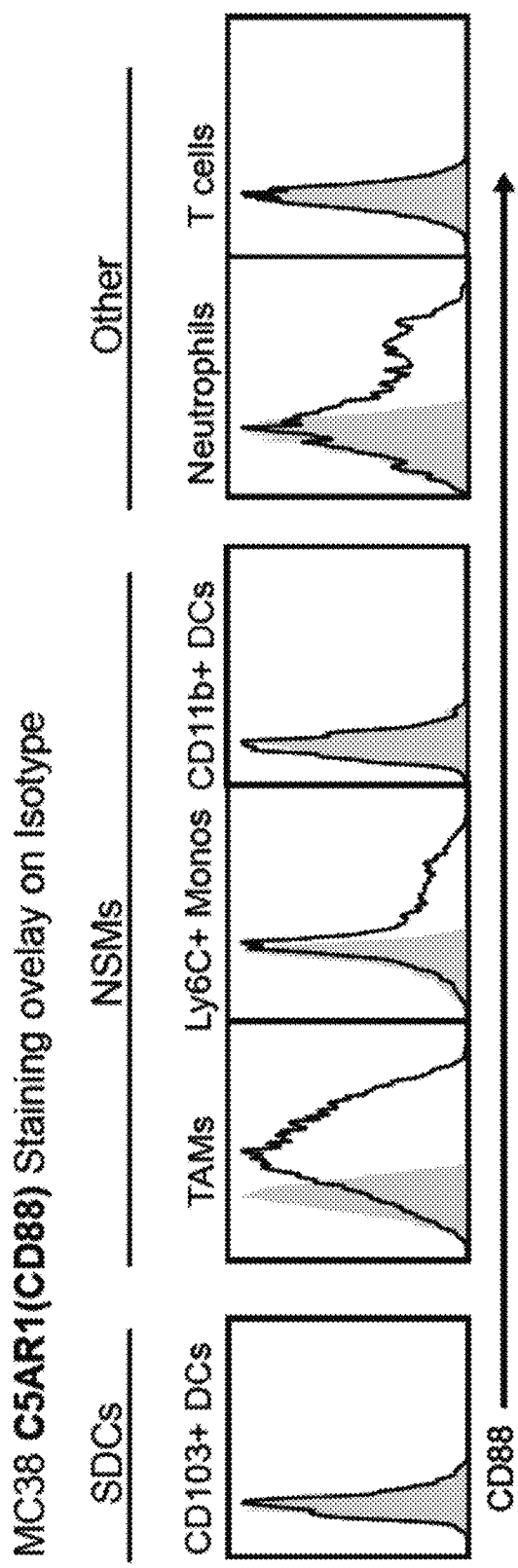

Mouse tumors were stained with NSM markers to demonstrate specificity of these markers for NSM but not SDC or other cell types or subsets. FIG. 14 shows labeling of the indicated cell subsets with various NSM markers, gating within the indicated cell subsets. Staining for the indicated markers is shown in the black histograms while staining control isotypes are shown by the gray shaded histograms. Top row: B16 melanoma stained with anti TREM2 (Pi1.2 clone 2); Second row: MC38 stained with anti TREM2 (Pi1.2 clone 2); Third row: MC38 stained with anti-MS4A7 (commercial polyclonal antibody, purchased from Human Protein Atlas, product code: HPA017418); Fourth row: B16 stained with anti-LILRB4 (Pi1.5 Clone 1); Fifth row: MC38 stained with anti-C5AR1. The data shows strong binding to inflammatory DCs, Ly6c+ monocytes and TAMs, and significant binding to the CD11b+ DCs. Little to no staining was observed on CD103+DC, T cells, B cells, and tumor cells.

Binding of a given NSM protein by an anti-NSM antibody directed against the given NSM protein indicates that NSMs will be depleted or killed via known antibody-based depletion mechanisms, e.g., by choosing an appropriate Fc domain to allow ADCC.

Example 15: CCR7 Expression in Human SDC and NSM Cells

Figure 15:
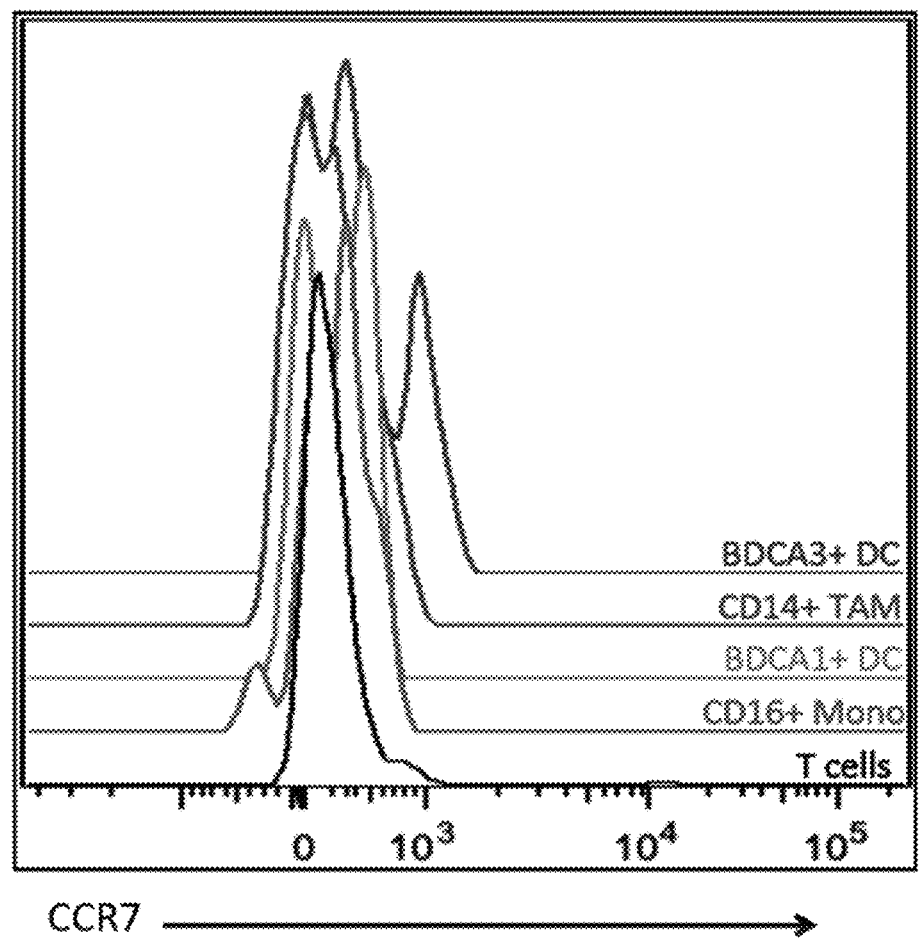
FIG. 15 shows CCR7 expression on human SDCs. Populations previously gated as in FIG. 13 gating strategy.

Specific expression of CCR7 on SDC and NSM populations, respectively, in digested tumor tissue was analyzed by flow cytometry. All data is from human metastatic melanoma cells. FIG. 15 shows specific expression on human SDCs of CCR7 relative to NSMs and other immune cells.

Example 16: SDC Protein Expression and Binding in Tumor

It was next determined whether certain SDC proteins are expressed on the cell surface of SDCs and whether those SDC proteins can be bound by anti-SDC antibodies. It was also determined whether certain SDC proteins are expressed on NSMs.

Figure 16:
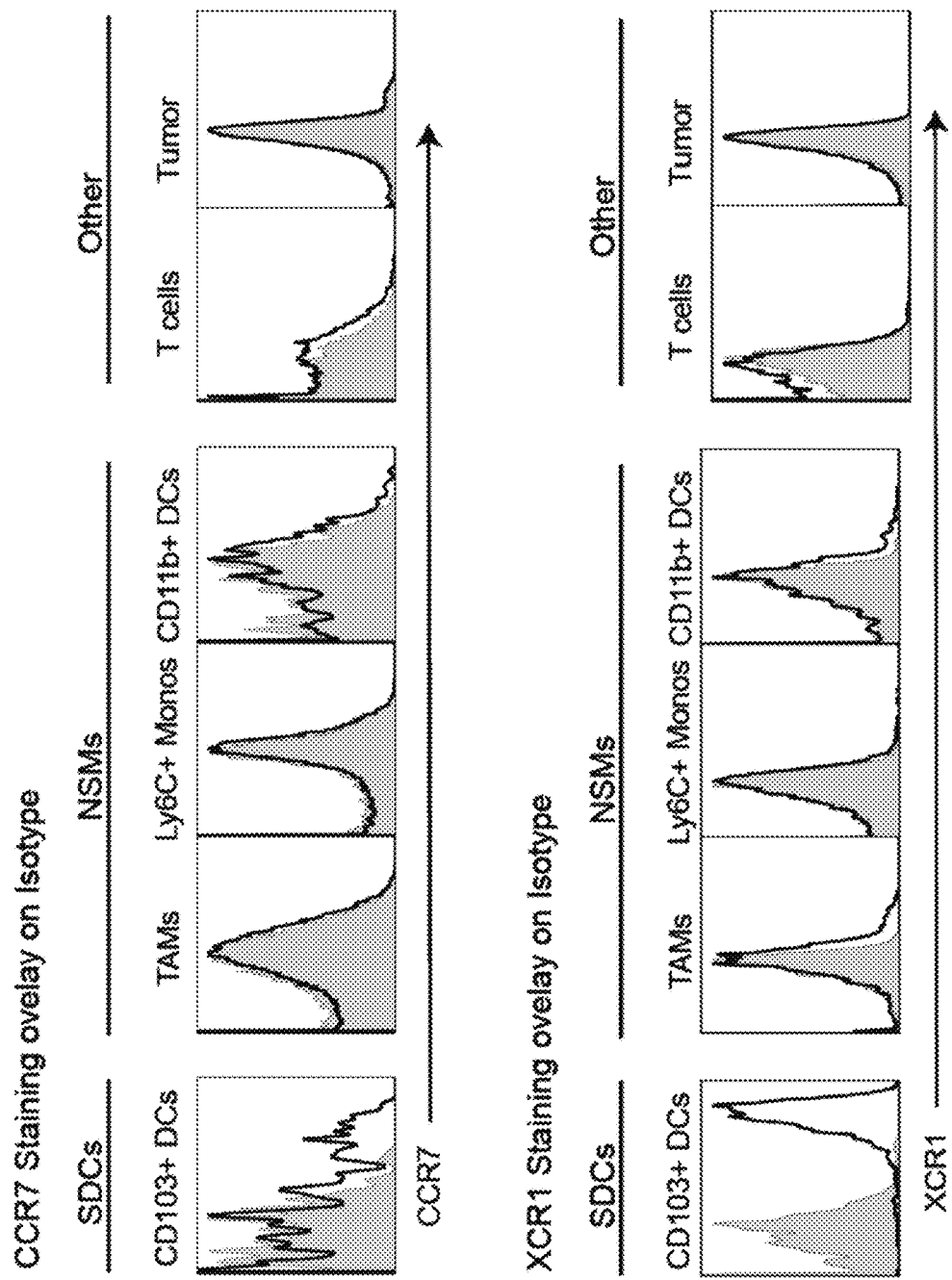
FIG. 16 shows specific expression of SDC gene products, CCR7 and XCR1 on SDC (CD103+ DCs) and the lack of SDC protein expression on NSMs (TAMs, Ly6C+ monocytes, CD11b+ DCs) in the tumor microenvironment of mouse ectopic B16-F10 tumors. Populations previously gated as in FIG. 1A, B gating strategy. The secondary control for each population is in shaded grey while the staining for SDC markers is over-laid by a solid black histogram for each population.

Specific expression of SDC and NSM Gene Products on SDC and NSM populations, respectively, in digested tumor tissue was analyzed by flow cytometry. All data is from the ectopic B78chOVA tumor model. Expression of SDC markers (CCR7 and XCR1; black line) compared to the respective isotype (grey shaded) across populations of cells in tumors. FIG. 16 shows specific expression of SDC gene products on SDC and the lack of SDC protein expression on NSMs.

Example 17: Absence of NSM Binding Outside of Tumor

Healthy wild type B6 mouse Bone Marrow (BM) and Spleens were analyzed by Flow cytometry for expression of TREM2 (clone 237920, RnD), and MS4A7 (Commercial Polyclonal, Human Protein Atlas).

Representative histograms show the levels of TREM2 and MS4A7 staining across several healthy tissue populations. The secondary control (anti-Rat-A488 and anti-Rabbit-A488, respectively from Jackson Immunoresearch) for each population is in shaded gray while the staining for target proteins is over-laid by a solid black line histogram for each population.

Healthy wild type B6 mouse Bone Marrow (BM) and Spleens were analyzed by Flow cytometry for expression of TREM2 (Pi1.2 Clone 2, Clone 5 and Clone 7) by antibody staining across a range of staining concentrations (2, 20, 200 nM), compared to control (human IgG1 Fc, labeled as 0 nM) across immune populations.

Figure 17A:
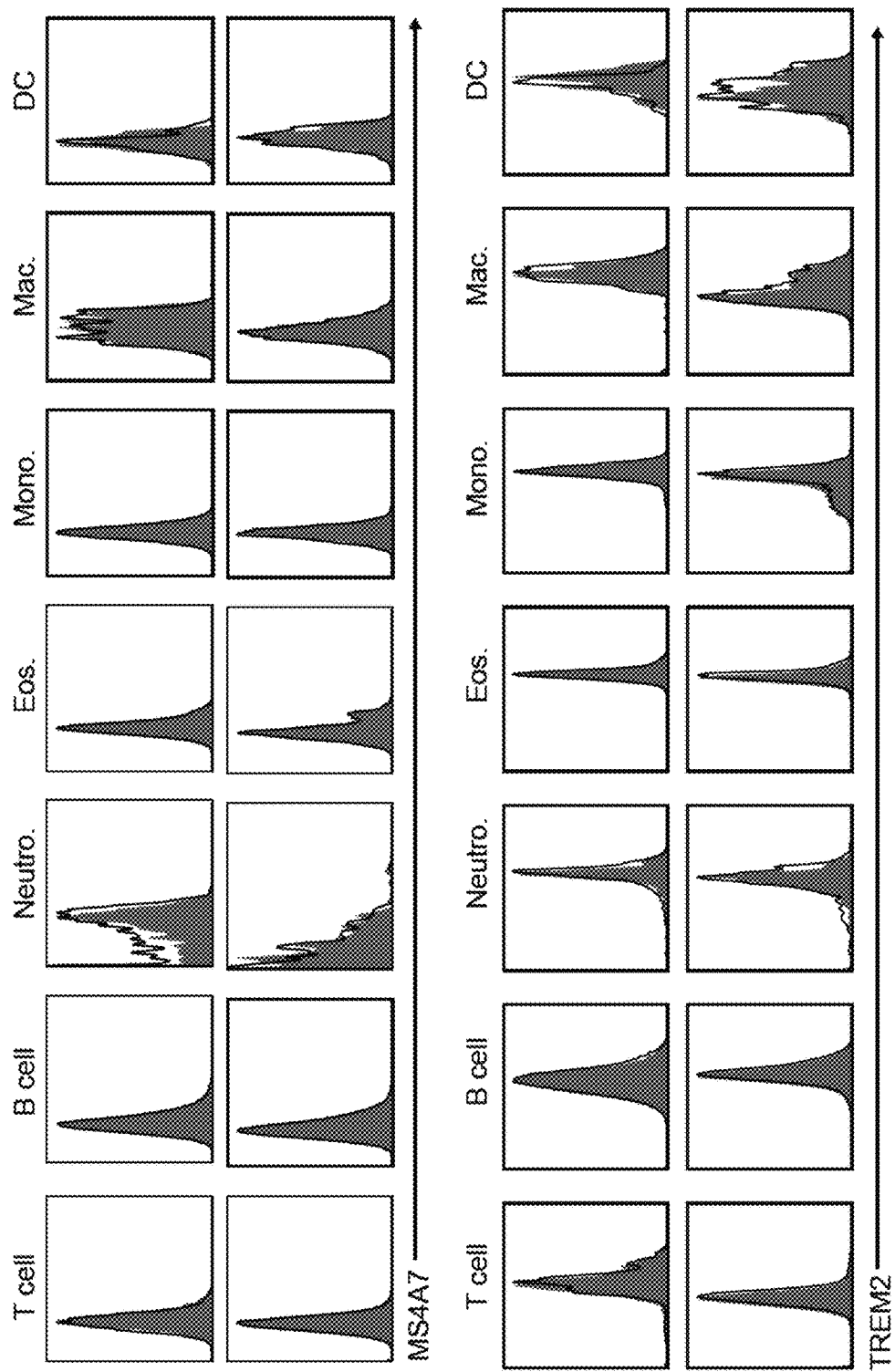
FIG. 17A, B, C shows the absence of staining for NSM markers, MS4A7 and TREM2 in healthy BM and spleen tissues from wild type C57BL/6 male mice as analyzed by flow cytometry. Populations previously gated as in FIG. 1A, B gating strategy. The secondary control for each population is in shaded gray while the staining for MS4A7 and TREM2 is over-laid by a solid black histogram for each population (top figure). Bottom half of the figure shows specific lack of staining in healthy BM and splenic mouse tissue with titered concentrations (0 nM, 2 nM, 20 nM and 200 nM) of aTREM2 antibody clones 2, 5 and 7 across immune populations.
Figure 17B:
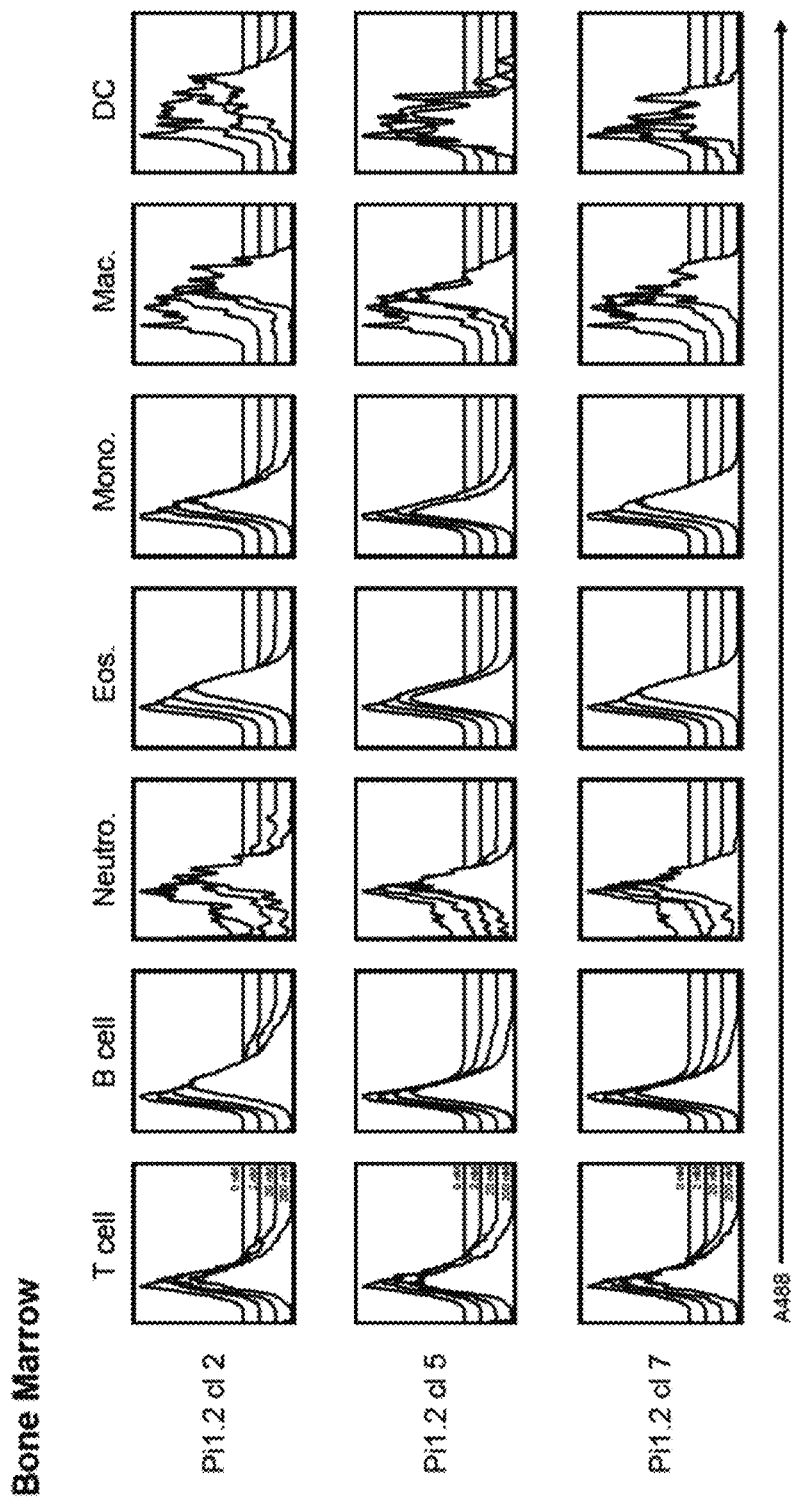
Figure 17C:
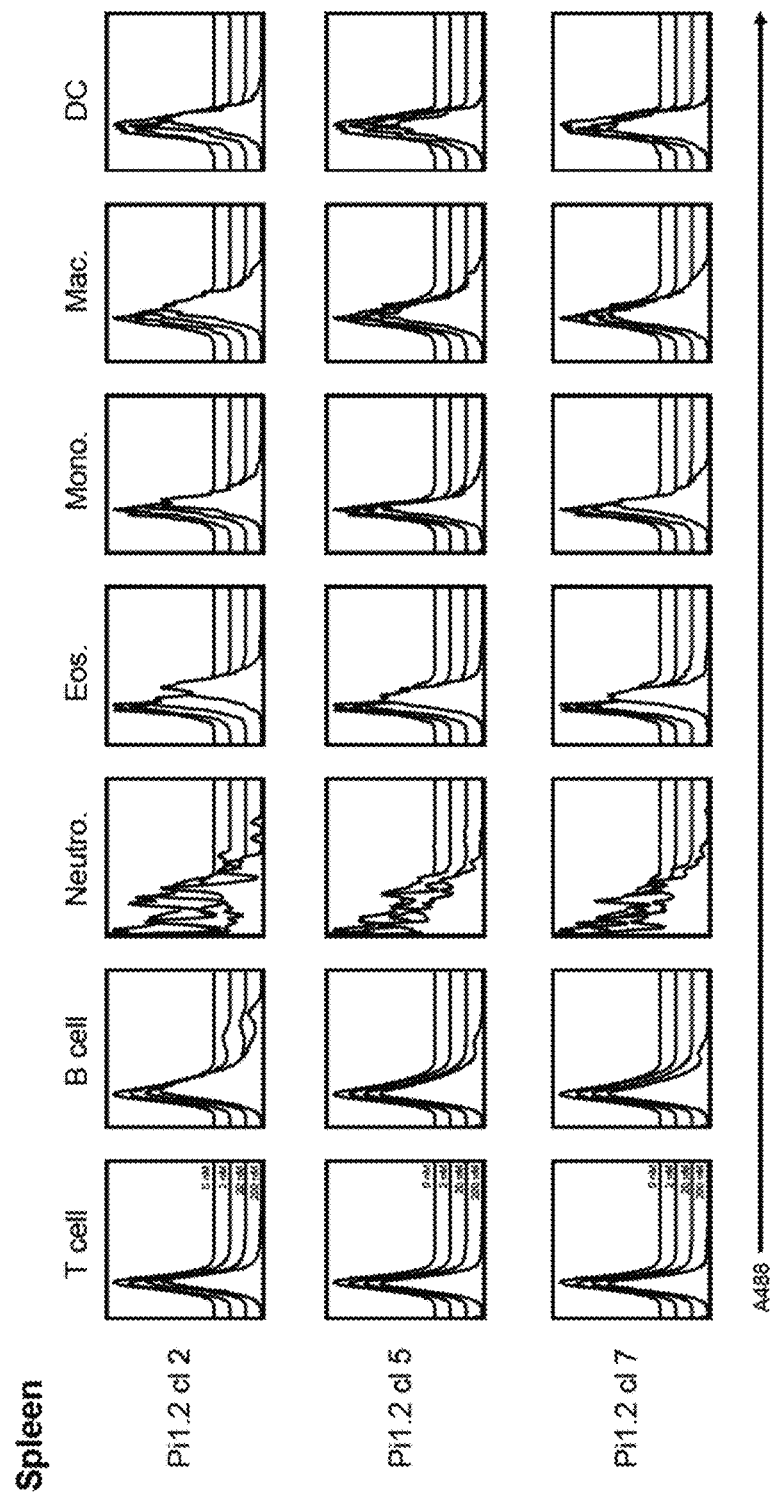

FIG. 17 shows the absence of substantial staining for multiple NSM markers in healthy BM and spleen tissues. This suggests that use of anti-NSM antibodies is unlikely to have significant off-target effects, e.g., during tumor treatment.

Example 18: NSM Depletion in Tumor Using Anti-TREM2 or Anti-LILRB4 Antibodies It was next determined whether anti-NSM antibodies can specifically deplete NSM bearing cells in vivo.

Figure 18A:
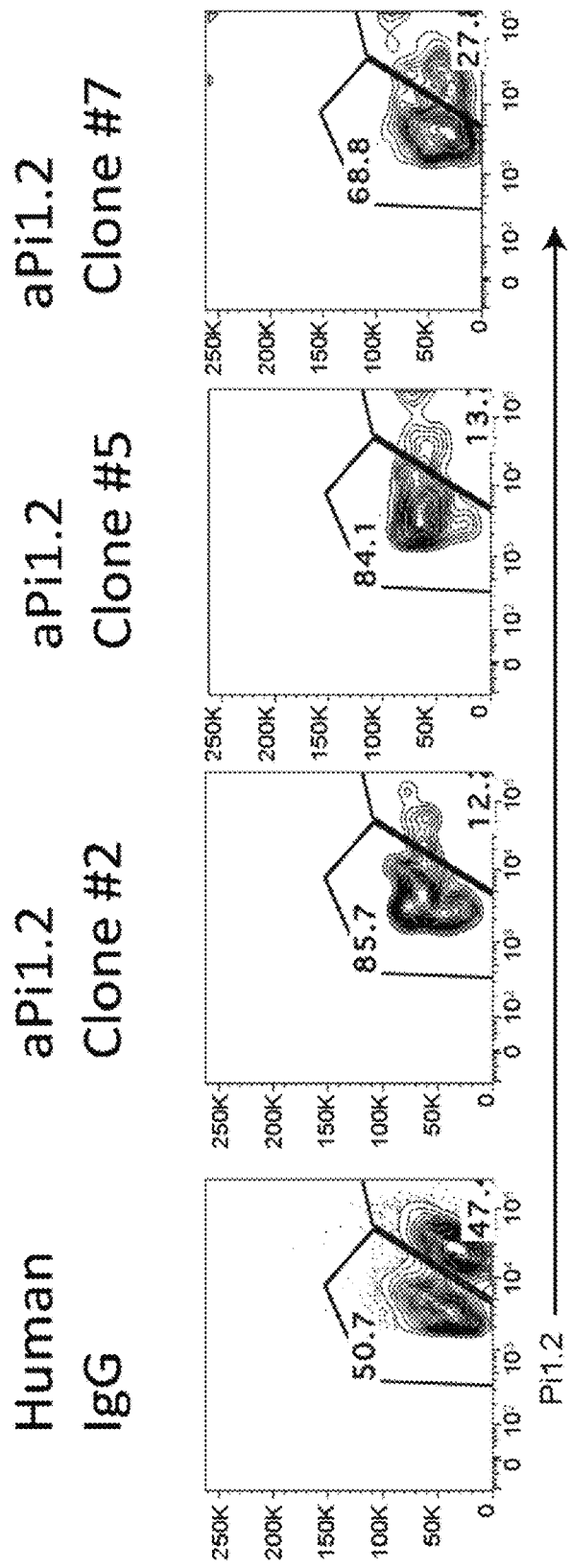
FIG. 18A, B, C shows that anti-TREM2 and anti-LILRB4 antibodies specifically deplete TREM2 and LILRB4 bearing cells in vivo, respectively. Control and TREM2 or LILRB4 expressing EL4 transfectants cells were mixed at a 1:1 ratio and injected IP into WT B6 male mice. Three hours later animals were injected with (anti-TREM2 or anti-LILRB4) antibody or control Human IgG1 or PBS. After 36 hours, mice were sacrificed and the recovered cells from the peritoneum, harvested by peritoneal lavage, were enumerated by flow cytometry.
Figure 18C:
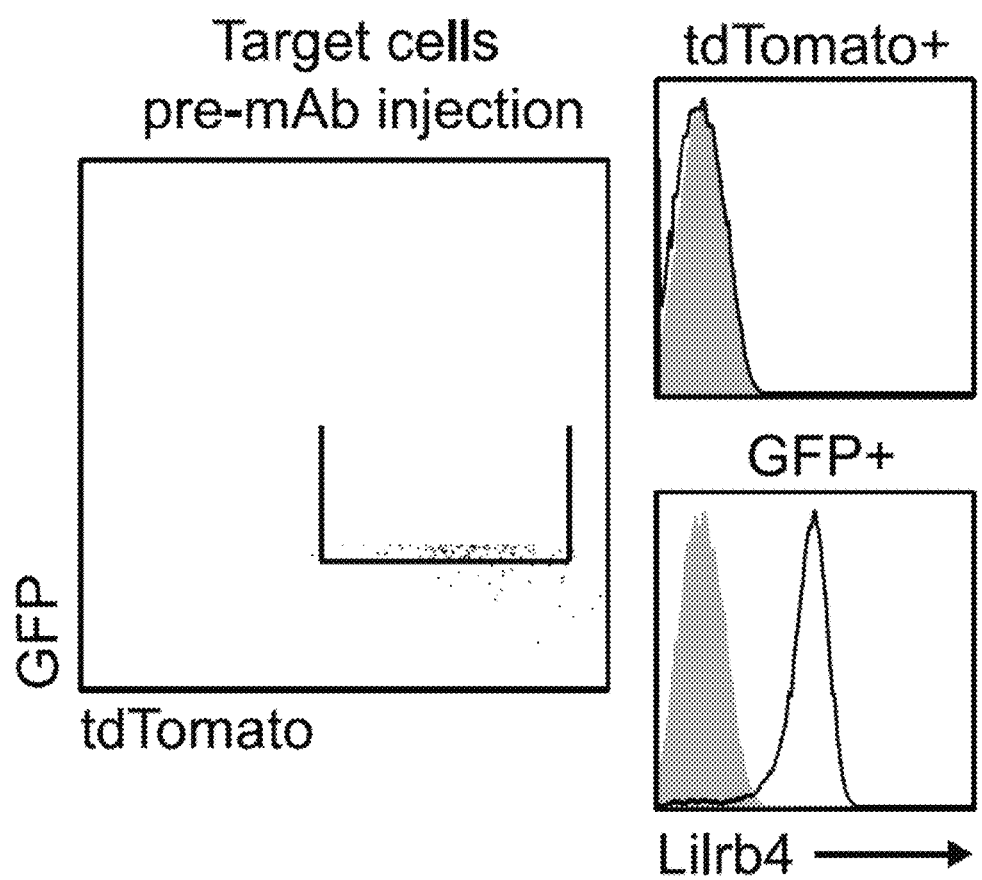

TREM2: Control and TREM2 (TREM2 can also be referred to as Pi1.2) expressing EL4 transfectants cells were dye labeled with CMTMR and Elfour670 respectively and mixed at a 1:1 ratio. 4×10^6 total cell mixtures were the injected IP into WT B6 male mice. 4 hours later animals were injected with 500 ug of anti-Pi1.2 (anti-TREM2) antibody or control Human IgG1. After 36 hours, mice were sacrificed and the recovered cells from the peritoneum, harvested by peritoneal lavage, and were enumerated by flow cytometry. FIG. 18 shows that anti-TREM2 antibodies specifically deplete TREM2 bearing cells in vivo while control antibody does not.

LILRB4 (ILT3): Control and LILRB4 expressing EL4 transfectants cells expressing TdTomato and GFP, respectively were mixed at a 1:1 ratio with 5×10^5 of each cell type and injected IP into WT B6 male mice. Two hours later animals were injected with 100 ug of anti-LILRB4 Clone 1 or PBS control. After 24 hours, mice were sacrificed and the recovered cells from the peritoneum, harvested by peritoneal lavage were enumerated by flow cytometry. FIG. 18 shows that anti-LILRB4 antibodies specifically deplete LILRB4 bearing cells in vivo.

Depletion of NSM by an anti-NSM antibody directed against a given NSM protein indicates that anti-NSM antibody will reduce tumor growth upon administration to a subject having a tumor.

Example 19: Reduced Tumor Growth Following Administration of Anti-TREM2 Antibodies It was next determined whether anti-NSM antibodies can reduce tumor growth in vivo.

Figure 19:
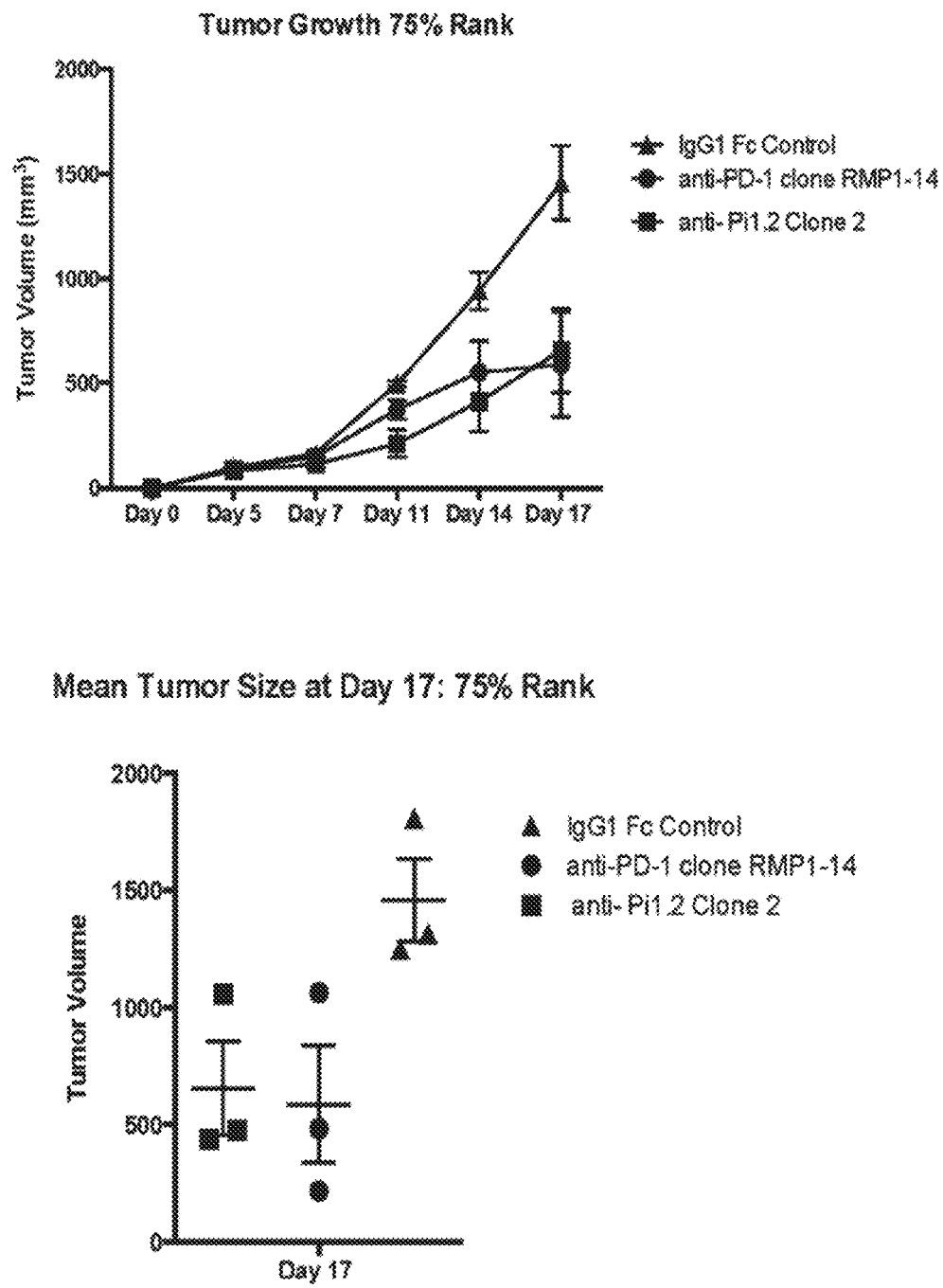
FIG. 19 indicates that anti-NSM antibodies reduce tumor growth relative to control, to the same extent as an anti-PD-1 therapy. MC38 colon carcinomas were injected into B6 6 week old male mice. Mice, randomized into treatment groups, were treated with the indicated antibodies on day 5, 7, 11, 15 by IP injection. Shown is the 75% rank (dropping the top outlier and plotting the bottom 3 out of 4 mice). Dosing: 200 ug/day for PD-1 and the Fc control, 40 ug, 20 ug, 20 ug and 40 ug injections were made for antiPi1.2 (aTREM2) antibody on days 5, 7, 11, and 15. Tumors were measured by caliper and tumor volume is shown.

MC38 colon carcinomas were injected into B6 6-week old male mice at T0. Mice, randomized into treatment groups, were treated with the indicated antibodies on day 5, 7, 11, 15 by IP injection following tumor implant. Dosing: 200 ug/day for anti-PD-1 and the Fc control, 40 ug, 20 ug, 20 ug and 40 ug injections were made for anti TREM2 (Pi1.2 Clone 2) antibody on days 5, 7, 11, and 15. Tumors were measured by caliper and tumor volume is shown. The top outlier was removed from each of the TREM2 and PD-1 groups for data analysis. FIG. 19 indicates that anti-NSM antibodies reduce tumor growth relative to control, to the same extent as an anti-PD-1 therapy.

Example 20: NSM Depletion in Tumor Using Anti-NSM Antibodies

Control and NSM protein expressing EL4 transfectants cells expressing TdTomato and GFP, respectively are mixed at a 1:1 ratio, e.g., with 5×10^5 of each cell type, and are injected IP into WT B6 male mice. Two hours later animals are injected with anti-NSM antibody (e.g., 100 ug), Fc control, or PBS control. After 24 hours, mice are sacrificed and the recovered cells from the peritoneum, harvested by peritoneal lavage are enumerated by flow cytometry. Anti-NSM antibodies specifically deplete NSM protein bearing cells in vivo. Anti-NSM antibodies bind TREM2, MS4A7, C5AR1, LYVE1, ABCC3, LILRB4, MRC1/CD206, SIGLEC1, STAB1, TMEM37, MERTK, and/or TMEM119. NSM proteins are selected from TREM2, MS4A7, C5AR1, LYVE1, ABCC3, LILRB4, MRC1/CD206, SIGLEC1, STAB1, TMEM37, MERTK, and TMEM119.

Example 21: Reduced Tumor Growth Following Administration of Anti-NSM Antibodies Cancer cells (e.g., MC38 colon carcinoma) are injected into B6 6 week old male mice at T0. Mice, randomized into treatment groups, are treated with Fc control or anti-NSM antibody on multiple days (e.g., day 5, 7, 11, 15) by IP injection following tumor implant. Dosing is determined, e.g., 200 ug/day for Fc control; 40 ug, 20 ug, 20 ug and 40 ug for anti NSM antibody on each day (e.g., days 5, 7, 11, and 15). Tumors are measured by caliper and tumor volume is determined. Anti-NSM antibodies reduce tumor growth relative to control. Anti-NSM antibodies enhance an immune response to the tumor in the experimental mice relative to control. Anti-NSM antibodies bind TREM2, MS4A7, C5AR1, LYVE1, ABCC3, LILRB4, MRC1/CD206, SIGLEC1, STAB1, TMEM37, MERTK, and/or TMEM119.

Example 22: Enhancement of Immunotherapy Via Co-Administration of Anti-NSM Antibodies Cancer cells (e.g., MC38 colon carcinoma) are injected into B6 6 week old male mice at T0. Mice, randomized into treatment groups, are treated with Fc control or anti-NSM antibody on multiple days (e.g., day 5, 7, 11, 15) by IP injection following tumor implant. The mice have previously received, concurrently receive, or will subsequently receive an immunotherapy. Immunotherapies can include an immunotherapy that inhibits a checkpoint inhibitor; an immunotherapy that inhibits a checkpoint inhibitor of T cells; anti-PD1; anti-PDL1; anti-CTLA4; adoptive T cell therapy; CAR-T cell therapy; a dendritic cell vaccine; a monocyte vaccine; an antigen binding protein that binds both a T cell and an antigen presenting cell; a BiTE antigen binding protein; a toll-like receipt ligand; and/or a cytokine. Dosing is determined using information available in the art and ordinary skill, e.g., 200 ug/day for Fc control; 40 ug, 20 ug, 20 ug and 40 ug for anti NSM antibody on each day (e.g., days 5, 7, 11, and 15). Tumors are measured by caliper and tumor volume is determined. Co-administration of anti-NSM antibodies with immunotherapy enhances reduction in tumor growth relative to non-co-administration control (e.g., monotherapy). Co-administration of anti-NSM antibodies with immunotherapy enhances an immune response to the tumor relative to non-co-administration control (e.g., monotherapy). Anti-NSM antibodies bind TREM2, MS4A7, C5AR1, LYVE1, ABCC3, LILRB4, MRC1/CD206, SIGLEC1, STAB1, TMEM37, MERTK, and/or TMEM119.

Example 23: SDC Threshold Analysis in Immunotherapy Responders Vs. Non-Responders It was next determined what SDC percent threshold value is statistically indicative of responder vs. non-responder status prior to initiation of immunotherapy in subjects having cancer via ROC curve.

The ROC curve used the data for % BDCA3 as a fraction of CD45+ or % BDCA3 as a fraction of HLA-DR+ taken from human melanoma patients prior to treatment with anti-PD-1. It plots the performance of the responder/non-responder binary system as the % BDCA3+ values are varied. The curve is created by plotting the true positive rate (TPR) against the false positive rate (FPR) at the optimal threshold settings. The true-positive rate is also known as sensitivity in signal detection. The false-positive rate is also known as the fall-out and can be calculated as (1−specificity). Large areas under the curve indicate a threshold value with high sensitivity versus specificity and thus high predictive value.

Figure 20A:
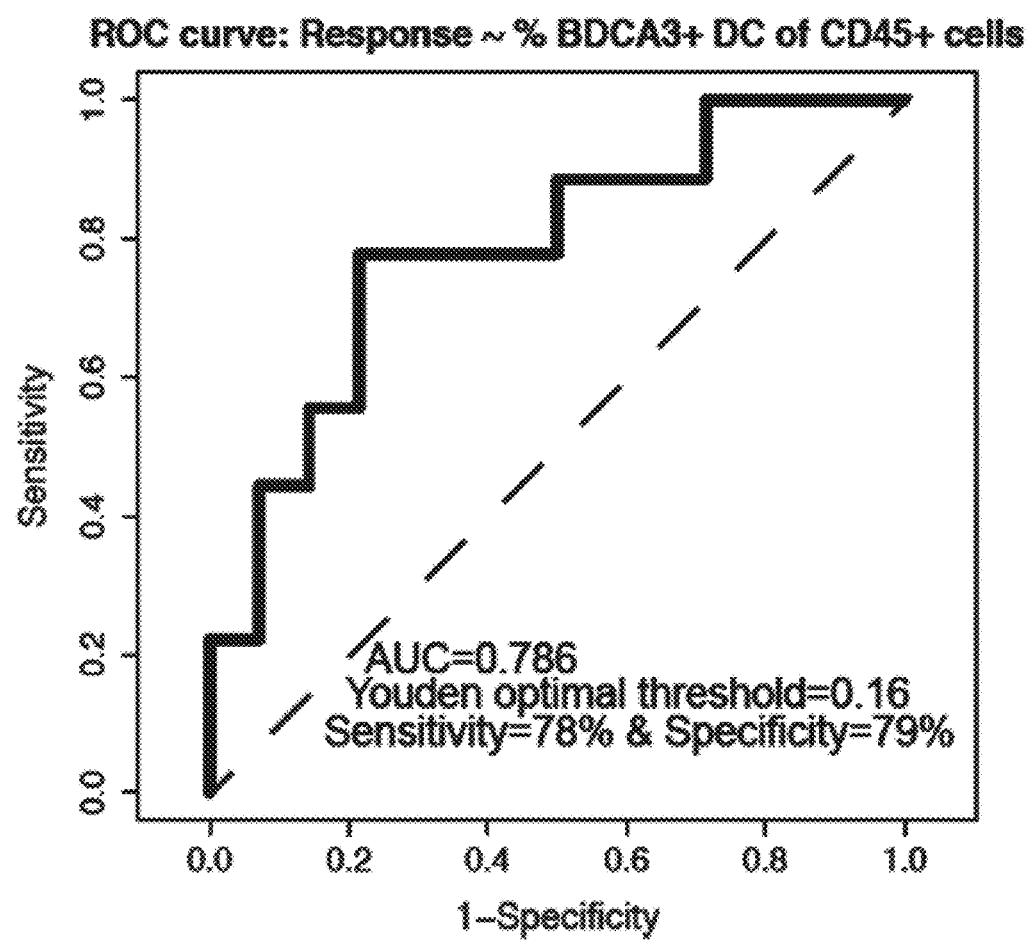
FIG. 20 shows Receiver Operating Characteristic (ROC) analysis of BDCA3+ in Human Melanoma. Staining data for % BDCA3 and anti-PD1 outcome data was used to perform (FIG. 20A) ROC analysis of BDCA3+ versus CD45+ ratio versus outcome.
(FIG. 20B) ROC analysis of BDCA3+ versus HLA-DR+ ratio versus outcome.
Figure 20B:
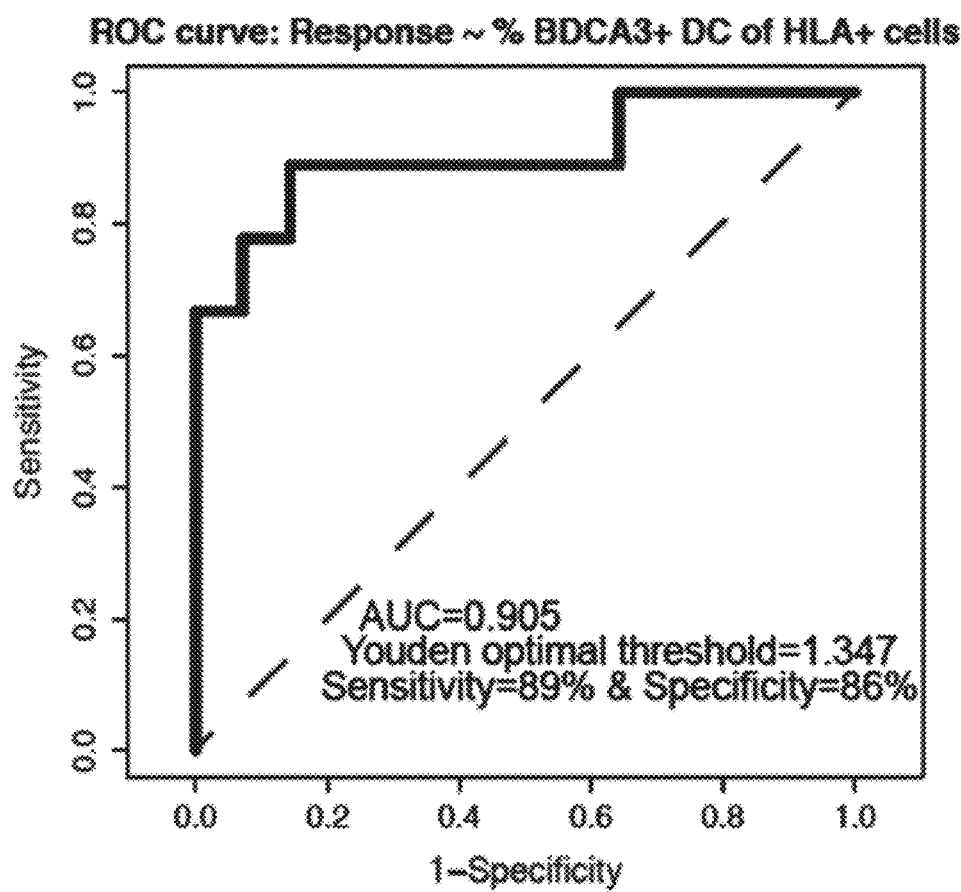

Further validation of BDCA3 as a predictor was obtained using the DeLong method as implemented by the pROC software package in R. For the percentage DC/HLA+, 95% CI of AUC is estimated to be [0.76-1] (AUC=0.905 [0.76-1]). Using the bootstrap method, with 2000 stratified bootstrapped replicates, the CI=[0.73-1] (AUC=0.905 [0.73-1]). For the pct/CD45+, the DeLong estimate is 95% CI:[0.59-0.98] (AUC=0.786 [0.59-0.98]), and the bootstrap [0.57-0.95] (AUC=0.786 [0.57-0.95]). FIG. 20 shows (A) ROC analysis of BDCA3$^+$ versus CD45$^+$ ratio versus outcome; and (B) ROC analysis of BDCA3$^+$ versus HLA-DR$^+$ ratio versus outcome.

This shows that using a threshold BDCA3+/HLADR+ percentage of 1.347% is one for which: the probability of a BDCA3+ high result given that the patient is a responder is 89% (so-called sensitivity) and probability of a BDCA3+ low result given that the patient is a non-responder is 86% (so-called specificity). This indicates that increasing the percentage of SDCs in the tumor to about 1.347% or greater among HLA-DR+ cells in the tumor is likely to result in an increase in response to cancer immunotherapy, previously administered, ongoing, upcoming, or otherwise. Such an increase can be achieved, e.g., by increasing SDC number (e.g., via use of FLT3L) and/or decreasing NSM number (e.g., via use of anti-NSM antibodies).

Example 24: Enhancement of SDC Populations in the Tumor with FLT3-L Treatments Cancer cells (e.g., MC38 colon carcinoma) are injected into B6 6 week old male mice at T0. Mice, randomized into treatment groups, are treated with injections of FLT3-L or PBS control on multiple days (e.g., day 5, 7, 11, 15) by I.P., I.V. and/or S.C. injection following tumor implant. Dosing is determined using information available in the art and ordinary skill (e.g., 10 ug in 100 ul of PBS). At multiple time points throughout tumor growth animals are scarified and SDC and NSM abundance is analyzed by flow cytometry. FLT3-L treatment through tumor development enhances SDC abundance in the tumor.

Examples 25: Reduced Tumor Growth Following Treatments with FLT3-L Due to Increased SDC Populations Cancer cells (e.g., MC38 colon carcinoma) are injected into B6 6 week old male mice at T0. Mice, randomized into treatment groups, are treated with injections of FLT3-L or PBS control on multiple days (e.g., day 5, 7, 11, 15) by I.P., I.V. and or S.C. injection following tumor implant. Dosing is determined using information available in the art and ordinary skill (e.g., 10 ug in 100 ul of PBS) Tumors are measured by caliper and tumor volume is determined. FLT3-L treatment reduces in tumor growth relative to control. FLT3-L treatment enhances SDC abundance in the tumor, as well as SDC populations in the dLN, Spleen and bone marrow (BM). FLT3-L enhances an immune response to the tumor in the experimental mice relative to control.

Example 26: Enhancement of Immunotherapy Via Co-Administration with FLT3-L

Cancer cells (e.g., MC38 colon carcinoma) are injected into B6 6 week old male mice at T0. Mice, randomized into treatment groups, are treated with injections of FLT3-L or PBS control on multiple days (e.g., day 5, 7, 11, 15) by I.P., I.V. and or S.C. injection following tumor implant. The mice have previously received, concurrently receive, or will subsequently receive an immunotherapy. Immunotherapies can include an immunotherapy that inhibits a checkpoint inhibitor; an immunotherapy that inhibits a checkpoint inhibitor of T cells; anti-PD1; anti-PDL1; anti-CTLA4; adoptive T cell therapy; CAR-T cell therapy; a dendritic cell vaccine; a monocyte vaccine; an antigen binding protein that binds both a T cell and an antigen presenting cell; a BiTE antigen binding protein; a toll-like receipt ligand; and/or a cytokine. Dosing is determined using information available in the art and ordinary skill (e.g., 10 ug in 100 ul of PBS) Tumors are measured by caliper and tumor volume is determined. Co-administration of FLT3-L with immunotherapy enhances reduction in tumor growth relative to non-co-administration control (e.g., monotherapy). Co-administration FLT3-L with immunotherapy enhances an immune response to the tumor relative to non-co-administration control (e.g., monotherapy). See also Curran et al., Lynch et al., Chen et al., Peron et al., and Shurin et al.

Example 27: SDC Targeted Stimulation Through Agonist Anti-FLT3 Antibodies

Cancer cells (e.g., MC38 colon carcinoma) are injected into B6 6 week old male mice at T0. Mice, randomized into treatment groups, are treated with injections of anti-FLT3 antibodies or Fc control antibodies on multiple days (e.g., day 5, 7, 11, 15) by I.P. injection following tumor implant. Dosing is determined using information available in the art and ordinary skill (e.g., 200 ug/day for Fc control; 40 ug, 20 ug, 20 ug and 40 ug for anti FLT3 antibodies). At multiple time points throughout tumor growth animals are scarified and SDC and NSM abundance is analyzed by flow cytometry. Anti-FLT3 agonist antibody treatment through tumor development enhances SDC abundance in the tumor, as well as SDC populations in the dLN, Spleen, and BM.

Examples 28: Reduced Tumor Growth Following Treatments with Agonist Anti-FLT3 Antibodies Due to Increased SDC Populations Cancer cells (e.g., MC38 colon carcinoma) are injected into B6 6 week old male mice at T0. Mice, randomized into treatment groups, are treated with injections of agonist anti-FLT3 antibodies or Fc control on multiple days (e.g., day 5, 7, 11, 15) by I.P. injection following tumor implant. Dosing is determined using information available in the art and ordinary skill (e.g., 200 ug/day for Fc control; 40 ug, 20 ug, 20 ug and 40 ug for anti FLT3 antibodies). Tumors are measured by caliper and tumor volume is determined. Anti-FLT3 antibody treatment reduces tumor growth relative to control. Anti-FLT3 antibody treatment enhances SDC abundance in the tumor, as well as SDC populations in the dLN, Spleen and BM. Anti-FLT3L agonist antibodies enhance an immune response to the tumor in the experimental mice relative to control.

Example 29: Enhancement of Immunotherapy Via Co-Administration with Agonist Anti-FLT3 Antibodies Cancer cells (e.g., MC38 colon carcinoma) are injected into B6 6 week old male mice at T0. Mice, randomized into treatment groups, are treated with injections of anti-FLT3 antibodies or PBS control on multiple days (e.g., day 5, 7, 11, 15) by I.P., I.V. and or S.C. injection following tumor implant. The mice have previously received, concurrently receive, or will subsequently receive an immunotherapy. Immunotherapies can include an immunotherapy that inhibits a checkpoint inhibitor; an immunotherapy that inhibits a checkpoint inhibitor of T cells; anti-PD1; anti-PDL1; anti-CTLA4; adoptive T cell therapy; CAR-T cell therapy; a dendritic cell vaccine; a monocyte vaccine; an antigen binding protein that binds both a T cell and an antigen presenting cell; a BiTE antigen binding protein; a toll-like receipt ligand; and/or a cytokine. Dosing is determined using information available in the art and ordinary skill (e.g., 10 ug in 100 ul of PBS) Tumors are measured by caliper and tumor volume is determined. Co-administration of anti-FLT3 antibodies with immunotherapy enhances reduction in tumor growth relative to non-co-administration control (e.g., monotherapy). Co-administration anti-FLT3 antibodies with immunotherapy enhances an immune response to the tumor relative to non-co-administration control (e.g., monotherapy).

Example 30: Expression of NSM Proteins on Human Cells

Figure 21:
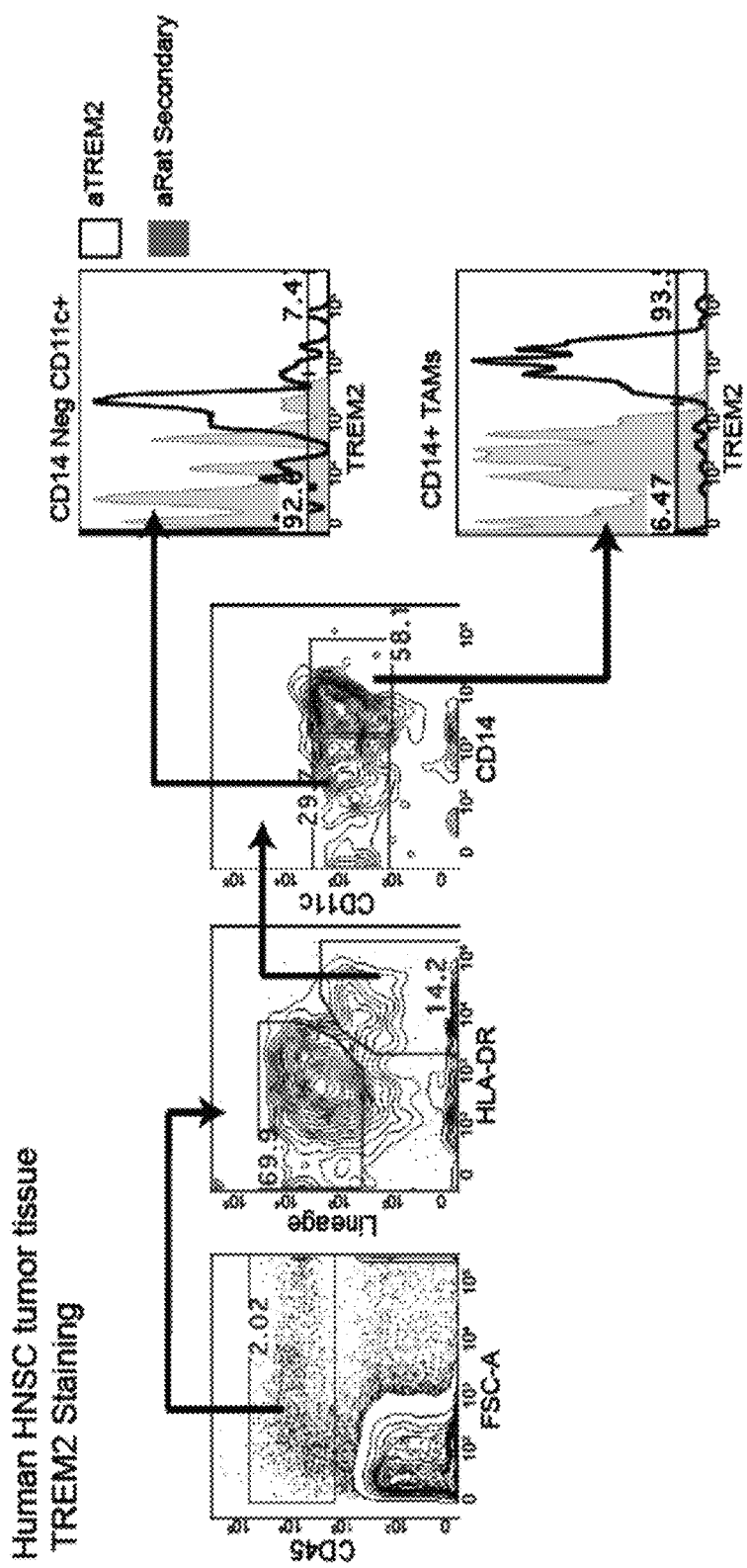
FIG. 21 demonstrates restricted expression of TREM2 protein to NSM populations (CD14+ TAMs) with little to no expression on CD14 negative CD11c positive cells which include SDC (BDCA3+DC) in primary human HNSC tumor tissue. TREM2 specific commercial antibody (RnD, clone 237920) staining was performed on digested human HNSC tumor tissue compared to secondary control staining (ant-Rat IgG, Jackson Immunoresearch) and analyzed by flow cytometry. This figure shows specific expression of NSM gene products on NSM cells and the lack of expression on SDC cells in human tumor tissue. Populations gated on live, CD45+, lineage negative, HLA-DR+, CD11c+ and split by CD14 expression.

FIG. 21 demonstrates restricted expression of TREM2 protein to NSM populations (CD14+ TAMs) with little to no expression on CD14 negative CD11c positive cells which include SDC (BDCA3+DC) in primary human HNSC tumor tissue. TREM2 specific commercial antibody (RnD, clone 237920) staining was performed on digested human HNSC tumor tissue compared to secondary control staining (ant-Rat IgG, Jackson Immunoresearch) and analyzed by flow cytometry. This figure shows specific expression of NSM gene products on NSM cells and the lack of expression on SDC cells in human tumor tissue. Populations gated on live, CD45+, lineage negative, HLA-DR+, CD11c+ and split by CD14 expression.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.
Sequences

TABLE AA

| | Name | | Mouse NCBI Accession # | Human NCBI Accession # |
|---|---|---|---|---|
| cKIT | v-kit Hardy-Zuckerman 4 feline sarcoma viral oncogene homolog (KIT) | | NM_001122733.1 | NM_000222.2 |
| CCR7 | chemokine (C-C motif) receptor 7 (CCR7) | | NM_001301713.1 | NM_001838.3 |
| BATF3 | basic leucine zipper transcription factor, ATF-like 3 (BATF3) | | NM_030060.2 | NM_018664.2 |
| FLT3 | fms-related tyrosine kinase 3 (FLT3) | | NM_010229.2 | NM_004119.2 |
| ZBTB46 | zinc finger and BTB domain containing 46 (ZBTB46) | | NM_027656.2 | NM_025224.3 |
| IRF8 | interferon regulatory factor 8 (IRF8) | | NM_001301811.1 | NM_002163.2 |
| BTLA | B and T lymphocyte associated (BTLA) | | NM_001301811.1 | NM_001085357.1 |

TABLE AA-continued

| Name | | Mouse NCBI Accession # | Human NCBI Accession # |
|---|---|---|---|
| MYCL1 | v-myc avian myelocytomatosis viral oncogene lung carcinoma derived homolog (MYCL) 1 | NM_001303121.1 | NM_001033081.2 |
| Clec9A | C-type lectin domain family 9, member A (CLEC9A) | NM_001205363.1 | NM_207345.3 |
| BDCA3/THBD | thrombomodulin (THBD) | NM_009378.3 | NM_000361.2 |
| XCR1 | chemokine (C motif) receptor 1 (XCR1) | NM_011798.4 | NM_001024644.1 |
| C5AR1 | complement component 5a receptor 1 (C5AR1) | NM_001173550.1 | NM_001736.3 |
| LYVE1 | lymphatic vessel endothelial hyaluronan receptor 1 (LYVE1) | NM_053247.4 | NM_006691.3 |
| ABCC3 | ATP-binding cassette, sub-family C (CFTR/MRP), member 3 (ABCC3) | NM_029600.3 | NM_001144070.1 |
| MRC1 | mannose receptor, C type 1 (MRC1) | NM_008625.2 | NM_002438.3 |
| SIGLEC1 | sialic acid binding Ig-like lectin 1, sialoadhesin (SIGLEC1) | NM_011426.3 | NM_023068.3 |
| STAB1 | stabilin 1 (STAB1) | NM_138672.2 | NM_015136.2 |
| C1QA | complement component 1, q subcomponent, A chain (C1QA) | NM_007572.2 | NM_015991.2 |
| C1QB | complement component 1, q subcomponent, B chain (C1QB) | NM_009777.2 | NM_000491.3 |
| TMEM37 | transmembrane protein 7 (TMEM37) | NM_019432.2 | NM_183240.2 |
| MERTK | MER proto-oncogene, tyrosine kinase (MERTK) | NM_008587.1 | NM_006343.2 |
| C1QC | complement component 1, q subcomponent, C chain (C1QC) | NM_007574.2 | NM_001114101.1 |
| TMEM119 | transmembrane protein 119 (Tmem119) | NM_146162.2 | NM_181724.2 |
| MS4A7 | membrane-spanning 4-domains, subfamily A, member 7 (MS4A7) | NM_001025610.4 | NM_021201.4 |
| APOE | apolipoprotein E (APOE) | NM_001305819.1 | NM_000041.3 |
| CYP4F18/ CYP4F2 | cytochrome P450, family 4, subfamily F, polypeptide 2 (CYP4F2) | NM_024444.2 | NM_001082.4 |
| TREM2 | triggering receptor expressed on myeloid cells 2 (TREM2) | NM_001272078.1 | NM_001271821.1 |
| TLR7 | toll-like receptor 7 (TLR7) | NM_001290755.1 | NM_016562.3 |
| LILRB4 | leukocyte immunoglobulin-like receptor, subfamily B (with TM and ITIM domains), member 4 (LILRB4) | NM_001013894.1 | NM_001278426.3 |

All NCBI accession numbers disclosed herein and the associated sequences are as of Sep. 25, 2015 as accessible via the publicly available NCBI website.

TABLE BB

CDR, variable and full length sequences of each anti-LILRB4 clone 1

| Clone | H1 | H2 | H3 | L1 | L2 | L3 |
|---|---|---|---|---|---|---|
| Anti-LILRB4 clone 1-1 | GFNLSSSY (SEQ ID NO: 1) | ISSSYGST (SEQ ID NO: 2) | ARAHYVWYGSVYAH SYGGMDY (SEQ ID NO: 3) | QSVSSA (SEQ ID NO: 4) | SAS (SEQ ID NO: 5) | QQWSGGYSG LIT (SEQ ID NO: 6) |

Anti-LILRB4.clone1-1.vL-
DIQMTQSPSSLSASVGDRVTITCRASQSVSSAVAWYQQKPGKAPKLLIYSASSLYSGVPSRFSGSRSGTDFTLTISSLQP
EDFATYYCQQWSGGYSGLITFGQGTKVEIK (SEQ ID NO: 7)

Anti-LILRB4.clone1-1.vH-
EVQLVESGGGLVQPGGSLRLSCAASGFNLSSSYMHWVRQAPGKGLEWVASISSSYGSTYYADSVKGRFTISADTSKN
TAYLQMNSLRAEDTAVYYCARAHYVWYGSVYAHSYGGMDYWGQGTLVTVSS (SEQ ID NO: 8)

Anti-LILRB4.clone1-1.hukappa-
DIQMTQSPSSLSASVGDRVTITCRASQSVSSAVAWYQQKPGKAPKLLIYSASSLYSGVPSRFSGSRSGTDFTLTISSLQP
EDFATYYCQQWSGGYSGLITFGQGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC (SEQ ID NO: 9)

Anti-LILRB4.clone1-1.huIgG1-
EVQLVESGGGLVQPGGSLRLSCAASGFNLSSSYMHWVRQAPGKGLEWVASISSSYGSTYYADSVKGRFTISADTSKN
TAYLQMNSLRAEDTAVYYCARAHYVWYGSVYAHSYGGMDYWGQGTLVTVSSASTKGPSVFPLAPSSKSTSGGTAA
LGCLVKDYFPEPVTVSWNSGALTSGVHTFPAVLQSSGLYSLSSVVTVPSSSLGTQTYICNVNHKPSNTKVDKKVEPKSC
DKTHTCPPCPAPELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMHEALHNHYTQKSLSLSPGK
(SEQ ID NO: 10)

REFERENCES

Bowles J A, Wang S Y, Link B K, Allan B, Beuerlein G, Campbell M A, Marquis D, Ondek B, Wooldridge J E, Smith B J, Breitmeyer J B, Weiner G J. Anti-CD20 monoclonal antibody with enhanced affinity for CD16 activates NK cells at lower concentrations and more effectively than rituximab. Blood. 2006 Oct. 15; 108(8): 2648-54. Epub 2006 Jul. 6.

Desjarlais J R, Lazar G A. Modulation of antibody effector function. Exp Cell Res. 2011 May 15; 317(9): 1278-85.

Ferrara C, Grau S, Jager C, Sondermann P, Brünker P, Waldhauer I, Hennig M, Ruf A, Rufer A C, Stihle M, Umaña P, Benz J. Unique carbohydrate-carbohydrate interactions are required for high affinity binding between FcgammaRIII and antibodies lacking core fucose. Proc Natl Acad Sci USA. 2011 Aug. 2; 108(31):12669-74.

Heider K H, Kiefer K, Zenz T, Volden M, Stilgenbauer S, Ostermann E, Baum A, Lamche H, Kupcu Z, Jacobi A, Müller S, Hirt U, Adolf G R, Borges E. A novel Fc-engineered monoclonal antibody to CD37 with enhanced ADCC and high proapoptotic activity for treatment of B-cell malignancies. Blood. 2011 Oct. 13; 118(15):4159-68. Epub 2011 Jul. 27. Blood. 2011 Oct. 13; 118(15): 4159-68. Epub 2011 Jul. 27.

Lazar G A, Dang W, Karki S, Vafa O, Peng J S, Hyun L, Chan C, Chung H S, Eivazi A, Yoder S C, Vielmetter J, Carmichael D F, Hayes R J, Dahiyat B I. Engineered antibody Fc variants with enhanced effector function. Proc Natl Acad Sci USA. 2006 Mar. 14; 103(11):4005-10. Epub 2006 Mar. 6.

Lu Y, Vernes J M, Chiang N, Ou Q, Ding J, Adams C, Hong K, Truong B T, Ng D, Shen A, Nakamura G, Gong Q, Presta L G, Beresini M, Kelley B, Lowman H, Wong W L, Meng Y G. Identification of IgG(1) variants with increased affinity to FcγRIIIa and unaltered affinity to FcγRI and FcRn: comparison of soluble receptor-based and cell-based binding assays. J Immunol Methods. 2011 Feb. 28; 365(1-2): 132-41. Epub 2010 Dec. 23.

Mizushima T, Yagi H, Takemoto E, Shibata-Koyama M, Isoda Y, Iida S, Masuda K, Satoh M, Kato K. Structural basis for improved efficacy of therapeutic antibodies on defucosylation of their Fc glycans. Genes Cells. 2011 November; 16(11):1071-1080.

Moore G L, Chen H, Karki S, Lazar G A. Engineered Fc variant antibodies with enhanced ability to recruit complement and mediate effector functions. MAbs. 2010 March-April; 2(2): 181-9.

Nordstrom J L, Gorlatov S, Zhang W, Yang Y, Huang L, Burke S, Li H, Ciccarone V, Zhang T, Stavenhagen J, Koenig S, Stewart S J, Moore P A, Johnson S, Bonvini E. Anti-tumor activity and toxicokinetics analysis of MGAH22, an anti-HER2 monoclonal antibody with enhanced Fc-gamma receptor binding properties. Breast Cancer Res. 2011 Nov. 30; 13(6):R123. [Epub ahead of print]

Richards J O, Karki S, Lazar G A, Chen H, Dang W, Desjarlais J R. Optimization of antibody binding to FcgammaRIIa enhances macrophage phagocytosis of tumor cells. Mol Cancer Ther. 2008 August; 7(8):2517-27.

Schneider S, Zacharias M. Atomic resolution model of the antibody Fc interaction with the complement C1q component. Mol Immunol. 2012 May; 51(1):66-72.

Shields R L, Namenuk A K, Hong K, Meng Y G, Rae J, Briggs J, Xie D, Lai J, Stadlen A, Li B, Fox J A, Presta L G. High resolution mapping of the binding site on human IgG1 for Fc gamma RI, Fc gamma RII, Fc gamma RIII, and FcRn and design of IgG1 variants with improved binding to the Fc gamma R. J Biol Chem. 2001 Mar. 2; 276(9):6591-604.

Stavenhagen J B, Gorlatov S, Tuaillon N, Rankin C T, Li H, Burke S, Huang L, Vijh S, Johnson S, Bonvini E, Koenig S. Fc optimization of therapeutic antibodies enhances their ability to kill tumor cells in vitro and controls tumor expansion in vivo via low-affinity activating Fcgamma receptors. Cancer Res. 2007 Sep. 15; 67(18):8882-90.

Stewart R, Thom G, Levens M, Güler-Gane G, Holgate R, Rudd P M, Webster C, Jermutus L, Lund J. A variant human IgG1-Fc mediates improved ADCC. Protein Eng Des Sel. 2011 September; 24(9):671-8. Epub 2011 May 18.

Bejamini, Y., and Hochberg, Y. (1995). Controlling the False Discovery Rate—a Practical and Powerful Approach to Multiple Testing. Journal of the Royal Statistical Society Series B—Methodological 57, 289-300.

Boissonnas, A., Licata, F., Poupel, L., Jacquelin, S., Fetler, L., Krumeich, S., Thery, C., Amigorena, S., and Combadiere, C. (2013). CD8+ tumor-infiltrating T cells are trapped in the tumor-dendritic cell network. Neoplasia 15, 85-94.

Cancer Genome Atlas Research, N., Weinstein, J. N., Collisson, E. A., Mills, G. B., Shaw, K. R., Ozenberger, B. A., Ellrott, K., Shmulevich, I., Sander, C., and Stuart, J. M. (2013). The Cancer Genome Atlas Pan-Cancer analysis project. Nat Genet 45, 1113-1120.

Chang, H. Y., Nuyten, D. S., Sneddon, J. B., Hastie, T., Tibshirani, R., Sorlie, T., Dai, H., He, Y. D., van't Veer, L. J., Bartelink, H., et al. (2005). Robustness, scalability, and integration of a wound-response gene expression signature in predicting breast cancer survival. Proc Natl Acad Sci USA 102, 3738-3743.

Cheong, C., Matos, I., Choi, J. H., Dandamudi, D. B., Shrestha, E., Longhi, M. P., Jeffrey, K. L., Anthony, R. M., Kluger, C., Nchinda, G., et al. (2010). Microbial stimulation fully differentiates monocytes to DC-SIGN/CD209 (+) dendritic cells for immune T cell areas. Cell 143, 416-429.

Cortez-Retamozo, V., Etzrodt, M., Newton, A., Rauch, P. J., Chudnovskiy, A., Berger, C., Ryan, R. J., Iwamoto, Y., Marinelli, B., Gorbatov, R., et al. (2012). Origins of tumor-associated macrophages and neutrophils. Proc Natl Acad Sci USA 109, 2491-2496.

Curran, M. A., and Allison, J. P. (2009). Tumor vaccines expressing flt3 ligand synergize with ctla-4 blockade to reject preimplanted tumors. Cancer Res 69, 7747-7755.

Curran, M. A., Montalvo, W., Yagita, H., and Allison, J. P. (2010). PD-1 and CTLA-4 combination blockade expands infiltrating T cells and reduces regulatory T and myeloid cells within B16 melanoma tumors. Proc Natl Acad Sci USA 107, 4275-4280.

DeNardo, D. G., Brennan, D. J., Rexhepaj, E., Ruffell, B., Shiao, S. L., Madden, S. F., Gallagher, W. M., Wadhwani, N., Keil, S. D., Junaid, S. A., et al. (2011). Leukocyte complexity predicts breast cancer survival and functionally regulates response to chemotherapy. Cancer discovery 1, 54-67.

Dranoff, G. (2002). GM-CSF-based cancer vaccines. Immunol Rev 188, 147-154.

Dzionek, A., Fuchs, A., Schmidt, P., Cremer, S., Zysk, M., Miltenyi, S., Buck, D. W., and Schmitz, J. (2000). BDCA-2, BDCA-3, and BDCA-4: three markers for distinct subsets of dendritic cells in human peripheral blood. J Immunol 165, 6037-6046.

Engelhardt, J. J., Boldajipour, B., Beemiller, P., Pandurangi, P., Sorensen, C., Werb, Z., Egeblad, M., and Krummel, M. F. (2012). Marginating dendritic cells of the tumor microenvironment cross-present tumor antigens and stably engage tumor-specific T cells. Cancer Cell 21, 402-417.

Gao, Y., Nish, S. A., Jiang, R., Hou, L., Licona-Limon, P., Weinstein, J. S., Zhao, H., and Medzhitov, R. (2013). Control of T helper 2 responses by transcription factor IRF4-dependent dendritic cells. Immunity 39, 722-732.

Gautier, E. L., Shay, T., Miller, J., Greter, M., Jakubzick, C., Ivanov, S., Helft, J., Chow, A., Elpek, K. G., Gordonov, S., et al. (2012). Gene-expression profiles and transcriptional regulatory pathways that underlie the identity and diversity of mouse tissue macrophages. Nat Immunol 13, 1118-1128.

Geissmann, F., Manz, M. G., Jung, S., Sieweke, M. H., Merad, M., and Ley, K. (2010). Development of monocytes, macrophages, and dendritic cells. Science 327, 656-661.

Ginhoux, F., Liu, K., Helft, J., Bogunovic, M., Greter, M., Hashimoto, D., Price, J., Yin, N., Bromberg, J., Lira, S. A., et al. (2009). The origin and development of nonlymphoid tissue CD103+ DCs. J Exp Med 206, 3115-3130.

Graf, L. H., Jr., Kaplan, P., and Silagi, S. (1984). Efficient DNA-mediated transfer of selectable genes and unselected sequences into differentiated and undifferentiated mouse melanoma clones. Somatic cell and molecular genetics 10, 139-151.

Guermonprez, P., Valladeau, J., Zitvogel, L., Thery, C., and Amigorena, S. (2002). Antigen presentation and T cell stimulation by dendritic cells. Annu Rev Immunol 20, 621-667.

Hanahan, D., and Weinberg, R. A. (2011). Hallmarks of cancer: the next generation. Cell 144, 646-674.

Haniffa, M., Shin, A., Bigley, V., McGovern, N., Teo, P., See, P., Wasan, P. S., Wang, X. N., Malinarich, F., Malleret, B., et al. (2012). Human tissues contain CD141hi cross-presenting dendritic cells with functional homology to mouse CD103+ nonlymphoid dendritic cells. Immunity 37, 60-73.

Hashimoto, D., Miller, J., and Merad, M. (2011). Dendritic cell and macrophage heterogeneity in vivo. Immunity 35, 323-335.

Helmich, B. K., and Dutton, R. W. (2001). The role of adoptively transferred CD8 T cells and host cells in the control of the growth of the EG7 thymoma: factors that determine the relative effectiveness and homing properties of Tc1 and Tc2 effectors. J Immunol 166, 6500-6508.

Hildner, K., Edelson, B. T., Purtha, W. E., Diamond, M., Matsushita, H., Kohyama, M., Calderon, B., Schraml, B. U., Unanue, E. R., Diamond, M. S., et al. (2008). Batf3 deficiency reveals a critical role for CD8alpha+ dendritic cells in cytotoxic T cell immunity. Science 322, 1097-1100.

Hoadley, K. A., Yau, C., Wolf, D. M., Cherniack, A. D., Tamborero, D., Ng, S., Leiserson, M. D., Niu, B., McLellan, M. D., Uzunangelov, V., et al. (2014). Multiplatform Analysis of 12 Cancer Types Reveals Molecular Classification within and across Tissues of Origin. Cell 158, 929-944.

Kraman, M., Bambrough, P. J., Arnold, J. N., Roberts, E. W., Magiera, L., Jones, J. O., Gopinathan, A., Tuveson, D. A., and Fearon, D. T. (2010). Suppression of antitumor immunity by stromal cells expressing fibroblast activation protein-alpha. Science 330, 827-830.

Kumamoto, Y., Linehan, M., Weinstein, J. S., Laidlaw, B. J., Craft, J. E., and Iwasaki, A. (2013). CD301b(+) dermal dendritic cells drive T helper 2 cell-mediated immunity. Immunity 39, 733-743.

Kusmartsev, S., Nagaraj, S., and Gabrilovich, D. I. (2005). Tumor-associated CD8+ T cell tolerance induced by bone marrow-derived immature myeloid cells. J Immunol 175, 4583-4592.

Leach, D. R., Krummel, M. F., and Allison, J. P. (1996). Enhancement of antitumor immunity by CTLA-4 blockade. Science 271, 1734-1736.

Lewis, C. E., and Pollard, J. W. (2006). Distinct role of macrophages in different tumor microenvironments. Cancer Res 66, 605-612.

Meredith, M. M., Liu, K., Darrasse-Jeze, G., Kamphorst, A. O., Schreiber, H. A., Guermonprez, P., Idoyaga, J., Cheong, C., Yao, K. H., Niec, R. E., and Nussenzweig, M. C. (2012). Expression of the zinc finger transcription factor zDC (Zbtb46, Btbd4) defines the classical dendritic cell lineage. J Exp Med 209, 1153-1165.

Miller, J. C., Brown, B. D., Shay, T., Gautier, E. L., Jojic, V., Cohain, A., Pandey, G., Leboeuf, M., Elpek, K. G., Helft, J., et al. (2012). Deciphering the transcriptional network of the dendritic cell lineage. Nat Immunol 13, 888-899.

Movahedi, K., Laoui, D., Gysemans, C., Baeten, M., Stange, G., Van den Bossche, J., Mack, M., Pipeleers, D., In't Veld, P., De Baetselier, P., and Van Ginderachter, J. A. (2010). Different tumor microenvironments contain functionally distinct subsets of macrophages derived from Ly6C(high) monocytes. Cancer Res 70, 5728-5739.

Palmer, C., Diehn, M., Alizadeh, A. A., and Brown, P. O. (2006). Cell-type specific gene expression profiles ofleukocytes in human peripheral blood. BMC genomics 7, 115.

Ries, C. H., Cannarile, M. A., Hoves, S., Benz, J., Wartha, K., Runza, V., Rey-Giraud, F., Pradel, L. P., Feuerhake, F., Klaman, I., et al. (2014). Targeting Tumor-Associated Macrophages with Anti-CSF-1R Antibody Reveals a Strategy for Cancer Therapy. Cancer Cell 25, 846-859.

Savina, A., Jancic, C., Hugues, S., Guermonprez, P., Vargas, P., Moura, I. C., Lennon-Dumenil, A. M., Seabra, M. C., Raposo, G., and Amigorena, S. (2006). NOX2 controls phagosomal pH to regulate antigen processing during crosspresentation by dendritic cells. Cell 126, 205-218.

Schulz, C., Gomez Perdiguero, E., Chorro, L., Szabo-Rogers, H., Cagnard, N., Kierdorf, K., Prinz, M., Wu, B., Jacobsen, S. E., Pollard, J. W., et al. (2012). A lineage of myeloid cells independent of Myb and hematopoietic stem cells. Science 336, 86-90.

Strachan, D. C., Ruffell, B., Oei, Y., Bissell, M. J., Coussens, L. M., Pryer, N., and Daniel, D. (2013). CSF1R inhibition delays cervical and mammary tumor growth in murine models by attenuating the turnover of tumor-associated macrophages and enhancing infiltration by CD8 T cells. Oncoimmunology 2, e26968.

Tamura, T., Tailor, P., Yamaoka, K., Kong, H. J., Tsujimura, H., O'Shea, J. J., Singh, H., and Ozato, K. (2005). IFN regulatory factor-4 and -8 govern dendritic cell subset development and their functional diversity. J Immunol 174, 2573-2581.

Tussiwand, R., Lee, W. L., Murphy, T. L., Mashayekhi, M., Kc, W., Albring, J. C., Satpathy, A. T., Rotondo, J. A., Edelson, B. T., Kretzer, N. M., et al. (2012). Compensatory dendritic cell development mediated by BATF-IRF interactions. Nature 490, 502-507.

Viigimaa, M., Vaverkova, H., Farnier, M., Averna, M., Missault, L., Hanson, M. E., Dong, Q., Shah, A., and Brudi, P. (2010). Ezetimibe/simvastatin 10/20 mg versus rosuvastatin 10 mg in high-risk hypercholesterolemic patients stratified by prior statin treatment potency. Lipids in health and disease 9, 127.

Williams, J. W., Tjota, M. Y., Clay, B. S., Vander Lugt, B., Bandukwala, H. S., Hrusch, C. L., Decker, D. C., Blaine, K. M., Fixsen, B. R., Singh, H., et al. (2013). Transcription factor IRF4 drives dendritic cells to promote Th2 differentiation. Nature communications 4, 2990.

Wolf, D. M., Lenburg, M. E., Yau, C., Boudreau, A., and van't Veer, L. J. (2014). Gene co-expression modules as clinically relevant hallmarks of breast cancer diversity. PLoS One 9, e88309.

Wyckoff, J., Wang, W., Lin, E. Y., Wang, Y., Pixley, F., Stanley, E. R., Graf, T., Pollard, J. W., Segall, J., and Condeelis, J. (2004). A paracrine loop between tumor cells and macrophages is required for tumor cell migration in mammary tumors. Cancer Res 64, 7022-7029.

Anders, S., and Huber, W. (2010). Differential expression analysis for sequence count data. Genome biology 11, R106.

Bertram, J. S., and Janik, P. (1980). Establishment of a cloned line of Lewis Lung Carcinoma cells adapted to cell culture. Cancer Lett 11, 63-73.

Curran, M. A., and Allison, J. P. (2009). Tumor vaccines expressing flt3 ligand synergize with ctla-4 blockade to reject preimplanted tumors. Cancer Res 69, 7747-7755.

Choi, C. H., Webb, B. A., Chimenti, M. S., Jacobson, M. P., and Barber, D. L. (2013). pH sensing by FAK-His58 regulates focal adhesion remodeling. J Cell Biol 202, 849-859.

Dranoff, G., Jaffee, E., Lazenby, A., Golumbek, P., Levitsky, H., Brose, K., Jackson, V., Hamada, H., Pardoll, D., and Mulligan, R. C. (1993). Vaccination with irradiated tumor cells engineered to secrete murine granulocyte-macrophage colony-stimulating factor stimulates potent, specific, and long-lasting anti-tumor immunity. Proc Natl Acad Sci USA 90, 3539-3543.

Fidler, I. J. (1975). Biological behavior of malignant melanoma cells correlated to their survival in vivo. Cancer Res 35, 218-224.

Friedman, R. S., Jacobelli, J., and Krummel, M. F. (2006). Surface-bound chemokines capture and prime T cells for synapse formation. Nat Immunol 7, 1101-1108.

Graf, L. H., Jr., Kaplan, P., and Silagi, S. (1984). Efficient DNA-mediated transfer of selectable genes and unselected sequences into differentiated and undifferentiated mouse melanoma clones. Somatic cell and molecular genetics 10, 139-151.

Hadjantonakis, A. K., Macmaster, S., and Nagy, A. (2002). Embryonic stem cells and mice expressing different GFP variants for multiple non-invasive reporter usage within a single animal. BMC Biotechnol 2, 11.

Halpern, J., Lynch, C. C., Fleming, J., Hamming, D., Martin, M. D., Schwartz, H. S., Matrisian, L. M., and Holt, G. E. (2006). The application of a murine bone bioreactor as a model of tumor: bone interaction. Clinical & experimental metastasis 23, 345-356.

Hoquist, K. A., Jameson, S. C., Heath, W. R., Howard, J. L., Bevan, M. J., and Carbone, F. R. (1994). T cell receptor antagonist peptides induce positive selection. Cell 76, 17-27.

Hyman, R., Ralph, P., and Sarkar, S. (1972). Cell-specific antigens and immunoglobulin synthesis of murine myeloma cells and their variants. Journal of the National Cancer Institute 48, 173-184.

Jung, S., Aliberti, J., Graemmel, P., Sunshine, M. J., Kreutzberg, G. W., Sher, A., and Littman, D. R. (2000). Analysis of fractalkine receptor CX(3)CR1 function by targeted deletion and green fluorescent protein reporter gene insertion. Molecular and cellular biology 20, 4106-4114.

Khanna, K. M., Blair, D. A., Vella, A. T., McSorley, S. J., Datta, S. K., and Lefrancois, L. (2010). T cell and APC dynamics in situ control the outcome of vaccination. J Immunol 185, 239-252.

Klein, U., Casola, S., Cattoretti, G., Shen, Q., Lia, M., Mo, T., Ludwig, T., Rajewsky, K., and Dalla-Favera, R. (2006). Transcription factor IRF4 controls plasma cell differentiation and class-switch recombination. Nat Immunol 7, 773-782.

Koivusalo, M., Welch, C., Hayashi, H., Scott, C. C., Kim, M., Alexander, T., Touret, N., Hahn, K. M., and Grinstein, S. (2010). Amiloride inhibits macropinocytosis by lowering submembranous pH and preventing Raci and Cdc42 signaling. J Cell Biol 188, 547-563.

Liu, F., Wu, H. Y., Wesselschmidt, R., Kornaga, T., and Link, D. C. (1996). Impaired production and increased apoptosis of neutrophils in granulocyte colony-stimulating factor receptor-deficient mice. Immunity 5, 491-501.

Meredith, M. M., Liu, K., Darrasse-Jeze, G., Kamphorst, A. O., Schreiber, H. A., Guermonprez, P., Idoyaga, J., Cheong, C., Yao, K. H., Niec, R. E., and Nussenzweig, M. C. (2012). Expression of the zinc finger transcription factor zDC (Zbtb46, Btbd4) defines the classical dendritic cell lineage. J Exp Med 209, 1153-1165.

Moore, M. W., Carbone, F. R., and Bevan, M. J. (1988). Introduction of soluble protein into the class I pathway of antigen processing and presentation. Cell 54, 777-785.

Moran, A. E., Holzapfel, K. L., Xing, Y., Cunningham, N. R., Maltzman, J. S., Punt, J., and Hogquist, K. A. (2011). T cell receptor signal strength in Treg and iNKT cell development demonstrated by a novel fluorescent reporter mouse. J Exp Med 208, 1279-1289.

Ouyang, X., Zhang, R., Yang, J., Li, Q., Qin, L., Zhu, C., Liu, J., Ning, H., Shin, M. S., Gupta, M., et al. (2011). Transcription factor IRF8 directs a silencing programme for TH17 cell differentiation. Nature communications 2, 314.

Robb, L., Drinkwater, C. C., Metcalf, D., Li, R., Kontgen, F., Nicola, N. A., and Begley, C. G. (1995). Hematopoietic and lung abnormalities in mice with a null mutation of the common beta subunit of the receptors for granulocyte-macrophage colony-stimulating factor and interleukins 3 and 5. Proc Natl Acad Sci USA 92, 9565-9569.

Ruffell, B., Au, A., Rugo, H. S., Esserman, L. J., Hwang, E. S., and Coussens, L. M. (2012). Leukocyte composition of human breast cancer. Proc Natl Acad Sci USA 109, 2796-2801.

Trapnell, C., Pachter, L., and Salzberg, S. L. (2009). TopHat: discovering splice junctions with RNA-Seq. Bioinformatics 25, 1105-1111.

Veiga-Fernandes, H., Coles, M. C., Foster, K. E., Patel, A., Williams, A., Natarajan, D., Barlow, A., Pachnis, V., and Kioussis, D. (2007). Tyrosine kinase receptor RET is a key regulator of Peyer's patch organogenesis. Nature 446, 547-551.

Webb, B. A., Chimenti, M., Jacobson, M. P., and Barber, D. L. (2011). Dysregulated pH: a perfect storm for cancer progression. Nat Rev Cancer 11, 671-677.

Williams, J. W., Tjota, M. Y., Clay, B. S., Vander Lugt, B., Bandukwala, H. S., Hrusch, C. L., Decker, D. C., Blaine, K. M., Fixsen, B. R., Singh, H., et al. (2013). Transcription factor IRF4 drives dendritic cells to promote Th2 differentiation. Nature communications 4, 2990.

Leach, D. R., Krummel, M. F. & Allison, J. P. Enhancement of antitumor immunity by CTLA-4 blockade. *Science* 271, 1734-1736 (1996).

Hodi, F. S., et al. Improved Survival with Ipilimumab in Patients with Metastatic Melanoma. *New England Journal of Medicine* 363, 711-723 (2010).

Wolchok, J. D., et al. Nivolumab plus ipilimumab in advanced melanoma. *The New England journal of medicine* 369, 122-133 (2013).

Pardoll, D. M. The blockade of immune checkpoints in cancer immunotherapy. *Nat Rev Cancer* 12, 252-264 (2012).

Topalian, S. L., et al. Safety, activity, and immune correlates of anti-PD-1 antibody in cancer. *The New England journal of medicine* 366, 2443-2454 (2012).

Hamid, O., et al. Safety and tumor responses with lambrolizumab (anti-PD-1) in melanoma. *The New England journal of medicine* 369, 134-144 (2013).

Broz, M. L., et al. Dissecting the tumor myeloid compartment reveals rare activating antigen-presenting cells critical for T cell immunity. *Cancer Cell* 26, 638-652 (2014).

DeNardo, D. G., et al. Leukocyte complexity predicts breast cancer survival and functionally regulates response to chemotherapy. *Cancer discovery* 1, 54-67 (2011).

Hanada, T., et al. Prognostic value of tumor-associated macrophage count in human bladder cancer. *International journal of urology: official journal of the Japanese Urological Association* 7, 263-269 (2000).

Sandel, M. H., et al. Prognostic value of tumor-infiltrating dendritic cells in colorectal cancer: role of maturation status and intratumoral localization. *Clin Cancer Res* 11, 2576-2582 (2005).

Bogunovic, D., et al. Immune profile and mitotic index of metastatic melanoma lesions enhance clinical staging in predicting patient survival. *Proc Natl Acad Sci USA* 106, 20429-20434 (2009).

Fridman, W. H., Pages, F., Sautes-Fridman, C. & Galon, J. The immune contexture in human tumours: impact on clinical outcome. *Nat Rev Cancer* 12, 298-306 (2012).

Ascierto, P. A., et al. The additional facet of immunoscore: immunoprofiling as a possible predictive tool for cancer treatment. *J Transl Med* 11, 54 (2013).

Angelo, M., et al. Multiplexed ion beam imaging of human breast tumors. *Nat Med* 20, 436-442 (2014).

Le, D. T., et al. PD-1 Blockade in Tumors with Mismatch-Repair Deficiency. *The New England journal of medicine* (2015).

Snyder, A., et al. Genetic Basis for Clinical Response to CTLA-4 Blockade in Melanoma. *New England Journal of Medicine* 371, 2189-2199 (2014).

Selby, M. J., et al. Anti-CTLA-4 antibodies of IgG2a isotype enhance antitumor activity through reduction of intratumoral regulatory T cells. *Cancer immunology research* 1, 32-42 (2013).

Bell, D., et al. In Breast Carcinoma Tissue, Immature Dendritic Cells Reside within the Tumor, Whereas Mature Dendritic Cells Are Located in Peritumoral Areas. *The Journal of Experimental Medicine* 190, 1417-1426 (1999).

Dieu-Nosjean, M. C., et al. Long-term survival for patients with non-small-cell lung cancer with intratumoral lymphoid structures. *J Clin Oncol* 26, 4410-4417 (2008).

Bejamini, Y. & Hochberg, Y. Controlling the False Discovery Rate—a Practical and Powerful Approach to Multiple Testing. *Journal of the Royal Statistical Society Series B—Methodological* 57, 289-300 (1995).

Ruffell, B., et al. Leukocyte composition of human breast cancer. *Proc Natl Acad Sci USA* 109, 2796-2801 (2012).

Graf, L. H., Jr., Kaplan, P. & Silagi, S. Efficient DNA-mediated transfer of selectable genes and unselected sequences into differentiated and undifferentiated mouse melanoma clones. *Somatic cell and molecular genetics* 10, 139-151 (1984).

Engelhardt, J. J., et al. Marginating dendritic cells of the tumor microenvironment cross-present tumor antigens and stably engage tumor-specific T cells. *Cancer Cell* 21, 402-417 (2012).

Meredith, M. M., et al. Expression of the zinc finger transcription factor zDC (Zbtb46, Btbd4) defines the classical dendritic cell lineage. *J Exp Med* 209, 1153-1165 (2012).

Curran and Allison. 'Tumor Vaccines Expressing Flt3-Ligand Synergize with CTLA-4 Blockade to Reject Pre-Implanted Tumors' Cancer Research 2009.

Lynch, D. H., A. Andreasen, E. Maraskovsky, J. Whitmore, R. E. Miller, J. C. Schuh. 1997. Flt3 ligand induces tumor regression and antitumor immune responses in vivo. *Nat. Med.* 3: 625.

Chen, K., S. Braun, S. Lyman, Y. Fan, C. M. Traycoff, E. A. Wiebke, J. Gaddy, G. Sledge, H. E. Broxmeyer, K. Cornetta. 1997. Antitumor activity and immunotherapeutic properties of Flt3-ligand in a murine breast cancer model. *Cancer Res.* 57: 3511.

Peron, J. M., C. Esche, V. M. Subbotin, C. Maliszewski, M. T. Lotze, M. R. Shurin. 1998. Flt3-ligand administration inhibits liver metastases: role of NK cells. *J Immunol.* 161: 6164.

Shurin, M. R., C. Esche, M. T. Lotze. 1998. FLT3: receptor and ligand: biology and potential clinical application. *Cytokine Growth Factor Rev.* 9: 3.

We claim:

1. A method of killing, disabling, or depleting Triggering Receptor Expressed on Myeloid Cells 2 (TREM2+) myeloid cells present in a cancer tissue of a subject, comprising: contacting the TREM2+ myeloid cells present in the cancer tissue of the subject with an antibody or antigen-binding fragment thereof comprising a human Fc domain, wherein the antibody or antigen-binding fragment thereof binds to the extracellular domain of TREM2; wherein the antibody or antigen-binding fragment thereof is present in an amount effective to kill, disable, or deplete the TREM2+ myeloid cells via antibody-dependent cell-mediated cytotoxicity activity, antibody-dependent phagocytosis activity, complement-dependent cytotoxicity activity, or antibody-mediated phagocytosis activity.

2. The method of claim 1, wherein the TREM2+ myeloid cells are CD45+, HLA-DR+, CD11c+, CD14+, and BDCA3−, wherein the TREM2+ myeloid cells are present in a population of immune cells comprising myeloid cells that are CD45+, HLA-DR+, CD14−, CD11c+, BDCA1−, and BDCA3+ and the TREM2+ myeloid cells, and wherein the killing, disabling, or depleting of the TREM2+ myeloid cells treats the cancer by enhancing an immune response to the cancer tissue.

3. The method of claim 1 wherein the TREM2+ myeloid cells present in the cancer tissue of the subject comprise at least one of: tumor-associated macrophages; tumor-associated dendritic cells; CD45+, HLA-DR+, CD11c+, CD14+, and BDCA3− cells; CD45+, HLA-DR+, and CD14+ cells; CD45+, HLA-DR+, CD14+, BDCA3−, CD11b+, and CD11c+ cells; CD45+, HLA-DR+, CD14−, CD11c+, and BDCA1+ cells; and wherein the TREM2+ myeloid cells are not BDCA3+ cells, as determined by flow cytometry or an equivalent assay.

4. The method of claim 1, wherein the antibody is at least one of a monoclonal antibody, an IgG1 antibody, an IgG4 antibody, an afucosylated antibody, a human antibody, a humanized antibody, a chimeric antibody, and a full length antibody.

5. The method of claim 1, wherein the contacting induces at least one of: death of the TREM2+ myeloid cells, apoptosis of the TREM2+ myeloid cells, lysis of the TREM2+ myeloid cells, phagocytosis of the TREM2+ myeloid cells, and growth arrest in the TREM2+ myeloid cells.

6. The method of claim 1, wherein the cancer tissue is a solid cancer or a liquid cancer.

7. The method of claim 6, wherein the cancer is selected from the group consisting of: melanoma, kidney cancer, hepatobiliary cancer, head-neck squamous carcinoma, pancreatic cancer, colon cancer, bladder cancer, glioblastoma, prostate cancer, lung cancer, and breast cancer.

8. The method of claim 1, wherein the subject has previously received an immunotherapy.

9. The method of claim 8, wherein the immunotherapy comprises the administration to the subject of at least one of: pembromizulab, nivolumab, and ipilimumab.

10. The method of claim 1, further comprising administering an immunotherapy to the subject concurrently with the antibody or antigen-binding fragment thereof, wherein the immunotherapy comprises at least one of pembromizulab, nivolumab, or ipilimumab.

11. The method of claim 1, further comprising administering an immunotherapy to the subject subsequently to the antibody or antigen-binding fragment thereof, wherein the immunotherapy comprises at least one of pembromizulab, nivolumab, or ipilimumab.

12. A method of treating a cancer in a subject, comprising administering to the subject an antibody or antigen-binding fragment thereof comprising a human Fc domain, wherein the antibody or antigen-binding fragment thereof binds to the extracellular domain Triggering Receptor Expressed on Myeloid Cells 2 (TREM2+), wherein TREM2+ myeloid cells are present in the cancer and the antibody or antigen-binding fragment thereof is present in an amount effective to kill, disable, or deplete the TREM2+ myeloid cells via antibody-dependent cell-mediated cytotoxicity activity, antibody-dependent phagocytosis activity, complement-dependent cytotoxicity activity, or antibody-mediated phagocytosis activity.

13. The method of claim 12, wherein the TREM2+ myeloid cells are CD45+, HLA-DR+, CD11c+, CD14+, and BDCA3−, wherein the TREM2+ myeloid cells are present in a population of immune cells comprising myeloid cells that are CD45+, HLA-DR+, CD14−, CD11c+, BDCA1−, and BDCA3+ and the TREM2+ myeloid cells, and wherein the killing, disabling, or depleting of the TREM2+ myeloid cells treats the cancer.

14. The method of claim 12, wherein the TREM2+ myeloid cells present in the cancer tissue of the subject comprise at least one of: tumor-associated macrophages; tumor-associated dendritic cells; CD45+, HLA-DR+, CD11c+, CD14+, and BDCA3− cells; CD45+, HLA-DR+, and CD14+ cells; CD45+, HLA-DR+, CD14+, BDCA3−, CD11b+, and CD11c+ cells; CD45+, HLA-DR+, CD14−, CD11c+, and BDCA1+ cells; and wherein the TREM2+ myeloid cells are not BDCA3+ cells, as determined by flow cytometry or an equivalent assay.

15. The method of claim 12, wherein the antibody is at least one of a monoclonal antibody, an IgG1 antibody, an IgG4 antibody, an afucosylated antibody, a human antibody, a humanized antibody, a chimeric antibody, and a full length antibody.

16. The method of claim 12, wherein the administering induces at least one of death of the TREM2+ myeloid cells, apoptosis of the TREM2+ myeloid cells, lysis of the TREM2+ myeloid cells, phagocytosis of the TREM2+ myeloid cells, and growth arrest in the TREM2+ myeloid cells.

17. The method of claim 12, wherein the cancer is a solid cancer or a liquid cancer.

18. The method of claim 17, wherein the cancer is selected from the group consisting of: melanoma, kidney cancer, hepatobiliary cancer, head-neck squamous carcinoma, pancreatic cancer, colon cancer, bladder cancer, glioblastoma, prostate cancer, lung cancer, and breast cancer.

19. The method of claim 12, wherein the subject has previously received an immunotherapy.

20. The method of claim 19, wherein the immunotherapy comprises the administration to the subject of at least one of: pembromizulab, nivolumab, and ipilimumab.

21. The method of claim 12, further comprising administering an immunotherapy to the subject concurrently with the antibody or antigen-binding fragment thereof, wherein the immunotherapy comprises at least one of pembromizulab, nivolumab, or ipilimumab.

22. The method of claim 12, further comprising administering an immunotherapy to the subject subsequently to the antibody or antigen-binding fragment thereof, wherein the immunotherapy comprises at least one of pembromizulab, nivolumab, or ipilimumab.

\* \* \* \* \*

SEQUENCE LISTING

<160> NUMBER OF SEQ ID NOS: 11

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Gly Phe Asn Leu Ser Ser Ser Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Ser Ser Ser Tyr Gly Ser Thr
1               5

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Arg Ala His Tyr Val Trp Tyr Gly Ser Val Tyr Ala His Ser Tyr
1               5                   10                  15

Gly Gly Met Asp Tyr
            20

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Val Ser Ser Ala
1               5

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Ala Ser
1

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Trp Ser Gly Gly Tyr Ser Gly Leu Ile Thr
1               5                   10

<210> SEQ ID NO 7
<211> LENGTH: 110

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Ser Gly Gly Tyr Ser
                85                  90                  95

Gly Leu Ile Thr Phe Gly Gln Gly Thr Lys Val Glu Ile Lys
            100                 105                 110

<210> SEQ ID NO 8
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Ser Ser
            20                  25                  30

Tyr Met His Trp Val Arg Gln Ala Pro Gly Lys Gly Leu Glu Trp Val
        35                  40                  45

Ala Ser Ile Ser Ser Ser Tyr Gly Ser Thr Tyr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ala His Tyr Val Trp Tyr Gly Ser Val Tyr Ala His Ser Tyr
            100                 105                 110

Gly Gly Met Asp Tyr Trp Gly Gln Gly Thr Leu Val Thr Val Ser Ser
        115                 120                 125

<210> SEQ ID NO 9
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
```

```
                    20                  25                  30
Val Ala Trp Tyr Gln Gln Lys Pro Gly Lys Ala Pro Lys Leu Leu Ile
             35                  40                  45

Tyr Ser Ala Ser Ser Leu Tyr Ser Gly Val Pro Ser Arg Phe Ser Gly
         50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Trp Ser Gly Gly Tyr Ser
                 85                  90                  95

Gly Leu Ile Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 10
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Leu Ser Ser Ser
             20                  25                  30

Tyr Met His Trp Val Arg Gln Ala Pro Gly Lys Gly Leu Glu Trp Val
         35                  40                  45

Ala Ser Ile Ser Ser Ser Tyr Gly Ser Thr Tyr Tyr Ala Asp Ser Val
     50                  55                  60

Lys Gly Arg Phe Thr Ile Ser Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Ala His Tyr Val Trp Tyr Gly Ser Val Tyr Ala His Ser Tyr
            100                 105                 110

Gly Gly Met Asp Tyr Trp Gly Gln Gly Thr Leu Val Thr Val Ser Ser
        115                 120                 125

Ala Ser Thr Lys Gly Pro Ser Val Phe Pro Leu Ala Pro Ser Ser Lys
130                 135                 140

Ser Thr Ser Gly Gly Thr Ala Ala Leu Gly Cys Leu Val Lys Asp Tyr
145                 150                 155                 160
```

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 11
<211> LENGTH: 8
<212> TYPE: PRT
<213> ORGANISM: Gallus gallus

<400> SEQUENCE: 11

Ser Ile Ile Asn Phe Glu Lys Leu
1               5